(12) United States Patent
Brunner et al.

(10) Patent No.: US 12,416,004 B2
(45) Date of Patent: Sep. 16, 2025

(54) RNA COMPOSITIONS AND METHODS FOR INHIBITING ANGPTL8

(71) Applicant: Sanofi, Paris (FR)

(72) Inventors: Bodo Brunner, Frankfurt am Main (DE); Mike Helms, Frankfurt am Main (DE); Armin Hofmeister, Frankfurt am Main (DE); Kerstin Jahn-Hofmann, Frankfurt am Main (DE); Christiane Metz-Weidmann, Frankfurt am Main (DE); Sabine Scheidler, Frankfurt am Main (DE); Pierrick Rival, Paris (FR)

(73) Assignee: Sanofi, Paris (FR)

( * ) Notice: Subject to any disclaimer, the term of this patent is extended or adjusted under 35 U.S.C. 154(b) by 1064 days.

(21) Appl. No.: 17/296,530

(22) PCT Filed: Nov. 22, 2019

(86) PCT No.: PCT/EP2019/082216
§ 371 (c)(1),
(2) Date: May 24, 2021

(87) PCT Pub. No.: WO2020/104649
PCT Pub. Date: May 28, 2020

(65) Prior Publication Data
US 2022/0025367 A1 Jan. 27, 2022

(30) Foreign Application Priority Data
Nov. 23, 2018 (EP) .................................... 18306562

(51) Int. Cl.
C12N 15/113 (2010.01)
(52) U.S. Cl.
CPC ........ *C12N 15/113* (2013.01); *C12N 2310/14* (2013.01); *C12N 2310/321* (2013.01); *C12N 2310/322* (2013.01); *C12N 2310/351* (2013.01); *C12N 2310/3515* (2013.01); *C12N 2320/30* (2013.01)

(58) Field of Classification Search
CPC .............. C12N 15/113; C12N 2310/14; C12N 2310/321; C12N 2310/322; C12N 2310/351; C12N 2310/3515; C12N 2320/30
See application file for complete search history.

(56) References Cited

U.S. PATENT DOCUMENTS

| | | | |
|---|---|---|---|
| 11,897,911 B2 | 2/2024 | Hofmeister et al. | |
| 2005/0246794 A1 | 11/2005 | Khvorova et al. | |
| 2007/0031844 A1* | 2/2007 | Khvorova | A61P 3/10 435/6.13 |
| 2017/0291937 A1* | 10/2017 | Gromada | A61P 5/00 |
| 2022/0025367 A1 | 1/2022 | Brunner et al. | |
| 2022/0290156 A1 | 9/2022 | Brunner et al. | |
| 2022/0372063 A1 | 11/2022 | Brunner et al. | |
| 2023/0383294 A1 | 11/2023 | Brunner et al. | |
| 2024/0035029 A1 | 2/2024 | Brunner et al. | |
| 2024/0092819 A1 | 3/2024 | Elshorst et al. | |
| 2024/0376137 A1 | 11/2024 | Hofmeister et al. | |

FOREIGN PATENT DOCUMENTS

| | | | |
|---|---|---|---|
| EP | 2213738 A2 | 8/2010 | |
| WO | 2004045543 A2 | 6/2004 | |
| WO | 2007127439 A2 | 11/2007 | |
| WO | 2008022309 A2 | 2/2008 | |
| WO | 2009004085 A2 | 1/2009 | |
| WO | WO-2014025805 A1 * | 2/2014 | ......... A61K 31/7088 |
| WO | 2019170731 A1 | 9/2019 | |

OTHER PUBLICATIONS

Dharmacon Inc. "JP 2006507841-A/1106881: Functional and Hyperfunctional siRNA." EMBL Jun. 28, 2011, retrieved from EBI accession No. EM_PAT:GB544472, Database accession No. GB544472.
Distefano, J.K. "Angiopoietin-like 8 (ANGPTL8) expression is regulated by miR-143-3p in human hepatocytes." Gene vol. 681 (2019): 1-6.
Gusarova, V. et al. "ANGPTL8/betatrophin does not control pancreatic beta cell expansion." Cell vol. 159,3 (2014): 691-6.
International Search Report and Written Opinion in International Patent Application No. PCT/EP2019/082216 dated May 18, 2020.
Lee, E.C. et al. "Identification of a new functional domain in angiopoietin-like 3 (ANGPTL3) and angiopoietin-like 4 (ANGPTL4) involved in binding and inhibition of lipoprotein lipase (LPL)." The Journal of Biological Chemistry vol. 284,20 (2009): 13735-13745.
Mysore, R. et al. "Angiopoietin-like 8 (Angptl8) controls adipocyte lipolysis and phospholipid composition." Chemistry and Physics of Lipids vol. 207, (2017): 246-252.
Quagliarini, F. et al. "Atypical angiopoietin-like protein that regulates ANGPTL3." Proceedings of the National Academy of Sciences of the United States of America vol. 109,48 (2012): 19751-6.
Wang, Y. et al. "Mice lacking ANGPTL8 (Betatrophin) manifest disrupted triglyceride metabolism without impaired glucose homeostasis." Proceedings of the National Academy of Sciences of the United States of America vol. 110,40 (2013): 16109-14.
Zhang Y. et al. "Angiopoietin-like protein 8 (betatrophin) is a stress-response protein that down-regulates expression of adipocyte triglyceride lipase." Biochimica Et Biophysica Acta vol. 1861, No. 2 (2015): 130-137.
Vatner, D. F. et al. "Angptl8 antisense oligonucleotide improves adipose lipid metabolism and prevents diet-induced NAFLD and hepatic insulin resistance in rodents." Diabetologia vol. 61,6 (2018): 1435-1446.

* cited by examiner

*Primary Examiner* — Abigail Vanhorn
*Assistant Examiner* — Stephanie L Sullivan
(74) *Attorney, Agent, or Firm* — K&L Gates LLP

(57) ABSTRACT

The present disclosure relates to dsRNAs targeting ANGPTL8, methods of inhibiting ANGPTL8 gene expression, and methods of treating one or more conditions associated with ANGPTL8 gene expression.

16 Claims, 17 Drawing Sheets
Specification includes a Sequence Listing.

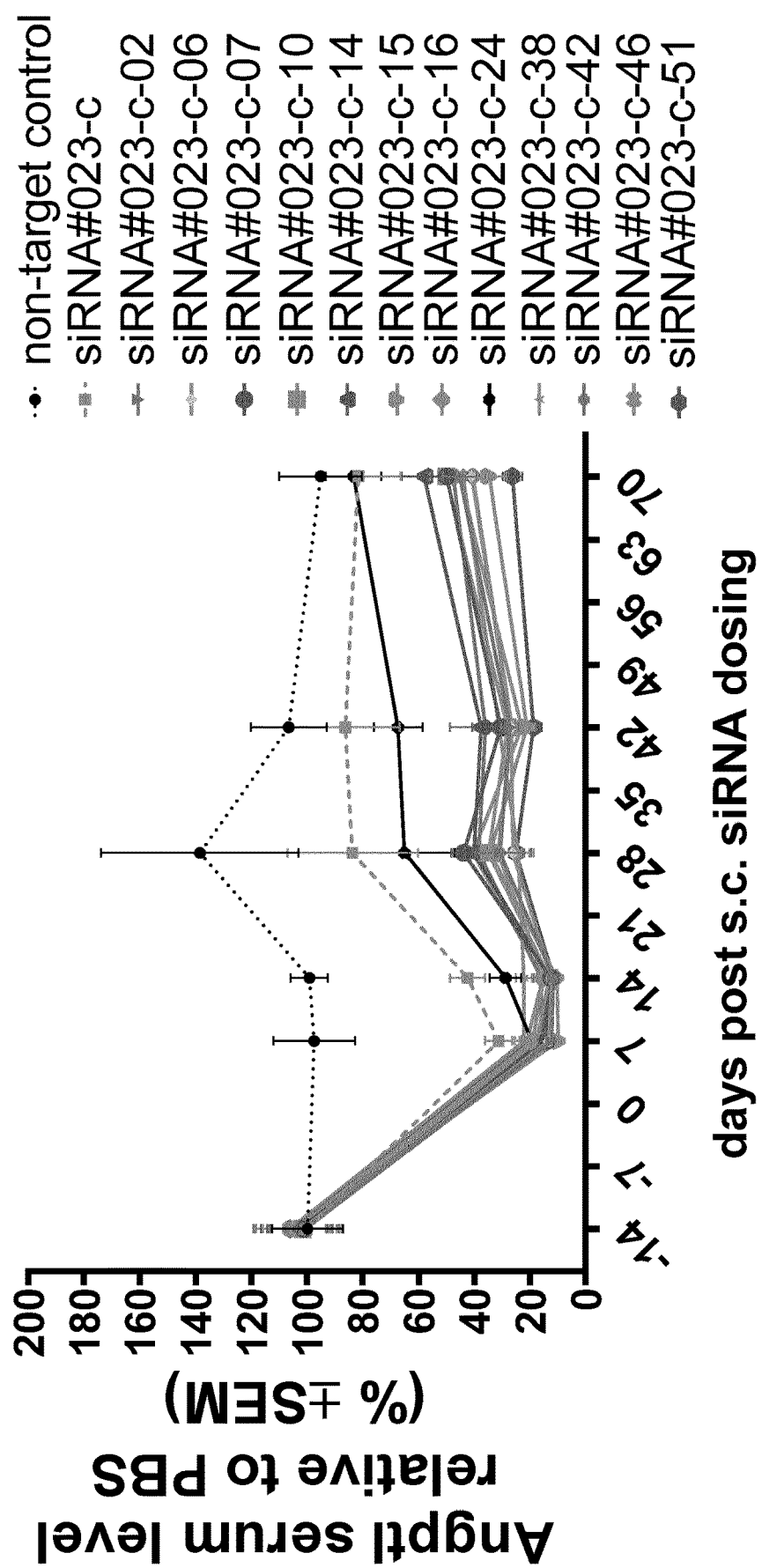

SEQUENCE LISTING

```
<160> NUMBER OF SEQ ID NOS: 750

<210> SEQ ID NO 1
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
cuuagacccu cagucaugc                                                19

<210> SEQ ID NO 2
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
cagaacuggc acagcauga                                                19

<210> SEQ ID NO 3
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
agaacuggca cagcaugag                                                19

<210> SEQ ID NO 4
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
cugacaaagg ccaggaaca                                                19

<210> SEQ ID NO 5
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ugacaaaggc caggaacag                                               19

<210> SEQ ID NO 6
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
gaacagccug ggucucuau                                               19

<210> SEQ ID NO 7
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
aacagccugg gucucuaug                                               19

<210> SEQ ID NO 8
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gucucuaugg ccgcacaau                                               19

<210> SEQ ID NO 9
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
aacuucgggc aagccuguu                                               19

<210> SEQ ID NO 10
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
caagccuguu ggagacuca                                               19
```

```
<210> SEQ ID NO 11
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
aagccuguug gagacucag                                                 19

<210> SEQ ID NO 12
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agccuguugg agacucaga                                                 19

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gccuguugga gacucagau                                                 19

<210> SEQ ID NO 14
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ccuguuggag acucagaug                                                 19

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cuguuggaga cucagaugg                                                 19

<210> SEQ ID NO 16
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

```
Synthetic oligonucleotide"

<400> SEQUENCE: 16
uguuggagac ucagaugga                                                19

<210> SEQ ID NO 17
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
guuggagacu cagauggag                                                19

<210> SEQ ID NO 18
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
uuggagacuc agauggagg                                                19

<210> SEQ ID NO 19
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gacucagaug gaggaggau                                                19

<210> SEQ ID NO 20
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
cucagaugga ggaggauau                                                19

<210> SEQ ID NO 21
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ucagauggag gaggauauu                                                19

<210> SEQ ID NO 22
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
cagauggagg aggauauuc                                                19

<210> SEQ ID NO 23
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
agauggagga ggauauucu                                                19

<210> SEQ ID NO 24
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
gauggaggag gauauucug                                                19

<210> SEQ ID NO 25
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
auggaggagg auauucugc                                                19

<210> SEQ ID NO 26
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uggaggagga uauucugca                                                19

<210> SEQ ID NO 27
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
```
ggaggaggau auucugcag                                                19

<210> SEQ ID NO 28
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gaggaggaua uucugcagc                                                19

<210> SEQ ID NO 29
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
aggaggauau ucugcagcu                                                19

<210> SEQ ID NO 30
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
uauucugcag cugcaggca                                                19

<210> SEQ ID NO 31
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
cuagaagucc agcugagga                                                19

<210> SEQ ID NO 32
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
uagaagucca gcugaggag                                                19

<210> SEQ ID NO 33
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 33
cccugccuac cgagaauuu                                                    19

<210> SEQ ID NO 34
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 34
ccugccuacc gagaauuug                                                    19

<210> SEQ ID NO 35
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 35
cugccuaccg agaauuuga                                                    19

<210> SEQ ID NO 36
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 36
ugccuaccga gaauuugag                                                    19

<210> SEQ ID NO 37
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 37
gccuaccgag aauuugagg                                                    19

<210> SEQ ID NO 38
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 38
ccuaccgaga auuugaggu                                                    19

<210> SEQ ID NO 39

<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 39
cuaccgagaa uuugagguc                    19

<210> SEQ ID NO 40
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 40
uaccgagaau uugaggucu                    19

<210> SEQ ID NO 41
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 41
accgagaauu ugaggucuu                    19

<210> SEQ ID NO 42
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
ccgagaauuu gaggucuua                    19

<210> SEQ ID NO 43
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43
cgagaauuug aggucuuaa                    19

<210> SEQ ID NO 44
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 44
gagaauuuga ggucuuaaa                                                    19

<210> SEQ ID NO 45
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
agaauuugag gucuuaaag                                                    19

<210> SEQ ID NO 46
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
gaauuugagg ucuuaaagg                                                    19

<210> SEQ ID NO 47
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
aauuugaggu cuuaaaggc                                                    19

<210> SEQ ID NO 48
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
auuugagguc uuaaaggcu                                                    19

<210> SEQ ID NO 49
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
uuugaggucu uaaaggcuc                                                    19

<210> SEQ ID NO 50
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 50
uugaggucuu aaaggcuca                                                     19

<210> SEQ ID NO 51
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ugaggucuua aaggcucac                                                     19

<210> SEQ ID NO 52
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
gaggucuuaa aggcucacg                                                     19

<210> SEQ ID NO 53
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aggucuuaaa ggcucacgc                                                     19

<210> SEQ ID NO 54
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
ggucuuaaag gcucacgcu                                                     19

<210> SEQ ID NO 55
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
gucuuaaagg cucacgcug                                                     19
```

-continued

```
<210> SEQ ID NO 56
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
ucuuaaaggc ucacgcuga                                                   19

<210> SEQ ID NO 57
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
cuuaaaggcu cacgcugac                                                   19

<210> SEQ ID NO 58
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
uuaaaggcuc acgcugaca                                                   19

<210> SEQ ID NO 59
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
uaaaggcuca cgcugacaa                                                   19

<210> SEQ ID NO 60
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
aaaggcucac gcugacaag                                                   19

<210> SEQ ID NO 61
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 61
cugacaagca gagccacau                                                    19

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ugacaagcag agccacauc                                                    19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
acaagcagag ccacauccu                                                    19

<210> SEQ ID NO 64
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
caagcagagc cacauccua                                                    19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
aagcagagcc acauccuau                                                    19

<210> SEQ ID NO 66
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
agcagagcca cauccuaug                                                    19

<210> SEQ ID NO 67
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 67
gacagaucca ggagagacu                                              19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
acagauccag gagagacuc                                              19

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
agauccagga gagacucca                                              19

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
agccugaauc ugccuggau                                              19

<210> SEQ ID NO 71
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
cugaaucugc cuggaugga                                              19

<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ugaaucugcc uggauggaa                                              19
```

```
<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
gaaucugccu ggauggaac                                                    19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
aaucugccug gauggaacu                                                    19

<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
aucugccugg auggaacug                                                    19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ucugccugga uggaacuga                                                    19

<210> SEQ ID NO 77
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
uggauggaac ugaggacca                                                    19

<210> SEQ ID NO 78
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 78
gauggaacug aggaccaau                                              19

<210> SEQ ID NO 79
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
auggaacuga ggaccaauc                                              19

<210> SEQ ID NO 80
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
uggaacugag gaccaauca                                              19

<210> SEQ ID NO 81
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
ggaacugagg accaaucau                                              19

<210> SEQ ID NO 82
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gaacugagga ccaaucaug                                              19

<210> SEQ ID NO 83
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
aacugaggac caaucaugc                                              19

<210> SEQ ID NO 84
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
acugaggacc aaucaugcu                                              19

<210> SEQ ID NO 85
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
cugaggacca aucaugcug                                              19

<210> SEQ ID NO 86
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ugaggaccaa ucaugcugc                                              19

<210> SEQ ID NO 87
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gaggaccaau caugcugca                                              19

<210> SEQ ID NO 88
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
aggaccaauc augcugcaa                                              19

<210> SEQ ID NO 89
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ggaccaauca ugcugcaag                                              19
```

```
<210> SEQ ID NO 90
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gaccaaucau gcugcaagg                                                   19

<210> SEQ ID NO 91
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
accaaucaug cugcaagga                                                   19

<210> SEQ ID NO 92
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ccaaucaugc ugcaaggaa                                                   19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
caaucaugcu gcaaggaac                                                   19

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
aaucaugcug caaggaaca                                                   19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 95
aucaugcugc aaggaacac                                                  19

<210> SEQ ID NO 96
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
ucaugcugca aggaacacu                                                  19

<210> SEQ ID NO 97
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
caugcugcaa ggaacacuu                                                  19

<210> SEQ ID NO 98
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
augcugcaag gaacacuuc                                                  19

<210> SEQ ID NO 99
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
ugcugcaagg aacacuucc                                                  19

<210> SEQ ID NO 100
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gcugcaagga acacuucca                                                  19

<210> SEQ ID NO 101
<211> LENGTH: 19

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
ugccuguuca cugggauca                                                19

<210> SEQ ID NO 102
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
uguucacugg gaucagcca                                                19

<210> SEQ ID NO 103
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
cacuucugag cacagagca                                                19

<210> SEQ ID NO 104
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
acuucugagc acagagcag                                                19

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
ugagcacaga gcagagaca                                                19

<210> SEQ ID NO 106
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
```
agcacagagc agagacaga                                                    19

<210> SEQ ID NO 107
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
ggacaaaggc agaggaugu                                                    19

<210> SEQ ID NO 108
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gacaaaggca gaggaugua                                                    19

<210> SEQ ID NO 109
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
acaaaggcag aggauguag                                                    19

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
caaaggcaga ggauguagc                                                    19

<210> SEQ ID NO 111
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
aaaggcagag gauguagcc                                                    19

<210> SEQ ID NO 112
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 112
cagaggaugu agccccauu                                              19

<210> SEQ ID NO 113
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
agaggaugua gccccauug                                              19

<210> SEQ ID NO 114
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
uguacccuuu caugccuac                                              19

<210> SEQ ID NO 115
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
guacccuuuc augccuaca                                              19

<210> SEQ ID NO 116
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
uacccuuuca ugccuacac                                              19

<210> SEQ ID NO 117
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
acccuuucau gccuacaca                                              19

<210> SEQ ID NO 118
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
cccuuucaug ccuacacac                                                  19

<210> SEQ ID NO 119
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
ccuuucaugc cuacacacc                                                  19

<210> SEQ ID NO 120
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
cuuucaugcc uacacaccc                                                  19

<210> SEQ ID NO 121
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
uuucaugccu acacacccc                                                  19

<210> SEQ ID NO 122
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
ccccucauua aagcagagu                                                  19

<210> SEQ ID NO 123
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
```
cccucauuaa agcagaguc                                              19

<210> SEQ ID NO 124
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
ccucauuaaa gcagagucg                                              19

<210> SEQ ID NO 125
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
cucauuaaag cagagucgu                                              19

<210> SEQ ID NO 126
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ucauuaaagc agagucgug                                              19

<210> SEQ ID NO 127
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
cauuaaagca gagucgugg                                              19

<210> SEQ ID NO 128
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
auuaaagcag agucguggc                                              19

<210> SEQ ID NO 129
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 129
uuaaagcaga gucguggca                                               19

<210> SEQ ID NO 130
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
uaaagcagag ucguggcau                                               19

<210> SEQ ID NO 131
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
aaagcagagu cguggcauc                                               19

<210> SEQ ID NO 132
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
aagcagaguc guggcaucu                                               19

<210> SEQ ID NO 133
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
gcaugacuga gggucuaag                                               19

<210> SEQ ID NO 134
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ucaugcugug ccaguucug                                               19
```

```
<210> SEQ ID NO 135
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
cucaugcugu gccaguucu                                                  19

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
uguuccuggc cuuugucag                                                  19

<210> SEQ ID NO 137
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cuguuccugg ccuuuguca                                                  19

<210> SEQ ID NO 138
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
auagagaccc aggcuguuc                                                  19

<210> SEQ ID NO 139
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
cauagagacc caggcuguu                                                  19

<210> SEQ ID NO 140
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 140
auugugcggc cauagagac                                                19

<210> SEQ ID NO 141
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
aacaggcuug cccgaaguu                                                19

<210> SEQ ID NO 142
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
ugagucucca acaggcuug                                                19

<210> SEQ ID NO 143
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
cugagucucc aacaggcuu                                                19

<210> SEQ ID NO 144
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
ucugagucuc caacaggcu                                                19

<210> SEQ ID NO 145
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
aucugagucu ccaacaggc                                                19

<210> SEQ ID NO 146
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 146
caucugaguc uccaacagg                                                    19

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
ccaucugagu cuccaacag                                                    19

<210> SEQ ID NO 148
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
uccaucugag ucuccaaca                                                    19

<210> SEQ ID NO 149
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
cuccaucuga gucuccaac                                                    19

<210> SEQ ID NO 150
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
ccuccaucug agucuccaa                                                    19

<210> SEQ ID NO 151
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
auccuccucc aucugaguc                                                    19
```

```
<210> SEQ ID NO 152
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
auauccuccu ccaucugag                                              19

<210> SEQ ID NO 153
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
aauauccucc uccaucuga                                              19

<210> SEQ ID NO 154
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
gaauauccuc cuccaucug                                              19

<210> SEQ ID NO 155
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
agaauauccu ccuccaucu                                              19

<210> SEQ ID NO 156
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cagaauaucc uccuccauc                                              19

<210> SEQ ID NO 157
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 157
gcagaauauc cuccuccau                                                19

<210> SEQ ID NO 158
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
ugcagaauau ccuccucca                                                19

<210> SEQ ID NO 159
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cugcagaaua uccuccucc                                                19

<210> SEQ ID NO 160
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gcugcagaau auccuccuc                                                19

<210> SEQ ID NO 161
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
agcugcagaa uauccuccu                                                19

<210> SEQ ID NO 162
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
ugccugcagc ugcagaaua                                                19

<210> SEQ ID NO 163
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
uccucagcug gacuucuag                                                     19

<210> SEQ ID NO 164
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
cuccucagcu ggacuucua                                                     19

<210> SEQ ID NO 165
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
aaauucucgg uaggcaggg                                                     19

<210> SEQ ID NO 166
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
caaauucucg guaggcagg                                                     19

<210> SEQ ID NO 167
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
ucaaauucuc gguaggcag                                                     19

<210> SEQ ID NO 168
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
cucaaauucu cgguaggca                                                     19
```

-continued

```
<210> SEQ ID NO 169
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
ccucaaauuc ucgguaggc                                                    19

<210> SEQ ID NO 170
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
accucaaauu cucgguagg                                                    19

<210> SEQ ID NO 171
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
gaccucaaau ucucgguag                                                    19

<210> SEQ ID NO 172
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
agaccucaaa uucucggua                                                    19

<210> SEQ ID NO 173
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
aagaccucaa auucucggu                                                    19

<210> SEQ ID NO 174
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 174
uaagaccuca aauucucgg                                                19

<210> SEQ ID NO 175
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
uuaagaccuc aaauucucg                                                19

<210> SEQ ID NO 176
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
uuuaagaccu caaauucuc                                                19

<210> SEQ ID NO 177
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
cuuuaagacc ucaaauucu                                                19

<210> SEQ ID NO 178
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
ccuuuaagac cucaaauuc                                                19

<210> SEQ ID NO 179
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gccuuuaaga ccucaaauu                                                19

<210> SEQ ID NO 180
<211> LENGTH: 19

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
agccuuuaag accucaaau                                                      19

<210> SEQ ID NO 181
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gagccuuuaa gaccucaaa                                                      19

<210> SEQ ID NO 182
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ugagccuuua agaccucaa                                                      19

<210> SEQ ID NO 183
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
gugagccuuu aagaccuca                                                      19

<210> SEQ ID NO 184
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
cgugagccuu uaagaccuc                                                      19

<210> SEQ ID NO 185
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
```
gcgugagccu uuaagaccu                                        19

<210> SEQ ID NO 186
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
agcgugagcc uuuaagacc                                        19

<210> SEQ ID NO 187
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
cagcgugagc cuuuaagac                                        19

<210> SEQ ID NO 188
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
ucagcgugag ccuuuaaga                                        19

<210> SEQ ID NO 189
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gucagcguga gccuuuaag                                        19

<210> SEQ ID NO 190
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
ugucagcgug agccuuuaa                                        19

<210> SEQ ID NO 191
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 191
uugucagcgu gagccuuua                                                    19

<210> SEQ ID NO 192
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
cuugucagcg ugagccuuu                                                    19

<210> SEQ ID NO 193
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
auguggcucu gcuugucag                                                    19

<210> SEQ ID NO 194
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gauguggcuc ugcuuguca                                                    19

<210> SEQ ID NO 195
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
aggauguggc ucugcuugu                                                    19

<210> SEQ ID NO 196
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
uaggaugugg cucugcuug                                                    19

<210> SEQ ID NO 197
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
auaggaugug gcucugcuu                                                    19

<210> SEQ ID NO 198
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
cauaggaugu ggcucugcu                                                    19

<210> SEQ ID NO 199
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
agucucuccu ggaucuguc                                                    19

<210> SEQ ID NO 200
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
gagucucucc uggaucugu                                                    19

<210> SEQ ID NO 201
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
uggagucucu ccuggaucu                                                    19

<210> SEQ ID NO 202
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
```
auccaggcag auucaggcu                                          19

<210> SEQ ID NO 203
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
uccauccagg cagauucag                                          19

<210> SEQ ID NO 204
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
uuccauccag gcagauuca                                          19

<210> SEQ ID NO 205
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
guuccaucca ggcagauuc                                          19

<210> SEQ ID NO 206
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aguuccaucc aggcagauu                                          19

<210> SEQ ID NO 207
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207 caguccauc caggcagau                                           19

<210> SEQ ID NO 208
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 208
ucaguuccau ccaggcaga                                              19

<210> SEQ ID NO 209
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ugguccucag uuccaucca                                              19

<210> SEQ ID NO 210
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
auugguccuc aguuccauc                                              19

<210> SEQ ID NO 211
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
gauugguccu caguuccau                                              19

<210> SEQ ID NO 212
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
ugauuggucc ucaguucca                                              19

<210> SEQ ID NO 213
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
augauugguc cucaguucc                                              19
```

```
<210> SEQ ID NO 214
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
caugauuggu ccucaguuc                                               19

<210> SEQ ID NO 215
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gcaugauugg uccucaguu                                               19

<210> SEQ ID NO 216
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
agcaugauug guccucagu                                               19

<210> SEQ ID NO 217
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
cagcaugauu gguccucag                                               19

<210> SEQ ID NO 218
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
gcagcaugau ugguccuca                                               19

<210> SEQ ID NO 219
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 219
ugcagcauga uugguccuc                                                  19

<210> SEQ ID NO 220
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
uugcagcaug auugguccu                                                  19

<210> SEQ ID NO 221
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
cuugcagcau gauuggucc                                                  19

<210> SEQ ID NO 222
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
ccuugcagca ugauugguc                                                  19

<210> SEQ ID NO 223
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
uccuugcagc augauuggu                                                  19

<210> SEQ ID NO 224
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
uuccuugcag caugauugg                                                  19

<210> SEQ ID NO 225
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 225
guuccuugca gcaugauug                                                    19

<210> SEQ ID NO 226
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
uguuccuugc agcaugauu                                                    19

<210> SEQ ID NO 227
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
guguuccuug cagcaugau                                                    19

<210> SEQ ID NO 228
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
aguguuccuu gcagcauga                                                    19

<210> SEQ ID NO 229
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
aaguguuccu ugcagcaug                                                    19

<210> SEQ ID NO 230
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
gaaguguucc uugcagcau                                                    19
```

```
<210> SEQ ID NO 231
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
ggaaguguuc cuugcagca                                                19

<210> SEQ ID NO 232
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
uggaaguguu ccuugcagc                                                19

<210> SEQ ID NO 233
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
ugaucccagu gaacaggca                                                19

<210> SEQ ID NO 234
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
uggcugaucc cagugaaca                                                19

<210> SEQ ID NO 235
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ugcucugugc ucagaagug                                                19

<210> SEQ ID NO 236
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 236
cugcucugug cucagaagu                                                19

<210> SEQ ID NO 237
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
ugucucugcu cugugcuca                                                19

<210> SEQ ID NO 238
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
ucugucucug cucugugcu                                                19

<210> SEQ ID NO 239
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
acauccucug ccuuugucc                                                19

<210> SEQ ID NO 240
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
uacauccucu gccuuuguc                                                19

<210> SEQ ID NO 241
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
cuacauccuc ugccuuugu                                                19

<210> SEQ ID NO 242
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gcuacauccu cugccuuug                                                       19

<210> SEQ ID NO 243
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ggcuacaucc ucugccuuu                                                       19

<210> SEQ ID NO 244
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244 aaugggcua cauccucug                                                        19

<210> SEQ ID NO 245
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245 caaugggcu acauccucu                                                        19

<210> SEQ ID NO 246
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
guaggcauga aagguaca                                                        19

<210> SEQ ID NO 247
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
uguaggcaug aaagggua                                                        19
```

<210> SEQ ID NO 248
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
guguaggcau gaaagggua                                                      19

<210> SEQ ID NO 249
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
uguguaggca ugaaagggu                                                      19

<210> SEQ ID NO 250
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
guguguaggc augaaaggg                                                      19

<210> SEQ ID NO 251
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
gguguguagg caugaaagg                                                      19

<210> SEQ ID NO 252
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
ggguguguag gcaugaaag                                                      19

<210> SEQ ID NO 253
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 253 gggguguguaggcaugaaa                              19

<210> SEQ ID NO 254
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254 acucugcuuuaaugagggg                              19

<210> SEQ ID NO 255
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255 gacucugcuuuaaugaggg                              19

<210> SEQ ID NO 256
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256 cgacucugcuuuaaugagg                              19

<210> SEQ ID NO 257
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257 acgacucugcuuuaaugag                              19

<210> SEQ ID NO 258
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258 cacgacucugcuuuaauga                              19

<210> SEQ ID NO 259
<211> LENGTH: 19

```
-continued

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ccacgacucu gcuuuaaug                                                    19

<210> SEQ ID NO 260
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gccacgacuc ugcuuuaau                                                    19

<210> SEQ ID NO 261
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
ugccacgacu cugcuuuaa                                                    19

<210> SEQ ID NO 262
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
augccacgac ucugcuuua                                                    19

<210> SEQ ID NO 263
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gaugccacga cucugcuuu                                                    19

<210> SEQ ID NO 264
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
```
agaugccacg acucugcuu                                          19

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 265
ccacuuagac ccucagucau gct                                     23

<210> SEQ ID NO 266
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 266
ccacagaacu ggcacagcau gat                                     23

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 267
ccaagaacug gcacagcaug agt                                     23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
ccacugacaa aggccaggaa cat                                     23

<210> SEQ ID NO 269
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269
ccaugacaaa ggccaggaac agt                                              23

<210> SEQ ID NO 270
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 270
ccagaacagc cuggucucu aut                                               23

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
ccaaacagcc ugggucucua ugt                                              23

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
ccagucucua uggccgcaca aut                                              23

<210> SEQ ID NO 273
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 273
ccaaacuucg ggcaagccug uut                                              23

<210> SEQ ID NO 274
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 274
ccacaagccu guuggagacu cat                                              23

<210> SEQ ID NO 275
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 275
ccaaagccug uuggagacuc agt                                              23

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 276
ccaagccugu uggagacuca gat                                              23

<210> SEQ ID NO 277
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: source
<223> OTHER INFORMATION: /note="Description of Combined DNA/RNA
       Molecule: Synthetic oligonucleotide"

<400> SEQUENCE: 277
ccagccuguu ggagacucag aut                                              23

```
<210> SEQ ID NO 278
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 278
ccaccuguug gagacucaga ugt                                          23

<210> SEQ ID NO 279
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 279
ccacuguugg agacucagau ggt                                          23

<210> SEQ ID NO 280
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280
ccauguugga gacucagaug gat                                          23

<210> SEQ ID NO 281
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 281
ccaguuggag acucagaugg agt                                          23

<210> SEQ ID NO 282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282
ccauuggaga cucagaugga ggt                                              23

<210> SEQ ID NO 283
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 283
ccagacucag auggaggagg aut                                              23

<210> SEQ ID NO 284
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 284
ccacucagau ggaggaggau aut                                              23

<210> SEQ ID NO 285
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285
ccaucagaug gaggaggaua uut                                              23

<210> SEQ ID NO 286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 286
```

```
ccacagaugg aggaggauau uct                                              23
```

<210> SEQ ID NO 287
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 287

```
ccaagaugga ggaggauauu cut                                              23
```

<210> SEQ ID NO 288
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 288

```
ccagauggag gaggauauuc ugt                                              23
```

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 289

```
ccauggagg aggauauucu gct                                               23
```

<210> SEQ ID NO 290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290

```
ccauggagga ggauauucug cat                                              23
```

<210> SEQ ID NO 291
<211> LENGTH: 23
<212> TYPE: DNA

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 291
ccaggaggag gauauucugc agt          23

<210> SEQ ID NO 292
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 292
ccagaggagg auauucugca gct          23

<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 293
ccaaggagga uauucugcag cut          23

<210> SEQ ID NO 294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 294
ccauauucug cagcugcagg cat          23

<210> SEQ ID NO 295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 295
ccacuagaag uccagcugag gat                                              23

<210> SEQ ID NO 296
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 296
ccauagaagu ccagcugagg agt                                              23

<210> SEQ ID NO 297
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 297
ccacccugcc uaccgagaau uut                                              23

<210> SEQ ID NO 298
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 298
ccaccugccu accgagaauu ugt                                              23

<210> SEQ ID NO 299
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 299
ccacugccua ccgagaauuu gat                                              23
```

```
<210> SEQ ID NO 300
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 300
ccaugccuac cgagaauuug agt                                              23

<210> SEQ ID NO 301
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 301
ccagccuacc gagaauuuga ggt                                              23

<210> SEQ ID NO 302
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 302
ccaccuaccg agaauuugag gut                                              23

<210> SEQ ID NO 303
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 303
ccacuaccga gaauuugagg uct                                              23

<210> SEQ ID NO 304
<211> LENGTH: 23
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 304
ccauaccgag aauuugaggu cut                                          23

<210> SEQ ID NO 305
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 305
ccaaccgaga auuugagguc uut                                          23

<210> SEQ ID NO 306
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 306
ccaccgagaa uuugaggucu uat                                          23

<210> SEQ ID NO 307
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 307
ccacgagaau uugaggucuu aat                                          23

<210> SEQ ID NO 308
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 308
ccagagaauu ugaggucuua aat                                        23

<210> SEQ ID NO 309
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 309 ccagaauuu gaggucuuaa agt                                         23

<210> SEQ ID NO 310
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 310
ccagaauuug aggucuuaaa ggt                                        23

<210> SEQ ID NO 311
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 311
ccaaauuuga ggucuuaaag gct                                        23

<210> SEQ ID NO 312
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 312
ccaauuugag gucuuaaagg cut                                        23

<210> SEQ ID NO 313
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 313
ccauuugagg ucuuaaaggc uct                                              23

<210> SEQ ID NO 314
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 314
ccauugaggu cuuaaaggcu cat                                              23

<210> SEQ ID NO 315
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 315
ccaugagguc uuaaaggcuc act                                              23

<210> SEQ ID NO 316
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 316
ccagaggucu uaaaggcuca cgt                                              23

<210> SEQ ID NO 317
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 317
ccaaggucuu aaaggcucac gct                                            23

<210> SEQ ID NO 318
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 318
ccaggucuua aaggcucacg cut                                            23

<210> SEQ ID NO 319
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 319
ccagucuuaa aggcucacgc ugt                                            23

<210> SEQ ID NO 320
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 320
ccaucuuaaa ggcucacgcu gat                                            23

<210> SEQ ID NO 321
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 321
ccacuuaaag gcucacgcug act                                            23
```

<210> SEQ ID NO 322
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 322
ccauuaaagg cucacgcuga cat                                           23

<210> SEQ ID NO 323
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 323
ccauaaaggc ucacgcugac aat                                           23

<210> SEQ ID NO 324
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 324
ccaaaaggcu cacgcugaca agt                                           23

<210> SEQ ID NO 325
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 325
ccacugacaa gcagagccac aut                                           23

<210> SEQ ID NO 326
<211> LENGTH: 23
<212> TYPE: DNA
<213> ORGANISM: Artificial Sequence
<220> FEATURE:

<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 326
ccaugacaag cagagccaca uct                                           23

<210> SEQ ID NO 327
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 327
ccaacaagca gagccacauc cut                                           23

<210> SEQ ID NO 328
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 328
ccacaagcag agccacaucc uat                                           23

<210> SEQ ID NO 329
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329
ccaaagcaga gccacauccu aut                                           23

<210> SEQ ID NO 330
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

```
<400> SEQUENCE: 330
ccaagcagag ccacauccua ugt                                            23

<210> SEQ ID NO 331
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 331
ccagacagau ccaggagaga cut                                            23

<210> SEQ ID NO 332
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 332
ccaacagauc caggagagac uct                                            23

<210> SEQ ID NO 333
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 333
ccaagaucca ggagagacuc cat                                            23

<210> SEQ ID NO 334
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 334
ccaagccuga aucugccugg aut                                            23

<210> SEQ ID NO 335
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 335
ccacugaauc ugccuggaug gat                                           23

<210> SEQ ID NO 336
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 336
ccaugaaucu gccuggaugg aat                                           23

<210> SEQ ID NO 337
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 337
ccagaaucug ccuggaugga act                                           23

<210> SEQ ID NO 338
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 338
ccaaaucugc cuggauggaa cut                                           23

<210> SEQ ID NO 339
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 339
ccaaucugcc uggauggaac ugt                                            23

<210> SEQ ID NO 340
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 340
ccaucugccu ggauggaacu gat                                            23

<210> SEQ ID NO 341
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 341
ccauggaugg aacugaggac cat                                            23

<210> SEQ ID NO 342
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 342
ccagauggaa cugaggacca aut                                            23

<210> SEQ ID NO 343
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 343
```
ccaauggaac ugaggaccaa uct                                                23

<210> SEQ ID NO 344
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 344
ccauggaacu gaggaccaau cat                                                23

<210> SEQ ID NO 345
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 345
ccaggaacug aggaccaauc aut                                                23

<210> SEQ ID NO 346
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 346
ccagaacuga ggaccaauca ugt                                                23

<210> SEQ ID NO 347
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 347
ccaaacugag gaccaaucau gct                                                23

<210> SEQ ID NO 348
<211> LENGTH: 23
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 348
ccaacugagg accaaucaug cut                                              23

<210> SEQ ID NO 349
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 349
ccacugagga ccaaucaugc ugt                                              23

<210> SEQ ID NO 350
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 350
ccaugaggac caaucaugcu gct                                              23

<210> SEQ ID NO 351
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 351
ccagaggacc aaucaugcug cat                                              23

<210> SEQ ID NO 352
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 352
ccaaggacca aucaugcugc aat    23

<210> SEQ ID NO 353
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 353
ccaggaccaa ucaugcugca agt    23

<210> SEQ ID NO 354
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 354
ccagaccaau caugcugcaa ggt    23

<210> SEQ ID NO 355
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 355
ccaaccaauc augcugcaag gat    23

<210> SEQ ID NO 356
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 356
ccaccaauca ugcugcaagg aat    23

```
<210> SEQ ID NO 357
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 357
ccacaaucau gcugcaagga act                                             23

<210> SEQ ID NO 358
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 358
ccaaaucaug cugcaaggaa cat                                             23

<210> SEQ ID NO 359
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 359
ccaaucaugc ugcaaggaac act                                             23

<210> SEQ ID NO 360
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 360
ccaucaugcu gcaaggaaca cut                                             23

<210> SEQ ID NO 361
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 361
ccacaugcug caaggaacac uut                                               23

<210> SEQ ID NO 362
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 362
ccaaugcugc aaggaacacu uct                                               23

<210> SEQ ID NO 363
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 363
ccaugcugca aggaacacuu cct                                               23

<210> SEQ ID NO 364
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 364
ccagcugcaa ggaacacuuc cat                                               23

<210> SEQ ID NO 365
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 365

-continued ccaugccugu ucacugggau cat					23

<210> SEQ ID NO 366
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 366
ccauguucac ugggaucagc cat					23

<210> SEQ ID NO 367
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 367
ccacacuucu gagcacagag cat					23

<210> SEQ ID NO 368
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 368
ccaacuucug agcacagagc agt					23

<210> SEQ ID NO 369
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 369
ccaugagcac agagcagaga cat					23

<210> SEQ ID NO 370
<211> LENGTH: 23
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 370
ccaagcacag agcagagaca gat                                            23

<210> SEQ ID NO 371
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 371
ccaggacaaa ggcagaggau gut                                            23

<210> SEQ ID NO 372
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 372
ccagacaaag gcagaggaug uat                                            23

<210> SEQ ID NO 373
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 373
ccaacaaagg cagaggaugu agt                                            23

<210> SEQ ID NO 374
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

-continued

```
<223> OTHER INFORMATION: /note="Description of Combined DNA/RNA
      Molecule: Synthetic oligonucleotide"

<400> SEQUENCE: 374
ccacaaaggc agaggaugua gct                                            23

<210> SEQ ID NO 375
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 375
ccaaaaggca gaggauguag cct                                            23

<210> SEQ ID NO 376
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 376
ccacagagga uguagcccca uut                                            23

<210> SEQ ID NO 377
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 377
ccaagaggau guagccccau ugt                                            23

<210> SEQ ID NO 378
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 378
ccauguaccc uuucaugccu act                                            23
```

```
<210> SEQ ID NO 379
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 379
ccaguacccu uucaugccua cat                                              23

<210> SEQ ID NO 380
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 380 ccaucccuu ucaugccuac act                                               23

<210> SEQ ID NO 381
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 381
ccaacccuuu caugccuaca cat                                              23

<210> SEQ ID NO 382
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 382
ccacccuuuc augccuacac act                                              23

<210> SEQ ID NO 383
<211> LENGTH: 23
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 383
ccaccuuuca ugccuacaca cct                                                23

<210> SEQ ID NO 384
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 384
ccacuuucau gccuacacac cct                                                23

<210> SEQ ID NO 385
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 385
ccauuucaug ccuacacacc cct                                                23

<210> SEQ ID NO 386
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 386
ccaccccuca uuaaagcaga gut                                                23

<210> SEQ ID NO 387
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 387
ccacccucau uaaagcagag uct                                               23

<210> SEQ ID NO 388
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 388
ccaccucauu aaagcagagu cgt                                               23

<210> SEQ ID NO 389
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 389
ccacucauua aagcagaguc gut                                               23

<210> SEQ ID NO 390
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 390
ccaucauuaa agcagagucg ugt                                               23

<210> SEQ ID NO 391
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 391
ccacauuaaa gcagagucgu ggt                                               23

<210> SEQ ID NO 392
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 392
ccaauuaaag cagagucgug gct                                         23

<210> SEQ ID NO 393
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 393
ccauuaaagc agagucgugg cat                                         23

<210> SEQ ID NO 394
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 394
ccauaaagca gagucguggc aut                                         23

<210> SEQ ID NO 395
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 395
ccaaaagcag agucguggca uct                                         23

<210> SEQ ID NO 396
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 396
ccaaagcaga gucguggcau cut                                              23

<210> SEQ ID NO 397
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 397
gcaugacuga gggucuaagt t                                                21

<210> SEQ ID NO 398
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 398
ucaugcugug ccaguucugt t                                                21

<210> SEQ ID NO 399
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 399
cucaugcugu gccaguucut t                                                21

<210> SEQ ID NO 400
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 400
uguuccuggc cuuugucagt t                                                21
```

<210> SEQ ID NO 401
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 401 cguuccugg ccuuugucat t                                              21

<210> SEQ ID NO 402
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 402
auagagaccc aggcuguuct t                                             21

<210> SEQ ID NO 403
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 403
cauagagacc caggcuguut t                                             21

<210> SEQ ID NO 404
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 404
auugugcggc cauagagact t                                             21

<210> SEQ ID NO 405
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 405
aacaggcuug cccgaaguut t                                              21

<210> SEQ ID NO 406
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 406
ugagucucca acaggcuugt t                                              21

<210> SEQ ID NO 407
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 407
cugagucucc aacaggcuut t                                              21

<210> SEQ ID NO 408
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligoncleotide"

<400> SEQUENCE: 408
ucugagucuc caacaggcut t                                              21

<210> SEQ ID NO 409
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 409
aucugagucu ccaacaggct t                                              21

<210> SEQ ID NO 410
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 410
caucugaguc uccaacaggt t                                              21

<210> SEQ ID NO 411
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 411
ccaucugagu cuccaacagt t                                              21

<210> SEQ ID NO 412
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 412
uccaucugag ucuccaacat t                                              21

<210> SEQ ID NO 413
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 413
cuccaucuga gucuccaact t                                              21

<210> SEQ ID NO 414
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 414
ccuccaucug agucuccaat t                                              21

<210> SEQ ID NO 415
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 415
auccuccucc aucugaguct t                                              21

<210> SEQ ID NO 416
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 416
auauccuccu ccaucugagt t                                              21

<210> SEQ ID NO 417
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 417
aauauccucc uccaucugat t                                              21

<210> SEQ ID NO 418
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 418
gaauauccuc cuccaucugt t                                              21

<210> SEQ ID NO 419
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 419
agaauauccu ccuccaucut t                                              21

<210> SEQ ID NO 420
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 420
cagaauaucc uccuccauct t                                              21

<210> SEQ ID NO 421
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 421
gcagaauauc cuccuccaut t                                              21

<210> SEQ ID NO 422
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 422
```
ugcagaauau ccuccuccat t                                            21

<210> SEQ ID NO 423
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 423
cugcagaaua uccuccucct t                                            21

<210> SEQ ID NO 424
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 424
gcugcagaau auccuccuct t                                            21

<210> SEQ ID NO 425
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 425
agcugcagaa uauccuccut t                                            21

<210> SEQ ID NO 426
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 426
ugccugcagc ugcagaauat t                                            21

<210> SEQ ID NO 427
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 427
uccucagcug gacuucuagt t                                              21

<210> SEQ ID NO 428
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 428
cuccucagcu ggacuucuat t                                              21

<210> SEQ ID NO 429
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 429
aaauucucgg uaggcagggt t                                              21

<210> SEQ ID NO 430
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 430
caaauucucg guaggcaggt t                                              21

<210> SEQ ID NO 431
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

Molecule: Synthetic oligonucleotide"

<400> SEQUENCE: 431
ucaaauucuc gguaggcagt t                                              21

<210> SEQ ID NO 432
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 432
cucaaauucu cgguaggcat t                                              21

<210> SEQ ID NO 433
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 433
ccucaaauuc ucgguaggct t                                              21

<210> SEQ ID NO 434
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 434
accucaaauu cucgguaggt t                                              21

<210> SEQ ID NO 435
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 435
gaccucaaau ucucgguagt t                                              21

```
<210> SEQ ID NO 436
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 436
agaccucaaa uucucgguat t                                              21

<210> SEQ ID NO 437
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 437
aagaccucaa auucucggut t                                              21

<210> SEQ ID NO 438
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 438
uaagaccuca aauucucggt t                                              21

<210> SEQ ID NO 439
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 439
uuaagaccuc aaauucucgt t                                              21

<210> SEQ ID NO 440
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 440
uuuaagaccu caaauucuct t                                              21

<210> SEQ ID NO 441
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 441
cuuuaagacc ucaaauucut t                                              21

<210> SEQ ID NO 442
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 442
ccuuuaagac cucaaauuct t                                              21

<210> SEQ ID NO 443
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 443
gccuuuaaga ccucaaauut t                                              21

<210> SEQ ID NO 444
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 444
```
agccuuuaag accucaaaut t          21

<210> SEQ ID NO 445
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 445
gagccuuuaa gaccucaaat t          21

<210> SEQ ID NO 446
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 446
ugagccuuua agaccucaat t          21

<210> SEQ ID NO 447
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 447
gugagccuuu aagaccucat t          21

<210> SEQ ID NO 448
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 448
cgugagccuu uaagaccuct t          21

<210> SEQ ID NO 449
<211> LENGTH: 21
<212> TYPE: DNA

-continued

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 449
gcgugagccu uuaagaccut t                                              21

<210> SEQ ID NO 450
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 450
agcgugagcc uuuaagacct t                                              21

<210> SEQ ID NO 451
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 451
cagcgugagc cuuuaagact t                                              21

<210> SEQ ID NO 452
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 452
ucagcgugag ccuuuaagat t                                              21

<210> SEQ ID NO 453
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 453
gucagcguga gccuuuaagt t         21

<210> SEQ ID NO 454
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 454
ugucagcgug agccuuuaat t         21

<210> SEQ ID NO 455
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 455
uugucagcgu gagccuuuat t         21

<210> SEQ ID NO 456
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 456
cuugucagcg ugagccuuut t         21

<210> SEQ ID NO 457
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 457
auguggcucu gcuugucagt t         21

<210> SEQ ID NO 458
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 458
gauguggcuc ugcuugucat t                                              21

<210> SEQ ID NO 459
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 459
aggauguggc ucugcuugut t                                              21

<210> SEQ ID NO 460
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 460
uaggaugugg cucugcuugt t                                              21

<210> SEQ ID NO 461
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 461
auaggaugug gcucugcuut t                                              21

<210> SEQ ID NO 462
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 462
cauaggaugu ggcucugcut t                                         21

<210> SEQ ID NO 463
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 463
agucucuccu ggaucuguct t                                         21

<210> SEQ ID NO 464
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 464
gagucucucc uggaucugut t                                         21

<210> SEQ ID NO 465
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 465
uggagucucu ccuggaucut t                                         21

<210> SEQ ID NO 466
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 466
auccaggcag auucaggcut t                                              21

<210> SEQ ID NO 467
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 467
uccauccagg cagauucagt t                                              21

<210> SEQ ID NO 468
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 468
uuccauccag gcagauucat t                                              21

<210> SEQ ID NO 469
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 469
guuccaucca ggcagauuct t                                              21

<210> SEQ ID NO 470
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 470
aguuccaucc aggcagauut t                                              21

<210> SEQ ID NO 471
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 471
caguuccauc caggcagaut t                                              21

<210> SEQ ID NO 472
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 472
ucaguuccau ccaggcagat t                                              21

<210> SEQ ID NO 473
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 473
ugguccucag uuccauccat t                                              21

<210> SEQ ID NO 474
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 474
auugguccuc aguuccauct t                                              21

<210> SEQ ID NO 475
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 475
gauugguccu caguuccaut t                                              21

<210> SEQ ID NO 476
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 476
ugauuggucc ucaguuccat t                                              21

<210> SEQ ID NO 477
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 477 augaugguc cucaguucct t                                               21

<210> SEQ ID NO 478
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 478
caugauuggu ccucaguuct t                                              21

<210> SEQ ID NO 479
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 479
gcaugauugg uccucaguut t                                              21

<210> SEQ ID NO 480
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 480
agcaugauug guccucagut t                                             21

<210> SEQ ID NO 481
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 481
cagcaugauu gguccucagt t                                             21

<210> SEQ ID NO 482
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 482
gcagcaugau ugguccucat t                                             21

<210> SEQ ID NO 483
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 483
ugcagcauga uugguccuct t                                             21

<210> SEQ ID NO 484
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 484
uugcagcaug auugguccut t                                              21

<210> SEQ ID NO 485
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 485
cuugcagcau gauuggucct t                                              21

<210> SEQ ID NO 486
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 486
ccuugcagca ugauugguct t                                              21

<210> SEQ ID NO 487
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 487
uccuugcagc augauuggut t                                              21

<210> SEQ ID NO 488
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 488
uuccuugcag caugauuggt t                                              21

<210> SEQ ID NO 489
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 489
guuccuugca gcaugauugt t                                              21

<210> SEQ ID NO 490
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 490 uguccuugc agcaugauut t                                               21

<210> SEQ ID NO 491
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 491
guguuccuug cagcaugaut t                                              21

<210> SEQ ID NO 492
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 492
aguguuccuu gcagcaugat t                                              21

<210> SEQ ID NO 493

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 493
aaguguuccu ugcagcaugt t                                           21

<210> SEQ ID NO 494
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 494
gaaguguucc uugcagcaut t                                           21

<210> SEQ ID NO 495
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 495
ggaaguguuc cuugcagcat t                                           21

<210> SEQ ID NO 496
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 496
uggaaguguu ccuugcagct t                                           21

<210> SEQ ID NO 497
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 497
ugaucccagu gaacaggcat t                                              21

<210> SEQ ID NO 498
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 498
uggcugaucc cagugaacat t                                              21

<210> SEQ ID NO 499
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 499
ugcucugugc ucagaagugt t                                              21

<210> SEQ ID NO 500
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 500
cugcucugug cucagaagut t                                              21

<210> SEQ ID NO 501
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 501
```
ugucucugcu cugugcucat t                                              21

<210> SEQ ID NO 502
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 502
ucugucucug cucugugcut t                                              21

<210> SEQ ID NO 503
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 503
acauccucug ccuuugucct t                                              21

<210> SEQ ID NO 504
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 504
uacauccucu gccuuuguct t                                              21

<210> SEQ ID NO 505
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 505
cuacauccuc ugccuuugut t                                              21

<210> SEQ ID NO 506
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 506
gcuacauccu cugccuuugt t                                              21

<210> SEQ ID NO 507
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 507
ggcuacaucc ucugccuuut t                                              21

<210> SEQ ID NO 508
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 508 aaugggcua cauccucugt t                                               21

<210> SEQ ID NO 509
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 509
caauggggcu acauccucut t                                              21

<210> SEQ ID NO 510
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 510
guaggcauga aaggguacat t                                                21

<210> SEQ ID NO 511
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 511
uguaggcaug aaaggguact t                                                21

<210> SEQ ID NO 512
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 512
guguaggcau gaaaggguat t                                                21

<210> SEQ ID NO 513
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 513
uguguaggca ugaaagggut t                                                21

<210> SEQ ID NO 514
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 514
guguguaggc augaaagggt t                                                21

```
<210> SEQ ID NO 515
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 515
gguguguagg caugaaaggt t                                              21

<210> SEQ ID NO 516
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 516
ggguguguag gcaugaaagt t                                              21

<210> SEQ ID NO 517
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 517
ggggugugua ggcaugaaat t                                              21

<210> SEQ ID NO 518
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 518
acucugcuuu aaugaggggt t                                              21

<210> SEQ ID NO 519
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 519
gacucugcuu uaaugagggt t                                                  21

<210> SEQ ID NO 520
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 520
cgacucugcu uuaaugaggt t                                                  21

<210> SEQ ID NO 521
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 521
acgacucugc uuuaaugagt t                                                  21

<210> SEQ ID NO 522
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 522
cacgacucug cuuuaaugat t                                                  21

<210> SEQ ID NO 523
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 523
ccacgacucu gcuuuaaugt t								21

<210> SEQ ID NO 524
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 524
gccacgacuc ugcuuuaaut t								21

<210> SEQ ID NO 525
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 525
ugccacgacu cugcuuuaat t								21

<210> SEQ ID NO 526
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 526
augccacgac ucugcuuuat t								21

<210> SEQ ID NO 527
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 527
gaugccacga cucugcuuut t								21

<210> SEQ ID NO 528
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 528
agaugccacg acucugcuut t                                             21

<210> SEQ ID NO 529
<211> LENGTH: 888
<212> TYPE: DNA
<213> ORGANISM: Homo sapiens

<400> SEQUENCE: 529
ataccttaga ccctcagtca tgccagtgcc tgctctgtgc ctgctctggg ccctggcaat    60
ggtgacccgg cctgcctcag cggcccccat gggcggccca gaactggcac agcatgagga   120
gctgaccctg ctcttccatg ggaccctgca gctgggccag gccctcaacg gtgtgtacag   180
gaccacggag ggacggctga caaaggccag gaacagcctg gtctctatg ccgcacaat    240 agaactcctg gggcaggagg tcagccgggg ccgggatgca gcccaggaac ttcgggcaag   300
cctgttggag actcagatgg aggaggatat tctgcagctg caggcagagg ccacagctga   360
ggtgctgggg gaggtggccc aggcacagaa ggtgctacgg gacagcgtgc agcggctaga   420
agtccagctg aggagcgcct ggctgggccc tgcctaccga gaatttgagg tcttaaaggc   480
tcacgctgac aagcagagcc acatcctatg ggccctcaca ggccacgtgc agcggcagag   540
gcgggagatg gtggcacagc agcatcggct gcgacagatc caggagagac tccacacagc   600
ggcgctccca gcctgaatct gcctggatgg aactgaggac caatcatgct gcaaggaaca   660
cttccacgcc ccgtgaggcc cctgtgcagg gaggagctgc ctgttcactg ggatcagcca   720
gggcgccggg ccccacttct gagcacagag cagagacaga cgcaggcggg gacaaaggca   780
gaggatgtag ccccattggg gaggggtgga ggaaggacat gtacccttc atgcctacac   840 accccctcatt aaagcagagt cgtggcatct caaaaaaaaa aaaaaaaa                888

<210> SEQ ID NO 530
<211> LENGTH: 198
<212> TYPE: PRT
<213> ORGANISM: Homo sapiens

<400> SEQUENCE: 530

Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
                20                  25                  30

Glu Glu Leu Thr Leu Leu Phe His Gly Thr Leu Gln Leu Gly Gln Ala
            35                  40                  45

Leu Asn Gly Val Tyr Arg Thr Thr Glu Gly Arg Leu Thr Lys Ala Arg
        50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
                85                  90                  95

Glu Thr Gln Met Glu Glu Asp Ile Leu Gln Leu Gln Ala Glu Ala Thr
```

```
                    100                 105                 110
Ala Glu Val Leu Gly Glu Val Ala Gln Ala Gln Lys Val Leu Arg Asp
            115                 120                 125

Ser Val Gln Arg Leu Glu Val Gln Leu Arg Ser Ala Trp Leu Gly Pro
        130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
        180                 185                 190

Thr Ala Ala Leu Pro Ala
        195
```

<210> SEQ ID NO 531
<211> LENGTH: 1023
<212> TYPE: DNA
<213> ORGANISM: Macaca fascicularis

<400> SEQUENCE: 531

```
atgggggatg ccctcccctc cttccctggg gtgcagtcac tgaccggcag ggcctggctg      60
gggtcctcgc ctgtcatgta ctgcactcgc acggcaaggt tgcgcacgga ccctggcgg     120
ctgctgaagt tgaggctgtg cgggtacacg tacagcagac cctcagtcat gctagtgcct    180
gctctgtgcc tgctgtgggc cctggcaatg gtgatccagc ctgcctcagc ggccccgtg     240
ggcagcccag aactggcaga gcatgaggag ctgaccctgc tcttccatgg gaccctgcag    300
ctgggccagg ccctcaatgg tgtgtacaag accacggagg acggctgac aaaggccagg     360
aacagcctgg gtctctatgg ccgcacagtg gaactcctgg ggcaggaggt cagccggggc    420
cgggatgcag cccaggaact tcgggcaagc ctgttggaga ctcagatgga ggaggatatt    480
ctgcagctga aggcagaggc catagccgag gtgctggagg aggtggccca ggcacagaag    540
gtgctacagg acagcgtgcg gcggctagaa gtccagctga ggagcgcctg gctgggccct    600
gcctaccaag aatttgaggt cttaaaggct cacgctgaca gcagagcca tcctgtgg      660
gccctcacag gccacgtgca gcggcagagg cgggagatgg tggcacagca gcatcggctg    720
cgacagatcc aggagagaat ccacaaagcg cgctcccag cctgaatctg cctggatgga    780
actgaggacc aaccatgctg caaggaacac ttccacgccc catgaggccc ctgaacaggg    840
aggagctgcc tgttcactgg gatcagccag ggcgcccggc cccacttctg agcacagagc    900
agagacagac gcaggcaggg acaaaggcag aggacgtagc cccattgggg aggggtggag    960
gaaggatgtg tacccttca tacctacaca ccccccttat taaagcagag tcgtggcatc   1020
tca                                                                1023
```

<210> SEQ ID NO 532
<211> LENGTH: 198
<212> TYPE: PRT
<213> ORGANISM: Macaca fascicularis

<400> SEQUENCE: 532

```
Met Leu Val Pro Ala Leu Cys Leu Leu Trp Ala Leu Ala Met Val Ile
1               5                  10                  15

Gln Pro Ala Ser Ala Ala Pro Val Gly Ser Pro Glu Leu Ala Glu His
            20                  25                  30

Glu Glu Leu Thr Leu Leu Phe His Gly Thr Leu Gln Leu Gly Gln Ala
```

```
                35                  40                  45
Leu Asn Gly Val Tyr Lys Thr Thr Glu Gly Arg Leu Thr Lys Ala Arg
    50                  55                  60
Asn Ser Leu Gly Leu Tyr Gly Arg Thr Val Glu Leu Leu Gly Gln Glu
65                  70                  75                  80
Val Ser Arg Gly Arg Asp Ala Ala Gln Glu Leu Arg Ala Ser Leu Leu
                85                  90                  95
Glu Thr Gln Met Glu Glu Asp Ile Leu Gln Leu Lys Ala Glu Ala Ile
            100                 105                 110
Ala Glu Val Leu Glu Glu Val Ala Gln Ala Gln Lys Val Leu Gln Asp
        115                 120                 125
Ser Val Arg Arg Leu Glu Val Gln Leu Arg Ser Ala Trp Leu Gly Pro
    130                 135                 140
Ala Tyr Gln Glu Phe Glu Val Leu Lys Ala His Ala Asp Lys Gln Ser
145                 150                 155                 160
His Ile Leu Trp Ala Leu Thr Gly His Val Gln Arg Gln Arg Arg Glu
                165                 170                 175
Met Val Ala Gln Gln His Arg Leu Arg Gln Ile Gln Glu Arg Ile His
            180                 185                 190
Lys Ala Ala Leu Pro Ala
        195
```

<210> SEQ ID NO 533
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
tttttttttt tttttt                                                    16

<210> SEQ ID NO 534
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 534
gccctgccta ccaagaattt g                                              21

<210> SEQ ID NO 535
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 535
tttagaugga ggaggauauu cu                                             22

```
<210> SEQ ID NO 536
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 536
tttagaugga ggaggauauu cu                                              22

<210> SEQ ID NO 537
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 537
tttagaugga ggaggauauu cu                                              22

<210> SEQ ID NO 538
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 538
tttagaugga ggaggauauu cu                                              22

<210> SEQ ID NO 539
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 539
tttagaugga ggaggauauu cu                                              22

<210> SEQ ID NO 540
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 540
tttagaugga ggaggauauu cu                                              22

<210> SEQ ID NO 541
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 541
tttagaugga ggaggauauu cu                                              22

<210> SEQ ID NO 542
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 542
tttagaugga ggaggauauu cu                                              22

<210> SEQ ID NO 543
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 543
tttagaugga ggaggauauu cu                                              22

<210> SEQ ID NO 544
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 544
tttagaugga ggaggauauu cu                                              22

<210> SEQ ID NO 545
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 545
tttagaugga ggaggauauu cu                                              22

<210> SEQ ID NO 546
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 546
tttagaugga ggaggauauu cu                                              22

<210> SEQ ID NO 547
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 547
tttagaugga ggaggauauu cu                                              22

<210> SEQ ID NO 548
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 548
tttagaugga ggaggauauu cu                                              22

<210> SEQ ID NO 549
<211> LENGTH: 22
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 549
tttagaugga ggaggauauu cu                                           22

<210> SEQ ID NO 550
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 550
tttagaugga ggaggauauu cu                                           22

<210> SEQ ID NO 551
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 551
tttagaugga ggaggauauu cu                                           22

<210> SEQ ID NO 552
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 552
tttagaugga ggaggauauu cu                                           22

<210> SEQ ID NO 553
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 553
tttagaugga ggaggauauu tt                                              22

<210> SEQ ID NO 554
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 554
tttagaugga ggaggauauu tt                                              22

<210> SEQ ID NO 555
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 555
tttagaugga ggaggauauu tt                                              22

<210> SEQ ID NO 556
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 556
tttagaugga ggaggauauu tt                                              22

<210> SEQ ID NO 557
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 557
tttagaugga ggaggauauu tt                                              22

-continued

<210> SEQ ID NO 558
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 558
tttagaugga ggaggauauu tt                                              22

<210> SEQ ID NO 559
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 559
tttagaugga ggaggauauu tt                                              22

<210> SEQ ID NO 560
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 560
tttagaugga ggaggauauu tt                                              22

<210> SEQ ID NO 561
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 561
tttagaugga ggaggauauu tt                                              22

<210> SEQ ID NO 562
<211> LENGTH: 22
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 562
tttagaugga ggaggauauu tt                                            22

<210> SEQ ID NO 563
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 563
tttagaugga ggaggauauu tt                                            22

<210> SEQ ID NO 564
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 564
tttagaugga ggaggauauu tt                                            22

<210> SEQ ID NO 565
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 565
tttagaugga ggaggauauu tt                                            22

<210> SEQ ID NO 566
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 566
tttagaugga ggaggauauu tt                                          22

<210> SEQ ID NO 567
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 567
tttagaugga ggaggauauu tt                                          22

<210> SEQ ID NO 568
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 568
tttagaugga ggaggauauu tt                                          22

<210> SEQ ID NO 569
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 569
tttagaugga ggaggauauu tt                                          22

<210> SEQ ID NO 570
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 570
tttagaugga ggaggauauu tt                                          22

<210> SEQ ID NO 571
<211> LENGTH: 24
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 571
tttagaugga ggaggauauu cutt                                            24

<210> SEQ ID NO 572
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 572
tttagaugga ggaggauauu cutt                                            24

<210> SEQ ID NO 573
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 573
tttagaugga ggaggauauu cutt                                            24

<210> SEQ ID NO 574
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 574
tttagaugga ggaggauauu cutt                                            24

<210> SEQ ID NO 575
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 575
tttagaugga ggaggauauu cutt                                              24

<210> SEQ ID NO 576
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 576
tttagaugga ggaggauauu cutt                                              24

<210> SEQ ID NO 577
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 577
tttagaugga ggaggauauu cutt                                              24

<210> SEQ ID NO 578
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 578
tttagaugga ggaggauauu cutt                                              24

<210> SEQ ID NO 579
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 579
tttagaugga ggaggauauu cutt                                              24
```

<210> SEQ ID NO 580
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 580
tttagaugga ggaggauauu cutt                                           24

<210> SEQ ID NO 581
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 581
tttagaugga ggaggauauu cutt                                           24

<210> SEQ ID NO 582
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 582
tttagaugga ggaggauauu cutt                                           24

<210> SEQ ID NO 583
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 583
tttagaugga ggaggauauu cutt                                           24

<210> SEQ ID NO 584
<211> LENGTH: 24
<212> TYPE: DNA
<213> ORGANISM: Artificial Sequence
<220> FEATURE:

<210> SEQ ID NO 584
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 584
tttagaugga ggaggauauu cutt                                         24

<210> SEQ ID NO 585
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 585
tttagaugga ggaggauauu cutt                                         24

<210> SEQ ID NO 586
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 586
tttagaugga ggaggauauu cutt                                         24

<210> SEQ ID NO 587
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 587
tttagaugga ggaggauauu cutt                                         24

<210> SEQ ID NO 588
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 588
tttagaugga ggaggauauu cutt                                              24

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
agaauauccu ccuccaucua a                                                 21

<210> SEQ ID NO 590
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
agaauauccu ccuccaucua a                                                 21

<210> SEQ ID NO 591
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
agaauauccu ccuccaucua a                                                 21

<210> SEQ ID NO 592
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 592
agaauauccu ccuccaucut t                                                 21

<210> SEQ ID NO 593
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
agaauauccu ccuccaucua a                                                 21
```

```
<210> SEQ ID NO 594
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
agaauauccu ccuccaucua a                                              21

<210> SEQ ID NO 595
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
agaauauccu ccuccaucua a                                              21

<210> SEQ ID NO 596
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 596
agaauauccu ccuccaucut t                                              21

<210> SEQ ID NO 597
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
agaauauccu ccuccaucua a                                              21

<210> SEQ ID NO 598
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
agaauauccu ccuccaucua a                                              21

<210> SEQ ID NO 599
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 599
agaauauccu ccuccaucua a                                              21

<210> SEQ ID NO 600
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
agaauauccu ccuccaucua a                                              21

<210> SEQ ID NO 601
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 601
agaauauccu ccuccaucut t                                              21

<210> SEQ ID NO 602
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
agaauauccu ccuccaucua a                                              21

<210> SEQ ID NO 603
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
agaauauccu ccuccaucua a                                              21

<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 604
agaauauccu ccuccaucua a                                              21

<210> SEQ ID NO 605
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
agaauauccu ccuccaucua a                                              21

<210> SEQ ID NO 606
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 606
agaauauccu ccuccaucut t                                              21

<210> SEQ ID NO 607
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
agaauauccu ccuccaucua a                                              21

<210> SEQ ID NO 608
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
agaauauccu ccuccaucua a                                              21

<210> SEQ ID NO 609
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
agaauauccu ccuccaucua a                                              21
```

-continued

<210> SEQ ID NO 610
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 610
agaauauccu ccuccaucut t                                              21

<210> SEQ ID NO 611
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
agaauauccu ccuccaucua a                                              21

<210> SEQ ID NO 612
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
agaauauccu ccuccaucua a                                              21

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
agaauauccu ccuccaucua a                                              21

<210> SEQ ID NO 614
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 614
agaauauccu ccuccaucut t                                              21

<210> SEQ ID NO 615

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
agaauauccu ccuccaucua a                                              21

<210> SEQ ID NO 616
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
agaauauccu ccuccaucua a                                              21

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
agaauauccu ccuccaucua a                                              21

<210> SEQ ID NO 618
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
agaauauccu ccuccaucua a                                              21

<210> SEQ ID NO 619
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 619
agaauauccu ccuccaucut t                                              21

<210> SEQ ID NO 620
<211> LENGTH: 21
<212> TYPE: RNA
<213> ORGANISM: Artificial Sequence
<220> FEATURE:
<221> NAME/KEY: source
```

-continued

<223> OTHER INFORMATION: /note="Description of Artificial Sequence:
      Synthetic oligonucleotide"

<400> SEQUENCE: 620
agaauauccu ccuccaucua a                                              21

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
agaauauccu ccuccaucua a                                              21

<210> SEQ ID NO 622
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
agaauauccu ccuccaucua a                                              21

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
agaauauccu ccuccaucua a                                              21

<210> SEQ ID NO 624
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 624
agaauauccu ccuccaucut t                                              21

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
agaauauccu ccuccaucua a                                               21

<210> SEQ ID NO 626
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
agaauauccu ccuccaucua a                                               21

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
agaauauccu ccuccaucua a                                               21

<210> SEQ ID NO 628
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 628
agaauauccu ccuccaucut t                                               21

<210> SEQ ID NO 629
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
agaauauccu ccuccaucua a                                               21

<210> SEQ ID NO 630
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
agaauauccu ccuccaucua a                                               21

<210> SEQ ID NO 631
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
agaauauccu ccuccaucua a                                              21

<210> SEQ ID NO 632
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 632
agaauauccu ccuccaucut t                                              21

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
agaauauccu ccuccaucua a                                              21

<210> SEQ ID NO 634
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
agaauauccu ccuccaucua a                                              21

<210> SEQ ID NO 635
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
agaauauccu ccuccaucua a                                              21

<210> SEQ ID NO 636
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 636
agaauauccu ccuccaucua a                                              21

<210> SEQ ID NO 637
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 637
agaauauccu ccuccaucut t                                              21

<210> SEQ ID NO 638
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
agaauauccu ccuccaucua a                                              21

<210> SEQ ID NO 639
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
agaauauccu ccuccaucua a                                              21

<210> SEQ ID NO 640
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
agaauauccu ccuccaucua a                                              21

<210> SEQ ID NO 641
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
agaauauccu ccuccaucua a                                              21

```
<210> SEQ ID NO 642
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 642
agaauauccu ccuccaucut t                                             21

<210> SEQ ID NO 643
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 643
tttccgagaa uuugaggucu ua                                            22

<210> SEQ ID NO 644
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 644
tttccgagaa uuugaggucu ua                                            22

<210> SEQ ID NO 645
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 645
tttccgagaa uuugaggucu ua                                            22

<210> SEQ ID NO 646
<211> LENGTH: 22
<212> TYPE: DNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 646
tttccgagaa uuugaggucu ua                                           22

<210> SEQ ID NO 647
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 647
tttccgagaa uuugaggucu ua                                           22

<210> SEQ ID NO 648
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 648
tttccgagaa uuugaggucu ua                                           22

<210> SEQ ID NO 649
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 649
tttccgagaa uuugaggucu ua                                           22

<210> SEQ ID NO 650
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

```
<400> SEQUENCE: 650
tttccgagaa uuugaggucu ua                                              22

<210> SEQ ID NO 651
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 651
tttccgagaa uuugaggucu ua                                              22

<210> SEQ ID NO 652
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 652
tttccgagaa uuugaggucu ua                                              22

<210> SEQ ID NO 653
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 653
tttccgagaa uuugaggucu ua                                              22

<210> SEQ ID NO 654
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 654
tttccgagaa uuugaggucu ua                                              22

<210> SEQ ID NO 655
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 655
tttccgagaa uuugaggucu ua                                             22

<210> SEQ ID NO 656
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 656
tttccgagaa uuugaggucu ua                                             22

<210> SEQ ID NO 657
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 657
tttccgagaa uuugaggucu ua                                             22

<210> SEQ ID NO 658
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 658
tttccgagaa uuugaggucu ua                                             22

<210> SEQ ID NO 659
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 659
tttccgagaa uuugaggucu ua                                              22

<210> SEQ ID NO 660
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 660
tttccgagaa uuugaggucu ua                                              22

<210> SEQ ID NO 661
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 661
tttccgagaa uuugaggucu tt                                              22

<210> SEQ ID NO 662
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 662
tttccgagaa uuugaggucu tt                                              22

<210> SEQ ID NO 663
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 663
tttccgagaa uuugaggucu tt                                            22

<210> SEQ ID NO 664
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 664
tttccgagaa uuugaggucu tt                                            22

<210> SEQ ID NO 665
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 665
tttccgagaa uuugaggucu tt                                            22

<210> SEQ ID NO 666
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 666
tttccgagaa uuugaggucu tt                                            22

<210> SEQ ID NO 667
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 667
tttccgagaa uuugaggucu tt                                            22

<210> SEQ ID NO 668
<211> LENGTH: 22
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 668
tttccgagaa uuugaggucu tt                                              22

<210> SEQ ID NO 669
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 669
tttccgagaa uuugaggucu tt                                              22

<210> SEQ ID NO 670
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 670
tttccgagaa uuugaggucu tt                                              22

<210> SEQ ID NO 671
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 671
tttccgagaa uuugaggucu tt                                              22

<210> SEQ ID NO 672
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 672
tttccgagaa uuugaggucu tt                                            22

<210> SEQ ID NO 673
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 673
tttccgagaa uuugaggucu tt                                            22

<210> SEQ ID NO 674
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 674
tttccgagaa uuugaggucu tt                                            22

<210> SEQ ID NO 675
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 675
tttccgagaa uuugaggucu tt                                            22

<210> SEQ ID NO 676
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 676
tttccgagaa uuugaggucu tt                                            22

```
<210> SEQ ID NO 677
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 677
tttccgagaa uuugaggucu tt                                                  22

<210> SEQ ID NO 678
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 678
tttccgagaa uuugaggucu tt                                                  22

<210> SEQ ID NO 679
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 679
tttccgagaa uuugaggucu uatt                                                24

<210> SEQ ID NO 680
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 680
tttccgagaa uuugaggucu uatt                                                24

<210> SEQ ID NO 681
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                        Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 681
tttccgagaa uuugaggucu uatt                                              24

<210> SEQ ID NO 682
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 682
tttccgagaa uuugaggucu uatt                                              24

<210> SEQ ID NO 683
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 683
tttccgagaa uuugaggucu uatt                                              24

<210> SEQ ID NO 684
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 684
tttccgagaa uuugaggucu uatt                                              24

<210> SEQ ID NO 685
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 685
```
tttccgagaa uuugaggucu uatt                              24

<210> SEQ ID NO 686
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 686
tttccgagaa uuugaggucu uatt                              24

<210> SEQ ID NO 687
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 687
tttccgagaa uuugaggucu uatt                              24

<210> SEQ ID NO 688
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 688
tttccgagaa uuugaggucu uatt                              24

<210> SEQ ID NO 689
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 689
tttccgagaa uuugaggucu uatt                              24

<210> SEQ ID NO 690
<211> LENGTH: 24
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 690
tttccgagaa uuugaggucu uatt                                            24

<210> SEQ ID NO 691
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 691
tttccgagaa uuugaggucu uatt                                            24

<210> SEQ ID NO 692
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 692
tttccgagaa uuugaggucu uatt                                            24

<210> SEQ ID NO 693
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 693
tttccgagaa uuugaggucu uatt                                            24

<210> SEQ ID NO 694
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 694
tttccgagaa uuugaggucu uatt                                              24

<210> SEQ ID NO 695
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 695
tttccgagaa uuugaggucu uatt                                              24

<210> SEQ ID NO 696
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 696
tttccgagaa uuugaggucu uatt                                              24

<210> SEQ ID NO 697
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
uaagaccuca aauucucgga a                                                 21

<210> SEQ ID NO 698
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
uaagaccuca aauucucgga a                                                 21

<210> SEQ ID NO 699
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 699
uaagaccuca aauucucgga a                                              21

<210> SEQ ID NO 700
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 700
uaagaccuca aauucucggt t                                              21

<210> SEQ ID NO 701
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
uaagaccuca aauucucgga a                                              21

<210> SEQ ID NO 702
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
uaagaccuca aauucucgga a                                              21

<210> SEQ ID NO 703
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
uaagaccuca aauucucgga a                                              21

<210> SEQ ID NO 704
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 704
uaagaccuca aauucucggt t                                              21

<210> SEQ ID NO 705
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
uaagaccuca aauucucgga a                                              21

<210> SEQ ID NO 706
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
uaagaccuca aauucucgga a                                              21

<210> SEQ ID NO 707
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
uaagaccuca aauucucgga a                                              21

<210> SEQ ID NO 708
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
uaagaccuca aauucucgga a                                              21

<210> SEQ ID NO 709
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 709
uaagaccuca aauucucggt t                                              21
```

```
<210> SEQ ID NO 710
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
uaagaccuca aauucucgga a                                              21

<210> SEQ ID NO 711
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
uaagaccuca aauucucgga a                                              21

<210> SEQ ID NO 712
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
uaagaccuca aauucucgga a                                              21

<210> SEQ ID NO 713
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
uaagaccuca aauucucgga a                                              21

<210> SEQ ID NO 714
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 714
uaagaccuca aauucucggt t                                              21

<210> SEQ ID NO 715
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 715
uaagaccuca aauucucgga a                                                    21

<210> SEQ ID NO 716
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
uaagaccuca aauucucgga a                                                    21

<210> SEQ ID NO 717
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
uaagaccuca aauucucgga a                                                    21

<210> SEQ ID NO 718
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 718
uaagaccuca aauucucggt t                                                    21

<210> SEQ ID NO 719
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
uaagaccuca aauucucgga a                                                    21

<210> SEQ ID NO 720
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 720
uaagaccuca aauucucgga a                                              21

<210> SEQ ID NO 721
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
uaagaccuca aauucucgga a                                              21

<210> SEQ ID NO 722
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 722
uaagaccuca aauucucggt t                                              21

<210> SEQ ID NO 723
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
uaagaccuca aauucucgga a                                              21

<210> SEQ ID NO 724
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
uaagaccuca aauucucgga a                                              21

<210> SEQ ID NO 725
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
uaagaccuca aauucucgga a                                              21
```

```
<210> SEQ ID NO 726
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
uaagaccuca aauucucgga a                                             21

<210> SEQ ID NO 727
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 727
uaagaccuca aauucucggt t                                             21

<210> SEQ ID NO 728
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
uaagaccuca aauucucgga a                                             21

<210> SEQ ID NO 729
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
uaagaccuca aauucucgga a                                             21

<210> SEQ ID NO 730
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
uaagaccuca aauucucgga a                                             21

<210> SEQ ID NO 731
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 731
uaagaccuca aauucucgga a                                              21

<210> SEQ ID NO 732
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 732
uaagaccuca aauucucggt t                                              21

<210> SEQ ID NO 733
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
uaagaccuca aauucucgga a                                              21

<210> SEQ ID NO 734
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
uaagaccuca aauucucgga a                                              21

<210> SEQ ID NO 735
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
uaagaccuca aauucucgga a                                              21

<210> SEQ ID NO 736
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 736
uaagaccuca aauucucggt t                                              21

<210> SEQ ID NO 737
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
uaagaccuca aauucucgga a                                              21

<210> SEQ ID NO 738
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
uaagaccuca aauucucgga a                                              21

<210> SEQ ID NO 739
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
uaagaccuca aauucucgga a                                              21

<210> SEQ ID NO 740
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 740
uaagaccuca aauucucggt t                                              21

<210> SEQ ID NO 741
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
```
uaagaccuca aauucucgga a                                          21

<210> SEQ ID NO 742
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
uaagaccuca aauucucgga a                                          21

<210> SEQ ID NO 743
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
uaagaccuca aauucucgga a                                          21

<210> SEQ ID NO 744
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
uaagaccuca aauucucgga a                                          21

<210> SEQ ID NO 745
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 745
uaagaccuca aauucucggt t                                          21

<210> SEQ ID NO 746
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
uaagaccuca aauucucgga a                                          21

<210> SEQ ID NO 747
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
uaagaccuca aauucucgga a                                              21

<210> SEQ ID NO 748
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
uaagaccuca aauucucgga a                                              21

<210> SEQ ID NO 749
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
uaagaccuca aauucucgga a                                              21

<210> SEQ ID NO 750
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 750
uaagaccuca aauucucggt t                                              21
```

RNA COMPOSITIONS AND METHODS FOR INHIBITING ANGPTL8

CROSS-REFERENCE TO RELATED APPLICATIONS

The present application is a national stage application under 35 U.S.C. § 371 of International Patent Application No. PCT/EP2019/082216, filed Nov. 22, 2019, which claims priority to EP patent application Ser. No. 18/306,562.2, filed Nov. 23, 2018. The contents of the aforementioned priority applications are incorporated herein by reference in their entirety.

SEQUENCE LISTING

Nucleic acid sequences are disclosed in the present specification that serve as references. The same sequences are also presented in a sequence listing formatted according to standard requirements for the purpose of patent matters. In case of any sequence discrepancy with the standard sequence listing, the sequences described in the present specification shall be the reference. The instant application contains a Sequence Listing that has been submitted electronically in ASCII format and is hereby incorporated by reference in its entirety. Said ASCII copy, created on 15 Nov. 2019, is named 022548_P1058_SL.txt and is 244,191 bytes in size.

BACKGROUND OF THE INVENTION

Angiopoietin-like protein 8 (ANGPTL8) is an ANGPTL family member believed to be involved in lipid and potentially glucose metabolism. ANGPTL8, a 22 kDa protein expressed primarily in liver tissue in humans, is also known as betatrophin, lipasin, refeeding-induced fat and liver protein, hepatocellular carcinoma-associated protein TD26, LOC55908RIFL, and C19ORF80. Levels of circulating ANGPTL8 are positively correlated with triglyceride levels. Overexpression of ANGPTL8 in the liver is associated with hypertriglyceridemia, whereas its inactivation reduces plasma triglyceride levels (Quagliarini et. al., *Proc. Natl. Acad. Sci.* (2012) 109(48):19751-6; Wang et. al., *Proc. Natl. Acad. Sci.* (2013) 110:16109-14). Elevated levels of blood triglycerides (e.g., 150 mg/dL or higher) significantly increase the risk of cardiovascular conditions such as heart disease, heart attack, stroke, and atherosclerosis, e.g., by contributing to risk factors such as obesity, hypertension, high cholesterol levels, high blood sugar, and metabolic syndrome. Very high levels of blood triglycerides (e.g., 500 mg/dL or higher) significantly increase the risk of pancreatitis.

Double-stranded RNA molecules (dsRNAs) have been shown to block gene expression in a highly conserved regulatory mechanism known as RNA interference (RNAi). This appears to be a different mechanism of action from that of single-stranded oligonucleotides such as antisense oligonucleotides, antimiRs, and antagomiRs. In RNA interference technology, double-stranded RNAs, such as small interfering RNAs (siRNAs), bind to the RNA-induced silencing complex ("RISC"), where one strand (the "passenger strand" or "sense strand") is displaced and the remaining strand (the "guide strand" or "antisense strand") cooperates with RISC to bind a complementary RNA (the target RNA). Once bound, the target RNA is cleaved by RNA endonuclease Argonaute (AGO) in RISC and then further degraded by RNA exonucleases. RNAi has now been used to develop a new class of therapeutic agents for treating disorders caused by the aberrant or unwanted expression of a gene.

Due to the importance of ANGPTL8 in regulating triglyceride and lipid metabolism, and the prevalence of diseases associated with elevated triglyceride levels, there is a continuing need to identify inhibitors of ANGPTL8 expression and to test such inhibitors for efficacy and unwanted side effects such as cytotoxicity.

SUMMARY OF THE INVENTION

Provided herein are dsRNAs useful for inhibiting expression of an ANGPTL8 gene. Compared to currently available treatments for conditions associated with elevated levels of triglycerides, the dsRNAs provided herein may provide a superior clinical efficacy. The RNA agents of the present disclosure may reduce elevated triglyceride levels into normal ranges, or maintain normal triglyceride levels, resulting in overall improved health. The RNA agents of the present disclosure may be used to treat conditions such as lipid metabolism disorders characterized in whole or in part by elevated triglyceride levels (e.g., hypertriglyceridemia and associated diseases such as pancreatitis).

Accordingly, provided herein is a double-stranded ribonucleic acid (dsRNA) that inhibits expression of the human angiopoietin-like protein 8 (ANGPTL8) gene by binding to a target sequence on an RNA transcript of the ANGPTL8 gene. The dsRNA contains a sense strand comprising a sense sequence, and an antisense strand comprising an antisense sequence, wherein the sense sequence is at least 90% identical to the target sequence. In some embodiments, the sense strand and the antisense strand of the present dsRNA are complementary to each other over a region of 15-25 contiguous nucleotides. In some embodiments, the sense strand and the antisense strand are no more than 30 nucleotides in length.

In some embodiments, the target sequence of the present dsRNA is nucleotides 211-229, 315-333, 455-473, 456-474, 457-475, 458-476, 459-477, 573-591, 648-666, 843-861, 844-862, 851-869, 455-474, 455-475, 455-476, 455-477, 456-475, 456-476, 456-477, 457-476, or 457-477 of SEQ ID NO: 529. In further embodiments, the target sequence is nucleotides 315-333, 457-475, 458-476, or 459-477 of SEQ ID NO: 529. In some embodiments, the target sequence of the present dsRNA is nucleotides 315-333, 457-475, 458-476, or 459-477 of SEQ ID NO: 529. As used herein, a target sequence defined as the range "x-y" of SEQ ID NO: Z consists of the target sequence beginning at the nucleotide in position x and ending at the nucleotide in position y of the nucleic acid sequence of SEQ ID NO: Z. Illustratively, for the sake of clarity, the target sequence defined as the range "211-229" consists of the target sequence beginning at the nucleotide in position 211 and ending at the nucleotide in position 229 of the nucleic acid sequence of SEQ ID NO: 529.

In some embodiments, the dsRNA comprises an antisense sequence that is at least 90% identical to a nucleotide sequence selected from the group consisting of SEQ ID NOs: 138, 155, 172-176, 199, 232, 255, 256, and 263.

In some embodiments, the sense sequence and the antisense sequence of the present dsRNA are complementary, wherein a) the sense sequence comprises a nucleotide sequence selected from the group consisting of SEQ ID NOs: 6, 23, 40-44, 67, 100, 123, 124, and 131; or b) the antisense sequence comprises a nucleotide sequence selected from the group consisting of SEQ ID NOs: 138, 155, 172-176, 199, 232, 255, 256, and 263.

In some embodiments, the sense strand and antisense strand of the dsRNA respectively comprise the nucleotide sequences of: a) SEQ ID NOs: 6 (sense strand) and 138 (antisense strand); b) SEQ ID NOs: 23 and 155; c) SEQ ID NOs: 40 and 172; d) SEQ ID NOs: 41 and 173; e) SEQ ID NOs: 42 and 174; f) SEQ ID NOs: 43 and 175; g) SEQ ID NOs: 44 and 176; h) SEQ ID NOs: 67 and 199; i) SEQ ID NOs: 100 and 232; j) SEQ ID NOs: 123 and 255; k) SEQ ID NOs: 124 and 256; or l) SEQ ID NOs: 131 and 263. In some embodiments, the sense strand and antisense strand of the dsRNA respectively comprise the nucleotide sequences of: a) SEQ ID NOs: 23 and 155; b) SEQ ID NOs: 42 and 174; c) SEQ ID NOs: 43 and 175; or d) SEQ ID NOs: 44 and 176.

In some embodiments, the dsRNA comprises one or more modified nucleotides, wherein at least one of the one or more modified nucleotides is 2'-deoxy-2'-fluoro-ribonucleotide, 2'-deoxyribonucleotide, or 2'-O-methyl-ribonucleotide. In further embodiments, the dsRNA comprises two or more 2'-O-methyl-ribonucleotides and two or more 2'-deoxy-2'-fluoro-ribonucleotides (e.g., in an alternating pattern). In some embodiments, the sense sequence and the antisense sequence comprise alternating 2'-O-methyl ribonucleotides and 2'-deoxy-2'-fluoro ribonucleotides.

In some embodiments, the dsRNA comprises an inverted 2'-deoxyribonucleotide at the 3'-end of its sense or antisense strand.

In some embodiments, one or both of the sense strand and antisense strand of the present dsRNA comprise a) a 5' overhang comprising one or more nucleotides; and/or b) a 3' overhang comprising one or more nucleotides. In further embodiments, an overhang in the dsRNA comprises two or three nucleotides. In certain embodiments, an overhang in the dsRNA comprises one or more thymines.

In some embodiments, in the present dsRNA, the sense strand comprises a nucleotide sequence selected from the group consisting of SEQ ID NOs: 270, 287, 304-308, 331, 364, 387, 388, and 395; and/or the antisense strand comprises a nucleotide sequence selected from the group consisting of SEQ ID NOs: 402, 419, 436-440, 463, 496, 519, 520, and 527. In further embodiments, the sense strand and antisense strand of the dsRNA respectively comprise the nucleotide sequences of: a) SEQ ID NOs: 270 and 402; b) SEQ ID NOs: 287 and 419; c) SEQ ID NOs: 304 and 436; d) SEQ ID NOs: 305 and 437; e) SEQ ID NOs: 306 and 438; f) SEQ ID NOs: 307 and 439; g) SEQ ID NOs: 308 and 440; h) SEQ ID NOs: 331 and 463; i) SEQ ID NOs: 364 and 496; j) SEQ ID NOs: 387 and 519; k) SEQ ID NOs: 388 and 520; or l) SEQ ID NOs: 395 and 527.

In some embodiments, the present dsRNA is conjugated to one or more ligands with or without a linker. The ligand may, for example, be a cholesterol derivative or a lipophilic moiety. The present dsRNA may also be conjugated to one or more N-acetylgalactosamine (GalNAc) groups.

In some embodiments, one or both strands of the present dsRNA comprise one or more compounds having the structure of

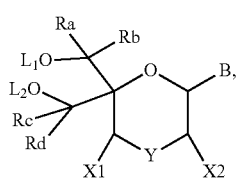

(I)

wherein:
B is a heterocyclic nucleobase,
one of L1 and L2 is an internucleoside linking group linking the compound of formula (I) to said strand(s) and the other of L1 and L2 is H, a protecting group, a phosphorus moiety or an internucleoside linking group linking the compound of formula (I) to said strand(s),
Y is O, NH, NR1 or N—C(=O)—R1, wherein R1 is:
  a (C1-C20) alkyl group, optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2, wherein
J is O or S,
each of Z1 and Z2 is, independently, H, a (C1-C6) alkyl group, optionally substituted by one or more groups selected from a halogen atom and a (C1-C6) alkyl group,
  a (C3-C8) cycloalkyl group, optionally substituted by one or more groups selected from a halogen atom and a (C1-C6) alkyl group,
  a group [C(=O)]m-R2-(O—CH2—CH2)p-R3, wherein
m is an integer meaning 0 or 1,
p is an integer ranging from 0 to 10,
R2 is a (C1-C20) alkylene group optionally substituted by a (C1-C6) alkyl group, —O—Z3, —N(Z3)(Z4), —S—Z3, —CN, —C(=K)—O—Z3, —O—C(=K)—Z3, —C(=K)—N(Z3)(Z4), or —N(Z3)-C(=K)—Z4, wherein
K is O or S,
each of Z3 and Z4 is, independently, H, a (C1-C6) alkyl group, optionally substituted by one or more groups selected from a halogen atom and a (C1-C6) alkyl group, and
R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group or a (C5-C14) heteroaryl group, or R3 is a cell targeting moiety,
X1 and X2 are each, independently, a hydrogen atom, a (C1-C6) alkyl group, and
each of Ra, Rb, Rc and Rd is, independently, H or a (C1-C6) alkyl group, or a pharmaceutically acceptable salt thereof.

In some embodiments, the dsRNA comprises one or more compounds of formula (I) wherein Y is a) NR1, R1 is a non-substituted (C1-C20) alkyl group; b) NR1, R1 is a non-substituted (C1-C16) alkyl group, which includes an alkyl group selected from a group comprising methyl, isopropyl, butyl, octyl, and hexadecyl; c) NR1, R1 is a (C3-C8) cycloalkyl group, optionally substituted by one or more groups selected from a halogen atom and a (C1-C6) alkyl group; d) NR1, R1 is a cyclohexyl group; e) NR1, R1 is a (C1-C20) alkyl group substituted by a (C6-C14) aryl group; f) NR1, R1 is a methyl group substituted by a phenyl group; g)N—C(=O)—R1, R1 is an optionally substituted (C1-C20) alkyl group; or h)N—C(=O)—R1, R1 is methyl or pentadecyl.

In some embodiments, the dsRNA comprises one or more compounds of formula (I) wherein B is selected from a group consisting of a pyrimidine, a substituted pyrimidine, a purine and a substituted purine, or a pharmaceutically acceptable salt thereof.

In some embodiments, R3 is of the formula (II):

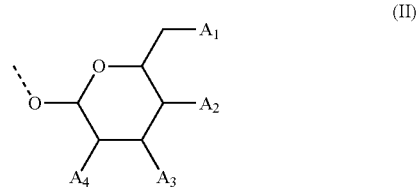

(II)

wherein A1, A2 and A3 are OH,
A4 is OH or NHC(=O)—R5, wherein R5 is a (C1-C6) alkyl group, optionally substituted by an halogen atom, or a pharmaceutically acceptable salt thereof.

In some embodiments, R3 is N-acetyl-galactosamine, or a pharmaceutically acceptable salt thereof.

In some embodiments, the present dsRNA comprises one or more nucleotides from Tables A and B.

In some embodiments, the present dsRNA comprises 2 to 10 compounds of formula (I), or a pharmaceutically acceptable salt thereof, wherein the compounds are optionally on the sense strand.

In some embodiments, the sense strand of the dsRNA comprises two to five compounds of formula (I) at the 5' end, and/or comprises one to three compounds of formula (I) at the 3' end. In further embodiments, the two to five compounds of formula (I) at the 5' end of the sense strand comprise lgT3 and/or lgT7, optionally comprising three consecutive lgT3 nucleotides; and/or the one to three compounds of formula (I) at the 3' end of the sense strand comprise lT4 or lT3; optionally comprising two consecutive lT4.

In some embodiments, the dsRNA of the present disclosure comprises one or more internucleoside linking groups independently selected from the group consisting of phosphodiester, phosphotriester, phosphorothioate, phosphorodithioate, alkyl-phosphonate and phosphoramidate backbone linking groups, or a pharmaceutically acceptable salt thereof.

In some embodiments, the present dsRNA is a small interfering RNA (siRNA). In some embodiments, the present dsRNA is a short hairpin RNA (shRNA). The present disclosure encompasses a DNA vector encoding such a dsRNA. In some embodiments, the dsRNA is selected from Tables 1-4.

The present disclosure further provides a pharmaceutical composition comprising a dsRNA or DNA vector described herein, and a pharmaceutically acceptable excipient.

Also provided in this disclosure is the present dsRNA, DNA vector, or composition for use in inhibiting ANGPTL8 expression in a human in need thereof, or for use in treating or preventing an ANGPTL8-associated condition in a human in need thereof.

Further provided in this disclosure is a method of inhibiting ANGPTL8 expression, or treating or preventing an ANGPTL8-associated condition, in a mammal (e.g., a human) in need thereof by administering the present dsRNA, DNA vector, or composition to the mammal.

Further provided in this disclosure is the use of the present dsRNA or DNA vector in the manufacture of a medicament for inhibiting ANGPTL8 expression, or treating or preventing an ANGPTL8-associated condition, in a mammal (e.g., a human) in need thereof, as well as articles of manufacture (e.g., kits).

In some embodiments, the dsRNA inhibits the expression of the ANGPTL8 gene in the liver of a human in the treatment methods. In certain embodiments, the ANGPTL8-associated condition is a lipid metabolism disorder such as hypertriglyceridemia and associated diseases such as pancreatitis.

Expression of mRNA is represented relative to cells treated with LV2. Error bars indicate standard deviation.

Figure 8:
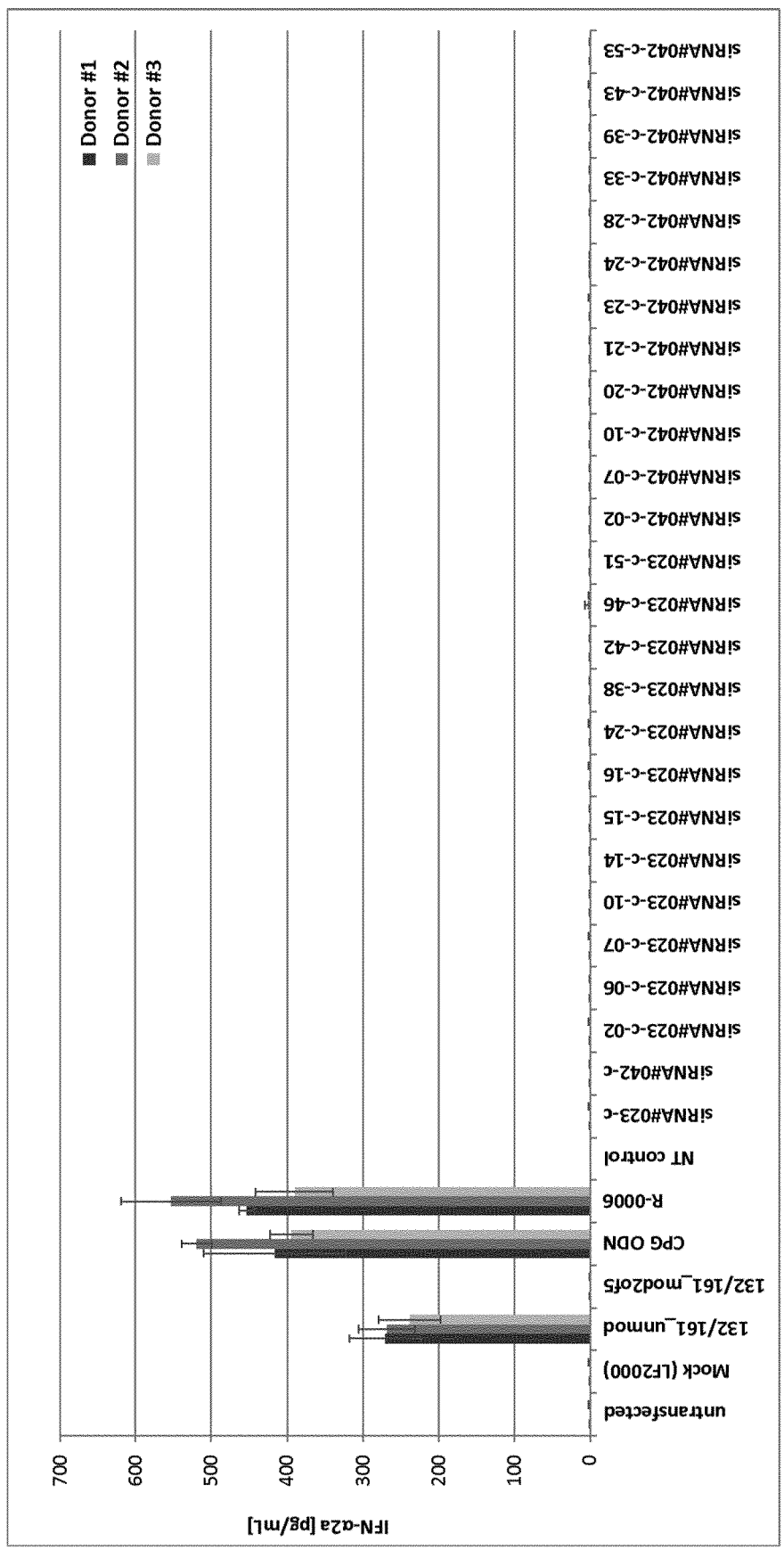

FIG. 8 is a graph showing immune stimulation indicated by the amount of interferon α2a (IFN-α2a) protein released into the supernatant of human peripheral blood mononuclear cells (PBMCs) isolated from three donors and transfected for 24 hours with 100 nM concentration of 24 selected modified GalNAc ANGPTL8 siRNAs together with respective parental sequences (siRNA#023-c and siRNA#042-c) or controls. Protein concentration was determined by ELISA. Error bars indicate standard deviation.

Figure 9:
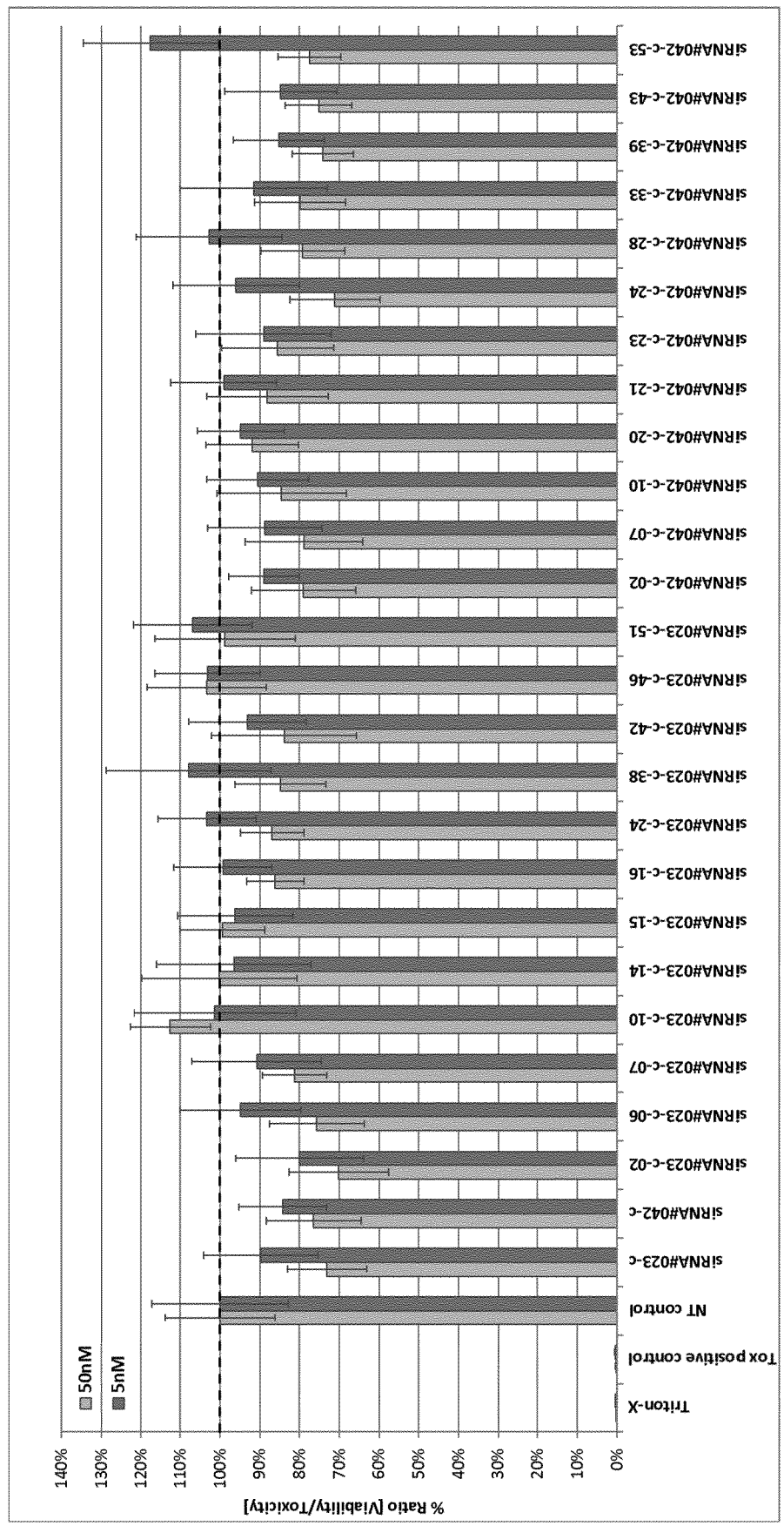

FIG. 9 is a graph showing cytotoxic effects of 24 selected modified GalNAc ANGPTL8 siRNAs together with respective parental sequences (siRNA#023-c and siRNA#042-c) in human Hep3B cells. Cells were transfected with siRNAs as indicated at 5 or 50 nM concentration for 72 hours before being analyzed for viability (CellTiter-Glo assay) and toxicity (ToxiLight assay). Ratios of the resulting readings are shown relative to results for a non-targeting siRNA control. Error bars indicate standard deviation.

Figure 10B:
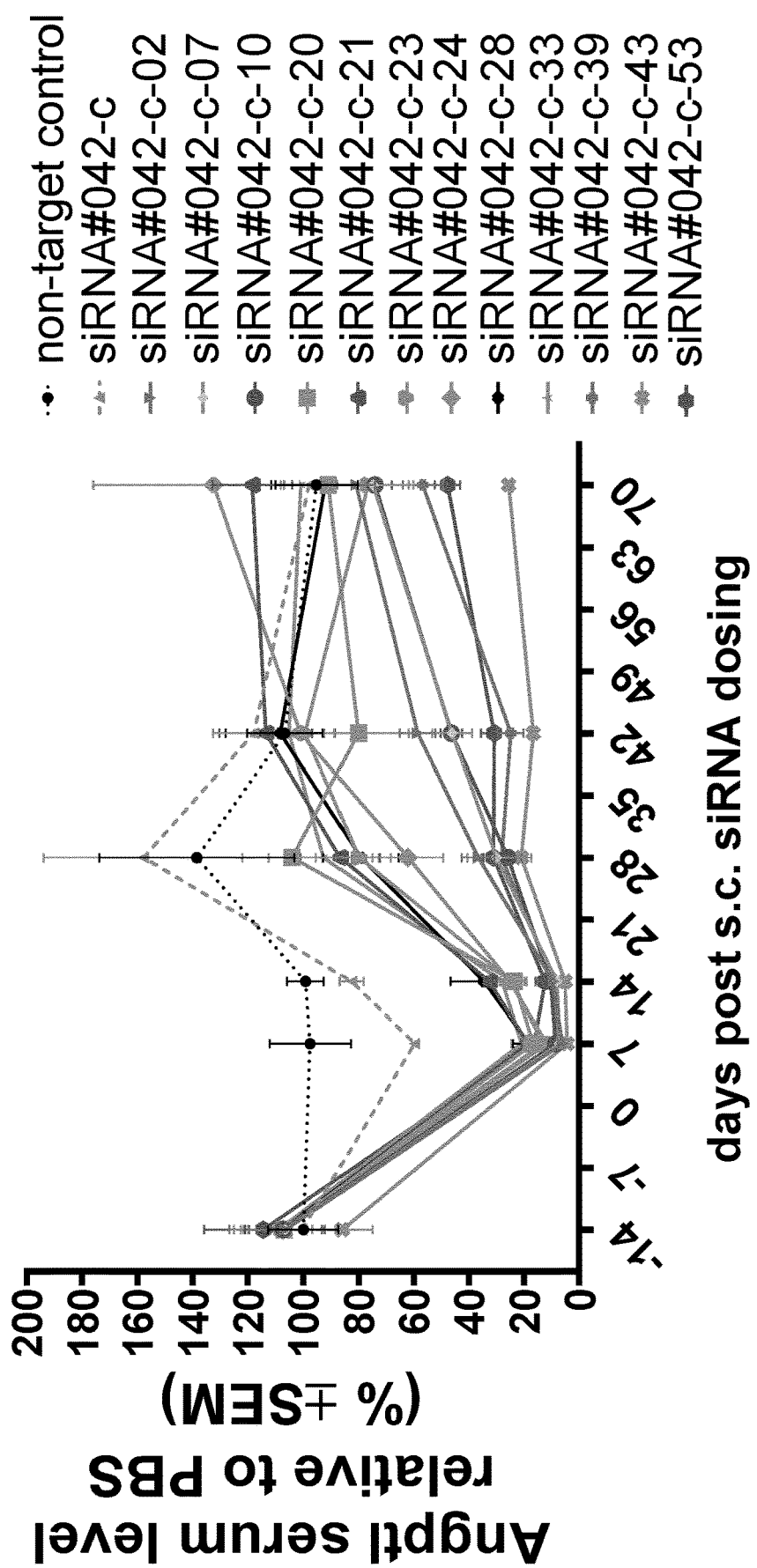

FIGS. 10A and 10B are graphs showing serum ANGPTL3 protein levels as a surrogate indicator for ANGPTL8 expression from a bicistronic ANGPTL3-ANGPTL8 AAV8 construct, over time in mice treated subcutaneously with selected GalNAc-siRNAs at 6 mg/kg at day 0. Serum ANGPTL3 levels were measured by ELISA. FIG. 10A: siRNA#023-c and modified variants thereof. FIG. 10B: siRNA#042-c and modified variants thereof. Error bars indicate standard error of the mean.

DETAILED DESCRIPTION OF THE INVENTION

The present disclosure provides novel double-stranded RNAs (dsRNAs) that inhibit expression of an angiopoietin-like protein 8 (ANGPTL8) gene. In some embodiments, the dsRNAs are small interfering RNAs (siRNAs). The dsRNAs can be used to treat conditions such as lipid metabolism disorders (e.g., dyslipidemia, hypertriglyceridemia, and associated diseases such as pancreatitis). Unless otherwise stated, "ANGPTL8" refers to human ANGPTL8 herein. An mRNA sequence of a human ANGPTL8 protein is available under NCBI Reference Sequence No. NM_018687.6 (SEQ ID NO: 529) and its polypeptide sequence is available under NCBI Reference Sequence No. NP_061157.3 (SEQ ID NO: 530). In certain embodiments, the present disclosure refers to cynomolgus ANGPTL8. An mRNA sequence of a cynomolgus ANGPTL8 protein is available under NCBI Reference Sequence No. XM_005588007.1 (SEQ ID NO: 531) and its polypeptide sequence is available under NCBI Reference Sequence No. XP_005588064.1 (SEQ ID NO: 532).

A dsRNA of the present disclosure may have one or more of the following properties: (i) has a half-life of at least 24, 28, 32, 48, 52, 56, 60, or 72 hours in vitro; (ii) does not increase production of interferon α secreted from human primary PBMCs; (iii) has an $IC_{50}$ value of at least 300, 325, 350, 375, 400, 425, 450, 475, 500, 525, 550, 575, or 600 nM for inhibition of human ANGPTL8 expression in vitro; and (iv) reduces protein levels of ANGPTL8 by at least 75%, 80%, 85%, 90%, 95%, 96%, 97%, 98%, or 99% in vivo in C57BL/6 mice expressing human ANGPTL3 and ANGPTL8.

In some embodiments, a dsRNA of the present disclosure has at least one of the following properties: (i) has a half-life of at least 24 hours in vitro; (ii) does not increase production of interferon α secreted from human primary PBMCs, (iii) has an $IC_{50}$ value of at least 475 nM for inhibition of human ANGPTL8 expression in vitro; and (iv) reduces protein levels of human ANGPTL8 by at least 80% in vivo in C57BL/6 mice expressing human ANGPTL3 and ANGPTL8. In certain embodiments, the dsRNA has all of said properties.

It will be understood by a person skilled in the art that the dsRNAs described herein do not occur in nature ("isolated" dsRNAs).

I. Double-Stranded RNAs

Certain aspects of the present disclosure relate to double-stranded ribonucleic acid (dsRNA) molecules targeting ANGPTL8. As used herein, the term "double-stranded RNA" or "dsRNA" refers to an oligoribonucleotide molecule comprising a duplex structure having two anti-parallel and substantially complementary nucleic acid strands. The two strands forming the duplex structure may be different portions of one larger RNA molecule, or they may be on separate RNA molecules. When the two strands are on separate RNA molecules, the dsRNA structure may function as a small interfering RNA (siRNA). Where the two strands are part of one larger molecule and are connected by an uninterrupted chain of nucleotides between the 3'-end of a first strand and the 5'-end of a second strand, the connecting RNA chain is referred to as a "hairpin loop" and the RNA molecule may be termed "short hairpin RNA," or "shRNA." The RNA strands may have the same or a different number of nucleotides. In addition to the duplex structure, a dsRNA may comprise overhangs of one or more (e.g., 1, 2, or 3) nucleotides.

As used herein, the term "polynucleotide" refers to a polymeric form of nucleotides (e.g., ribonucleotides, deoxyribonucleotides, or modified forms of either type of nucleotide) of at least 10 bases in length. The term includes single and double stranded forms.

A "dsRNA" may include naturally occurring ribonucleotides, and/or chemically modified analogs thereof. As used herein, "dsRNAs" are not limited to those with ribose-containing nucleotides. A dsRNA herein encompasses a double-stranded polynucleotide molecule where the ribose moiety in some or all of its nucleotides has been replaced by another moiety, so long as the resultant double-stranded molecule can inhibit the expression of a target gene by RNA interference. The dsRNA may also include one or more, but not more than 60% (e.g., not more than 50%, 40%, 30%, 20%, or 10%) deoxyribonucleotides or chemically modified analogs thereof.

A dsRNA of the present disclosure comprises a sense strand comprising a sense sequence, and an antisense strand comprising an antisense sequence, wherein the sense strand and the antisense strand are sufficiently complementary to hybridize to form a duplex structure. The term "antisense sequence" refers to a sequence that is substantially or fully complementary, and binds under physiological conditions, to a target RNA sequence in a cell. A "target sequence" refers to a nucleotide sequence on an RNA molecule (e.g., a primary RNA transcript or a messenger RNA transcript) transcribed from a target gene, e.g., an ANGPTL8 gene. The term "sense sequence" refers to a sequence that is substantially or fully complementary to the antisense sequence.

The ANGPTL8-targeting dsRNA of the present disclosure comprises a sense strand comprising a sense sequence and an antisense strand comprising an antisense sequence, wherein the sense and antisense sequences are substantially or fully complementary to each other. Unless otherwise indicated, the term "complementary" refers herein to the ability of a polynucleotide comprising a first contiguous nucleotide sequence, under certain conditions, e.g., physiological conditions, to hybridize to and form a duplex structure with another polynucleotide comprising a second contiguous nucleotide sequence. This may include base-pairing of the two polynucleotides over the entire length of the first or second contiguous nucleotide sequence; in this case, the two nucleotide sequences are considered "fully complementary" to each other. For example, in a case where a dsRNA comprises a first oligonucleotide 21 nucleotides in length and a second oligonucleotide 23 nucleotides in length, and where the two oligonucleotides form 21 contiguous base-pairs, the two oligonucleotides may be referred to as "fully complementary" to each other. Where a first polynucleotide sequence is referred to as "substantially complementary" to a second polynucleotide sequence, the two sequences may base-pair with each other over 80% or more (e.g., 90% or more) of their length of hybridization, with no more than 20% (e.g., no more than 10%) of mismatching base-pairs (e.g., for a duplex of 20 nucleotides, no more than 4 or no more than 2 mismatched base-pairs). Where two oligonucleotides are designed to form a duplex with one or more single-stranded overhangs, such overhangs shall not be regarded as mismatches for the determination of complementarity. Complementarity of two sequences may be based on Watson-Crick base-pairs and/or non-Watson-Crick base-pairs. As used herein, a polynucleotide which is "substantially complementary to at least part of" an mRNA refers to a polynucleotide which is substantially complementary to a contiguous portion of an mRNA of interest (e.g., an mRNA encoding ANGPTL8).

In some embodiments, the ANGPTL8-targeting dsRNA is an siRNA where the sense and antisense strands are not covalently linked to each other. In some embodiments, the sense and antisense strands of the ANGPTL8-targeting dsRNA are covalently linked to each other, e.g., through a hairpin loop (such as in the case of shRNA), or by means other than a hairpin loop (such as by a connecting structure referred to as a "covalent linker").

I.1 Lengths

In some embodiments, each of the sense sequence (in the sense strand) and the antisense sequence (in the antisense strand) is 9-30 nucleotides in length. For example, each sequence can be any of a range of nucleotide lengths having an upper limit of 21, 22, 23, 24, 25, 26, 27, 28, 29, or 30 and an independently selected lower limit of 9, 10, 11, 12, 13, 14, 15, 16, 17, 18, 19, or 20. In some embodiments, the number of nucleotides in each sequence may be 15-25 (i.e., 15 to 25 nucleotides in each sequence), 15-30, 16-29, 17-28, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, or 19-21.

In some embodiments, each sequence is greater than 8, 9, 10, 11, 12, 13, 14, 15, 16, 17, 18, 19, 20, 21, 22, 23, 24, 25, 26, 27, 28, 29, or 30 nucleotides in length. In some embodiments, each sequence is less than 21, 22, 23, 24, 25, 26, 27, 28, 29, 30, or 31 nucleotides in length. In some embodiments, each sequence is 9, 10, 11, 12, 13, 14, 15, 16, 17, 18, 19, 20, 21, 22, 23, 24, 25, 26, 27, 28, 29, or 30 nucleotides in length.

In some embodiments, the sense and antisense sequences are each at least 15 and no greater than 25 nucleotides in length. In some embodiments, the sense and antisense sequences are each at least 17 (e.g. at least 19) and no greater than 23 nucleotides in length. For example, the sequences are 15, 16, 17, 18, 19, 20, 21, 22, 23, 24, or 25 nucleotides in length.

The sense sequence and antisense sequence may be of the same or different lengths. For example, the antisense sequence may have 19 nucleotides while the sense sequence may have 17 nucleotides. In another example, the antisense sequence and the sense sequence both have 19 nucleotides.

In some embodiments, the ANGPTL8-targeting dsRNA has sense and antisense strands of the same length or different lengths. For example, the sense strand may be 1, 2, 3, 4, 5, 6, or 7 nucleotides longer than the antisense strand. Alternatively, the sense strand may be 1, 2, 3, 4, 5, 6, or 7 nucleotides shorter than the antisense strand.

In some embodiments, each of the sense strand and the antisense strand is 9-36 nucleotides in length. For example, each strand can be any of a range of nucleotide lengths having an upper limit of 21, 22, 23, 24, 25, 26, 27, 28, 29, 30, 31, 32, 33, 34, 35, or 36 and an independently selected lower limit of 9, 10, 11, 12, 13, 14, 15, 16, 17, 18, 19, or 20. In some embodiments, the number of nucleotides in each strand may be 15-25, 15-30, 16-29, 17-28, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, or 19-21.

In some embodiments, each strand is greater than 8, 9, 10, 11, 12, 13, 14, 15, 16, 17, 18, 19, 20, 21, 22, 23, 24, 25, 26, 27, 28, 29, or 30 nucleotides in length. In some embodiments, each strand is less than 20, 21, 22, 23, 24, 25, 26, 27, 28, 29, 30, 31, 32, 33, 34, 35, 36, or 37 nucleotides in length. In some embodiments, each strand is 9, 10, 11, 12, 13, 14, 15, 16, 17, 18, 19, 20, 21, 22, 23, 24, 25, 26, 27, 28, 29, 30, 31, 32, 33, 34, 35, or 36 nucleotides in length.

In some embodiments, the sense and antisense strands are each at least 15 and no greater than 25 nucleotides in length. In some embodiments, the sense and antisense strands are each at least 19 and no greater than 23 nucleotides in length. For example, the strands are 19, 20, 21, 22, or 23 nucleotides in length.

In some embodiments, the sense strand may have 21, 22, 23, or 24 nucleotides, including any modified nucleotides, while the antisense strand may have 21 nucleotides, including any modified nucleotides; in certain embodiments, the sense strand may have a sense sequence having 17, 18, or 19 nucleotides, while the antisense strand may have an antisense sequence having 19 nucleotides.

I.2 Overhangs

In some embodiments, a dsRNA of the present disclosure comprises one or more overhangs at the 3'-end, 5'-end, or both ends of one or both of the sense and antisense strands. In some embodiments, the one or more overhangs improve the stability and/or inhibitory activity of the dsRNA.

"Overhang" refers herein to the unpaired nucleotide(s) that protrude from the duplex structure of a dsRNA when a 3' end of a first strand of the dsRNA extends beyond the 5' end of a second strand, or vice versa. "Blunt end" means that there are no unpaired nucleotides at that end of the dsRNA, i.e., no nucleotide overhang. A "blunt-ended" dsRNA is a dsRNA that is double-stranded over its entire length, i.e., no nucleotide overhang at either end of the duplex molecule. Chemical caps or non-nucleotide chemical moieties conjugated to the 3' end and/or the 5' end of a dsRNA are not considered herein in determining whether a dsRNA has an overhang or not.

In some embodiments, an overhang comprises one or more, two or more, three or more, or four or more nucleotides. For example, the overhang may comprise 1, 2, 3, or 4 nucleotides.

In some embodiments, an overhang of the present disclosure comprises one or more nucleotides (e.g., ribonucleotides or deoxyribonucleotides, naturally occurring or chemically modified analogs thereof). In some embodiments, the overhang comprises one or more thymines or chemically modified analogs thereof. In certain embodiments, the overhang comprises one or more thymines.

In some embodiments, the dsRNA comprises an overhang located at the 3'-end of the antisense strand. In some embodiments, the dsRNA comprises a blunt end at the 5'-end of the antisense strand. In some embodiments, the dsRNA comprises an overhang located at the 3'-end of the antisense strand and a blunt end at the 5'-end of the antisense strand. In some embodiments, the dsRNA comprises an overhang located at the 3'-end of the sense strand. In some embodiments, the dsRNA comprises a blunt end at the 5'-end of the sense strand. In some embodiments, the dsRNA comprises an overhang located at the 3'-end of the sense strand and a blunt end at the 5'-end of the sense strand. In some embodiments, the dsRNA comprises overhangs located at the 3'-end of both the sense and antisense strands of the dsRNA.

In some embodiments, the dsRNA comprises an overhang located at the 5'-end of the antisense strand. In some embodiments, the dsRNA comprises a blunt end at the 3'-end of the antisense strand. In some embodiments, the dsRNA comprises an overhang located at the 5'-end of the antisense strand and a blunt end at the 3'-end of the antisense strand. In some embodiments, the dsRNA comprises an overhang located at the 5'-end of the sense strand. In some embodiments, the dsRNA comprises a blunt end at the 3'-end of the sense strand. In some embodiments, the dsRNA comprises an overhang located at the 5'-end of the sense strand and a blunt end at the 3'-end of the sense strand. In some embodiments, the dsRNA comprises overhangs located at both the 5'-end of the sense and antisense strands of the dsRNA.

In some embodiments, the dsRNA comprises an overhang located at the 3'-end of the antisense strand and an overhang at the 5'-end of the antisense strand. In some embodiments, the dsRNA comprises an overhang located at the 3'-end of the sense strand and an overhang at the 5'-end of the sense strand.

In some embodiments, the dsRNA has two blunt ends.

In some embodiments, the overhang is the result of the sense strand being longer than the antisense strand. In some embodiments, the overhang is the result of the antisense strand being longer than the sense strand. In some embodiments, the overhang is the result of sense and antisense strands of the same length being staggered. In some embodiments, the overhang forms a mismatch with the target mRNA. In some embodiments, the overhang is complementary to the target mRNA.

In certain embodiments, a dsRNA of the present disclosure contains a sense strand having the sequence of 5'-CCA-[sense sequence]-invdT, and the antisense strand having the sequence of 5'-[antisense sequence]-dTdT-3', where the trinucleotide CCA may be modified (e.g., 2'-O-Methyl-C and 2'-O-Methyl-A).

I.3 Target and dsRNA Sequences

The antisense strand of a dsRNA of the present disclosure comprises an antisense sequence that may be substantially or fully complementary to a target sequence of 12-30 nucleotides in length in an ANGPTL8 RNA (e.g., an mRNA). For example, the target sequence can be any of a range of nucleotide lengths having an upper limit of 19, 20, 21, 22, 23, 24, 25, 26, 27, 28, 29, or 30 and an independently selected lower limit of 12, 13, 14, 15, 16, 17, 18, or 19. In some embodiments, the number of nucleotides in the target sequence may be 15-25, 15-30, 16-29, 17-28, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, or 19-21.

In some embodiments, the target sequence is greater than 12, 13, 14, 15, 16, 17, 18, 19, or 20 nucleotides in length. In some embodiments, the target sequence is less than 21, 22, 23, 24, 25, 26, 27, 28, 29, or 30 nucleotides in length. In some embodiments, the target sequence is 12, 13, 14, 15, 16, 17, 18, 19, 20, 21, 22, 23, 24, 25, 26, 27, 28, 29, or 30 nucleotides in length. In certain embodiments, the target sequence is at least 15 and no greater than 25 nucleotides in length; for example, at least 19 and no greater than 23 nucleotides in length, or 15, 16, 17, 18, 19, 20, 21, 22, 23, 24, or 25 nucleotides in length.

The target sequence may be in the 5' noncoding region, the coding region, or the 3' noncoding region of the ANGPTL8 mRNA transcript. The target sequence may also be located at the junction of the non-coding and coding regions.

In some embodiments, the dsRNA antisense strand comprises an antisense sequence having one or more mismatch (e.g., one, two, three, or four mismatches) to the target sequence. In certain embodiments, the antisense sequence is fully complementary to the corresponding portion in the human ANGPTL8 mRNA sequence and is fully complementary or substantially complementary (e.g., comprises at least one or two mismatches) to the corresponding portion in a cynomolgus ANGPTL8 mRNA sequence. One advantage of such dsRNAs is to allow pre-clinical in vivo studies of the dsRNAs in non-human primates such as cynomolgus monkeys. In certain embodiments, the dsRNA sense strand comprises a sense sequence that is at least 70%, 75%, 80%, 85%, 90%, 95%, 96%, 97%, 98%, or 99% identical to the target sequence (e.g., in human or cynomolgus ANGPTL8 mRNA).

In some embodiments, the target sequence in a human ANGPTL8 mRNA sequence (SEQ ID NO: 529) has the start and end nucleotide positions at or around (e.g., within 3 nucleotides of) the following nucleotides: 211 and 229, 315 and 333, 455 and 473, 456 and 474, 457 and 475, 458 and 476, 459 and 477, 573 and 591, 648 and 666, 843 and 861, 844 and 862, 851 and 869, 455 and 474, 455 and 475, 455 and 476, 455 and 477, 456 and 475, 456 and 476, 456 and 477, 457 and 476, or 457 and 477, respectively. In certain embodiments, the target sequence corresponds to nucleotide positions 315-333, 457-475, 458-476, or 459-477 of the human ANGPTL8 mRNA sequence, where the start and end positions may vary within 3 nucleotides of the numbered positions. In some embodiments, the target sequence is a sequence listed in Table 1 as a sense sequence, or a sequence that includes at least 80% nucleotides (e.g., at least 90%) of the listed sequence.

In some embodiments, a dsRNA of the present disclosure comprises a sense strand comprising a sense sequence shown in Table 1. For example, the sense strand comprises a sequence selected from SEQ ID NOs: 6, 23, 40-44, 67, 100, 123, 124, and 131, or a sequence having at least 15, 16, 17, or 18 contiguous nucleotides derived from said selected sequence. In certain embodiments, the sense strand comprises a sequence selected from SEQ ID NOs: 23 and 42-44.

In some embodiments, a dsRNA of the present disclosure comprises an antisense strand comprising an antisense sequence shown in Table 1. In some embodiments, the antisense strand comprises a sequence selected from SEQ ID NOs: 138, 155, 172-176, 199, 232, 255, 256, and 263, or a sequence having at least 15, 16, 17, or 18 contiguous nucleotides derived from said selected sequence. In certain embodiments, the antisense strand comprises a sequence selected from SEQ ID NOs: 155 and 174-176.

In some embodiments, a dsRNA of the present disclosure comprises a sense strand comprising a sense sequence shown in Table 1 and an antisense strand comprising an antisense sequence shown in Table 1. In some embodiments, the sense and antisense strands respectively comprise the sequences of:
SEQ ID NOs: 6 and 138;
SEQ ID NOs: 23 and 155;
SEQ ID NOs: 40 and 172;
SEQ ID NOs: 41 and 173;
SEQ ID NOs: 42 and 174;
SEQ ID NOs: 43 and 175;
SEQ ID NOs: 44 and 176;
SEQ ID NOs: 67 and 199;
SEQ ID NOs: 100 and 232;
SEQ ID NOs: 123 and 255;
SEQ ID NOs: 124 and 256; or
SEQ ID NOs: 131 and 263.

In certain embodiments, the sense and antisense strands respectively comprise the sequences of:
SEQ ID NOs: 23 and 155;
SEQ ID NOs: 42 and 174;
SEQ ID NOs: 43 and 175; or
SEQ ID NOs: 44 and 176.

In some embodiments, the antisense sequence is fully complementary to a sequence selected from SEQ ID NOs: 6, 23, 40-44, 67, 100, 123, 124, and 131. In some embodiments, the antisense sequence is substantially complementary to a sequence selected from SEQ ID NOs: 6, 23, 40-44, 67, 100, 123, 124, and 131, wherein the antisense sequence comprises at least one mismatch (e.g., one, two, three, or four mismatches) to the selected sequence.

In some embodiments, the antisense sequence is fully complementary to a sequence selected from SEQ ID NOs: 23 and 42-44. In some embodiments, the antisense sequence is substantially complementary to a sequence selected from SEQ ID NOs: 23 and 42-44, wherein the antisense sequence comprises at least one mismatch (e.g., one, two, three, or four mismatches) to the selected sequence.

In some embodiments, the antisense sequence of the ANGPTL8-targeting dsRNA comprises one or more mismatches to the target sequence (for example, due to allelic differences among individuals in a general population). For example, the antisense sequence comprises one or more mismatches (e.g., one, two, three, or four mismatches) to the target sequence. In some embodiments, the one or more mismatches are not located in the center of the region of complementarity. In some embodiments, the one or more mismatches are located within five, four, three, two, or one nucleotide of the 5' and/or 3' ends of the region of complementarity. For example, for a dsRNA containing a 19 nucleotide antisense sequence, in some embodiments the antisense sequence may not contain any mismatch within the central 9 nucleotides of the region of complementarity between it and its target sequence in the ANGPTL8 mRNA.

Table 1 below lists the sense and antisense sequences of exemplary siRNA constructs (CNST). The start (ST) and end (ED) nucleotide positions in NM_018687.6 (SEQ ID NO: 529) are indicated. "SEQ" denotes SEQ ID NOs.

TABLE 1

Sequences of Exemplary siRNA Constructs

| CNST# | ST | ED | Sense Sequence (5'-3') | SEQ | Antisense Sequence (5'-3') | SEQ |
|---|---|---|---|---|---|---|
| 001 | 5 | 23 | CUUAGACCCUCAGUCAUGC | 1 | GCAUGACUGAGGGUCUAAG | 133 |
| 002 | 99 | 117 | CAGAACUGGCACAGCAUGA | 2 | UCAUGCUGUGCCAGUUCUG | 134 |
| 003 | 100 | 118 | AGAACUGGCACAGCAUGAG | 3 | CUCAUGCUGUGCCAGUUCU | 135 |
| 004 | 197 | 215 | CUGACAAAGGCCAGGAACA | 4 | UGUUCCUGGCCUUUGUCAG | 136 |
| 005 | 198 | 216 | UGACAAAGGCCAGGAACAG | 5 | CUGUUCCUGGCCUUUGUCA | 137 |
| 006 | 211 | 229 | GAACAGCCUGGGUCUCUAU | 6 | AUAGAGACCCAGGCUGUUC | 138 |
| 007 | 212 | 230 | AACAGCCUGGGUCUCUAUG | 7 | CAUAGAGACCCAGGCUGUU | 139 |
| 008 | 222 | 240 | GUCUCUAUGGCCGCACAAU | 8 | AUUGUGCGGCCAUAGAGAC | 140 |
| 009 | 288 | 306 | AACUUCGGGCAAGCCUGUU | 9 | AACAGGCUUGCCCGAAGUU | 141 |
| 010 | 297 | 315 | CAAGCCUGUUGGAGACUCA | 10 | UGAGUCUCCAACAGGCUUG | 142 |
| 011 | 298 | 316 | AAGCCUGUUGGAGACUCAG | 11 | CUGAGUCUCCAACAGGCUU | 143 |
| 012 | 299 | 317 | AGCCUGUUGGAGACUCAGA | 12 | UCUGAGUCUCCAACAGGCU | 144 |
| 013 | 300 | 318 | GCCUGUUGGAGACUCAGAU | 13 | AUCUGAGUCUCCAACAGGC | 145 |
| 014 | 301 | 319 | CCUGUUGGAGACUCAGAUG | 14 | CAUCUGAGUCUCCAACAGG | 146 |
| 015 | 302 | 320 | CUGUUGGAGACUCAGAUGG | 15 | CCAUCUGAGUCUCCAACAG | 147 |
| 016 | 303 | 321 | UGUUGGAGACUCAGAUGGA | 16 | UCCAUCUGAGUCUCCAACA | 148 |
| 017 | 304 | 322 | GUUGGAGACUCAGAUGGAG | 17 | CUCCAUCUGAGUCUCCAAC | 149 |
| 018 | 305 | 323 | UUGGAGACUCAGAUGGAGG | 18 | CCUCCAUCUGAGUCUCCAA | 150 |
| 019 | 310 | 328 | GACUCAGAUGGAGGAGGAU | 19 | AUCCUCCUCCAUCUGAGUC | 151 |

TABLE 1-continued

Sequences of Exemplary siRNA Constructs

| CNST# | ST | ED | Sense Sequence (5'-3') | SEQ | Antisense Sequence (5'-3') | SEQ |
|---|---|---|---|---|---|---|
| 020 | 312 | 330 | CUCAGAUGGAGGAGGAUAU | 20 | AUAUCCUCCUCCAUCUGAG | 152 |
| 021 | 313 | 331 | UCAGAUGGAGGAGGAUAUU | 21 | AAUAUCCUCCUCCAUCUGA | 153 |
| 022 | 314 | 332 | CAGAUGGAGGAGGAUAUUC | 22 | GAAUAUCCUCCUCCAUCUG | 154 |
| 023 | 315 | 333 | AGAUGGAGGAGGAUAUUCU | 23 | AGAAUAUCCUCCUCCAUCU | 155 |
| 024 | 316 | 334 | GAUGGAGGAGGAUAUUCUG | 24 | CAGAAUAUCCUCCUCCAUC | 156 |
| 025 | 317 | 335 | AUGGAGGAGGAUAUUCUGC | 25 | GCAGAAUAUCCUCCUCCAU | 157 |
| 026 | 318 | 336 | UGGAGGAGGAUAUUCUGCA | 26 | UGCAGAAUAUCCUCCUCCA | 158 |
| 027 | 319 | 337 | GGAGGAGGAUAUUCUGCAG | 27 | CUGCAGAAUAUCCUCCUCC | 159 |
| 028 | 320 | 338 | GAGGAGGAUAUUCUGCAGC | 28 | GCUGCAGAAUAUCCUCCUC | 160 |
| 029 | 321 | 339 | AGGAGGAUAUUCUGCAGCU | 29 | AGCUGCAGAAUAUCCUCCU | 161 |
| 030 | 328 | 346 | UAUUCUGCAGCUGCAGGCA | 30 | UGCCUGCAGCUGCAGAAUA | 162 |
| 031 | 416 | 434 | CUAGAAGUCCAGCUGAGGA | 31 | UCCUCAGCUGGACUUCUAG | 163 |
| 032 | 417 | 435 | UAGAAGUCCAGCUGAGGAG | 32 | CUCCUCAGCUGGACUUCUA | 164 |
| 033 | 448 | 466 | CCCUGCCUACCGAGAAUUU | 33 | AAAUUCUCGGUAGGCAGGG | 165 |
| 034 | 449 | 467 | CCUGCCUACCGAGAAUUUG | 34 | CAAAUUCUCGGUAGGCAGG | 166 |
| 035 | 450 | 468 | CUGCCUACCGAGAAUUUGA | 35 | UCAAAUUCUCGGUAGGCAG | 167 |
| 036 | 451 | 469 | UGCCUACCGAGAAUUUGAG | 36 | CUCAAAUUCUCGGUAGGCA | 168 |
| 037 | 452 | 470 | GCCUACCGAGAAUUUGAGG | 37 | CCUCAAAUUCUCGGUAGGC | 169 |
| 038 | 453 | 471 | CCUACCGAGAAUUUGAGGU | 38 | ACCUCAAAUUCUCGGUAGG | 170 |
| 039 | 454 | 472 | CUACCGAGAAUUUGAGGUC | 39 | GACCUCAAAUUCUCGGUAG | 171 |
| 040 | 455 | 473 | UACCGAGAAUUUGAGGUCU | 40 | AGACCUCAAAUUCUCGGUA | 172 |
| 041 | 456 | 474 | ACCGAGAAUUUGAGGUCUU | 41 | AAGACCUCAAAUUCUCGGU | 173 |
| 042 | 457 | 475 | CCGAGAAUUUGAGGUCUUA | 42 | UAAGACCUCAAAUUCUCGG | 174 |
| 043 | 458 | 476 | CGAGAAUUUGAGGUCUUAA | 43 | UUAAGACCUCAAAUUCUCG | 175 |
| 044 | 459 | 477 | GAGAAUUUGAGGUCUUAAA | 44 | UUUAAGACCUCAAAUUCUC | 176 |
| 045 | 460 | 478 | AGAAUUUGAGGUCUUAAAG | 45 | CUUUAAGACCUCAAAUUCU | 177 |
| 046 | 461 | 479 | GAAUUUGAGGUCUUAAAGG | 46 | CCUUUAAGACCUCAAAUUC | 178 |
| 047 | 462 | 480 | AAUUUGAGGUCUUAAAGGC | 47 | GCCUUUAAGACCUCAAAUU | 179 |
| 048 | 463 | 481 | AUUUGAGGUCUUAAAGGCU | 48 | AGCCUUUAAGACCUCAAAU | 180 |
| 049 | 464 | 482 | UUUGAGGUCUUAAAGGCUC | 49 | GAGCCUUUAAGACCUCAAA | 181 |
| 050 | 465 | 483 | UUGAGGUCUUAAAGGCUCA | 50 | UGAGCCUUUAAGACCUCAA | 182 |
| 051 | 466 | 484 | UGAGGUCUUAAAGGCUCAC | 51 | GUGAGCCUUUAAGACCUCA | 183 |
| 052 | 467 | 485 | GAGGUCUUAAAGGCUCACG | 52 | CGUGAGCCUUUAAGACCUC | 184 |
| 053 | 468 | 486 | AGGUCUUAAAGGCUCACGC | 53 | GCGUGAGCCUUUAAGACCU | 185 |
| 054 | 469 | 487 | GGUCUUAAAGGCUCACGCU | 54 | AGCGUGAGCCUUUAAGACC | 186 |
| 055 | 470 | 488 | GUCUUAAAGGCUCACGCUG | 55 | CAGCGUGAGCCUUUAAGAC | 187 |
| 056 | 471 | 489 | UCUUAAAGGCUCACGCUGA | 56 | UCAGCGUGAGCCUUUAAGA | 188 |

TABLE 1-continued

Sequences of Exemplary siRNA Constructs

| CNST# | ST | ED | Sense Sequence (5'-3') | SEQ | Antisense Sequence (5'-3') | SEQ |
|---|---|---|---|---|---|---|
| 057 | 472 | 490 | CUUAAAGGCUCACGCUGAC | 57 | GUCAGCGUGAGCCUUUAAG | 189 |
| 058 | 473 | 491 | UUAAAGGCUCACGCUGACA | 58 | UGUCAGCGUGAGCCUUUAA | 190 |
| 059 | 474 | 492 | UAAAGGCUCACGCUGACAA | 59 | UUGUCAGCGUGAGCCUUUA | 191 |
| 060 | 475 | 493 | AAAGGCUCACGCUGACAAG | 60 | CUUGUCAGCGUGAGCCUUU | 192 |
| 061 | 486 | 504 | CUGACAAGCAGAGCCACAU | 61 | AUGUGGCUCUGCUUGUCAG | 193 |
| 062 | 487 | 505 | UGACAAGCAGAGCCACAUC | 62 | GAUGUGGCUCUGCUUGUCA | 194 |
| 063 | 489 | 507 | ACAAGCAGAGCCACAUCCU | 63 | AGGAUGUGGCUCUGCUUGU | 195 |
| 064 | 490 | 508 | CAAGCAGAGCCACAUCCUA | 64 | UAGGAUGUGGCUCUGCUUG | 196 |
| 065 | 491 | 509 | AAGCAGAGCCACAUCCUAU | 65 | AUAGGAUGUGGCUCUGCUU | 197 |
| 066 | 492 | 510 | AGCAGAGCCACAUCCUAUG | 66 | CAUAGGAUGUGGCUCUGCU | 198 |
| 067 | 573 | 591 | GACAGAUCCAGGAGAGACU | 67 | AGUCUCUCCUGGAUCUGUC | 199 |
| 068 | 574 | 592 | ACAGAUCCAGGAGAGACUC | 68 | GAGUCUCUCCUGGAUCUGU | 200 |
| 069 | 576 | 594 | AGAUCCAGGAGAGACUCCA | 69 | UGGAGUCUCUCCUGGAUCU | 201 |
| 070 | 610 | 628 | AGCCUGAAUCUGCCUGGAU | 70 | AUCCAGGCAGAUUCAGGCU | 202 |
| 071 | 613 | 631 | CUGAAUCUGCCUGGAUGGA | 71 | UCCAUCCAGGCAGAUUCAG | 203 |
| 072 | 614 | 632 | UGAAUCUGCCUGGAUGGAA | 72 | UUCCAUCCAGGCAGAUUCA | 204 |
| 073 | 615 | 633 | GAAUCUGCCUGGAUGGAAC | 73 | GUUCCAUCCAGGCAGAUUC | 205 |
| 074 | 616 | 634 | AAUCUGCCUGGAUGGAACU | 74 | AGUUCCAUCCAGGCAGAUU | 206 |
| 075 | 617 | 635 | AUCUGCCUGGAUGGAACUG | 75 | CAGUUCCAUCCAGGCAGAU | 207 |
| 076 | 618 | 636 | UCUGCCUGGAUGGAACUGA | 76 | UCAGUUCCAUCCAGGCAGA | 208 |
| 077 | 624 | 642 | UGGAUGGAACUGAGGACCA | 77 | UGGUCCUCAGUUCCAUCCA | 209 |
| 078 | 626 | 644 | GAUGGAACUGAGGACCAAU | 78 | AUUGGUCCUCAGUUCCAUC | 210 |
| 079 | 627 | 645 | AUGGAACUGAGGACCAAUC | 79 | GAUUGGUCCUCAGUUCCAU | 211 |
| 080 | 628 | 646 | UGGAACUGAGGACCAAUCA | 80 | UGAUUGGUCCUCAGUUCCA | 212 |
| 081 | 629 | 647 | GGAACUGAGGACCAAUCAU | 81 | AUGAUUGGUCCUCAGUUCC | 213 |
| 082 | 630 | 648 | GAACUGAGGACCAAUCAUG | 82 | CAUGAUUGGUCCUCAGUUC | 214 |
| 083 | 631 | 649 | AACUGAGGACCAAUCAUGC | 83 | GCAUGAUUGGUCCUCAGUU | 215 |
| 084 | 632 | 650 | ACUGAGGACCAAUCAUGCU | 84 | AGCAUGAUUGGUCCUCAGU | 216 |
| 085 | 633 | 651 | CUGAGGACCAAUCAUGCUG | 85 | CAGCAUGAUUGGUCCUCAG | 217 |
| 086 | 634 | 652 | UGAGGACCAAUCAUGCUGC | 86 | GCAGCAUGAUUGGUCCUCA | 218 |
| 087 | 635 | 653 | GAGGACCAAUCAUGCUGCA | 87 | UGCAGCAUGAUUGGUCCUC | 219 |
| 088 | 636 | 654 | AGGACCAAUCAUGCUGCAA | 88 | UUGCAGCAUGAUUGGUCCU | 220 |
| 089 | 637 | 655 | GGACCAAUCAUGCUGCAAG | 89 | CUUGCAGCAUGAUUGGUCC | 221 |
| 090 | 638 | 656 | GACCAAUCAUGCUGCAAGG | 90 | CCUUGCAGCAUGAUUGGUC | 222 |
| 091 | 639 | 657 | ACCAAUCAUGCUGCAAGGA | 91 | UCCUUGCAGCAUGAUUGGU | 223 |
| 092 | 640 | 658 | CCAAUCAUGCUGCAAGGAA | 92 | UUCCUUGCAGCAUGAUUGG | 224 |
| 093 | 641 | 659 | CAAUCAUGCUGCAAGGAAC | 93 | GUUCCUUGCAGCAUGAUUG | 225 |
| 094 | 642 | 660 | AAUCAUGCUGCAAGGAACA | 94 | UGUUCCUUGCAGCAUGAUU | 226 |

TABLE 1-continued

Sequences of Exemplary siRNA Constructs

| CNST# | ST | ED | Sense Sequence (5'-3') | SEQ | Antisense Sequence (5'-3') | SEQ |
|---|---|---|---|---|---|---|
| 095 | 643 | 661 | AUCAUGCUGCAAGGAACAC | 95 | GUGUUCCUUGCAGCAUGAU | 227 |
| 096 | 644 | 662 | UCAUGCUGCAAGGAACACU | 96 | AGUGUUCCUUGCAGCAUGA | 228 |
| 097 | 645 | 663 | CAUGCUGCAAGGAACACUU | 97 | AAGUGUUCCUUGCAGCAUG | 229 |
| 098 | 646 | 664 | AUGCUGCAAGGAACACUUC | 98 | GAAGUGUUCCUUGCAGCAU | 230 |
| 099 | 647 | 665 | UGCUGCAAGGAACACUUCC | 99 | GGAAGUGUUCCUUGCAGCA | 231 |
| 100 | 648 | 666 | GCUGCAAGGAACACUUCCA | 100 | UGGAAGUGUUCCUUGCAGC | 232 |
| 101 | 698 | 716 | UGCCUGUUCACUGGGAUCA | 101 | UGAUCCCAGUGAACAGGCA | 233 |
| 102 | 702 | 720 | UGUUCACUGGGAUCAGCCA | 102 | UGGCUGAUCCCAGUGAACA | 234 |
| 103 | 734 | 752 | CACUUCUGAGCACAGAGCA | 103 | UGCUCUGUGCUCAGAAGUG | 235 |
| 104 | 735 | 753 | ACUUCUGAGCACAGAGCAG | 104 | CUGCUCUGUGCUCAGAAGU | 236 |
| 105 | 740 | 758 | UGAGCACAGAGCAGAGACA | 105 | UGUCUCUGCUCUGUGCUCA | 237 |
| 106 | 742 | 760 | AGCACAGAGCAGAGACAGA | 106 | UCUGUCUCUGCUCUGUGCU | 238 |
| 107 | 770 | 788 | GGAcAAAGGcAGAGGAuGU | 107 | ACAUCCUCUGCCUUUGUCC | 239 |
| 108 | 771 | 789 | GACAAAGGCAGAGGAUGUA | 108 | UACAUCCUCUGCCUUUGUC | 240 |
| 109 | 772 | 790 | ACAAAGGCAGAGGAUGUAG | 109 | CUACAUCCUCUGCCUUUGU | 241 |
| 110 | 773 | 791 | CAAAGGCAGAGGAUGUAGC | 110 | GCUACAUCCUCUGCCUUUG | 242 |
| 111 | 774 | 792 | AAAGGCAGAGGAUGUAGCC | 111 | GGCUACAUCCUCUGCCUUU | 243 |
| 112 | 779 | 797 | CAGAGGAUGUAGCCCCAUU | 112 | AAUGGGGCUACAUCCUCUG | 244 |
| 113 | 780 | 798 | AGAGGAUGUAGCCCCAUUG | 113 | CAAUGGGGCUACAUCCUCU | 245 |
| 114 | 820 | 838 | UGUACCCUUUCAUGCCUAC | 114 | GUAGGCAUGAAAGGGUACA | 246 |
| 115 | 821 | 839 | GUACCCUUUCAUGCCUACA | 115 | UGUAGGCAUGAAAGGGUAC | 247 |
| 116 | 822 | 840 | UACCCUUUCAUGCCUACAC | 116 | GUGUAGGCAUGAAAGGGUA | 248 |
| 117 | 823 | 841 | ACCCUUUCAUGCCUACACA | 117 | UGUGUAGGCAUGAAAGGGU | 249 |
| 118 | 824 | 842 | CCCUUUCAUGCCUACACAC | 118 | GUGUGUAGGCAUGAAAGGG | 250 |
| 119 | 825 | 843 | CCUUUCAUGCCUACACACC | 119 | GGUGUGUAGGCAUGAAAGG | 251 |
| 120 | 826 | 844 | CUUUCAUGCCUACACACCC | 120 | GGGUGUGUAGGCAUGAAAG | 252 |
| 121 | 827 | 845 | UUUCAUGCCUACACACCCC | 121 | GGGGUGUGUAGGCAUGAAA | 253 |
| 122 | 842 | 860 | CCCCUCAUUAAAGCAGAGU | 122 | ACUCUGCUUUAAUGAGGGG | 254 |
| 123 | 843 | 861 | CCCUCAUUAAAGCAGAGUC | 123 | GACUCUGCUUUAAUGAGGG | 255 |
| 124 | 844 | 862 | CCUCAUUAAAGCAGAGUCG | 124 | CGACUCUGCUUUAAUGAGG | 256 |
| 125 | 845 | 863 | CUCAUUAAAGCAGAGUCGU | 125 | ACGACUCUGCUUUAAUGAG | 257 |
| 126 | 846 | 864 | UCAUUAAAGCAGAGUCGUG | 126 | CACGACUCUGCUUUAAUGA | 258 |
| 127 | 847 | 865 | CAUUAAAGCAGAGUCGUGG | 127 | CCACGACUCUGCUUUAAUG | 259 |
| 128 | 848 | 866 | AUUAAAGCAGAGUCGUGGC | 128 | GCCACGACUCUGCUUUAAU | 260 |
| 129 | 849 | 867 | UUAAAGCAGAGUCGUGGCA | 129 | UGCCACGACUCUGCUUUAA | 261 |

TABLE 1-continued

Sequences of Exemplary siRNA Constructs

| CNST# | ST | ED | Sense Sequence (5'-3') | SEQ | Antisense Sequence (5'-3') | SEQ |
|---|---|---|---|---|---|---|
| 130 | 850 | 868 | UAAAGCAGAGUCGUGGCAU | 130 | AUGCCACGACUCUGCUUUA | 262 |
| 131 | 851 | 869 | AAAGCAGAGUCGUGGCAUC | 131 | GAUGCCACGACUCUGCUUU | 263 |
| 132 | 852 | 870 | AAGCAGAGUCGUGGCAUCU | 132 | AGAUGCCACGACUCUGCUU | 264 |

I.4 Nucleotide Modifications

A dsRNA of the present disclosure may comprise one or more modifications, e.g., to enhance cellular uptake, affinity for the target sequence, inhibitory activity, and/or stability. Modifications may include any modification known in the art, including, for example, end modifications, base modifications, sugar modifications/replacements, and backbone modifications. End modifications may include, for example, 5' end modifications (e.g., phosphorylation, conjugation, and inverted linkages) and 3' end modifications (e.g., conjugation, DNA nucleotides, and inverted linkages). Base modifications may include, e.g., replacement with stabilizing bases, destabilizing bases or bases that base-pair with an expanded repertoire of partners, removal of bases (abasic modifications of nucleotides), or conjugated bases. Sugar modifications or replacements may include, e.g., modifications at the 2' or 4' position of the sugar moiety, or replacement of the sugar moiety. Backbone modifications may include, for example, modification or replacement of the phosphodiester linkages, e.g., with one or more phosphorothioates, phosphorodithioates, phosphotriesters, methyl and other alkyl phosphonates, phosphinates, and phosphoramidates.

As used herein, the term "nucleotide" includes naturally occurring or modified nucleotide, or a surrogate replacement moiety. A modified nucleotide is a non-naturally occurring nucleotide and is also referred to herein as a "nucleotide analog." One of ordinary skill in the art would understand that guanine, cytosine, adenine, uracil, or thymine in a nucleotide may be replaced by other moieties without substantially altering the base-pairing properties of the modified nucleotide. For example, a nucleotide comprising inosine as its base may base-pair with nucleotides containing adenine, cytosine, or uracil. Hence, nucleotides containing uracil, guanine, or adenine may be replaced in the nucleotide sequences of the present disclosure by a nucleotide containing, for example, inosine. Sequences comprising such replacement moieties are included as embodiments of the present disclosure. A modified nucleotide may also be a nucleotide whose ribose moiety is replaced with a non-ribose moiety.

The dsRNAs of the present disclosure may include one or more modified nucleotides known in the art, including, without limitation, 2'-O-methyl modified nucleotides, 2'-fluoro modified nucleotides, 2'-deoxy modified nucleotides, 2'-O-methoxyethyl modified nucleotides, modified nucleotides comprising alternate internucleotide linkages such as thiophosphates and phosphorothioates, phosphotriester modified nucleotides, modified nucleotides terminally linked to a cholesterol derivative or lipophilic moiety, peptide nucleic acids (PNAs; see, e.g., Nielsen et al., Science (1991) 254:1497-1500), constrained ethyl (cEt) modified nucleotides, inverted deoxy modified nucleotides, inverted dideoxy modified nucleotides, locked nucleic acid modified nucleotides, abasic modifications of nucleotides, 2'-amino modified nucleotides, 2'-alkyl modified nucleotides, morpholino-modified nucleotides, phosphoramidate modified nucleotides, modified nucleotides comprising modifications at other sites of the sugar or base of an oligonucleotide, and non-natural base-containing modified nucleotides. In some embodiments, at least one of the one or more modified nucleotides is a 2'-O-methyl nucleotide, a 5'-phosphorothioate nucleotide, or a terminal nucleotide linked to a cholesterol derivative, lipophilic or other targeting moiety. The incorporation of 2'-O-methyl, 2'-O-ethyl, 2'-O-propryl, 2'-O-alkyl, 2'-O-aminoalkyl, or 2'-deoxy-2'-fluoro (i.e., 2'-fluoro) groups in nucleosides of an oligonucleotide may confer enhanced hybridization properties and/or enhanced nuclease stability to the oligonucleotide. Further, oligonucleotides containing phosphorothioate backbones (e.g., phosphorothioate linkage between two neighboring nucleotides at one or more positions of the dsRNA) may have enhanced nuclease stability. In some embodiments, the dsRNA may contain nucleotides with a modified ribose, such as locked nucleic acid (LNA) units.

In some embodiments, a dsRNA of the present disclosure comprises one or more 2'-O-methyl nucleotides and one or more 2'-fluoro nucleotides. In some embodiments, the dsRNA comprises two or more 2'-O-methyl nucleotides and two or more 2'-fluoro nucleotides. In some embodiments, the dsRNA comprises two or more 2'-O-methyl nucleotides (OMe) and two or more 2'-fluoro nucleotides (F) in an alternating pattern, e.g., the pattern OMe-F-OMe-F or the pattern F-OMe-F-OMe. In some embodiments, the dsRNA comprises up to 10 contiguous nucleotides that are each a 2'-O-methyl nucleotide. In some embodiments, the dsRNA comprises up to 10 contiguous nucleotides that are each a 2'-fluoro nucleotide. In some embodiments, the dsRNA comprises two or more 2'-fluoro nucleotides at the 5'- or 3'-end of the antisense strand.

In some embodiments, a dsRNA of the present disclosure comprises one or more phosphorothioate groups. In some embodiments, a dsRNA of the present disclosure comprises two or more, three or more, four or more, five or more, six or more, seven or more, eight or more, nine or more, or 10 or more phosphorothioate groups. In some embodiments, the dsRNA does not comprise any phosphorothioate group.

In some embodiments, the dsRNA comprises one or more phosphotriester groups. In some embodiments, the dsRNA comprises two or more, three or more, four or more, five or more, six or more, seven or more, eight or more, nine or more, or 10 or more phosphotriester groups. In some embodiments, the dsRNA does not comprise any phosphotriester group.

In some embodiments, the dsRNA comprises a modified ribonucleoside such as a deoxyribonucleoside, including, for example, deoxyribonucleoside overhang(s), and one or more deoxyribonucleosides within the double-stranded portion of a dsRNA. However, it is self-evident that under no circumstances is a double-stranded DNA molecule encompassed by the term "dsRNA."

In some embodiments, the dsRNA comprises two or more, three or more, four or more, five or more, six or more, seven or more, eight or more, nine or more, or 10 or more different modified nucleotides described herein. In some embodiments, the dsRNA comprises up to two contiguous modified nucleotides, up to three contiguous modified nucleotides, up to four contiguous modified nucleotides, up to five contiguous modified nucleotides, up to six contiguous modified nucleotides, up to seven contiguous modified nucleotides, up to eight contiguous modified nucleotides, up to nine contiguous modified nucleotides, or up to 10 contiguous modified nucleotides. In some embodiments, the contiguous modified nucleotides are the same modified nucleotide. In some embodiments, the contiguous modified nucleotides are two or more, three or more, four or more, five or more, six or more, seven or more, eight or more, nine or more, or ten or more different modified nucleotides.

Table 2 below lists the sequences of exemplary siRNA constructs (CNST) with modified nucleotides. The start (ST) and end (ED) nucleotide positions in NM_018687.6 (SEQ ID NO: 529) are indicated. Abbreviations are as follows: SEQ=SEQ ID NO; mX=2'-O-Me nucleotide; fX=2'-F nucleotide; dX=DNA nucleotide; invdX=inverted dX; PO=phosphodiester linkage; and Hy=hydroxyl group. In these constructs, the sequences of their sense strands and antisense strands correspond to the sense and antisense sequences of the constructs in Table 1 with the same construct numbers, but for the inclusion of (1) the modified nucleotides mX and fX, (2) "Hy" at the 5' and 3' ends of both strands, (3) mC-mC-mA at the 5' end of the sense strand nucleotide sequence, (4) invdT at the 3' end of the sense strand nucleotide sequence, and (5) dT-dT at the 3' end of the antisense strand nucleotide sequence. In these constructs, a base-pair of nucleotides may be modified differently in some embodiments, e.g., one nucleotide in the base-pair is a 2'-O-Me ribonucleotide and the other is a 2'-F nucleotide. In some embodiments, the antisense strand comprises two 2'-F nucleotides at its 5' end.

TABLE 2

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 001 | 5 | 23 | Hy-mC-PO-mC-PO-mA-PO-fC-PO-mU-PO-fU-PO-mA-PO-fG-PO-mA-PO-fC-PO-mC-PO-fC-PO-mU-PO-fC-PO-mA-PO-fG-PO-mU-PO-fC-PO-mA-PO-fU-PO-mG-PO-fC-PO-invdT-Hy | 265 | Hy-fG-PO-fC-PO-mA-PO-fU-PO-mG-PO-fA-PO-mC-PO-fU-PO-mG-PO-fA-PO-mG-PO-fG-PO-mG-PO-fU-PO-mC-PO-fU-PO-mA-PO-fA-PO-mG-PO-dT-PO-dT-Hy | 397 |
| 002 | 99 | 117 | Hy-mC-PO-mC-PO-mA-PO-fC-PO-mA-PO-fG-PO-mA-PO-fA-PO-mC-PO-fU-PO-mG-PO-fG-PO-mC-PO-fA-PO-mC-PO-fA-PO-mG-PO-fC-PO-mA-PO-fU-PO-mG-PO-fA-PO-invdT-Hy | 266 | Hy-fU-PO-fC-PO-mA-PO-fU-PO-mG-PO-fC-PO-mU-PO-fG-PO-mU-PO-fG-PO-mC-PO-fC-PO-mA-PO-fG-PO-mU-PO-fU-PO-mC-PO-fU-PO-mG-PO-dT-PO-dT-Hy | 398 |
| 003 | 100 | 118 | Hy-mC-PO-mC-PO-mA-PO-fA-PO-mG-PO-fA-PO-mA-PO-fC-PO-mU-PO-fG-PO-mG-PO-fC-PO-mA-PO-fC-PO-mA-PO-fG-PO-mC-PO-fA-PO-mU-PO-fG-PO-mA-PO-fG-PO-invdT-Hy | 267 | Hy-fC-PO-fU-PO-mC-PO-fA-PO-mU-PO-fG-PO-mC-PO-fU-PO-mG-PO-fU-PO-mG-PO-fC-PO-mC-PO-fA-PO-mG-PO-fU-PO-mU-PO-fC-PO-mU-PO-dT-PO-dT-Hy | 399 |
| 004 | 197 | 215 | Hy-mC-PO-mC-PO-mA-PO-fC-PO-mU-PO-fG-PO-mA-PO-fC-PO-mA-PO-fA-PO-mA-PO-fG-PO-mG-PO-fC-PO-mC-PO-fA-PO-mG-PO-fG-PO-mA-PO-fA-PO-mC-PO-fA-PO-invdT-Hy | 268 | Hy-fU-PO-fG-PO-mU-PO-fU-PO-mC-PO-fC-PO-mU-PO-fG-PO-mG-PO-fC-PO-mC-PO-fU-PO-mU-PO-fU-PO-mG-PO-fU-PO-mC-PO-fA-PO-mG-PO-dT-PO-dT-Hy | 400 |
| 005 | 198 | 216 | Hy-mC-PO-mC-PO-mA-PO-fU-PO-mG-PO-fA-PO-mC-PO-fA-PO-mA-PO-fA-PO-mG-PO-fG-PO-mC-PO-fC-PO-mA-PO-fG-PO-mG-PO-fA-PO-mA-PO-fC-PO-mA-PO-fG-PO-invdT-Hy | 269 | Hy-fC-PO-fU-PO-mG-PO-fU-PO-mU-PO-fC-PO-mC-PO-fU-PO-mG-PO-fG-PO-mC-PO-fC-PO-mU-PO-fU-PO-mU-PO-fG-PO-mU-PO-fC-PO-mA-PO-dT-PO-dT-Hy | 401 |
| 006 | 211 | 229 | Hy-mC-PO-mC-PO-mA-PO-fG-PO-mA-PO-fA-PO-mC-PO-fA-PO-mG-PO-fC-PO-mC-PO-fU-PO-mG-PO-fG-PO-mG-PO-fU-PO-mC-PO-fU-PO-mU-PO-fU-PO-invdT-Hy | 270 | Hy-fA-PO-fU-PO-mA-PO-fG-PO-mA-PO-fG-PO-mA-PO-fC-PO-mC-PO-fC-PO-mA-PO-fG-PO-mG-PO-fC-PO-mU-PO-fG-PO-mU-PO-fU-PO-mC-PO-dT-PO-dT-Hy | 402 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 007 | 212 | 230 | Hy-mC-PO-mC-PO-mA-PO-fA-PO-mA-PO-fC-PO-mA-PO-fG-PO-mC-PO-fC-PO-mU-PO-fG-PO-mG-PO-fG-PO-mU-PO-fC-PO-mU-PO-fC-PO-mU-PO-fA-PO-mU-PO-fG-PO-invdT-Hy | 271 | Hy-fC-PO-fA-PO-mU-PO-fA-PO-mG-PO-fA-PO-mG-PO-fA-PO-mC-PO-fC-PO-mC-PO-fA-PO-mG-PO-fG-PO-mC-PO-fU-PO-mG-PO-fU-PO-mU-PO-dT-PO-dT-Hy | 403 |
| 008 | 222 | 240 | Hy-mC-PO-mC-PO-mA-PO-fG-PO-mU-PO-fC-PO-mU-PO-fC-PO-mU-PO-fA-PO-mU-PO-fG-PO-mA-PO-fC-PO-mC-PO-fG-PO-mC-PO-fA-PO-mC-PO-fA-PO-mA-PO-fU-PO-invdT-Hy | 272 | Hy-fA-PO-fU-PO-mU-PO-fG-PO-mU-PO-fG-PO-mC-PO-fG-PO-mG-PO-fC-PO-mC-PO-fA-PO-mU-PO-fA-PO-mG-PO-fA-PO-mG-PO-fA-PO-mC-PO-dT-PO-dT-Hy | 404 |
| 009 | 288 | 306 | Hy-mC-PO-mC-PO-mA-PO-fA-PO-mA-PO-fC-PO-mU-PO-fU-PO-mC-PO-fG-PO-mG-PO-fG-PO-mC-PO-fA-PO-mA-PO-fG-PO-mC-PO-fC-PO-mU-PO-fG-PO-mU-PO-fU-PO-invdT-Hy | 273 | Hy-fA-PO-fA-PO-mC-PO-fA-PO-mG-PO-fG-PO-mC-PO-fU-PO-mU-PO-fG-PO-mC-PO-fC-PO-mG-PO-fG-PO-mA-PO-fA-PO-mG-PO-fU-PO-mU-PO-dT-PO-dT-Hy | 405 |
| 010 | 297 | 315 | Hy-mC-PO-mC-PO-mA-PO-fC-PO-mA-PO-fA-PO-mG-PO-fC-PO-mC-PO-fU-PO-mG-PO-fU-PO-mU-PO-fG-PO-mG-PO-fA-PO-mG-PO-fA-PO-mC-PO-fU-PO-mC-PO-fA-PO-invdT-Hy | 274 | Hy-fU-PO-fG-PO-mA-PO-fG-PO-mU-PO-fC-PO-mU-PO-fC-PO-mC-PO-fA-PO-mA-PO-fC-PO-mA-PO-fG-PO-fU-PO-mG-PO-dT-PO-dT-Hy | 406 |
| 011 | 298 | 316 | Hy-mC-PO-mC-PO-mA-PO-fA-PO-mA-PO-fG-PO-mC-PO-fC-PO-mU-PO-fG-PO-mU-PO-fU-PO-mG-PO-fG-PO-mA-PO-fG-PO-mC-PO-fC-PO-mU-PO-fC-PO-mA-PO-fG-PO-invdT-Hy | 275 | Hy-fC-PO-fU-PO-mG-PO-fA-PO-mG-PO-fU-PO-mC-PO-fU-PO-mC-PO-fC-PO-mA-PO-fA-PO-mC-PO-fA-PO-mG-PO-fG-PO-mC-PO-fU-PO-mU-PO-dT-PO-dT-Hy | 407 |
| 012 | 299 | 317 | Hy-mC-PO-mC-PO-mA-PO-fA-PO-mG-PO-fC-PO-mC-PO-fU-PO-mG-PO-fU-PO-mU-PO-fG-PO-mG-PO-fA-PO-mG-PO-fA-PO-mC-PO-fU-PO-mC-PO-fA-PO-mG-PO-fA-PO-invdT-Hy | 276 | Hy-fU-PO-fC-PO-mU-PO-fG-PO-mA-PO-fG-PO-mU-PO-fC-PO-mU-PO-fC-PO-mC-PO-fA-PO-mA-PO-fC-PO-mA-PO-fG-PO-mG-PO-fC-PO-mU-PO-dT-PO-dT-Hy | 408 |
| 013 | 300 | 318 | Hy-mC-PO-mC-PO-mA-PO-fG-PO-mC-PO-fC-PO-mU-PO-fG-PO-mU-PO-fU-PO-mG-PO-fG-PO-mA-PO-fG-PO-mA-PO-fC-PO-mU-PO-fC-PO-mA-PO-fG-PO-mA-PO-fU-PO-invdT-Hy | 277 | Hy-fA-PO-fU-PO-mC-PO-fU-PO-mG-PO-fA-PO-mG-PO-fU-PO-mC-PO-fU-PO-mC-PO-fC-PO-mA-PO-fA-PO-mC-PO-fA-PO-mG-PO-fG-PO-mC-PO-dT-PO-dT-Hy | 409 |
| 014 | 301 | 319 | Hy-mC-PO-mC-PO-mA-PO-fC-PO-mC-PO-fU-PO-mG-PO-fU-PO-mU-PO-fG-PO-mG-PO-fA-PO-mG-PO-fA-PO-mC-PO-fU-PO-mC-PO-fA-PO-mG-PO-fA-PO-mU-PO-fG-PO-invdT-Hy | 278 | Hy-fC-PO-fA-PO-mU-PO-fC-PO-mU-PO-fG-PO-mA-PO-fG-PO-mU-PO-fC-PO-mU-PO-fC-PO-mC-PO-fA-PO-mA-PO-fC-PO-mA-PO-fG-PO-mG-PO-dT-PO-dT-Hy | 410 |
| 015 | 302 | 320 | Hy-mC-PO-mC-PO-mA-PO-fC-PO-mU-PO-fG-PO-mU-PO-fU-PO-mG-PO-fG-PO-mA-PO-fG-PO-mA-PO-fC-PO-mU-PO-fC-PO-mA-PO-fG-PO-mA-PO-fU-PO-mG-PO-invdT-Hy | 279 | Hy-fC-PO-fC-PO-mA-PO-fU-PO-mC-PO-fU-PO-mG-PO-fA-PO-mG-PO-fU-PO-mC-PO-fU-PO-mC-PO-fC-PO-mA-PO-fA-PO-mC-PO-fA-PO-mG-PO-dT-PO-dT-Hy | 411 |
| 016 | 303 | 321 | Hy-mC-PO-mC-PO-mA-PO-fU-PO-mG-PO-fU-PO-mU-PO-fG-PO-mG-PO-fA-PO- | 280 | Hy-fU-PO-fC-PO-mC-PO-fA-PO-mU-PO-fC-PO-mU-PO-fG-PO-mA-PO-fG-PO- | 412 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mG-PO-fA-PO-mC-PO-fU-PO-mC-PO-fA-PO-mG-PO-fA-PO-mU-PO-fG-PO-mG-PO-fA-PO-invdT-Hy | | mU-PO-fC-PO-mU-PO-fC-PO-mC-PO-fA-PO-mA-PO-fC-PO-mA-PO-dT-PO-dT-Hy | |
| 017 | 304 | 322 | Hy-mC-PO-mC-PO-mA-PO-fG-PO-mU-PO-fU-PO-mG-PO-fG-PO-mA-PO-fG-PO-mA-PO-fC-PO-mU-PO-fC-PO-mA-PO-fG-PO-mA-PO-fU-PO-mG-PO-fG-PO-mA-PO-fG-PO-invdT-Hy | 281 | Hy-fC-PO-fU-PO-mC-PO-fC-PO-mA-PO-fU-PO-mC-PO-fU-PO-mG-PO-fA-PO-mG-PO-fU-PO-mC-PO-fU-PO-mC-PO-fC-PO-mA-PO-fA-PO-mC-PO-dT-PO-dT-Hy | 413 |
| 018 | 305 | 323 | Hy-mC-PO-mC-PO-mA-PO-fU-PO-mU-PO-fG-PO-mG-PO-fA-PO-mG-PO-fA-PO-mC-PO-fU-PO-mC-PO-fA-PO-mG-PO-fA-PO-mU-PO-fG-PO-mG-PO-fA-PO-mG-PO-fG-PO-invdT-Hy | 282 | Hy-fC-PO-fC-PO-mU-PO-fC-PO-mC-PO-fA-PO-mU-PO-fU-PO-mG-PO-mA-PO-fG-PO-mU-PO-fC-PO-mU-PO-fC-PO-mC-PO-fA-PO-mA-PO-dT-PO-dT-Hy | 414 |
| 019 | 310 | 328 | Hy-mC-PO-mC-PO-mA-PO-fG-PO-mA-PO-fC-PO-mU-PO-fC-PO-mA-PO-fG-PO-mA-PO-fU-PO-mG-PO-fG-PO-mA-PO-fG-PO-mG-PO-fA-PO-mG-PO-fG-PO-mA-PO-fU-PO-invdT-Hy | 283 | Hy-fA-PO-fU-PO-mC-PO-fC-PO-mU-PO-fC-PO-mC-PO-fU-PO-mC-PO-fC-PO-mA-PO-fU-PO-mC-PO-fU-PO-mG-PO-fA-PO-mG-PO-fU-PO-mC-PO-dT-PO-dT-Hy | 415 |
| 020 | 312 | 330 | Hy-mC-PO-mC-PO-mA-PO-fC-PO-mU-PO-fC-PO-mA-PO-fG-PO-mA-PO-fU-PO-mG-PO-fG-PO-mA-PO-fG-PO-mG-PO-fA-PO-mG-PO-fG-PO-mA-PO-fU-PO-mA-PO-fU-PO-invdT-Hy | 284 | Hy-fA-PO-fU-PO-mA-PO-fU-PO-mC-PO-fC-PO-mU-PO-fC-PO-mC-PO-fU-PO-mC-PO-fC-PO-mA-PO-fU-PO-mC-PO-fU-PO-mG-PO-fA-PO-mG-PO-dT-PO-dT-Hy | 416 |
| 021 | 313 | 331 | Hy-mC-PO-mC-PO-mA-PO-fU-PO-mC-PO-fA-PO-mG-PO-fA-PO-mU-PO-fG-PO-mG-PO-fA-PO-mG-PO-fG-PO-mA-PO-fG-PO-mG-PO-fA-PO-mU-PO-fA-PO-mU-PO-fU-PO-invdT-Hy | 285 | Hy-fA-PO-fA-PO-mU-PO-fA-PO-mU-PO-fC-PO-mC-PO-fU-PO-mC-PO-fC-PO-mA-PO-fU-PO-mC-PO-fU-PO-mG-PO-fA-PO-mT-PO-dT-Hy | 417 |
| 022 | 314 | 332 | Hy-mC-PO-mC-PO-mA-PO-fC-PO-mA-PO-fG-PO-mA-PO-fU-PO-mG-PO-fG-PO-mA-PO-fG-PO-mG-PO-fA-PO-mG-PO-fG-PO-mA-PO-fU-PO-mA-PO-fU-PO-mU-PO-fC-PO-invdT-Hy | 286 | Hy-fG-PO-fA-PO-mA-PO-fU-PO-mA-PO-fU-PO-mC-PO-fC-PO-mU-PO-fC-PO-mC-PO-fU-PO-mC-PO-fC-PO-mA-PO-fU-PO-mC-PO-fU-PO-mG-PO-dT-PO-dT-Hy | 418 |
| 023 | 315 | 333 | Hy-mC-PO-mC-PO-mA-PO-fA-PO-mG-PO-fA-PO-mU-PO-fG-PO-mG-PO-fA-PO-mG-PO-fG-PO-mA-PO-fG-PO-mG-PO-fA-PO-mU-PO-fA-PO-mU-PO-fU-PO-mC-PO-fU-PO-invdT-Hy | 287 | Hy-fA-PO-fG-PO-mA-PO-fA-PO-mU-PO-fA-PO-mU-PO-fC-PO-mC-PO-fU-PO-mC-PO-fC-PO-mU-PO-fC-PO-mC-PO-fA-PO-mU-PO-fC-PO-mU-PO-dT-PO-dT-Hy | 419 |
| 024 | 316 | 334 | Hy-mC-PO-mC-PO-mA-PO-fG-PO-mA-PO-fU-PO-mG-PO-fG-PO-mA-PO-fG-PO-mG-PO-fA-PO-mG-PO-fG-PO-mA-PO-fU-PO-mA-PO-fU-PO-mU-PO-fC-PO-mU-PO-fG-PO-invdT-Hy | 288 | Hy-fC-PO-fA-PO-mG-PO-fA-PO-mA-PO-fU-PO-mA-PO-fU-PO-mC-PO-fC-PO-mU-PO-fC-PO-mc-PO-fU-PO-mC-PO-fC-PO-mA-PO-fU-PO-mC-PO-dT-PO-dT-Hy | 420 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 025 | 317 | 335 | Hy-mC-PO-mC-PO-mA-PO-fA-PO-mU-PO-fG-PO-mG-PO-fA-PO-mG-PO-mA-PO-fG-PO-mG-PO-fA-PO-mU-PO-fA-PO-mU-PO-fU-PO-mC-PO-fU-PO-mG-PO-fC-PO-invdT-Hy | 289 | Hy-fG-PO-fC-PO-mA-PO-fG-PO-mA-PO-fA-PO-mU-PO-fA-PO-mU-PO-fC-PO-mC-PO-fU-PO-mC-PO-fC-PO-mU-PO-fC-PO-mC-PO-fA-PO-mU-PO-dT-PO-dT-Hy | 421 |
| 026 | 318 | 336 | Hy-mC-PO-mC-PO-mA-PO-fU-PO-mG-PO-fG-PO-mA-PO-fG-PO-mG-PO-fA-PO-mG-PO-fG-PO-mA-PO-fU-PO-mA-PO-fU-PO-mU-PO-fC-PO-mU-PO-fG-PO-mC-PO-fA-PO-invdT-Hy | 290 | Hy-fU-PO-fG-PO-mC-PO-fA-PO-mG-PO-fA-PO-mA-PO-fU-PO-mA-PO-fU-PO-mC-PO-fC-PO-mU-PO-fC-PO-mC-PO-fU-PO-mC-PO-fC-PO-mA-PO-dT-PO-dT-Hy | 422 |
| 027 | 319 | 337 | Hy-mC-PO-mC-PO-mA-PO-fG-PO-mG-PO-fA-PO-mG-PO-fG-PO-mA-PO-fG-PO-mG-PO-fA-PO-mU-PO-fA-PO-mU-PO-fU-PO-mC-PO-fU-PO-mG-PO-fC-PO-mA-PO-fG-PO-invdT-Hy | 291 | Hy-fC-PO-fU-PO-mG-PO-fC-PO-mA-PO-fG-PO-mA-PO-fA-PO-mU-PO-fA-PO-mU-PO-fC-PO-mC-PO-fU-PO-mC-PO-fC-PO-mU-PO-fC-PO-mC-PO-dT-PO-dT-Hy | 423 |
| 028 | 320 | 338 | Hy-mC-PO-mC-PO-mA-PO-fG-PO-mA-PO-fG-PO-mG-PO-fA-PO-mG-PO-fG-PO-mA-PO-fU-PO-mA-PO-fU-PO-mU-PO-fC-PO-mU-PO-fG-PO-mC-PO-fA-PO-mG-PO-fC-PO-invdT-Hy | 292 | Hy-fG-PO-fC-PO-mU-PO-fG-PO-mC-PO-fA-PO-mG-PO-fA-PO-mA-PO-fU-PO-mA-PO-fU-PO-mC-PO-fC-PO-mU-PO-fC-PO-mC-PO-dT-PO-dT-Hy | 424 |
| 029 | 321 | 339 | Hy-mC-PO-mC-PO-mA-PO-fA-PO-mG-PO-fG-PO-mA-PO-fG-PO-mG-PO-fA-PO-mU-PO-fA-PO-mU-PO-fU-PO-mC-PO-fU-PO-mG-PO-fC-PO-mA-PO-fG-PO-mC-PO-fU-PO-invdT-Hy | 293 | Hy-fA-PO-fG-PO-mC-PO-fU-PO-mG-PO-fC-PO-mA-PO-fG-PO-mA-PO-fA-PO-mU-PO-fA-PO-mU-PO-fC-PO-mC-PO-fU-PO-mC-PO-fC-PO-mU-PO-dT-PO-dT-Hy | 425 |
| 030 | 328 | 346 | Hy-mC-PO-mC-PO-mA-PO-fU-PO-mA-PO-fU-PO-mU-PO-fC-PO-mU-PO-fG-PO-mC-PO-fA-PO-mG-PO-fC-PO-mU-PO-fG-PO-mC-PO-fA-PO-mG-PO-fG-PO-mC-PO-fA-PO-invdT-Hy | 294 | Hy-fU-PO-fG-PO-mC-PO-fC-PO-mU-PO-fG-PO-mC-PO-fA-PO-mG-PO-fC-PO-mU-PO-fG-PO-mC-PO-fA-PO-mG-PO-fA-PO-mA-PO-fU-PO-mA-PO-dT-PO-dT-Hy | 426 |
| 031 | 416 | 434 | Hy-mC-PO-mC-PO-mA-PO-fC-PO-mU-PO-fA-PO-mG-PO-fA-PO-mA-PO-fG-PO-mU-PO-fC-PO-mC-PO-fA-PO-mG-PO-fC-PO-mU-PO-fG-PO-mA-PO-fG-PO-mG-PO-fA-PO-invdT-Hy | 295 | Hy-fU-PO-fC-PO-mC-PO-fU-PO-mC-PO-fA-PO-mG-PO-fC-PO-mU-PO-fG-PO-mG-PO-fA-PO-mC-PO-fU-PO-mU-PO-fC-PO-mU-PO-fA-PO-mG-PO-dT-PO-dT-Hy | 427 |
| 032 | 417 | 435 | Hy-mC-PO-mC-PO-mA-PO-fU-PO-mA-PO-fG-PO-mA-PO-fA-PO-mG-PO-fU-PO-mC-PO-fC-PO-mA-PO-fG-PO-mC-PO-fU-PO-mG-PO-fA-PO-mG-PO-fG-PO-mA-PO-invdT-Hy | 296 | Hy-fC-PO-fU-PO-mC-PO-fC-PO-mU-PO-fC-PO-mA-PO-fG-PO-mC-PO-fU-PO-mG-PO-fG-PO-mA-PO-fC-PO-mU-PO-fU-PO-mC-PO-fU-PO-mA-PO-dT-PO-dT-Hy | 428 |
| 033 | 448 | 466 | Hy-mC-PO-mC-PO-mA-PO-fC-PO-mC-PO-fC-PO-mU-PO-fG-PO-mC-PO-fC-PO-mU-PO-fA-PO-mC-PO-fC-PO-mG-PO-fA-PO-mG-PO-fA-PO-mA-PO-fU-PO-mU-PO-fU-PO-invdT-Hy | 297 | Hy-fA-PO-fA-PO-mA-PO-fU-PO-mU-PO-fC-PO-mU-PO-fC-PO-mG-PO-fG-PO-mU-PO-fA-PO-mG-PO-fG-PO-mC-PO-fA-PO-mG-PO-fG-PO-mG-PO-dT-PO-dT-Hy | 429 |
| 034 | 449 | 467 | Hy-mC-PO-mC-PO-mA-PO-fC-PO-mC-PO-fU-PO-mG-PO-fC-PO-mC-PO-fU-PO- | 298 | Hy-fC-PO-fA-PO-mA-PO-fA-PO-mU-PO-fU-PO-mC-PO-fG-PO- | 430 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mA-PO-fC-PO-mC-PO-fG-PO-mA-PO-fG-PO-mA-PO-fA-PO-mU-PO-fU-PO-mU-PO-fG-PO-invdT-Hy | | mG-PO-fU-PO-mA-PO-fG-PO-mG-PO-fC-PO-mA-PO-fG-PO-mG-PO-dT-PO-dT-Hy | |
| 035 | 450 | 468 | Hy-mC-PO-mC-PO-mA-PO-fC-PO-mU-PO-fG-PO-mC-PO-fC-PO-mU-PO-fA-PO-mC-PO-fC-PO-mG-PO-fA-PO-mG-PO-fA-PO-mA-PO-fU-PO-mU-PO-fU-PO-mG-PO-fA-PO-invdT-Hy | 299 | Hy-fU-PO-fC-PO-mA-PO-fA-PO-mA-PO-fU-PO-mU-PO-fC-PO-mU-PO-fC-PO-mG-PO-fG-PO-mU-PO-fA-PO-mG-PO-fG-PO-mC-PO-fA-PO-mG-PO-dT-PO-dT-Hy | 431 |
| 036 | 451 | 469 | Hy-mC-PO-mC-PO-mA-PO-fU-PO-mG-PO-fC-PO-mC-PO-fU-PO-mA-PO-fC-PO-mC-PO-fG-PO-mA-PO-fG-PO-mA-PO-fA-PO-mU-PO-fU-PO-mU-PO-fG-PO-mA-PO-fG-PO-invdT-Hy | 300 | Hy-fC-PO-fU-PO-mC-PO-fA-PO-mA-PO-fA-PO-mU-PO-fU-PO-mC-PO-fU-PO-mC-PO-fG-PO-mG-PO-fU-PO-mA-PO-fG-PO-mG-PO-fC-PO-mA-PO-dT-PO-dT-Hy | 432 |
| 037 | 452 | 470 | Hy-mC-PO-mC-PO-mA-PO-fG-PO-mC-PO-fC-PO-mU-PO-fA-PO-mC-PO-fC-PO-mG-PO-fA-PO-mG-PO-fA-PO-mA-PO-fU-PO-mU-PO-fU-PO-mG-PO-fA-PO-mG-PO-invdT-Hy | 301 | Hy-fC-PO-fC-PO-mU-PO-fC-PO-mA-PO-fA-PO-mA-PO-fU-PO-mU-PO-fC-PO-mU-PO-fC-PO-mG-PO-fG-PO-mU-PO-fA-PO-mG-PO-fG-PO-mC-PO-dT-PO-dT-Hy | 433 |
| 038 | 453 | 471 | Hy-mC-PO-mC-PO-mA-PO-fC-PO-mC-PO-fU-PO-mA-PO-fC-PO-mC-PO-fG-PO-mA-PO-fG-PO-mA-PO-fA-PO-mU-PO-fU-PO-mU-PO-fG-PO-mA-PO-fG-PO-mG-PO-fU-PO-invdT-Hy | 302 | Hy-fA-PO-fC-PO-mC-PO-fU-PO-mC-PO-fA-PO-mA-PO-fA-PO-mU-PO-fU-PO-mC-PO-fU-PO-mC-PO-fG-PO-mG-PO-fU-PO-mA-PO-fG-PO-mG-PO-dT-PO-dT-Hy | 434 |
| 039 | 454 | 472 | Hy-mC-PO-mC-PO-mA-PO-fC-PO-mU-PO-fA-PO-mC-PO-fC-PO-mG-PO-fA-PO-mG-PO-fA-PO-mA-PO-fU-PO-mU-PO-fU-PO-mG-PO-fA-PO-mG-PO-fG-PO-mU-PO-fC-PO-invdT-Hy | 303 | Hy-fG-PO-fA-PO-mC-PO-fC-PO-mU-PO-fC-PO-mA-PO-fA-PO-mA-PO-fU-PO-mU-PO-fC-PO-mU-PO-fC-PO-mG-PO-fG-PO-mU-PO-fA-PO-mG-PO-dT-PO-dT-Hy | 435 |
| 040 | 455 | 473 | Hy-mC-PO-mC-PO-mA-PO-fU-PO-mA-PO-fC-PO-mC-PO-fG-PO-mA-PO-fG-PO-mA-PO-fA-PO-mU-PO-fU-PO-mU-PO-fG-PO-mA-PO-fG-PO-mG-PO-fU-PO-mC-PO-fU-PO-invdT-Hy | 304 | Hy-fA-PO-fG-PO-mA-PO-fC-PO-mC-PO-fU-PO-mC-PO-fA-PO-mA-PO-fA-PO-mU-PO-fU-PO-mC-PO-fU-PO-mC-PO-fG-PO-mG-PO-fU-PO-mA-PO-dT-PO-dT-Hy | 436 |
| 041 | 456 | 474 | Hy-mC-PO-mC-PO-mA-PO-fA-PO-mC-PO-fC-PO-mG-PO-fA-PO-mG-PO-fA-PO-mA-PO-fU-PO-mU-PO-fU-PO-mG-PO-fA-PO-mG-PO-fG-PO-mU-PO-fC-PO-mU-PO-fU-PO-invdT-Hy | 305 | Hy-fA-PO-fA-PO-mG-PO-fA-PO-mC-PO-fC-PO-mU-PO-fC-PO-mA-PO-fA-PO-mA-PO-fU-PO-mU-PO-fC-PO-mU-PO-fC-PO-mG-PO-fG-PO-mU-PO-dT-PO-dT-Hy | 437 |
| 042 | 457 | 475 | Hy-mC-PO-mC-PO-mA-PO-fC-PO-mC-PO-fG-PO-mA-PO-fG-PO-mA-PO-fA-PO-mU-PO-fU-PO-mU-PO-fG-PO-mA-PO-fG-PO-mG-PO-fU-PO-mC-PO-fU-PO-mU-PO-fA-PO-invdT-Hy | 306 | Hy-fU-PO-fA-PO-mA-PO-fG-PO-mA-PO-fC-PO-mC-PO-fU-PO-mC-PO-fA-PO-mA-PO-fA-PO-mU-PO-fU-PO-mC-PO-fU-PO-mC-PO-fG-PO-mG-PO-dT-PO-dT-Hy | 438 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 043 | 458 | 476 | Hy-mC-PO-mC-PO-mA-PO-fC-PO-mG-PO-fA-PO-mG-PO-fA-PO-mA-PO-fU-PO-mU-PO-fU-PO-mG-PO-fA-PO-fC-PO-mU-PO-fU-PO-mA-PO-fA-PO-invdT-Hy | 307 | Hy-fU-PO-fU-PO-mA-PO-fA-PO-mG-PO-fA-PO-mC-PO-fC-PO-mU-PO-fC-PO-mA-PO-fA-PO-mA-PO-fU-PO-mU-PO-fC-PO-mU-PO-fC-PO-mG-PO-dT-PO-dT-Hy | 439 |
| 044 | 459 | 477 | Hy-mC-PO-mC-PO-mA-PO-fG-PO-mA-PO-fG-PO-mA-PO-fA-PO-mU-PO-fU-PO-mU-PO-fG-PO-mA-PO-fG-PO-mG-PO-fU-PO-mC-PO-fU-PO-mU-PO-fA-PO-mA-PO-fA-PO-invdT-Hy | 308 | Hy-fU-PO-fU-PO-mU-PO-fA-PO-mA-PO-fG-PO-mA-PO-fC-PO-mC-PO-fU-PO-mC-PO-fA-PO-mA-PO-fA-PO-mU-PO-fU-PO-mC-PO-fU-PO-mC-PO-dT-PO-dT-Hy | 440 |
| 045 | 460 | 478 | Hy-mC-PO-mC-PO-mA-PO-fA-PO-mG-PO-fA-PO-mA-PO-fU-PO-mU-PO-fU-PO-mG-PO-fA-PO-mG-PO-fG-PO-mU-PO-fC-PO-mU-PO-fU-PO-mA-PO-fA-PO-mA-PO-fG-PO-invdT-Hy | 309 | Hy-fC-PO-fU-PO-mU-PO-fU-PO-mA-PO-fA-PO-mG-PO-fA-PO-mC-PO-fC-PO-mU-PO-fC-PO-mA-PO-fA-PO-mA-PO-fU-PO-mU-PO-fC-PO-mU-PO-dT-PO-dT-Hy | 441 |
| 046 | 461 | 479 | Hy-mC-PO-mC-PO-mA-PO-fG-PO-mA-PO-fA-PO-mU-PO-fU-PO-mU-PO-fG-PO-mA-PO-fG-PO-mG-PO-fU-PO-mC-PO-fU-PO-mU-PO-fA-PO-mA-PO-fA-PO-mG-PO-fG-PO-invdT-Hy | 310 | Hy-fC-PO-fC-PO-mU-PO-fU-PO-mU-PO-fA-PO-mA-PO-fG-PO-mA-PO-fC-PO-mC-PO-fU-PO-mC-PO-fA-PO-mA-PO-fA-PO-mU-PO-fU-PO-mC-PO-dT-PO-dT-Hy | 442 |
| 047 | 462 | 480 | Hy-mC-PO-mC-PO-mA-PO-fA-PO-mA-PO-fU-PO-mU-PO-fU-PO-mG-PO-fA-PO-mG-PO-fG-PO-mU-PO-fC-PO-mU-PO-fU-PO-mA-PO-fA-PO-mA-PO-fG-PO-mG-PO-fC-PO-invdT-Hy | 311 | Hy-fG-PO-fC-PO-mC-PO-fU-PO-mU-PO-fU-PO-mA-PO-fA-PO-mG-PO-fA-PO-mC-PO-fC-PO-mU-PO-fC-PO-mA-PO-fA-PO-mA-PO-fU-PO-mU-PO-dT-PO-dT-Hy | 443 |
| 048 | 463 | 481 | Hy-mC-PO-mC-PO-mA-PO-fA-PO-mU-PO-fU-PO-mU-PO-fG-PO-mA-PO-fG-PO-mG-PO-fU-PO-mC-PO-fU-PO-mU-PO-fA-PO-mA-PO-fA-PO-mG-PO-fG-PO-mC-PO-fU-PO-invdT-Hy | 312 | Hy-fA-PO-fG-PO-mC-PO-fC-PO-mU-PO-fU-PO-mU-PO-fA-PO-mA-PO-fG-PO-mA-PO-fC-PO-mC-PO-fU-PO-mC-PO-fA-PO-mA-PO-fA-PO-mU-PO-dT-PO-dT-Hy | 444 |
| 049 | 464 | 482 | Hy-mC-PO-mC-PO-mA-PO-fU-PO-mU-PO-fU-PO-mG-PO-fA-PO-mG-PO-fG-PO-mU-PO-fC-PO-mU-PO-fU-PO-mA-PO-fA-PO-mA-PO-fG-PO-mG-PO-fC-PO-mU-PO-fC-PO-invdT-Hy | 313 | Hy-fG-PO-fA-PO-mG-PO-fC-PO-mC-PO-fU-PO-mU-PO-fU-PO-mA-PO-fA-PO-mG-PO-fA-PO-mC-PO-fC-PO-mU-PO-fC-PO-mA-PO-fA-PO-mA-PO-dT-PO-dT-Hy | 445 |
| 050 | 465 | 483 | Hy-mC-PO-mC-PO-mA-PO-fU-PO-mU-PO-fG-PO-mA-PO-fG-PO-mG-PO-fU-PO-mC-PO-fU-PO-mU-PO-fA-PO-mA-PO-fA-PO-mG-PO-fG-PO-mC-PO-fU-PO-mC-PO-fA-PO-invdT-Hy | 314 | Hy-fU-PO-fG-PO-mA-PO-fG-PO-mC-PO-fC-PO-mU-PO-fU-PO-mU-PO-fA-PO-mA-PO-fG-PO-mA-PO-fC-PO-mC-PO-fU-PO-mC-PO-fA-PO-mA-PO-dT-PO-dT-Hy | 446 |
| 051 | 466 | 484 | Hy-mC-PO-mC-PO-mA-PO-fU-PO-mG-PO-fA-PO-mG-PO-fG-PO-mU-PO-fC-PO-mU-PO-fU-PO-mA-PO-fA-PO-mA-PO-fG-PO-mG-PO-fC-PO-mU-PO-fC-PO-mA-PO-fC-PO-invdT-Hy | 315 | Hy-fG-PO-fU-PO-mG-PO-fA-PO-mG-PO-fC-PO-mC-PO-fU-PO-mU-PO-fU-PO-mA-PO-fA-PO-mG-PO-fA-PO-mC-PO-fC-PO-mU-PO-fC-PO-mA-PO-dT-PO-dT-Hy | 447 |
| 052 | 467 | 485 | Hy-mC-PO-mC-PO-mA-PO-fG-PO-mA-PO-fG-PO-mG-PO-fU-PO-mC-PO-fU-PO- | 316 | Hy-fC-PO-fG-PO-mU-PO-fG-PO-mA-PO-fG-PO-mC-PO-fC-PO-mU-PO-fU-PO- | 448 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mU-PO-fA-PO-mA-PO-fA-PO-mG-PO-fG-PO-mC-PO-fU-PO-mC-PO-fA-PO-mC-PO-fG-PO-invdT-Hy | | mU-PO-fA-PO-mA-PO-fG-PO-mA-PO-fC-PO-mC-PO-fU-PO-mC-PO-dT-PO-dT-Hy | |
| 053 | 468 | 486 | Hy-mC-PO-mC-PO-mA-PO-fA-PO-mG-PO-fG-PO-mU-PO-fC-PO-mU-PO-fU-PO-mA-PO-fA-PO-mA-PO-fG-PO-mG-PO-fC-PO-mU-PO-fC-PO-mA-PO-fC-PO-mG-PO-fC-PO-invdT-Hy | 317 | Hy-fG-PO-fC-PO-mG-PO-fU-PO-mG-PO-fA-PO-mG-PO-fC-PO-mC-PO-fU-PO-mU-PO-fU-PO-mA-PO-fA-PO-mG-PO-fA-PO-mC-PO-fC-PO-mU-PO-dT-PO-dT-Hy | 449 |
| 054 | 469 | 487 | Hy-mC-PO-mC-PO-mA-PO-fG-PO-mG-PO-fU-PO-mC-PO-fU-PO-mU-PO-fA-PO-mA-PO-fA-PO-mG-PO-fG-PO-mC-PO-fU-PO-mC-PO-fA-PO-mC-PO-fG-PO-mC-PO-fU-PO-invdT-Hy | 318 | Hy-fA-PO-fG-PO-mC-PO-fG-PO-mU-PO-fG-PO-mA-PO-fG-PO-mC-PO-fC-PO-mU-PO-fU-PO-mU-PO-fA-PO-mA-PO-fG-PO-mA-PO-fC-PO-mC-PO-dT-PO-dT-Hy | 450 |
| 055 | 470 | 488 | Hy-mC-PO-mC-PO-mA-PO-fG-PO-mU-PO-fC-PO-mU-PO-fU-PO-mA-PO-fA-PO-mA-PO-fG-PO-mG-PO-fC-PO-mU-PO-fC-PO-mA-PO-fC-PO-mG-PO-fC-PO-mU-PO-fG-PO-invdT-Hy | 319 | Hy-fC-PO-fA-PO-mG-PO-fC-PO-mG-PO-fU-PO-mG-PO-fA-PO-mG-PO-fC-PO-mC-PO-fU-PO-mU-PO-fU-PO-mA-PO-fA-PO-mG-PO-fA-PO-mC-PO-dT-PO-dT-Hy | 451 |
| 056 | 471 | 489 | Hy-mC-PO-mC-PO-mA-PO-fU-PO-mC-PO-fU-PO-mU-PO-fA-PO-mA-PO-fA-PO-mG-PO-fG-PO-mC-PO-fU-PO-mC-PO-fA-PO-mC-PO-fG-PO-mC-PO-fU-PO-mG-PO-fA-PO-invdT-Hy | 320 | Hy-fU-PO-fC-PO-mA-PO-fG-PO-mC-PO-fG-PO-mU-PO-fG-PO-mA-PO-fG-PO-mC-PO-fC-PO-mU-PO-fU-PO-mU-PO-fA-PO-mA-PO-fG-PO-mA-PO-dT-PO-dT-Hy | 452 |
| 057 | 472 | 490 | Hy-mC-PO-mC-PO-mA-PO-fC-PO-mU-PO-fU-PO-mA-PO-fA-PO-mA-PO-fG-PO-mG-PO-fC-PO-mU-PO-fC-PO-mA-PO-fC-PO-mG-PO-fC-PO-mU-PO-fG-PO-mA-PO-fC-PO-invdT-Hy | 321 | Hy-fG-PO-fU-PO-mC-PO-fA-PO-mG-PO-fC-PO-mG-PO-fU-PO-mG-PO-fA-PO-mG-PO-fC-PO-mC-PO-fU-PO-mU-PO-fU-PO-mA-PO-fA-PO-mG-PO-dT-PO-dT-Hy | 453 |
| 058 | 473 | 491 | Hy-mC-PO-mC-PO-mA-PO-fU-PO-mU-PO-fA-PO-mA-PO-fA-PO-mG-PO-fG-PO-mC-PO-fU-PO-mC-PO-fA-PO-mC-PO-fG-PO-mC-PO-fU-PO-mG-PO-fA-PO-mC-PO-fA-PO-invdT-Hy | 322 | Hy-fU-PO-fG-PO-mU-PO-fC-PO-mA-PO-fG-PO-mC-PO-fG-PO-mU-PO-fG-PO-mA-PO-fG-PO-mC-PO-fC-PO-mU-PO-fU-PO-mU-PO-fA-PO-mA-PO-dT-PO-dT-Hy | 454 |
| 059 | 474 | 492 | Hy-mC-PO-mC-PO-mA-PO-fU-PO-mA-PO-fA-PO-mA-PO-fG-PO-mG-PO-fC-PO-mU-PO-fC-PO-mA-PO-fC-PO-mG-PO-fC-PO-mU-PO-fG-PO-mA-PO-fC-PO-mA-PO-fA-PO-invdT-Hy | 323 | Hy-fU-PO-fU-PO-mG-PO-fU-PO-mC-PO-fA-PO-mG-PO-fC-PO-mG-PO-fU-PO-mG-PO-fA-PO-mG-PO-fC-PO-mC-PO-fU-PO-mU-PO-fU-PO-mA-PO-dT-PO-dT-Hy | 455 |
| 060 | 475 | 493 | Hy-mC-PO-mC-PO-mA-PO-fA-PO-mA-PO-fA-PO-mG-PO-fG-PO-mC-PO-fU-PO-mC-PO-fA-PO-mC-PO-fG-PO-mC-PO-fU-PO-mG-PO-fA-PO-mC-PO-fA-PO-mA-PO-fG-PO-invdT-Hy | 324 | Hy-fC-PO-fU-PO-mU-PO-fG-PO-mU-PO-fC-PO-mA-PO-fG-PO-mC-PO-fG-PO-mU-PO-fG-PO-mA-PO-fG-PO-mC-PO-fC-PO-mU-PO-fU-PO-mU-PO-dT-PO-dT-Hy | 456 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 061 | 486 | 504 | Hy-mC-PO-mC-PO-mA-PO-fC-PO-mU-PO-fG-PO-mA-PO-fC-PO-mA-PO-fA-PO-mG-PO-fC-PO-mA-PO-fG-PO-mA-PO-fG-PO-mC-PO-fC-PO-mA-PO-fC-PO-mA-PO-fU-PO-invdT-Hy | 325 | Hy-fA-PO-fU-PO-mG-PO-fU-PO-mG-PO-fG-PO-mC-PO-fC-PO-mU-PO-fU-PO-mG-PO-fC-PO-mU-PO-fU-PO-mG-PO-fU-PO-mC-PO-fA-PO-mG-PO-dT-PO-dT-Hy | 457 |
| 062 | 487 | 505 | Hy-mC-PO-mC-PO-mA-PO-fU-PO-mG-PO-fA-PO-mC-PO-fA-PO-mA-PO-fG-PO-mC-PO-fA-PO-mG-PO-fA-PO-mG-PO-fC-PO-mC-PO-fA-PO-mC-PO-fA-PO-mU-PO-fC-PO-invdT-Hy | 326 | Hy-fG-PO-fA-PO-mU-PO-fG-PO-mU-PO-fG-PO-mG-PO-fC-PO-mU-PO-fC-PO-mU-PO-fG-PO-mG-PO-fU-PO-mU-PO-fG-PO-mU-PO-fC-PO-mA-PO-dT-PO-dT-Hy | 458 |
| 063 | 489 | 507 | Hy-mC-PO-mC-PO-mA-PO-fA-PO-mC-PO-fA-PO-mA-PO-fG-PO-mC-PO-fA-PO-mG-PO-fA-PO-mG-PO-fC-PO-mC-PO-fA-PO-mC-PO-fA-PO-mU-PO-fC-PO-mC-PO-fU-PO-invdT-Hy | 327 | Hy-fA-PO-fG-PO-mG-PO-fA-PO-mU-PO-fG-PO-mU-PO-fG-PO-mG-PO-fC-PO-mU-PO-fC-PO-mU-PO-fG-PO-mC-PO-fU-PO-mU-PO-fG-PO-mU-PO-dT-PO-dT-Hy | 459 |
| 064 | 490 | 508 | Hy-mC-PO-mC-PO-mA-PO-fC-PO-mA-PO-fA-PO-mG-PO-fC-PO-mA-PO-fG-PO-mA-PO-fG-PO-mC-PO-fC-PO-mA-PO-fC-PO-mA-PO-fU-PO-mC-PO-fC-PO-mU-PO-fA-PO-invdT-Hy | 328 | Hy-fU-PO-fA-PO-mG-PO-fG-PO-mA-PO-fU-PO-mG-PO-fU-PO-mG-PO-fG-PO-mC-PO-fU-PO-mC-PO-fU-PO-mG-PO-fC-PO-mU-PO-fU-PO-mG-PO-dT-PO-dT-Hy | 460 |
| 065 | 491 | 509 | Hy-mC-PO-mC-PO-mA-PO-fA-PO-mA-PO-fG-PO-mC-PO-fA-PO-mG-PO-fA-PO-mG-PO-fC-PO-mC-PO-fA-PO-mC-PO-fA-PO-mU-PO-fC-PO-mC-PO-fU-PO-mA-PO-fU-PO-invdT-Hy | 329 | Hy-fA-PO-fU-PO-mA-PO-fG-PO-mG-PO-fA-PO-mU-PO-fG-PO-mU-PO-fG-PO-mG-PO-fC-PO-mU-PO-fC-PO-mU-PO-fG-PO-mC-PO-fU-PO-mU-PO-dT-PO-dT-Hy | 461 |
| 066 | 492 | 510 | Hy-mC-PO-mC-PO-mA-PO-fA-PO-mG-PO-fC-PO-mA-PO-fG-PO-mA-PO-fG-PO-mC-PO-fC-PO-mA-PO-fC-PO-mA-PO-fU-PO-mC-PO-fC-PO-mU-PO-fA-PO-mU-PO-fG-PO-invdT-Hy | 330 | Hy-fC-PO-fA-PO-mU-PO-fA-PO-mG-PO-fG-PO-mA-PO-fU-PO-mG-PO-fU-PO-mG-PO-fG-PO-mC-PO-fU-PO-mC-PO-fU-PO-mG-PO-fC-PO-mU-PO-dT-PO-dT-Hy | 462 |
| 067 | 573 | 591 | Hy-mC-PO-mC-PO-mA-PO-fG-PO-mA-PO-fC-PO-mA-PO-fG-PO-mA-PO-fU-PO-mC-PO-fC-PO-mA-PO-fG-PO-mG-PO-fA-PO-mG-PO-fA-PO-mC-PO-fU-PO-invdT-Hy | 331 | Hy-fA-PO-fG-PO-mU-PO-fC-PO-mU-PO-fC-PO-mU-PO-fC-PO-mC-PO-fU-PO-mG-PO-fG-PO-mA-PO-fU-PO-mC-PO-fU-PO-mG-PO-fU-PO-mC-PO-dT-PO-dT-Hy | 463 |
| 068 | 574 | 592 | Hy-mC-PO-mC-PO-mA-PO-fA-PO-mC-PO-fA-PO-mG-PO-fA-PO-mU-PO-fC-PO-mC-PO-fA-PO-mG-PO-fG-PO-mA-PO-fG-PO-mA-PO-fG-PO-mA-PO-fC-PO-mU-PO-fC-PO-invdT-Hy | 332 | Hy-fG-PO-fA-PO-mG-PO-fU-PO-mC-PO-fU-PO-mC-PO-fU-PO-mC-PO-fC-PO-mU-PO-fG-PO-mG-PO-fA-PO-mU-PO-fC-PO-mU-PO-fG-PO-mU-PO-dT-PO-dT-Hy | 464 |
| 069 | 576 | 594 | Hy-mC-PO-mC-PO-mA-PO-fA-PO-mG-PO-fA-PO-mU-PO-fC-PO-mC-PO-fA-PO-mG-PO-fG-PO-mA-PO-fG-PO-mA-PO-fG-PO-mA-PO-fC-PO-mU-PO-fC-PO-mC-PO-fA-PO-invdT-Hy | 333 | Hy-fU-PO-fG-PO-mG-PO-fA-PO-mG-PO-fU-PO-mC-PO-fU-PO-mC-PO-fU-PO-mC-PO-fC-PO-mU-PO-fG-PO-mG-PO-fA-PO-mU-PO-fC-PO-mU-PO-dT-PO-dT-Hy | 465 |
| 070 | 610 | 628 | Hy-mC-PO-mC-PO-mA-PO-fA-PO-mG-PO-fC-PO-mC-PO-fU-PO-mG-PO-fA-PO- | 334 | Hy-fA-PO-fU-PO-mC-PO-fC-PO-mA-PO-fG-PO-mG-PO-fC-PO-mA-PO-fG-PO- | 466 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mA-PO-fU-PO-mC-PO-fU-PO-mG-PO-fC-PO-mC-PO-fU-PO-mG-PO-fG-PO-mA-PO-fU-PO-invdT-Hy | | mA-PO-fU-PO-mU-PO-fC-PO-mA-PO-fG-PO-mG-PO-fC-PO-mU-PO-dT-PO-dT-Hy | |
| 071 | 613 | 631 | Hy-mC-PO-mC-PO-mA-PO-fC-PO-mU-PO-fG-PO-mA-PO-fA-PO-mU-PO-fC-PO-mU-PO-fG-PO-mC-p0-fc-PO-mU-PO-fG-PO-mG-PO-fA-PO-mU-PO-fG-PO-mG-PO-fA-PO-invdT-Hy | 335 | Hy-fU-PO-fC-PO-mC-PO-fA-PO-mU-PO-fC-PO-mC-PO-fA-PO-mG-PO-fG-PO-mc-PO-fA-Po-mG-PO-fA-PO-mU-PO-fU-PO-mC-PO-fA-PO-mG-PO-dT-PO-dT-Hy | 467 |
| 072 | 614 | 632 | Hy-mC-PO-mC-PO-mA-PO-fU-PO-mG-PO-fA-PO-mA-PO-fU-PO-mC-PO-fU-PO-mG-PO-fC-PO-mC-PO-fU-PO-mG-PO-fG-PO-mA-PO-fU-PO-mG-PO-fG-PO-mA-PO-fA-PO-invdT-Hy | 336 | Hy-fU-PO-fU-PO-mC-PO-fC-PO-mA-PO-fU-PO-mC-PO-fC-PO-mA-PO-fG-PO-mG-PO-fC-PO-mA-PO-fG-PO-mA-PO-fU-PO-mU-PO-fC-PO-mA-PO-dT-PO-dT-Hy | 468 |
| 073 | 615 | 633 | Hy-mC-PO-mC-PO-mA-PO-fG-PO-mA-PO-fA-PO-mU-PO-fC-PO-mU-PO-fG-PO-mC-PO-fC-PO-mU-PO-fG-PO-mG-PO-fA-PO-mU-PO-fG-PO-mG-PO-fA-PO-mA-PO-invdT-Hy | 337 | Hy-fG-PO-fU-PO-mU-PO-fC-PO-mC-PO-fA-PO-mU-PO-fC-PO-mC-PO-fA-PO-mG-PO-fG-PO-mC-PO-fA-PO-mG-PO-fA-PO-mU-PO-fU-PO-mC-PO-dT-PO-dT-Hy | 469 |
| 074 | 616 | 634 | Hy-mC-PO-mC-PO-mA-PO-fA-PO-mA-PO-fU-PO-mC-PO-fU-PO-mG-PO-fC-PO-mC-PO-fU-PO-mG-PO-fG-PO-mA-PO-fU-PO-mG-PO-fG-PO-mA-PO-fA-PO-mC-PO-fU-PO-invdT-Hy | 338 | Hy-fA-PO-fG-PO-mU-PO-fU-PO-mC-PO-fC-PO-mA-PO-fU-PO-mC-PO-fC-PO-mA-PO-fG-PO-mG-PO-fC-PO-mA-PO-fG-PO-mA-PO-fU-PO-mU-PO-dT-PO-dT-Hy | 470 |
| 075 | 617 | 635 | Hy-mC-PO-mC-PO-mA-PO-fA-PO-mU-PO-fC-PO-mU-PO-fG-PO-mC-PO-fC-PO-mU-PO-fG-PO-mG-PO-fA-PO-mU-PO-fG-PO-mG-PO-fA-PO-mA-PO-fC-PO-mU-PO-fG-PO-invdT-Hy | 339 | Hy-fC-PO-fA-PO-mG-PO-fU-PO-mU-PO-fC-PO-mC-PO-fA-PO-mU-PO-fC-PO-mC-PO-fA-PO-mG-PO-fG-PO-mC-PO-fA-PO-mG-PO-fA-PO-mU-PO-dT-PO-dT-Hy | 471 |
| 076 | 618 | 636 | Hy-mC-PO-mC-PO-mA-PO-fU-PO-mC-PO-fU-PO-mG-PO-fC-PO-mC-PO-fU-PO-mG-PO-fG-Po-mA-PO-fU-PO-mG-PO-fG-PO-mA-PO-fA-PO-mC-PO-fU-PO-mG-PO-fA-PO-invdT-Hy | 340 | Hy-fU-PO-fC-PO-mA-PO-fG-PO-mU-PO-fU-PO-mC-PO-fC-PO-mA-PO-fU-PO-mC-PO-fC-PO-mA-PO-fG-PO-mG-PO-fC-PO-mA-PO-fG-PO-mA-PO-dT-PO-dT-Hy | 472 |
| 077 | 624 | 642 | Hy-mC-PO-mC-PO-mA-PO-fU-PO-mG-PO-fG-PO-mA-PO-fU-PO-mG-PO-fG-PO-mA-PO-fA-PO-mC-PO-fU-PO-mG-PO-fA-PO-mG-PO-fG-PO-mA-PO-fC-PO-mC-PO-fA-PO-invdT-Hy | 341 | Hy-fU-PO-fG-PO-mG-PO-fU-PO-mC-PO-fC-PO-mU-PO-fC-PO-mA-PO-fG-PO-mU-PO-fU-PO-mC-PO-fC-PO-mA-PO-fU-PO-mC-PO-fC-PO-mA-PO-dT-PO-dT-Hy | 473 |
| 078 | 626 | 644 | Hy-mC-PO-mC-PO-mA-PO-fG-PO-mA-PO-fU-PO-mG-PO-fG-PO-mA-PO-fA-PO-mC-PO-fU-PO-mG-PO-fA-PO-mG-PO-fG-PO-mA-PO-fC-PO-mC-PO-fA-PO-mA-PO-fU-PO-invdT-Hy | 342 | Hy-fA-PO-fU-PO-mU-PO-fG-PO-mG-PO-fU-PO-mC-PO-fC-PO-mU-PO-fC-PO-mA-PO-fG-PO-mU-PO-fU-PO-mC-PO-fC-PO-mA-PO-fU-PO-mC-PO-dT-PO-dT-Hy | 474 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 079 | 627 | 645 | Hy-mC-PO-mC-PO-mA-PO-fA-PO-mU-PO-fG-PO-mG-PO-fA-PO-mA-PO-fC-PO-mU-PO-fG-PO-mA-PO-fG-PO-mG-PO-fA-PO-mC-PO-fC-PO-mA-PO-fA-PO-mU-PO-fC-PO-invdT-Hy | 343 | Hy-fG-PO-fA-PO-mU-PO-fU-PO-mG-PO-fG-PO-mU-PO-fC-PO-mC-PO-fU-PO-mC-PO-fA-PO-mG-PO-fU-PO-mU-PO-fC-PO-mC-PO-fA-PO-mU-PO-dT-PO-dT-Hy | 475 |
| 080 | 628 | 646 | Hy-mC-PO-mC-PO-mA-PO-fU-PO-mG-PO-fG-PO-mA-PO-fA-PO-mC-PO-fU-PO-mG-PO-fA-PO-mG-PO-fG-PO-mA-PO-fC-PO-mC-PO-fA-PO-mA-PO-fU-PO-mC-PO-fA-PO-invdT-Hy | 344 | Hy-fU-PO-fG-PO-mA-PO-fU-PO-mU-PO-fG-PO-mG-PO-fU-PO-mC-PO-fC-PO-mU-PO-fC-PO-mA-PO-fG-PO-mU-PO-fU-PO-mC-PO-fC-PO-mA-PO-dT-PO-dT-Hy | 476 |
| 081 | 629 | 647 | Hy-mC-PO-mC-PO-mA-PO-fG-PO-mG-PO-fA-PO-mA-PO-fC-PO-mU-PO-fG-PO-mA-PO-fG-PO-mG-PO-fA-PO-mC-PO-fC-PO-mA-PO-fA-PO-mU-PO-fC-PO-mA-PO-fU-PO-invdT-Hy | 345 | Hy-fA-PO-fU-PO-mG-PO-fA-PO-mU-PO-fU-PO-mG-PO-fG-PO-mU-PO-fC-PO-mC-PO-fU-PO-mC-PO-fA-PO-mG-PO-fU-PO-mU-PO-fC-PO-mC-PO-dT-PO-dT-Hy | 477 |
| 082 | 630 | 648 | Hy-mC-PO-mC-PO-mA-PO-fG-PO-mA-PO-fA-PO-mC-PO-fU-PO-mG-PO-fA-PO-mG-PO-fG-PO-mA-PO-fC-PO-mC-PO-fA-PO-mA-PO-fU-PO-mC-PO-fA-PO-mU-PO-fG-PO-invdT-Hy | 346 | Hy-fC-PO-fA-PO-mU-PO-fG-PO-mA-PO-fU-PO-mU-PO-fG-PO-mG-PO-fU-PO-mC-PO-fC-PO-mU-PO-fC-PO-mA-PO-fG-PO-mU-PO-fU-PO-mC-PO-dT-PO-dT-Hy | 478 |
| 083 | 631 | 649 | Hy-mC-PO-mC-PO-mA-PO-fA-PO-mA-PO-fC-PO-mU-PO-fG-PO-mA-PO-fG-PO-mG-PO-fA-PO-mC-PO-fC-PO-mA-PO-fA-PO-mU-PO-fC-PO-mA-PO-fU-PO-mG-PO-fC-PO-invdT-Hy | 347 | Hy-fG-PO-fC-PO-mA-PO-fU-PO-mG-PO-fA-PO-mU-PO-fU-PO-mG-PO-fG-PO-mU-PO-fC-PO-mC-PO-fU-PO-mC-PO-fA-PO-mG-PO-fU-PO-mU-PO-dT-PO-dT-Hy | 479 |
| 084 | 632 | 650 | Hy-mC-PO-mC-PO-mA-PO-fA-PO-mC-PO-fU-PO-mG-PO-fA-PO-mG-PO-fG-PO-mA-PO-fC-PO-mC-PO-fA-PO-mA-PO-fU-PO-mC-PO-fA-PO-mU-PO-fG-PO-mC-PO-fU-PO-invdT-Hy | 348 | Hy-fA-PO-fG-PO-mC-PO-fA-PO-mU-PO-fG-PO-mA-PO-fU-PO-mU-PO-fG-PO-mG-PO-fU-PO-mC-PO-fC-PO-mU-PO-fC-PO-mA-PO-fG-PO-mU-PO-dT-PO-dT-Hy | 480 |
| 085 | 633 | 651 | Hy-mC-PO-mC-PO-mA-PO-fC-PO-mU-PO-fG-PO-mA-PO-fG-PO-mG-PO-fA-PO-mC-PO-fC-PO-mA-PO-fA-PO-mU-PO-fC-PO-mA-PO-fU-PO-mG-PO-fC-PO-mU-PO-fG-PO-invdT-Hy | 349 | Hy-fC-PO-fA-PO-mG-PO-fC-PO-mA-PO-fU-PO-mG-PO-fA-PO-mU-PO-fU-PO-mG-PO-fG-PO-mU-PO-fC-PO-mC-PO-fU-PO-mC-PO-fA-PO-mG-PO-dT-PO-dT-Hy | 481 |
| 086 | 634 | 652 | Hy-mC-PO-mC-PO-mA-PO-fU-PO-mG-PO-fA-PO-mG-PO-fG-PO-mA-PO-fC-PO-mC-PO-fA-PO-mA-PO-fU-PO-mC-PO-fA-PO-mU-PO-fG-PO-mC-PO-fU-PO-mG-PO-invdT-Hy | 350 | Hy-fG-PO-fC-PO-mA-PO-fG-PO-mC-PO-fA-PO-mU-PO-fG-PO-mA-PO-fU-PO-mU-PO-fG-PO-mG-PO-fU-PO-mC-PO-fC-PO-mU-PO-fC-PO-mA-PO-dT-PO-dT-Hy | 482 |
| 087 | 635 | 653 | Hy-mC-PO-mC-PO-mA-PO-fG-PO-mA-PO-fG-PO-mG-PO-fA-PO-mC-PO-fC-PO-mA-PO-fA-PO-mU-PO-fC-PO-mA-PO-fU-PO-mG-PO-fC-PO-mU-PO-fG-PO-mC-PO-fA-PO-invdT-Hy | 351 | Hy-fU-PO-fG-PO-mC-PO-fA-PO-mG-PO-fC-PO-mA-PO-fU-PO-mG-PO-fA-PO-mU-PO-fU-PO-mG-PO-fG-PO-mU-PO-fC-PO-mC-PO-dT-PO-dT-Hy | 483 |
| 088 | 636 | 654 | Hy-mC-PO-mC-PO-mA-PO-fA-PO-mG-PO-fG-PO-mA-PO-fC-PO-mC-PO-fA-PO- | 352 | Hy-fU-PO-fU-PO-mG-PO-fC-PO-mA-PO-fG-PO-mC-PO-fA-PO-mU-PO-fG-PO- | 484 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mA-PO-fU-PO-mC-PO-fA-PO-mU-PO-fG-PO-mC-PO-fU-PO-mG-PO-fC-PO-mA-PO-fA-PO-invdT-Hy | | mA-PO-fU-PO-mU-PO-fG-PO-mG-PO-fU-PO-mC-PO-fC-PO-mU-PO-dT-PO-dT-Hy | |
| 089 | 637 | 655 | Hy-mC-PO-mC-PO-mA-PO-fG-PO-mG-PO-fA-PO-mC-PO-fC-PO-mA-PO-fA-PO-mU-PO-fC-PO-mA-PO-fU-PO-mG-PO-fC-PO-mU-PO-fG-PO-mC-PO-fA-PO-mA-PO-fG-PO-invdT-Hy | 353 | Hy-fC-PO-fU-PO-mU-PO-fG-PO-mC-PO-fA-PO-mG-PO-fC-PO-mA-PO-fU-PO-mG-PO-fA-PO-mU-PO-fU-PO-mG-PO-fG-PO-mU-PO-fC-PO-mC-PO-dT-PO-dT-Hy | 485 |
| 090 | 638 | 656 | Hy-mC-PO-mC-PO-mA-PO-fG-PO-mA-PO-fC-PO-mC-PO-fA-PO-mA-PO-fU-PO-mC-PO-fA-PO-mU-PO-fG-PO-mC-PO-fU-PO-mG-PO-fC-PO-mA-PO-fA-PO-mG-PO-fG-PO-invdT-Hy | 354 | Hy-fC-PO-fC-PO-mU-PO-fU-PO-mG-PO-fC-PO-mA-PO-fA-PO-mU-PO-fG-PO-mA-PO-fU-PO-mU-PO-fG-PO-mG-PO-fU-PO-mC-PO-dT-PO-dT-Hy | 486 |
| 091 | 639 | 657 | Hy-mC-PO-mC-PO-mA-PO-fA-PO-mC-PO-fC-PO-mA-PO-fA-PO-mU-PO-fC-PO-mA-PO-fU-PO-mG-PO-fC-PO-mU-PO-fG-PO-mC-PO-fA-PO-mA-PO-fG-PO-mG-PO-fA-PO-invdT-Hy | 355 | Hy-fU-PO-fC-PO-mC-PO-fU-PO-mU-PO-fG-PO-mC-PO-fA-PO-mA-PO-fG-PO-mC-PO-fA-PO-mU-PO-fU-PO-mG-PO-fG-PO-mU-PO-dT-PO-dT-Hy | 487 |
| 092 | 640 | 658 | Hy-mC-PO-mC-PO-mA-PO-fC-PO-mC-PO-fA-PO-mA-PO-fU-PO-mC-PO-fA-PO-mU-PO-fG-PO-mC-PO-fU-PO-mG-PO-fC-PO-mA-PO-fA-PO-mG-PO-fG-PO-mA-PO-invdT-Hy | 356 | Hy-fU-PO-fU-PO-mC-PO-fC-PO-mU-PO-fU-PO-mG-PO-fC-PO-mA-PO-fG-PO-mC-PO-fA-PO-mU-PO-fG-PO-mA-PO-fU-PO-mU-PO-fG-PO-mG-PO-dT-PO-dT-Hy | 488 |
| 093 | 641 | 659 | Hy-mC-PO-mC-PO-mA-PO-fC-PO-mA-PO-fA-PO-mU-PO-fC-PO-mA-PO-fU-PO-mG-PO-fC-PO-mU-PO-fG-PO-mC-PO-fA-PO-mA-PO-fG-PO-mG-PO-fA-PO-mA-PO-fC-PO-invdT-Hy | 357 | Hy-fG-PO-fU-PO-mU-PO-fC-PO-mC-PO-fU-PO-mU-PO-fG-PO-mC-PO-fA-PO-mG-PO-fC-PO-mA-PO-fU-PO-mG-PO-fA-PO-mU-PO-fU-PO-mG-PO-dT-PO-dT-Hy | 489 |
| 094 | 642 | 660 | Hy-mC-PO-mC-PO-mA-PO-fA-PO-mA-PO-fU-PO-mC-PO-fA-PO-mU-PO-fG-PO-mC-PO-fU-PO-mG-PO-fC-PO-mA-PO-fA-PO-mG-PO-fG-PO-mA-PO-fA-PO-mC-PO-fA-PO-invdT-Hy | 358 | Hy-fU-PO-fG-PO-mU-PO-fU-PO-mC-PO-fC-PO-mU-PO-fU-PO-mG-PO-fC-PO-mA-PO-fG-PO-mC-PO-fA-PO-mU-PO-fG-PO-mA-PO-fU-PO-mU-PO-dT-PO-dT-Hy | 490 |
| 095 | 643 | 661 | Hy-mC-PO-mC-PO-mA-PO-fA-PO-mU-PO-fC-PO-mA-PO-fU-PO-mG-PO-fC-PO-mU-PO-fG-PO-mC-PO-fA-PO-mA-PO-fG-PO-mG-PO-fA-PO-mA-PO-fC-PO-mA-PO-fC-PO-invdT-Hy | 359 | Hy-fG-PO-fU-PO-mG-PO-fU-PO-mU-PO-fC-PO-mC-PO-fU-PO-mU-PO-fG-PO-mC-PO-fA-PO-mG-PO-fC-PO-mA-PO-fU-PO-mG-PO-fA-PO-mU-PO-dT-PO-dT-Hy | 491 |
| 096 | 644 | 662 | Hy-mC-PO-mC-PO-mA-PO-fU-PO-mC-PO-fA-PO-mU-PO-fG-PO-mC-PO-fU-PO-mG-PO-fC-PO-mA-PO-fA-PO-mG-PO-fG-PO-mA-PO-fA-PO-mC-PO-fA-PO-mC-PO-fU-PO-invdT-Hy | 360 | Hy-fA-PO-fG-PO-mU-PO-fG-PO-mU-PO-fU-PO-mC-PO-fC-PO-mU-PO-fU-PO-mG-PO-fC-PO-mA-PO-fG-PO-mC-PO-fA-PO-mU-PO-fG-PO-mA-PO-dT-PO-dT-Hy | 492 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 097 | 645 | 663 | Hy-mC-PO-mC-PO-mA-PO-fC-PO-mA-PO-fU-PO-mG-PO-fC-PO-mU-PO-fG-PO-mC-PO-fA-PO-mA-PO-fG-PO-mG-PO-fA-PO-mA-PO-fC-PO-mA-PO-fC-PO-mU-PO-fU-PO-invdT-Hy | 361 | Hy-fA-PO-fA-PO-mG-PO-fU-PO-mG-PO-fU-PO-mU-PO-fC-PO-mC-PO-fU-PO-mU-PO-fG-PO-mC-PO-fA-PO-mG-PO-fC-PO-mA-PO-fU-PO-mG-PO-dT-PO-dT-Hy | 493 |
| 098 | 646 | 664 | Hy-mC-PO-mC-PO-mA-PO-fA-PO-mU-PO-fG-PO-mC-PO-fU-PO-mG-PO-fC-PO-mA-PO-fA-PO-mG-PO-fC-PO-mA-PO-fA-PO-mC-PO-fA-PO-mC-PO-fU-PO-mU-PO-fC-PO-invdT-Hy | 362 | Hy-fG-PO-fA-PO-mA-PO-fG-PO-mU-PO-fG-PO-mU-PO-fU-PO-mC-PO-fC-PO-mU-PO-fU-PO-mG-PO-fC-PO-mA-PO-fG-PO-mC-PO-fA-PO-mU-PO-dT-PO-dT-Hy | 494 |
| 099 | 647 | 665 | Hy-mC-PO-mC-PO-mA-PO-fU-PO-mG-PO-fC-PO-mU-PO-fG-PO-mC-PO-fA-PO-mA-PO-fG-PO-mG-PO-fA-PO-mA-PO-fC-PO-mA-PO-fC-PO-mU-PO-fU-PO-mC-PO-fC-PO-invdT-Hy | 363 | Hy-fG-PO-fG-PO-mA-PO-fA-PO-mG-PO-fU-PO-mG-PO-fU-PO-mU-PO-fC-PO-mC-PO-fU-PO-mU-PO-fG-PO-mC-PO-fA-PO-mG-PO-fC-PO-mA-PO-dT-PO-dT-Hy | 495 |
| 100 | 648 | 666 | Hy-mC-PO-mC-PO-mA-PO-fG-PO-mC-PO-fU-PO-mG-PO-fC-PO-mA-PO-fA-PO-mG-PO-fG-PO-mA-PO-fA-PO-mC-PO-fA-PO-mC-PO-fU-PO-mU-PO-fC-PO-mC-PO-fA-PO-invdT-Hy | 364 | Hy-fU-PO-fG-PO-mG-PO-fA-PO-mA-PO-fG-PO-mU-PO-fG-PO-mU-PO-fU-PO-mC-PO-fC-PO-mU-PO-fU-PO-mG-PO-fC-PO-mA-PO-fG-PO-mC-PO-dT-PO-dT-Hy | 496 |
| 101 | 698 | 716 | Hy-mC-PO-mC-PO-mA-PO-fU-PO-mG-PO-fC-PO-mC-PO-fU-PO-mG-PO-fU-PO-mU-PO-fC-PO-mA-PO-fC-PO-fG-PO-mG-PO-fG-PO-mA-PO-fU-PO-mC-PO-fA-PO-invdT-Hy | 365 | Hy-fU-PO-fG-PO-mA-PO-fU-PO-mC-PO-fC-PO-mC-PO-fA-PO-mG-PO-fU-PO-mG-PO-fA-PO-mA-PO-fC-PO-mA-PO-fG-PO-mG-PO-fC-PO-mA-PO-dT-PO-dT-Hy | 497 |
| 102 | 702 | 720 | Hy-mC-PO-mC-PO-mA-PO-fU-PO-mG-PO-fU-PO-mU-PO-fC-PO-mA-PO-fC-PO-mU-PO-fG-PO-mG-PO-fG-PO-mA-PO-fU-PO-mC-PO-fA-PO-mG-PO-fC-PO-mC-PO-fA-PO-invdT-Hy | 366 | Hy-fU-PO-fG-PO-mG-PO-fC-PO-mU-PO-fG-PO-mA-PO-fU-PO-mC-PO-fC-PO-mC-PO-fA-PO-mG-PO-fU-PO-mG-PO-fA-PO-mA-PO-fC-PO-mA-PO-dT-PO-dT-Hy | 498 |
| 103 | 734 | 752 | Hy-mC-PO-mC-PO-mA-PO-fC-PO-mA-PO-fC-PO-mU-PO-fU-PO-mC-PO-fU-PO-mG-PO-fA-PO-mG-PO-fC-PO-mA-PO-fC-PO-mA-PO-fG-PO-mC-PO-fA-PO-invdT-Hy | 367 | Hy-fU-PO-fG-PO-mC-PO-fU-PO-mC-PO-fU-PO-mG-PO-fU-PO-mG-PO-fC-PO-mU-PO-fC-PO-mA-PO-fG-PO-mA-PO-fA-PO-mG-PO-fU-PO-mG-PO-dT-PO-dT-Hy | 499 |
| 104 | 735 | 753 | Hy-mC-PO-mC-PO-mA-PO-fA-PO-mC-PO-fU-PO-mU-PO-fC-PO-mU-PO-fG-PO-mA-PO-fG-PO-mC-PO-fA-PO-mC-PO-fA-PO-mG-PO-fA-PO-mG-PO-fC-PO-mA-PO-fG-PO-invdT-Hy | 368 | Hy-fC-PO-fU-PO-mG-PO-fC-PO-mU-PO-fC-PO-mU-PO-fG-PO-mU-PO-fG-PO-mC-PO-fU-PO-mC-PO-fA-PO-mG-PO-fA-PO-mA-PO-fG-PO-mU-PO-dT-PO-dT-Hy | 500 |
| 105 | 740 | 758 | Hy-mC-PO-mC-PO-mA-PO-fU-PO-mG-PO-fA-PO-mG-PO-fC-PO-mA-PO-fC-PO-mA-PO-fG-PO-mA-PO-fG-PO-mC-PO-fA-PO-mG-PO-fA-PO-mC-PO-fA-PO-invdT-Hy | 369 | Hy-fU-PO-fG-PO-mU-PO-fC-PO-mU-PO-fG-PO-mC-PO-fU-PO-mC-PO-fU-PO-mG-PO-fU-PO-mG-PO-fC-PO-mU-PO-fC-PO-mA-PO-dT-PO-dT-Hy | 501 |
| 106 | 742 | 760 | Hy-mC-PO-mC-PO-mA-PO-fA-PO-mG-PO-fC-PO-mA-PO-fC-PO-mA-PO-fG-PO- | 370 | Hy-fU-PO-fC-PO-mU-PO-fG-PO-mU-PO-fC-PO-mU-PO-fG-PO- | 502 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mA-PO-fG-PO-mC-PO-fA-PO-mG-PO-fA-PO-mG-PO-fA-PO-mC-PO-fA-PO-mG-PO-fA-PO-invdT-Hy | | mC-PO-fU-PO-mC-PO-fU-PO-mG-PO-fU-PO-mG-PO-fC-PO-mU-PO-dT-PO-dT-Hy | |
| 107 | 770 | 788 | Hy-mC-PO-mC-PO-mA-PO-fG-PO-mG-PO-fA-PO-mC-PO-fA-PO-mA-PO-fA-PO-mG-PO-fG-PO-mC-PO-fA-PO-mG-PO-fA-PO-mG-PO-fG-PO-mA-PO-fU-PO-mG-PO-fU-PO-invdT-Hy | 371 | Hy-fA-PO-fC-PO-mA-PO-fU-PO-mC-PO-fC-PO-mU-PO-fC-PO-mU-PO-fG-PO-mC-PO-fC-PO-mU-PO-fU-PO-mU-PO-fG-PO-mU-PO-fC-PO-mC-PO-dT-PO-dT-Hy | 503 |
| 108 | 771 | 789 | Hy-mC-PO-mC-PO-mA-PO-fG-PO-mA-PO-fC-PO-mA-PO-fA-PO-mA-PO-fG-PO-mG-PO-fC-PO-mA-PO-fG-PO-mA-PO-fG-PO-mG-PO-fA-PO-mU-PO-fG-PO-mU-PO-fA-PO-invdT-Hy | 372 | Hy-fU-PO-fA-PO-mC-PO-fA-PO-mU-PO-fC-PO-mC-PO-fU-PO-mG-PO-fC-PO-mC-PO-fU-PO-mU-PO-fU-PO-mG-PO-fU-PO-mC-PO-dT-PO-dT-Hy | 504 |
| 109 | 772 | 790 | Hy-mC-PO-mC-PO-mA-PO-fA-PO-mC-PO-fA-PO-mA-PO-fA-PO-mG-PO-fG-PO-mC-PO-fA-PO-mG-PO-fA-PO-mG-PO-fG-PO-mA-PO-fU-PO-mG-PO-fU-PO-mA-PO-fG-PO-invdT-Hy | 373 | Hy-fC-PO-fU-PO-mA-PO-fC-PO-mA-PO-fU-PO-mC-PO-fC-PO-mU-PO-fC-PO-mU-PO-fG-PO-mC-PO-fC-PO-mU-PO-fU-PO-mU-PO-fG-PO-mU-PO-dT-PO-dT-Hy | 505 |
| 110 | 773 | 791 | Hy-mC-PO-mC-PO-mA-PO-fC-PO-mA-PO-fA-PO-mA-PO-fG-PO-mG-PO-fC-PO-mA-PO-fG-PO-mA-PO-fG-PO-mG-PO-fA-PO-mU-PO-fG-PO-mU-PO-fA-PO-mG-PO-fC-PO-invdT-Hy | 374 | Hy-fG-PO-fC-PO-mU-PO-fA-PO-mC-PO-fA-PO-mU-PO-fC-PO-mC-PO-fU-PO-mC-PO-fU-PO-mG-PO-fC-PO-mC-PO-fU-PO-mU-PO-fU-PO-mG-PO-dT-PO-dT-Hy | 506 |
| 111 | 774 | 792 | Hy-mC-PO-mC-PO-mA-PO-fA-PO-mA-PO-fA-PO-mG-PO-fG-PO-mC-PO-fA-PO-mG-PO-fA-PO-mG-PO-fG-PO-mA-PO-fU-PO-mG-PO-fU-PO-mA-PO-fG-PO-mC-PO-fC-PO-invdT-Hy | 375 | Hy-fG-PO-fG-PO-mC-PO-fU-PO-mA-PO-fC-PO-mA-PO-fU-PO-mC-PO-fC-PO-mU-PO-fC-PO-mU-PO-fG-PO-mC-PO-fC-PO-mU-PO-fU-PO-mU-PO-dT-PO-dT-Hy | 507 |
| 112 | 779 | 797 | Hy-mC-PO-mC-PO-mA-PO-fC-PO-mA-PO-fG-PO-mA-PO-fG-PO-mG-PO-fA-PO-mU-PO-fG-PO-mU-PO-fA-PO-mG-PO-fC-PO-mC-PO-fC-PO-mC-PO-fA-PO-mU-PO-fU-PO-invdT-Hy | 376 | Hy-fA-PO-fA-PO-mU-PO-fG-PO-mG-PO-fG-PO-mG-PO-fC-PO-mU-PO-fA-PO-mC-PO-fA-PO-mU-PO-fC-PO-mC-PO-fU-PO-mC-PO-fU-PO-mG-PO-dT-PO-dT-Hy | 508 |
| 113 | 780 | 798 | Hy-mC-PO-mC-PO-mA-PO-fA-PO-mG-PO-fA-PO-mG-PO-fG-PO-mA-PO-fU-PO-mG-PO-fU-PO-mA-PO-fG-PO-mC-PO-fC-PO-mC-PO-fC-PO-mA-PO-fU-PO-mU-PO-fG-PO-invdT-Hy | 377 | Hy-fC-PO-fA-PO-mA-PO-fU-PO-mG-PO-fG-PO-mG-PO-fG-PO-mC-PO-fU-PO-mA-PO-fC-PO-mA-PO-fU-PO-mC-PO-fC-PO-mU-PO-fC-PO-mU-PO-dT-PO-dT-Hy | 509 |
| 114 | 820 | 838 | Hy-mC-PO-mC-PO-mA-PO-fU-PO-mG-PO-fU-PO-mA-PO-fC-PO-mC-PO-fC-PO-mU-PO-fU-PO-mU-PO-fC-PO-mA-PO-fU-PO-mG-PO-fC-PO-mC-PO-fU-PO-mA-PO-fC-PO-invdT-Hy | 378 | Hy-fG-PO-fU-PO-mA-PO-fG-PO-mG-PO-fC-PO-mA-PO-fU-PO-mG-PO-fA-PO-mA-PO-fA-PO-mG-PO-fG-PO-mG-PO-fU-PO-mA-PO-fC-PO-mA-PO-dT-PO-dT-Hy | 510 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| 115 | 821 | 839 | Hy-mC-PO-mC-PO-mA-PO-fG-PO-mU-PO-fA-PO-mC-PO-fC-PO-mC-PO-fU-PO-mU-PO-fU-PO-mC-PO-fA-PO-mU-PO-fG-PO-mC-PO-fC-PO-mU-PO-fA-PO-mC-PO-fA-PO-invdT-Hy | 379 | Hy-fU-PO-fG-PO-mU-PO-fA-PO-mG-PO-fG-PO-mC-PO-fA-PO-mU-PO-fG-PO-mA-PO-fA-PO-mA-PO-fG-PO-mG-PO-fG-PO-mU-PO-fA-PO-mC-PO-dT-PO-dT-Hy | 511 |
| 116 | 822 | 840 | Hy-mC-PO-mC-PO-mA-PO-fU-PO-mA-PO-fC-PO-mC-PO-fC-PO-mU-PO-fU-PO-mU-PO-fC-PO-mA-PO-fU-PO-mG-PO-fC-PO-mC-PO-fU-PO-mA-PO-fC-PO-mA-PO-fC-PO-invdT-Hy | 380 | Hy-fG-PO-fU-PO-mG-PO-fU-PO-mA-PO-fG-PO-mG-PO-fC-PO-mA-PO-fU-PO-mG-PO-fA-PO-mA-PO-fA-PO-mG-PO-fG-PO-mG-PO-fU-PO-mA-PO-dT-PO-dT-Hy | 512 |
| 117 | 823 | 841 | Hy-mC-PO-mC-PO-mA-PO-fA-PO-mC-PO-fC-PO-mC-PO-fU-PO-mU-PO-fU-PO-mC-PO-fA-PO-mU-PO-fG-PO-mC-PO-fC-PO-mU-PO-fA-PO-mC-PO-fA-PO-mC-PO-fA-PO-invdT-Hy | 381 | Hy-fU-PO-fG-PO-mU-PO-fG-PO-mU-PO-fA-PO-mG-PO-fG-PO-mC-PO-fA-PO-mU-PO-fG-PO-mA-PO-fA-PO-mA-PO-fG-PO-mG-PO-fG-PO-mU-PO-dT-PO-dT-Hy | 513 |
| 118 | 824 | 842 | Hy-mC-PO-mC-PO-mA-PO-fC-PO-mC-PO-fC-PO-mU-PO-fU-PO-mU-PO-fC-PO-mA-PO-fU-PO-mG-PO-fC-PO-mC-PO-fU-PO-mA-PO-fC-PO-mA-PO-fC-PO-mA-PO-fC-PO-invdT-Hy | 382 | Hy-fG-PO-fU-PO-mG-PO-fU-PO-mG-PO-fU-PO-mA-PO-fG-PO-mG-PO-fC-PO-mA-PO-fU-PO-mG-PO-fA-PO-mA-PO-fA-PO-mG-PO-fG-PO-mG-PO-dT-PO-dT-Hy | 514 |
| 119 | 825 | 843 | Hy-mC-PO-mC-PO-mA-PO-fC-PO-mC-PO-fU-PO-mU-PO-fU-PO-mC-PO-fA-PO-mU-PO-fG-PO-mC-PO-fC-PO-mU-PO-fA-PO-mC-PO-fA-PO-mA-PO-mC-PO-fA-PO-mC-PO-invdT-Hy | 383 | Hy-fG-PO-fG-PO-mU-PO-fG-PO-mU-PO-fG-PO-mU-PO-fA-PO-mG-PO-fG-PO-mC-PO-fA-PO-mU-PO-fG-PO-mA-PO-fA-PO-mA-PO-fG-PO-mG-PO-dT-PO-dT-Hy | 515 |
| 120 | 826 | 844 | Hy-mC-PO-mC-PO-mA-PO-fC-PO-mU-PO-fU-PO-mU-PO-fC-PO-mA-PO-fU-PO-mG-PO-fC-PO-mC-PO-fU-PO-mA-PO-fC-PO-mA-PO-fC-PO-mA-PO-fC-PO-mC-PO-fC-PO-invdT-Hy | 384 | Hy-fG-PO-fG-PO-mG-PO-fU-PO-mG-PO-fU-PO-mG-PO-fU-PO-mA-PO-fG-PO-mG-PO-fC-PO-mA-PO-fU-PO-mG-PO-mA-PO-fA-PO-mG-PO-dT-PO-dT-Hy | 516 |
| 121 | 827 | 845 | Hy-mC-PO-mC-PO-mA-PO-fU-PO-mU-PO-fU-PO-mC-PO-fA-PO-mU-PO-fG-PO-mC-PO-fC-PO-mU-PO-fA-PO-mC-PO-fA-PO-mC-PO-fC-PO-mC-PO-invdT-Hy | 385 | Hy-fG-PO-fG-PO-mG-PO-fG-PO-mU-PO-fG-PO-mU-PO-fG-PO-mU-PO-fA-PO-mG-PO-fG-PO-mC-PO-fA-PO-mU-PO-fG-PO-mA-PO-fA-PO-mA-PO-dT-PO-dT-Hy | 517 |
| 122 | 842 | 860 | Hy-mC-PO-mC-PO-mA-PO-fC-PO-mC-PO-fC-PO-mC-PO-fU-PO-mC-PO-fA-PO-mU-PO-fU-PO-mA-PO-fA-PO-mA-PO-fG-PO-mC-PO-fA-PO-fA-PO-mG-PO-fU-PO-invdT-Hy | 386 | Hy-fA-PO-fC-PO-mU-PO-fC-PO-mC-PO-fU-PO-mU-PO-fU-PO-mA-PO-fA-PO-mU-PO-fG-PO-mA-PO-fG-PO-mG-PO-fG-PO-mG-PO-dT-PO-dT-Hy | 518 |
| 123 | 843 | 861 | Hy-mC-PO-mC-PO-mA-PO-fC-PO-mC-PO-fC-PO-mU-PO-fC-PO-mA-PO-fU-PO-mU-PO-fA-PO-mA-PO-fA-PO-mG-PO-fC-PO-mA-PO-fG-PO-mC-PO-fG-PO-mU-PO-fC-PO-invdT-Hy | 387 | Hy-fG-PO-fA-PO-mC-PO-fU-PO-mC-PO-fU-PO-mU-PO-mG-PO-fC-PO-mU-PO-fU-PO-mU-PO-fA-PO-mA-PO-fU-PO-mG-PO-fA-PO-mG-PO-fG-PO-mG-PO-dT-PO-dT-Hy | 519 |
| 124 | 844 | 862 | Hy-mC-PO-mC-PO-mA-PO-fC-PO-mC-PO-fU-PO-mC-PO-fA-PO-mU-PO-fU-PO- | 388 | Hy-fC-PO-fG-PO-mA-PO-fC-PO-mU-PO-fC-PO-mU-PO-fG-PO-mC-PO-fU-PO- | 520 |

TABLE 2-continued

Sequences of Exemplary Modified siRNA Constructs

| CNST # | ST | ED | Sense strand sequence (5'-3') | SEQ | Antisense strand sequence (5'-3') | SEQ |
|---|---|---|---|---|---|---|
| | | | mA-PO-fA-PO-mA-PO-fG-PO-mC-PO-fA-PO-mG-PO-fA-PO-mG-PO-fU-PO-mC-PO-fG-PO-invdT-Hy | | mU-PO-fU-PO-mA-PO-fA-PO-mU-PO-fG-PO-mA-PO-fG-PO-mG-PO-dT-PO-dT-Hy | |
| 125 | 845 | 863 | Hy-mC-PO-mC-PO-mA-PO-fC-PO-mU-PO-fC-PO-mA-PO-fU-PO-mU-PO-fA-PO-mA-PO-fA-PO-mG-PO-fC-PO-mA-PO-fG-PO-mA-PO-fG-PO-mU-PO-fC-PO-mG-PO-fU-PO-invdT-Hy | 389 | Hy-fA-PO-fC-PO-mG-PO-fA-PO-mC-PO-fU-PO-mC-PO-fU-PO-mG-PO-fC-PO-mU-PO-fU-PO-mU-PO-fA-PO-mA-PO-fU-PO-mG-PO-fA-PO-mG-PO-dT-PO-dT-Hy | 521 |
| 126 | 846 | 864 | Hy-mC-PO-mC-PO-mA-PO-fU-PO-mC-PO-fA-PO-mU-PO-fU-PO-mA-PO-fA-PO-mA-PO-fG-PO-mC-PO-fA-PO-mG-PO-fA-PO-mG-PO-fU-PO-mC-PO-fG-PO-mU-PO-fG-PO-invdT-Hy | 390 | Hy-fC-PO-fA-PO-mC-PO-fG-PO-mA-PO-fC-PO-mU-PO-fC-PO-mU-PO-fG-PO-mC-PO-fU-PO-mU-PO-fU-PO-mA-PO-fA-PO-mU-PO-fG-PO-mA-PO-dT-PO-dT-Hy | 522 |
| 127 | 847 | 865 | Hy-mC-PO-mC-PO-mA-PO-fC-PO-mA-PO-fU-PO-mU-PO-fA-PO-mA-PO-fA-PO-mG-PO-fC-PO-mA-PO-fG-PO-mA-PO-fG-PO-mU-PO-fC-PO-mG-PO-fU-PO-mG-PO-invdT-Hy | 391 | Hy-fC-PO-fC-PO-mA-PO-fC-PO-mG-PO-fA-PO-mC-PO-fU-PO-mC-PO-fU-PO-mG-PO-fC-PO-mU-PO-fU-PO-mU-PO-fA-PO-mA-PO-fU-PO-mG-PO-dT-PO-dT-Hy | 523 |
| 128 | 848 | 866 | Hy-mC-PO-mC-PO-mA-PO-fA-PO-mU-PO-fU-PO-mA-PO-fA-PO-mA-PO-fG-PO-mC-PO-fA-PO-mG-PO-fA-PO-mG-PO-fU-PO-mC-PO-fG-PO-mU-PO-fG-PO-mG-PO-fC-PO-invdT-Hy | 392 | Hy-fG-PO-fC-PO-mC-PO-fA-PO-mC-PO-fG-PO-mA-PO-fC-PO-mU-PO-fC-PO-mU-PO-fG-PO-mC-PO-fU-PO-mU-PO-fU-PO-mA-PO-fA-PO-mU-PO-dT-PO-dT-Hy | 524 |
| 129 | 849 | 867 | Hy-mC-PO-mC-PO-mA-PO-fU-PO-mU-PO-fA-PO-mA-PO-fA-PO-mG-PO-fC-PO-mA-PO-fG-PO-mA-PO-fG-PO-mU-PO-fC-PO-mG-PO-fU-PO-mG-PO-fG-PO-mC-PO-fA-PO-invdT-Hy | 393 | Hy-fU-PO-fG-PO-mC-PO-fC-PO-mA-PO-fC-PO-mG-PO-fA-PO-mC-PO-fU-PO-mC-PO-fU-PO-mG-PO-fC-PO-mU-PO-fU-PO-mU-PO-fA-PO-mA-PO-dT-PO-dT-Hy | 525 |
| 130 | 850 | 868 | Hy-mC-PO-mC-PO-mA-PO-fU-PO-mA-PO-fA-PO-mA-PO-fG-PO-mC-PO-fA-PO-mG-PO-fA-PO-mG-PO-fU-PO-mC-PO-fG-PO-mU-PO-fG-PO-mG-PO-fC-PO-mA-PO-fU-PO-invdT-Hy | 394 | Hy-fA-PO-fU-PO-mG-PO-fC-PO-mC-PO-fA-PO-mC-PO-fG-PO-mA-PO-fC-PO-mU-PO-fC-PO-mU-PO-fG-PO-mC-PO-fU-PO-mU-PO-fU-PO-mA-PO-dT-PO-dT-Hy | 526 |
| 131 | 851 | 869 | Hy-mC-PO-mC-PO-mA-PO-fA-PO-mA-PO-fA-PO-mG-PO-fC-PO-mA-PO-fG-PO-mA-PO-fG-PO-mU-PO-fC-PO-mG-PO-fU-PO-mG-PO-fG-PO-mC-PO-fA-PO-mU-PO-fC-PO-invdT-Hy | 395 | Hy-fG-PO-fA-PO-mU-PO-fG-PO-mC-PO-fC-PO-mA-PO-fC-PO-mG-PO-fA-PO-mC-PO-fU-PO-mC-PO-fU-PO-mG-PO-fC-PO-mU-PO-fU-PO-mU-PO-dT-PO-dT-Hy | 527 |
| 132 | 852 | 870 | Hy-mC-PO-mC-PO-mA-PO-fA-PO-mA-PO-fG-PO-mC-PO-fA-PO-mG-PO-fA-PO-mG-PO-fU-PO-mC-PO-fG-PO-mU-PO-fG-PO-mG-PO-fC-PO-mA-PO-fU-PO-mC-PO-fU-PO-invdT-Hy | 396 | Hy-fA-PO-fG-PO-mA-PO-fU-PO-mG-PO-fC-PO-mC-PO-fA-PO-mC-PO-fG-PO-mA-PO-fC-PO-mU-PO-fC-PO-mU-PO-fG-PO-mC-PO-fU-PO-mU-PO-dT-PO-dT-Hy | 528 |

In some embodiments, the dsRNA comprises one or more modified nucleotides described in PCT Publication WO 2019/170731, the disclosure of which is incorporated herein in its entirety. In such modified nucleotides, the ribose ring has been replaced by a six-membered heterocyclic ring. Such a modified nucleotide has the structure of formula (I):

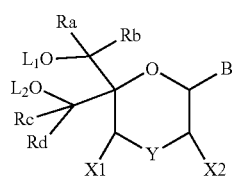

wherein:
B is a heterocyclic nucleobase;
one of L1 and L2 is an internucleoside linking group linking the compound of formula (I) to a polynucleotide and the other of L1 and L2 is H, a protecting group, a phosphorus moiety or an internucleoside linking group linking the compound of formula (I) to a polynucleotide,
Y is O, NH, NR1 or N—C(=O)—R1, wherein R1 is:
a (C1-C20) alkyl group, optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2,
wherein
J is O or S,
each of Z1 and Z2 is, independently, H, a (C1-C6) alkyl group, optionally substituted by one or more groups selected from a halogen atom and a (C1-C6) alkyl group, a (C3-C8) cycloalkyl group, optionally substituted by one or more groups selected from a halogen atom and a (C1-C6) alkyl group,
a group [C(=O)]m-R2-(O—CH2—CH2)p-R3, wherein
m is an integer meaning 0 or 1,
p is an integer ranging from 0 to 10,
R2 is a (C1-C20) alkylene group optionally substituted by a (C1-C6) alkyl group, —O—Z3, —N(Z3)(Z4), —S—Z3, —CN, —C(=K)—O—Z3, —O—C(=K)—Z3, —C(=K)—N(Z3)(Z4), or —N(Z3)-C(=K)—Z4, wherein
K is O or S,
each of Z3 and Z4 is, independently, H, a (C1-C6) alkyl group, optionally substituted by one or more groups selected from a halogen atom and a (C1-C6) alkyl group, and R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group or a (C5-C14) heteroaryl group, or R3 is a cell targeting moiety,
X1 and X2 are each, independently, a hydrogen atom, a (C1-C6) alkyl group, and
each of Ra, Rb, Rc and Rd is, independently, H or a (C1-C6) alkyl group, or is a pharmaceutically acceptable salt thereof.

In some embodiments, Y is NR1, R1 is a non-substituted (C1-C20) alkyl group, and L1, L2, Ra, Rb, Rc, Rd, X1, X2, R2, R3 and B have the same meaning as defined for the general formula (I), or a pharmaceutically acceptable salt thereof.

In some embodiments, Y is NR1, R1 is a non-substituted (C1-C16) alkyl group, which includes an alkyl group selected from a group comprising methyl, isopropyl, butyl, octyl, hexadecyl, and L1, L2, Ra, Rb, Rc, Rd, X1, X2, R2, R3 and B have the same meaning as defined for the general formula (I), or a pharmaceutically acceptable salt thereof.

In some embodiments, Y is NR1, R1 is a (C3-C8) cycloalkyl group, optionally substituted by one or more groups selected from a halogen atom and a (C1-C6) alkyl group, and L1, L2, Ra, Rb, Rc, Rd, X1, X2, R2, R3 and B have the same meaning as defined for the general formula (I), or a pharmaceutically acceptable salt thereof.

In some embodiments, Y is NR1, R1 is a cyclohexyl group, and L1, L2, Ra, Rb, Rc, Rd, X1, X2, R2, R3 and B have the same meaning as defined for the general formula (I), or a pharmaceutically acceptable salt thereof.

In some embodiments, Y is NR1, R1 is a (C1-C20) alkyl group substituted by a (C6-C14) aryl group and L1, L2, Ra, Rb, Rc, Rd, X1, X2, R2, R3 and B have the same meaning as defined for the general formula (I), or a pharmaceutically acceptable salt thereof.

In some embodiments, Y is NR1, R1 is a methyl group substituted by a phenyl group, and L1, L2, Ra, Rb, Rc, Rd, X1, X2, R2, R3 and B have the same meaning as defined for the general formula (I), or a pharmaceutically acceptable salt thereof.

In some embodiments, Y is N—C(=O)—R1, R1 is an optionally substituted (C1-C20) alkyl group, and L1, L2, Ra, Rb, Rc, Rd, X1, X2, R2, R3 and B have the same meaning as defined for the general formula (I), or a pharmaceutically acceptable salt thereof.

In some embodiments, Y is N—C(=O)—R1, R1 is selected from a group comprising methyl and pentadecyl and L1, L2, Ra, Rb, Rc, Rd, X1, X2, R2, R3 and B have the same meaning as defined for the general formula (I), or a pharmaceutically acceptable salt thereof.

In some embodiments, B is selected from a group comprising a pyrimidine, a substituted pyrimidine, a purine and a substituted purine, or a pharmaceutically acceptable salt thereof.

In some embodiments, the internucleoside linking group in the dsRNA is independently selected from the group consisting of phosphodiester, phosphotriester, phosphorothioate, phosphorodithioate, alkyl-phosphonate and phosphoramidate backbone linking groups, or a pharmaceutically acceptable salt thereof.

In some embodiments, the dsRNA comprises from 2 to 10 compounds of formula (I), or a pharmaceutically acceptable salt thereof.

In further embodiments, the dsRNA comprises one or more targeted nucleotides or a pharmaceutically acceptable salt thereof.

In some embodiments, R3 is of the formula (II):

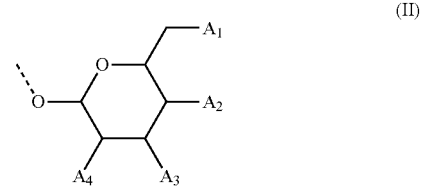

wherein A1, A2 and A3 are OH,
A4 is OH or NHC(=O)—R5, wherein R5 is a (C1-C6) alkyl group, optionally substituted by a halogen atom.

In some embodiments, R3 is N-acetyl-galactosamine.

The precursors that can be used to make modified siRNAs having nucleotides of formula (I) are exemplified in Tables A and B below. Table A shows examples of phosphoramidite nucleotide analogs for oligonucleotide synthesis; Table B shows some solid support of nucleotide analogs for oligonucleotide synthesis. In the (2S,6R) diastereomeric series, the phosphoramidites as nucleotide precursors are abbreviated with a "pre-l", the nucleotide analogs are abbreviated with an "l", followed by the nucleobase and a number, which specifies the group Y in formula (I). To distinguish both stereochemistries, the analogues (2R,6R)-diastereoisomers are indicated with an additional "b." For solid supports, the abbreviation "CPG-l" is used with the additional information as described above. Targeted nucleotide precursors, targeted nucleotide analogs and solid supports are abbreviated as described above, but with an "lg" instead of the "l."

TABLE A

| No | Structure | Precursor name | Name in oligo-sequence | Stereochemistry |
|---|---|---|---|---|
| 1 | 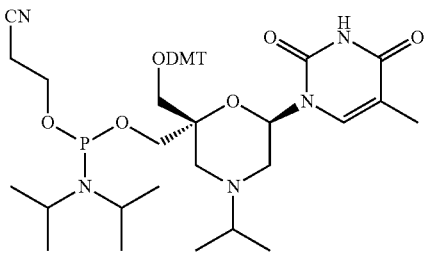 | pre-1T3 | 1T3 | (2S,6R) |
| 2 | 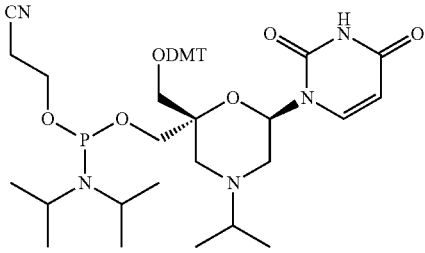 | pre-1U3 | 1U3 | (2S,6R) |
| 3 | 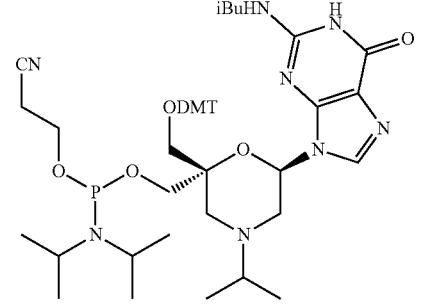 | pre-1G3 | 1G3 | (2S,6R) |
| 4 | 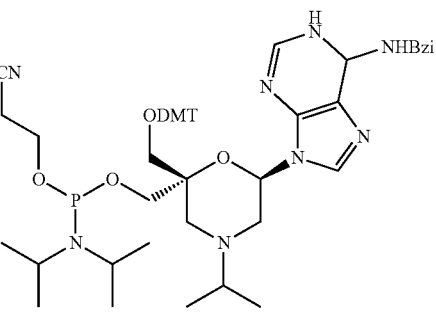 | pre-1A3 | 1A3 | (2S,6R) |

TABLE A-continued

| No | Structure | Precursor name | Name in oligo-sequence | Stereochemistry |
|---|---|---|---|---|
| 5 | 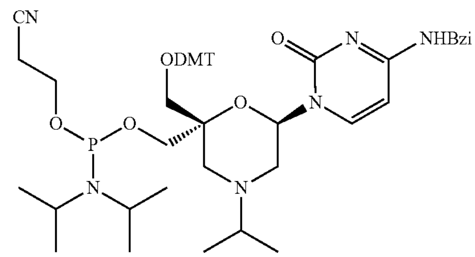 | pre-1C3 | 1C3 | (2S,6R) |
| 6 | 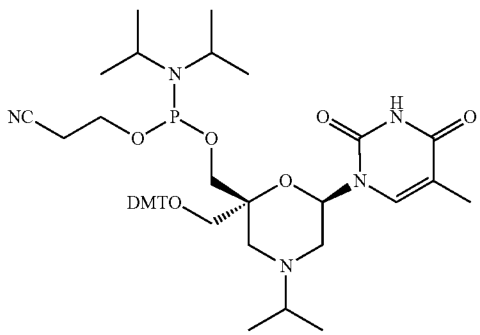 | pre-1T3b | 1T3b | (2R,6R) |
| 7 | 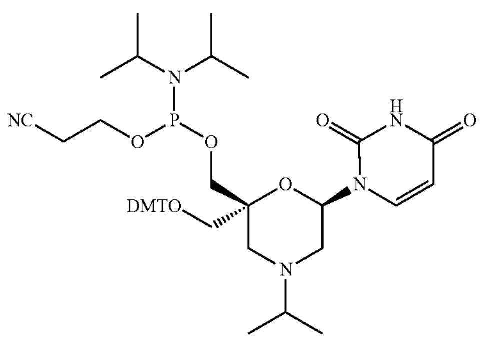 | pre-1U3b | 1U3b | (2R,6R) |
| 8 | 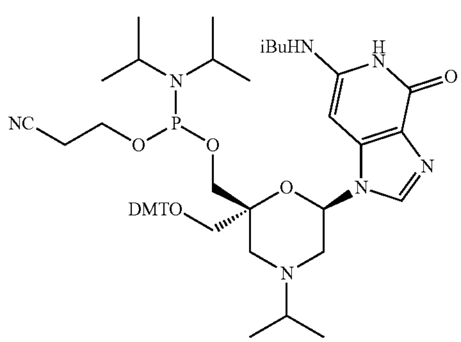 | pre-1G3b | 1G3b | (2R,6R) |

TABLE A-continued

| No | Structure | Precursor name | Name in oligo-sequence | Stereochemistry |
|----|-----------|----------------|------------------------|-----------------|
| 9  | 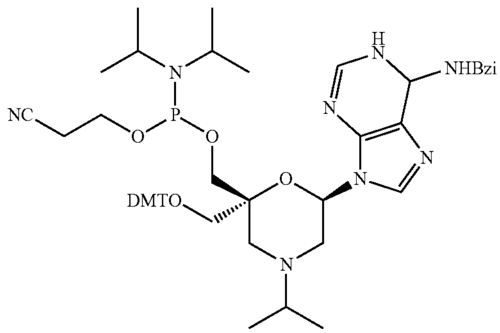          | pre-1A3b       | 1A3b                   | (2R,6R)         |
| 10 | 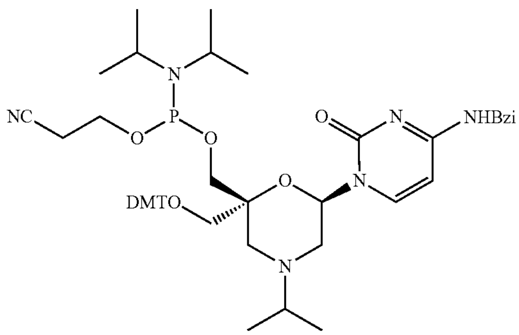          | pre-1C3b       | 1C3b                   | (2R,6R)         |
| 11 | 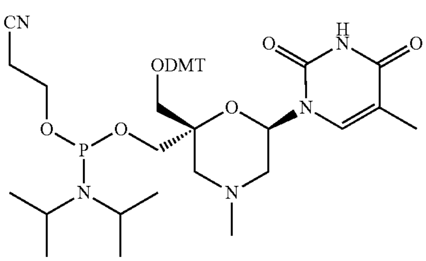          | pre-1T2        | 1T2                    | (2S,6R)         |
| 12 | 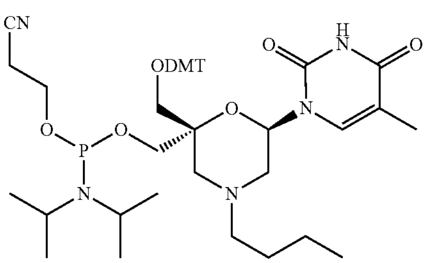          | pre-1T6        | 1T6                    | (2S,6R)         |
| 13 | 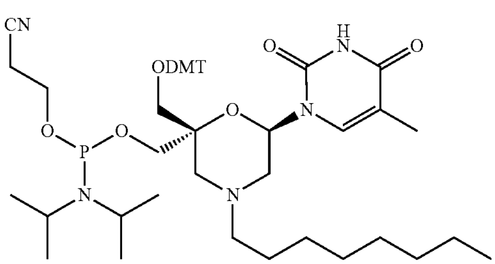          | pre-1T7        | 1T7                    | (2S,6R)         |

TABLE A-continued
| No | Structure | Precursor name | Name in oligo-sequence | Stereochemistry |
|---|---|---|---|---|
| 14 | 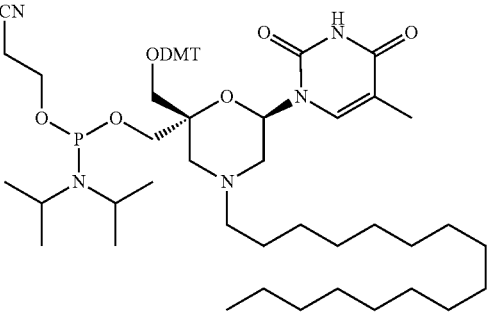 | pre-1T8 | 1T8 | (2S,6R) |
| 15 | 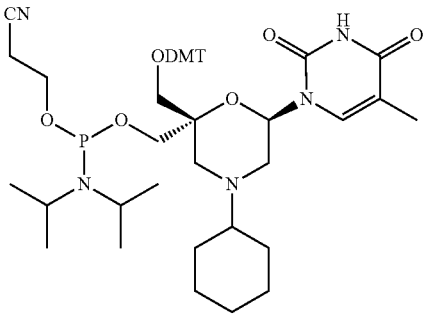 | pre-1T4 | 1T4 | (2S,6R) |
| 16 | 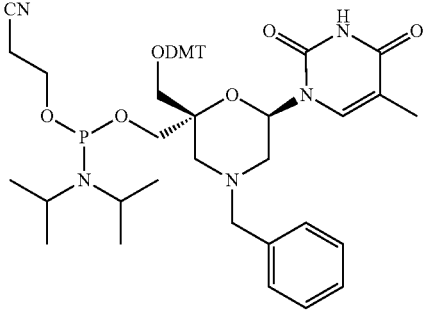 | pre-1T5 | 1T5 | (2S,6R) |
| 17 | 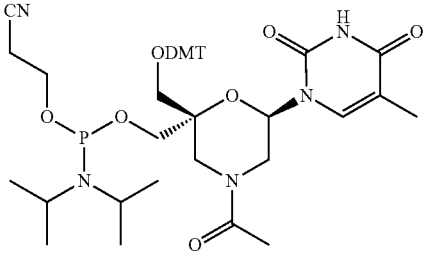 | pre-1T9 | 1T9 | (2S,6R) |
| 18 | 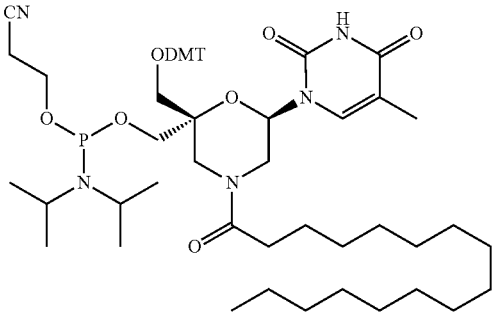 | pre-1T10 | 1T10 | (2S,6R) |

TABLE A-continued
| No | Structure | Precursor name | Name in oligo-sequence | Stereochemistry |
|---|---|---|---|---|
| 19 | 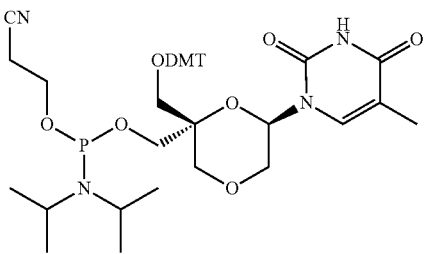 | pre-1T1 | 1T1 | (2S,6R) |
| 20 | 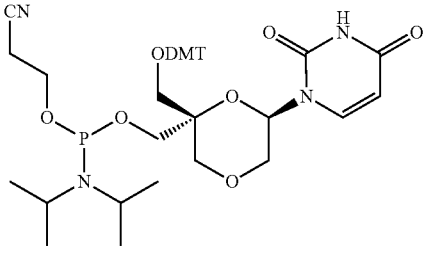 | pre-1U1 | 1U1 | (2S,6R) |
| 21 | 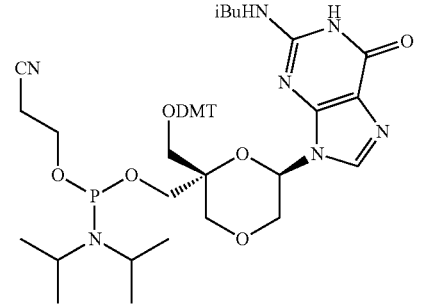 | pre-1G1 | 1G1 | (2S,6R) |
| 22 | 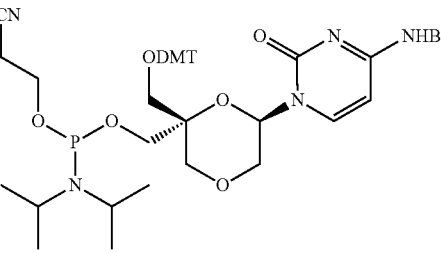 | pre-1C1 | 1C1 | (2S,6R) |
| 23 | 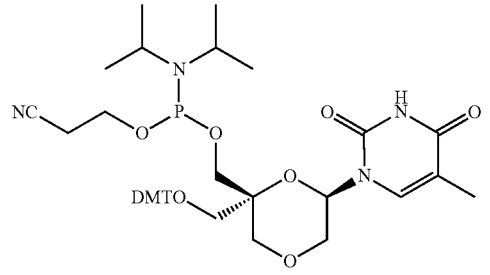 | pre-1T1b | 1T1b | (2R,6R) |

TABLE A-continued

| No | Structure | Precursor name | Name in oligo-sequence | Stereochemistry |
|---|---|---|---|---|
| 24 | 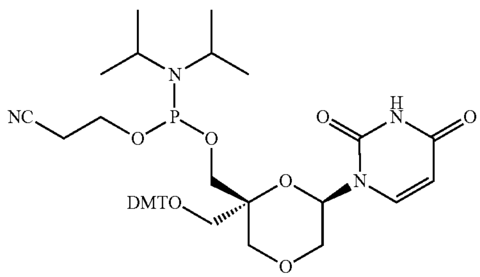 | pre-1U1b | 1U1b | (2R,6R) |
| 25 | 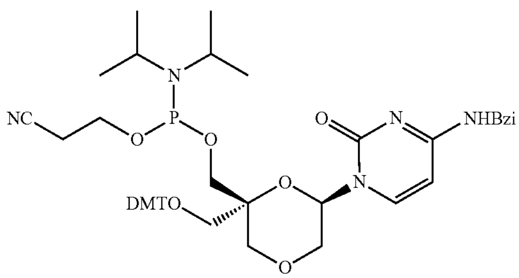 | pre-1C1b | 1C1b | (2R,6R) |
| 26 | 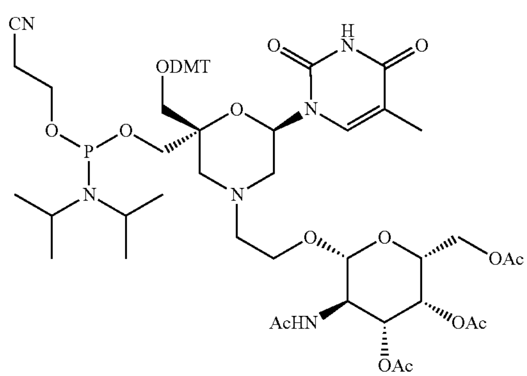 | pre-1gT9 | 1gT9 | (2S,6R) |
| 27 | 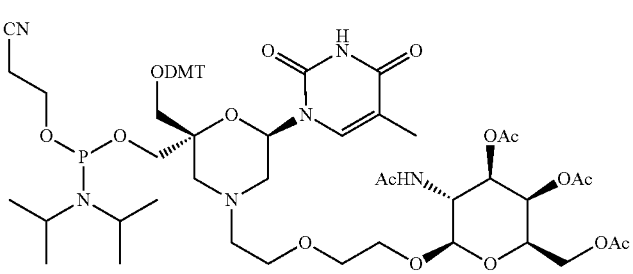 | pre-1gT8 | 1gT8 | (2S,6R) |

TABLE A-continued

| No | Structure | Precursor name | Name in oligo-sequence | Stereochemistry |
|---|---|---|---|---|
| 28 | 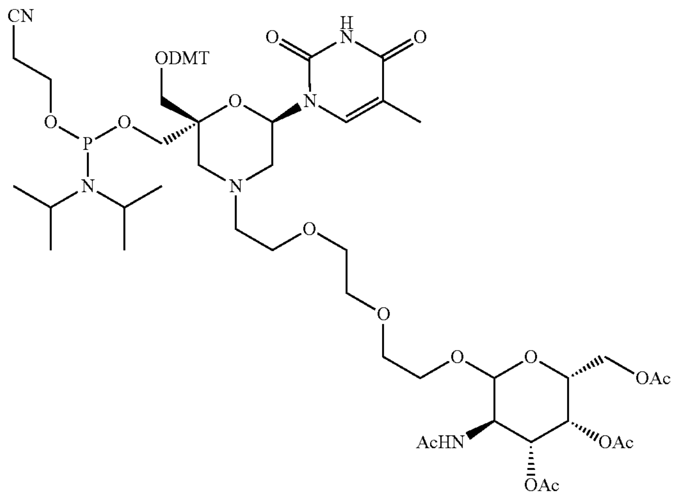 | pre-1gT7 | 1gT7 | (2S,6R) |
| 29 | 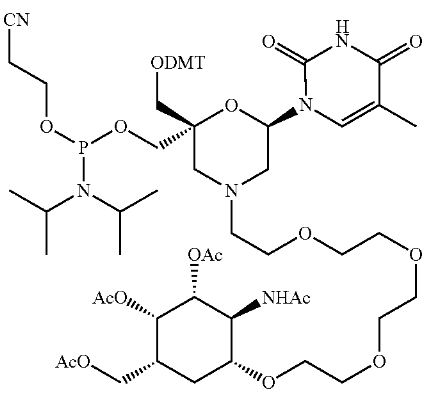 | pre-1gT6 | 1gT6 | (2S,6R) |
| 30 | 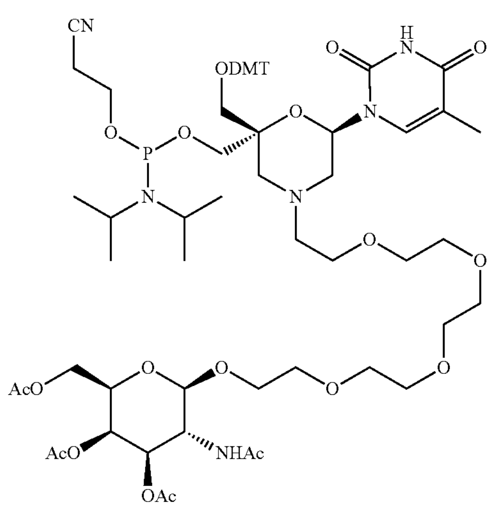 | pre-1gT5 | 1gT5 | (2S,6R) |

TABLE A-continued

| No | Structure | Precursor name | Name in oligo-sequence | Stereochemistry |
|---|---|---|---|---|
| 31 | 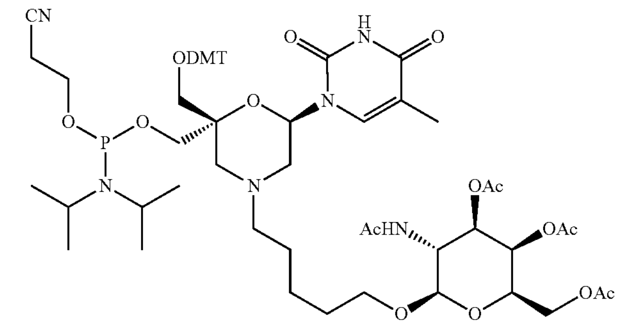 | pre-1gT3 | 1gT3 | (2S,6R) |
| 32 | 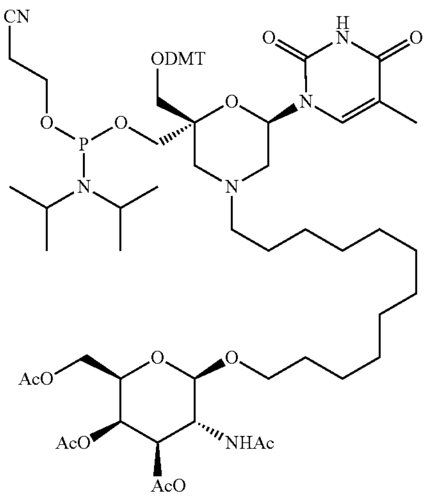 | pre-1gT4 | 1gT4 | (2S,6R) |
| 33 | 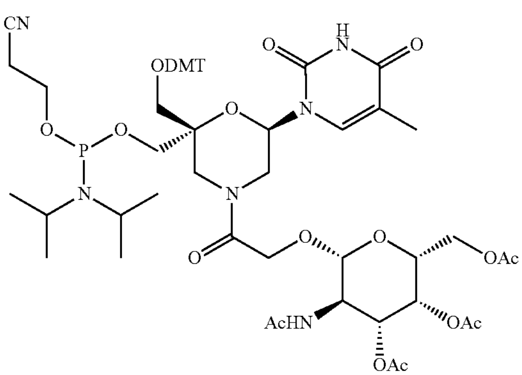 | pre-1gT12 | 1gT12 | (2S,6R) |
| 34 | 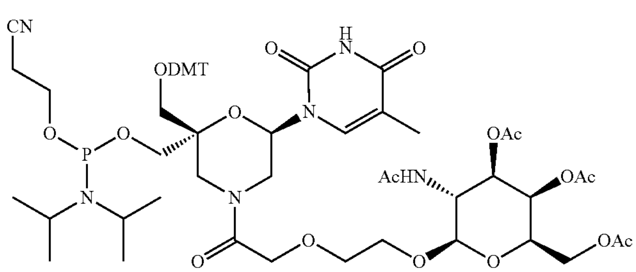 | pre-1gT11 | 1gT11 | (2S,6R) |

TABLE A-continued
| No | Structure | Precursor name | Name in oligo-sequence | Stereochemistry |
|---|---|---|---|---|
| 35 | 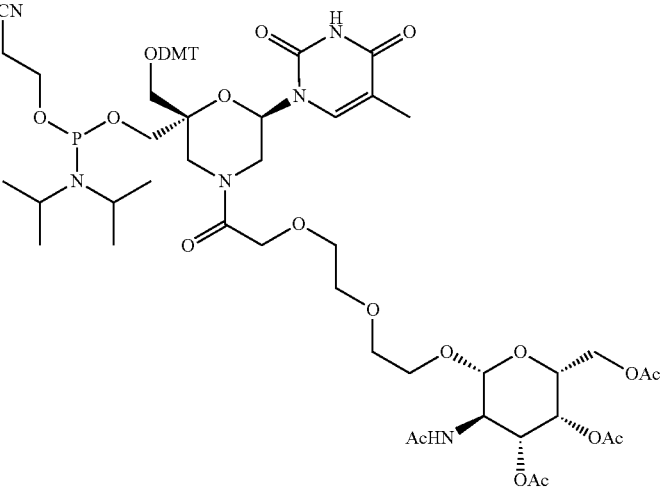 | pre-1gT10 | 1gT10 | (2S,6R) |
| 36 | 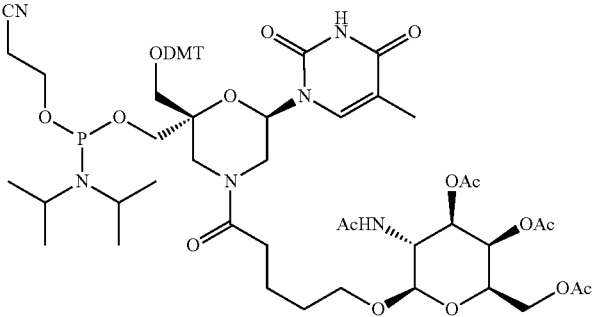 | pre-1gT1 | 1gT1 | (2S,6R) |
| 37 | 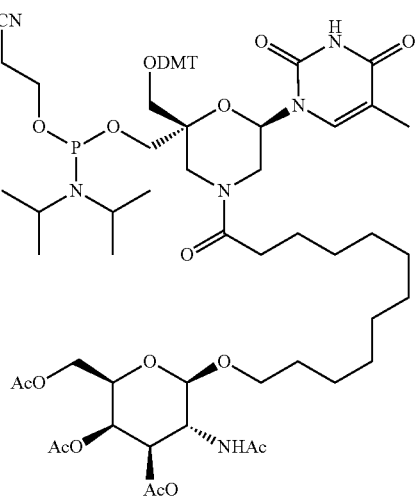 | pre-1gT2 | 1gT2 | (2S,6R) |

TABLE A-continued

| No | Structure | Precursor name | Name in oligo-sequence | Stereochemistry |
|----|-----------|----------------|------------------------|-----------------|
| 38 | 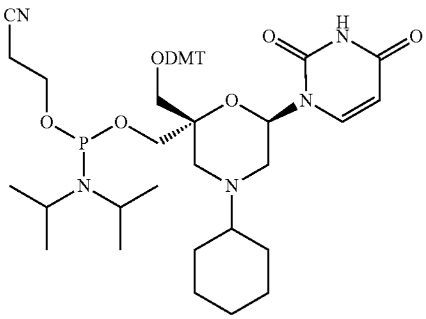 | pre-1U4 | 1U4 | (2S,6R) |
| 39 | 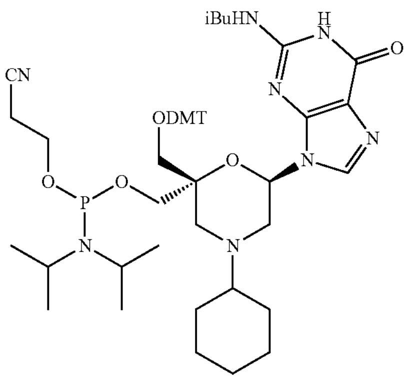 | pre-1G4 | 1G4 | (2S,6R) |
| 40 | 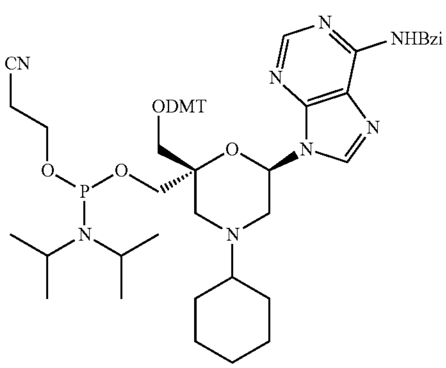 | pre-1A4 | 1A4 | (2S,6R) |
| 41 | 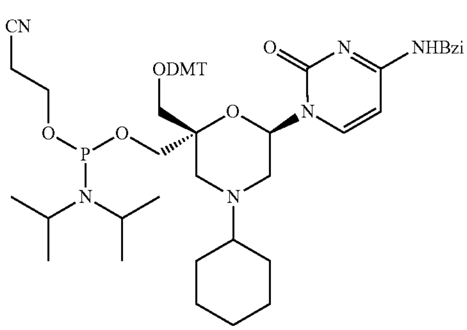 | pre-1C4 | 1C4 | (2S,6R) |

TABLE A-continued

| No | Structure | Precursor name | Name in oligo-sequence | Stereochemistry |
|----|-----------|----------------|------------------------|-----------------|
| 42 | 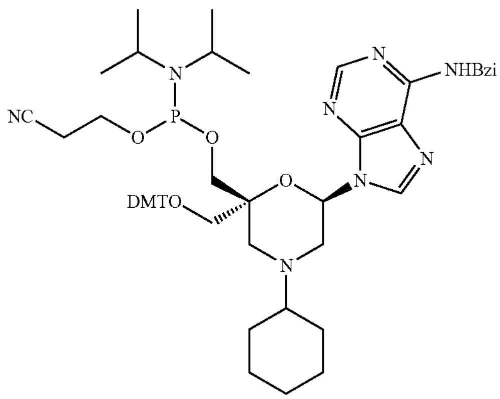 | pre-1A4b | 1A4b | (2R,6R) |
| 43 | 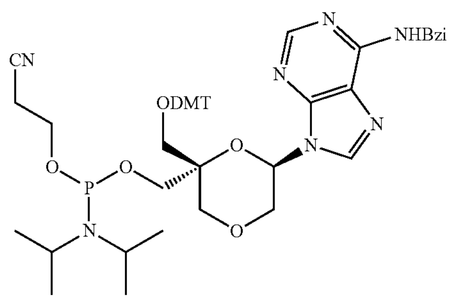 | pre-1A1 | 1A1 | (2S,6R) |
| 44 | 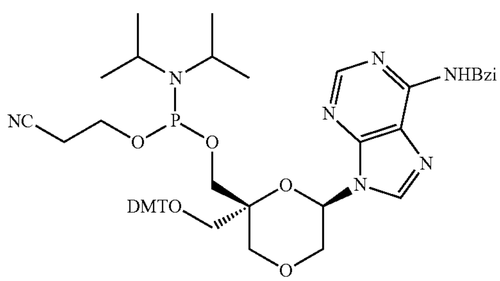 | pre-1A1b | 1A1b | (2R,6R) |
| 45 | 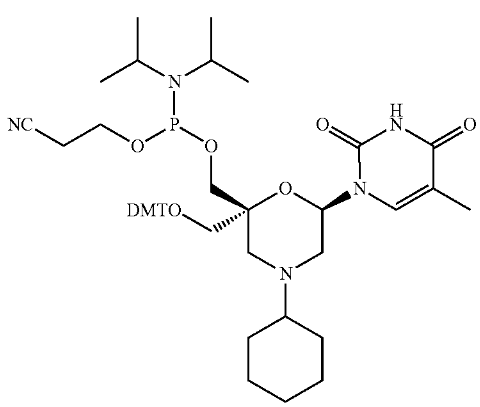 | pre-1T4b | 1T4b | (2R,6R) |

TABLE A-continued

| No | Structure | Precursor name | Name in oligo-sequence | Stereochemistry |
|---|---|---|---|---|
| 46 | 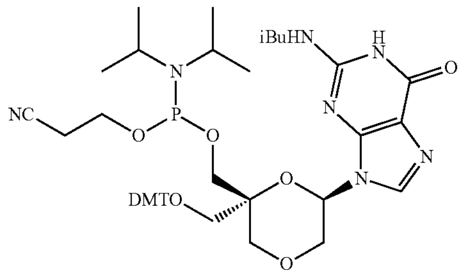 | pre-1G1b | 1G1b | (2R,6R) |

TABLE B

| No | Structure | Name | Name in oligo-sequence | Stereochemistry |
|---|---|---|---|---|
| 1 | 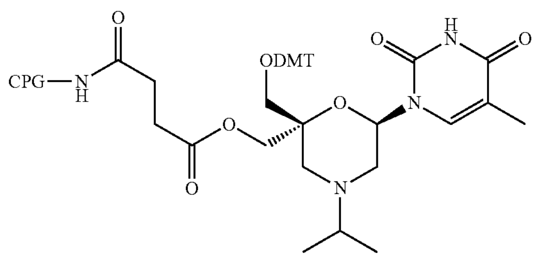 | cpg-1T3 | 1T3 | (2S,6R) |
| 2 | 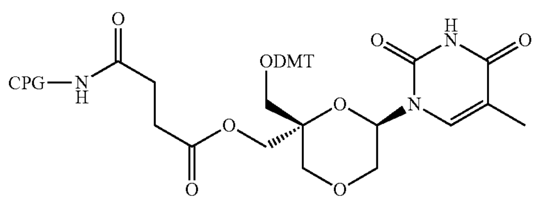 | cpg-1T1 | 1T1 | (2S,6R) |
| 3 | 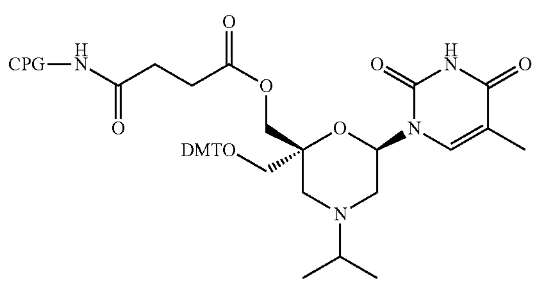 | cpg-1T3b | 1T3b | (2R,6R) |
| 4 | 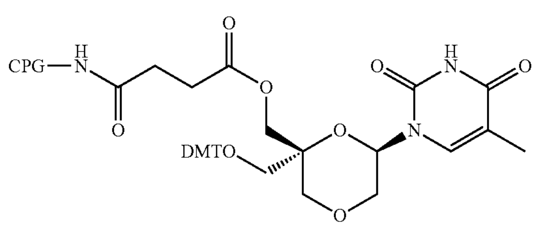 | cpg-1T1b | 1T1b | (2R,6R) |

TABLE B-continued

| No | Structure | Name | Name in oligo-sequence | Stereochemistry |
|---|---|---|---|---|
| 5 | 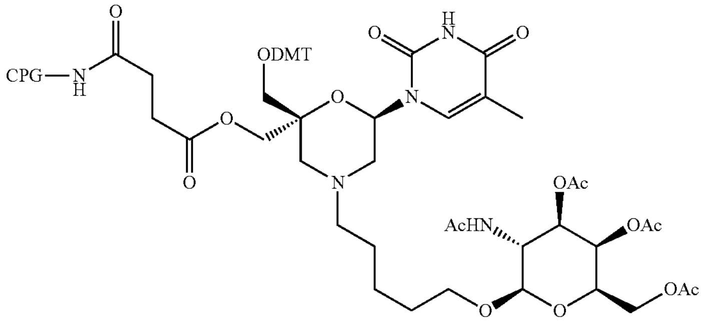 | cpg-1gT3 | 1gT3 | (2S,6R) |
| 6 | 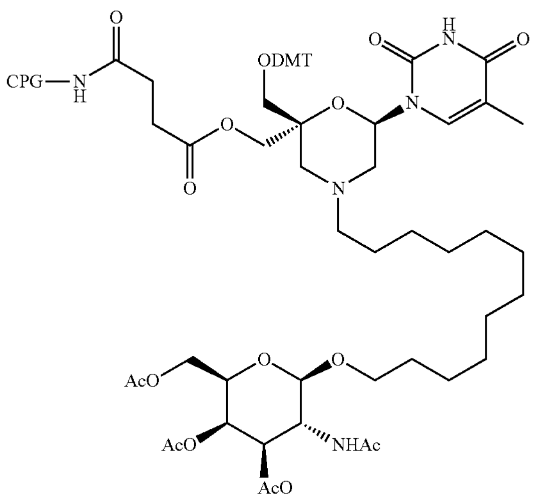 | cpg-1gT4 | 1gT4 | (2S,6R) |
| 7 | 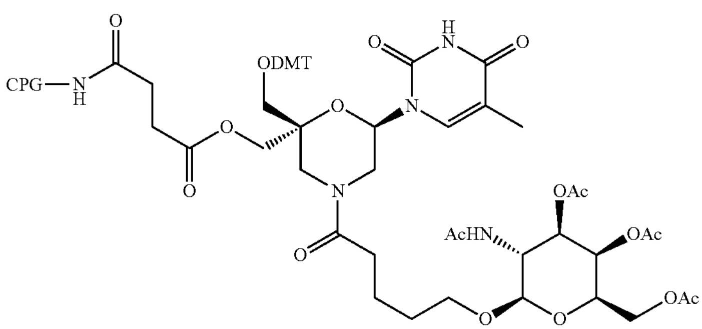 | cpg-1gT1 | 1gT1 | (2S,6R) |

TABLE B-continued

| No | Structure | Name | Name in oligo-sequence | Stereochemistry |
|---|---|---|---|---|
| 8 | 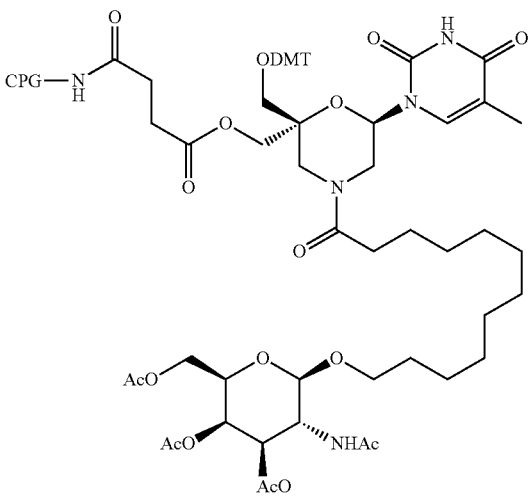 | cpg-1gT2 | 1gT2 | (2S,6R) |
| 9 | 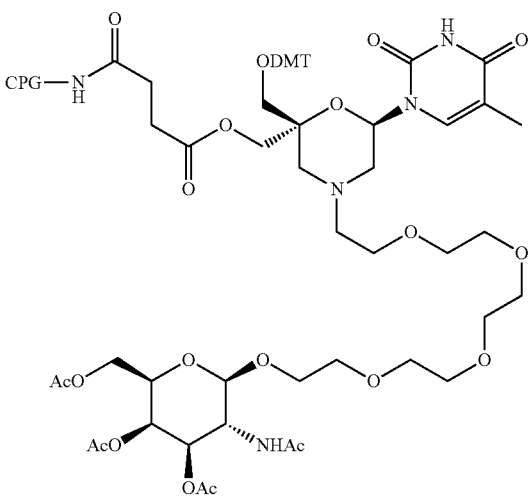 | cpg-1gT5 | 1gT5 | (2S,6R) |

The modified nucleotides of formula (I) may be incorporated at the 5', 3', or both ends of the sense strand and/or antisense strand of the dsRNA. By way of example, one or more (e.g., 1, 2, 3, 4, or 5 or more) modified nucleotides may be incorporated at the 5' end of the sense strand of the dsRNA. In some embodiments, one or more (e.g., 1, 2, 3, or more) modified nucleotides are positioned in the 5' end of the sense strand, where the modified nucleotides do not complement the antisense sequence but may be optionally paired with an equal or smaller number of complementary nucleotides at the corresponding 3' end of the antisense strand.

In some embodiments, the dsRNA may comprise a sense strand having a sense sequence of 17, 18, or 19 nucleotides in length, where three to five nucleotides of formula (I) (e.g., three consecutive 1gT3 or 1gT7 with or without additional nucleotides of formula (I)) are placed in the 5' end of the sense sequence, making the sense strand 20, 21, or 22 nucleotides in length. In such embodiments, the sense strand may additionally comprise two consecutive nucleotides of formula (I) (e.g., 1T4 or 1T3) at the 3' of the sense sequence, making the sense strand 22, 23, or 24 nucleotides in length.

The dsRNA may comprise an antisense sequence of 19 nucleotides in length, where the antisense sequence may additionally be linked to 2 modified nucleotides or deoxyribonucleotides (e.g., dT) at its 3' end, making the antisense strand 21 nucleotides in length. In further embodiments, the sense strand of the dsRNA contains only naturally occurring internucleotide bonds (phosphodiester bond), where the antisense strand may optionally contain non-naturally occurring internucleotide bonds. For example, the antisense strand may contain phosphoro-thioate bonds in the backbone near or at its 5' and/or 3' ends. In some embodiments, the dsRNA may contain nucleotides with a modified ribose, such as locked nucleic acid (LNA) units.

In some embodiments, the use of modified nucleotides of formula (I) circumvents the need for other RNA modifications such as the use of non-naturally occurring internucleotide bonds, thereby simplifying the chemical synthesis of dsRNAs. Moreover, the modified nucleotides of formula (I) can be readily made to contain cell targeted moieties such as GalNAc derivatives (which include GalNAc itself), enhancing the delivery efficiency of dsRNAs incorporating such nucleotides. Further, it has been shown that dsRNAs incorporating modified nucleotides of formula (I), e.g., at the sense strand, significantly improve the stability and therapeutic potency of the dsRNAs.

Tables 3 and 4 below list the sequences of exemplary modified GalNAc-siRNA constructs derived from constructs siRNA#023 and siRNA#042 listed in Table 2. In some embodiments, the dsRNA may contain nucleotides with a modified ribose, such as locked nucleic acid (LNA) units (abbreviated with an "1", followed by the corresponding nucleobase, in tables below).

TABLE 3

Sequences of Exemplary Modified GalNAc-siRNA Constructs from siRNA#023

| CNST # | Sense strand sequence (5'-3') | SEQ | Antisense strand sequence (5'-3') | SEQ |
|---|---|---|---|---|
| 023-c-01 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 535 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 589 |
| 023-c-02 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 536 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 590 |
| 023-c-03 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 537 | Hy-mA-PS-fG-PS-mA-PO-fA-PO-mU-PO-mA-PO-mU-PO-mC-PO-fC-PO-mU-PO-mC-PO-mC-PO-mU-PO-fC-PO-mC-PO-fA-PO-mU-PO-mC-PO-mU-PS-mA-PS-mA-Hy | 591 |
| 023-c-04 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 538 | Hy-fA-PS-fG-PS-mA-PO-fA-PO-mU-PO-fA-PO-mU-PO-fC-PO-fU-PO-mC-PO-mC-PO-mU-PO-fC-PO-mC-PO-fA-PO-mU-PO-fC-PO-mU-PS-dT-PS-dT-Hy | 592 |
| 023-c-05 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 539 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 593 |
| 023-c-06 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 540 | Hy-mA-PS-fG-PS-mA-PO-mA-PO-mU-PO-fA-PO-mU-PO-mC-PO-mC-PO-mU-PO-mC-PO-mC-PO-mU-PO-fc-PO-mC-PO-fA-PO-mU-PO-mC-PO-mU-PS-mA-PS-mA-Hy | 594 |
| 023-c-07 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 541 | Hy-mA-PS-fG-PS-mA-PO-fA-PO-mU-PO-mA-PO-mU-PO-mC-PO-fC-PO-mU-PO-mC-PO-mC-PO-mU-PO-fC-PO-mC-PO-fA-PO-mU-PO-mC-PO-mU-PS-mA-PS-mA-Hy | 595 |
| 023-c-08 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PS-mC-PS-mU-Hy | 542 | Hy-fA-PS-fG-PS-mA-PO-fA-PO-mU-PO-fA-PO-mU-PO-fC-PO-fU-PO-mC-PO-mC-PO-mU-PO-fC-PO-mC-PO-fA-PO-mU-PO-fC-PO-mU-PS-dT-PS-dT-Hy | 596 |
| 023-c-09 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 543 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 597 |
| 023-c-10 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG- | 544 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA- | 598 |

TABLE 3-continued

Sequences of Exemplary Modified GalNAc-siRNA Constructs from siRNA#023

| CNST # | Sense strand sequence (5'-3') | SEQ | Antisense strand sequence (5'-3') | SEQ |
|---|---|---|---|---|
| | PO-mA-PO-mU-PO-mA-PO-mU-PO-mU-PS-mC-PS-mU-Hy | | PO-mU-PO-mC-PO-mU-PS-mA-PS-mA-Hy | |
| 023-c-11 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 545 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 599 |
| 023-c-12 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 546 | Hy-mA-PS-fG-PS-mA-PO-mA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 600 |
| 023-c-13 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 547 | Hy-fA-PS-fG-PS-mA-PO-fA-PO-mU-PO-fA-PO-mU-PO-fC-PO-mC-PO-mU-PO-mC-PO-fC-PO-mU-PO-fC-PO-mC-PO-fA-PO-mU-PO-fC-PO-mU-PS-dT-PS-dT-Hy | 601 |
| 023-c-14 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 548 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 602 |
| 023-c-15 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 549 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 603 |
| 023-c-16 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 550 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 604 |
| 023-c-17 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 551 | Hy-mA-PS-fG-PS-mA-PO-mA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 605 |
| 023-c-18 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PS-mC-PS-mU-Hy | 552 | Hy-fA-PS-fG-PS-mA-PO-fA-PO-mU-PO-fA-PO-mU-PO-fC-PO-mC-PO-mU-PO-mC-PO-fC-PO-mU-PO-fC-PO-mC-PO-fA-PO-mU-PO-fC-PO-mU-PS-dT-PS-dT-Hy | 606 |
| 023-c-19 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 553 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 607 |
| 023-c-20 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 554 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 608 |

TABLE 3-continued

Sequences of Exemplary Modified GalNAc-siRNA Constructs from siRNA#023

| CNST # | Sense strand sequence (5'-3') | SEQ | Antisense strand sequence (5'-3') | SEQ |
|---|---|---|---|---|
| 023-c-21 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 555 | Hy-mA-PS-fG-PS-mA-PO-fA-PO-mU-PO-mA-PO-mU-PO-mC-PO-fC-PO-mU-PO-mC-PO-mC-PO-mU-PO-fC-PO-mC-PO-fA-PO-mU-PO-mC-PO-mU-PS-mA-PS-mA-Hy | 609 |
| 023-c-22 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 556 | Hy-fA-PS-fG-PS-mA-PO-fA-PO-mU-PO-fA-PO-mU-PO-fC-PO-mC-PO-fU-PO-mC-PO-mC-PO-mU-PO-fC-PO-mC-PO-fA-PO-mU-PO-fC-PO-mU-PS-dT-PS-dT-Hy | 610 |
| 023-c-23 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 557 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 611 |
| 023-c-24 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 558 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 612 |
| 023-c-25 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 559 | Hy-mA-PS-fG-PS-mA-PO-fA-PO-mU-PO-mA-PO-mU-PO-mC-PO-fC-PO-mU-PO-mC-PO-mC-PO-mU-PO-fC-PO-mC-PO-fA-PO-mU-PO-mC-PO-mU-PS-mA-PS-mA-Hy | 613 |
| 023-c-26 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-lT4-PO-lT4-Hy | 560 | Hy-fA-PS-fG-PS-mA-PO-fA-PO-mU-PO-fA-PO-mU-PO-fC-PO-mC-PO-fU-PO-mC-PO-mC-PO-mU-PO-fC-PO-mC-PO-fA-PO-mU-PO-fC-PO-mU-PS-dT-PS-dT-Hy | 614 |
| 023-c-27 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 561 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-•Hy | 615 |
| 023-c-28 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 562 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 616 |
| 023-c-29 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 563 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 617 |
| 023-c-30 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 564 | Hy-mA-PS-fG-PS-mA-PO-mA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 618 |
| 023-c-31 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG- | 565 | Hy-fA-PS-fG-PS-mA-PO-fA-PO-mU-PO-fA-PO-mU-PO-fC-PO-mC-PO-mU-PO-mC-PO-fc-PO-mU-PO-fC-PO-mC-PO-fA- | 619 |

TABLE 3-continued

Sequences of Exemplary Modified GalNAc-siRNA Constructs from siRNA#023

| CNST # | Sense strand sequence (5'-3') | SEQ | Antisense strand sequence (5'-3') | SEQ |
|---|---|---|---|---|
| | PO-mA-PO-mU-PO-mA-PO-mU-PO-mU-PO-lT4-PO-lT4-Hy | | PO-mU-PO-fC-PO-mU-PS-dT-PS-dT-Hy | |
| 023-c-32 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 566 | Hy-mA-PS-fG-PS-mA-PO-fA-PO-mU-PO-mA-PO-mU-PO-mC-PO-mC-PO-mU-PO-mC-PO-mC-PO-mU-PO-mC-PO-mC-PO-fA-PO-mU-PO-mC-PO-mU-PS-mA-PS-mA-Hy | 620 |
| 023-c-33 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 567 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 621 |
| 023-c-34 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 568 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 622 |
| 023-c-35 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 569 | Hy-mA-PS-fG-PS-mA-PO-mA-PO-mU-PO-mA-PO-mU-PO-fC-PO-mC-PO-mU-PO-mC-PO-mC-PO-fA-PO-mU-PO-fC-PO-mC-PO-fA-PO-mU-PO-mC-PO-mU-PS-mA-PS-mA-Hy | 623 |
| 023-c-36 | Hy-lgT3-PO-lgT3-PO-lgT3-PO-lA-PO-lG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-lT4-PO-lT4-Hy | 570 | Hy-fA-PS-fG-PS-mA-PO-fA-PO-mU-PO-fA-PO-mU-PO-fC-PO-mC-PO-mU-PO-mC-PO-fC-PO-mU-PO-fC-PO-mC-PO-fA-PO-mU-PO-fC-PO-mU-PS-dT-PS-dT-Hy | 624 |
| 023-c-37 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 571 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 625 |
| 023-c-38 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 572 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 626 |
| 023-c-39 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 573 | Hy-mA-PS-fG-PS-mA-PO-fA-PO-mU-PO-mA-PO-mU-PO-mC-PO-fC-PO-mU-PO-mC-PO-mC-PO-mU-PO-fc-PO-mC-PO-fA-PO-mU-PO-mC-PO-mU-PS-mA-PS-mA-Hy | 627 |
| 023-c-40 | Hy-lgT3-PO-lgT3-PO-lgT3-PO-mA-PO-mG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 574 | Hy-fA-PS-fG-PS-mA-PO-fA-PO-mU-PO-fA-PO-mU-PO-fC-PO-mC-PO-fU-PO-mC-PO-mC-PO-mU-PO-fC-PO-mC-PO-fA-PO-mU-PO-fC-PO-mU-PS-dT-PS-dT-Hy | 628 |
| 023-c-41 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG- | 575 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA- | 629 |

TABLE 3-continued

Sequences of Exemplary Modified GalNAc-siRNA
Constructs from siRNA#023

| CNST # | Sense strand sequence (5'-3') | SEQ | Antisense strand sequence (5'-3') | SEQ |
|---|---|---|---|---|
| | PO-mA-PO-mU-PO-mA-PO-mU-PO-mU-PO-mC-PO-mU-PO-lT4-PO-lT4-Hy | | PO-mU-PO-mC-PO-mU-PS-mA-PS-mA-Hy | |
| 023-c-42 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 576 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 630 |
| 023-c-43 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 577 | Hy-mA-PS-fG-PS-mA-PO-fA-PO-mU-PO-mA-PO-mU-PO-mC-PO-fC-PO-mU-PO-mC-PO-mC-PO-mU-PO-fC-PO-mC-PO-fA-PO-mU-PO-mC-PO-mU-PS-mA-PS-mA-Hy | 631 |
| 023-c-44 | Hy-lgT3-PO-lgT3-PO-lgT3-PO-lA-PO-lG-PO-mA-PO-mU-PO-fG-PO-mG-PO-fA-PO-fG-PO-fG-PO-mA-PO-mG-PO-mG-PO-mA-PO-mU-PO-mA-PO-mU-PO-mU-PO-mC-PO-mU-PO-lT4-PO-lT4-Hy | 578 | Hy-fA-PS-fG-PS-mA-PO-fA-PO-mU-PO-fA-PO-mU-PO-fC-PO-mC-PO-fU-PO-mC-PO-mC-PO-mU-PO-fC-PO-mC-PO-fA-PO-mU-PO-fC-PO-mU-PS-dT-PS-dT-Hy | 632 |
| 023-c-45 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-lT4-PO-lT4-Hy | 579 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 633 |
| 023-c-46 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-lT4-PO-lT4-Hy | 580 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 634 |
| 023-c-47 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-lT4-PO-lT4-Hy | 581 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 635 |
| 023-c-48 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-lT4-PO-lT4-Hy | 582 | Hy-mA-PS-fG-PS-mA-PO-mA-PO-mU-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 636 |
| 023-c-49 | Hy-lgT3-PO-lgT3-PO-lgT3-PO-mA-PO-mG-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-lT4-PO-lT4-Hy | 583 | Hy-fA-PS-fG-PS-mA-PO-fA-PO-mU-PO-fA-PO-mU-PO-fC-PO-mC-PO-mU-PO-mC-PO-fC-PO-mU-PO-fC-PO-mC-PO-fA-PO-mU-PO-fC-PO-mU-PS-dT-PS-dT-Hy | 637 |

TABLE 3-continued

Sequences of Exemplary Modified GalNAc-siRNA Constructs from siRNA#023

| CNST # | Sense strand sequence (5'-3') | SEQ | Antisense strand sequence (5'-3') | SEQ |
|---|---|---|---|---|
| 023-c-50 | Hy-lgT3-PO-lgT3-PO-lgT3-PO-1A-PO-1G-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-1T4-PO-1T4-Hy | 584 | Hy-mA-PS-fG-PS-mA-PO-fA-PO-mU-PO-mA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 638 |
| 023-c-51 | Hy-lgT3-PO-lgT3-PO-lgT3-PO-1A-PO-1G-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-1T4-PO-1T4-Hy | 585 | Hy-mA-PS-fG-PS-mA-PO-mA-PO-mU-PO-fA-PO-mU-PO-mC-PO-mC-PO-mU-PO-mC-PO-mC-PO-mU-PO-fC-PO-mC-PO-fA-PO-mU-PO-mC-PO-mU-PS-mA-PS-mA-Hy | 639 |
| 023-c-52 | Hy-lgT3-PO-lgT3-PO-lgT3-PO-1A-PO-1G-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-1T4-PO-1T4-Hy | 586 | Hy-mA-PS-fG-PS-mA-PO-fA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 640 |
| 023-c-53 | Hy-lgT3-PO-lgT3-PO-lgT3-PO-1A-PO-1G-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-1T4-PO-1T4-Hy | 587 | Hy-mA-PS-fG-PS-mA-PO-mA-PO-mU-PO-mA-PO-mU-PO-fC-PO-mC-PO-mU-PO-mC-PO-mC-PO-mU-PO-fC-PO-mC-PO-fA-PO-mU-PO-mC-PO-mU-PS-mA-PS-mA-Hy | 641 |
| 023-c-54 | Hy-lgT3-PO-lgT3-PO-lgT3-PO-1A-PO-1G-PO-mA-PO-mU-PO-fG-PO-mG-PO-fA-PO-mG-PO-fG-PO-fA-PO-fG-PO-mG-PO-mA-PO-mU-PO-mA-PO-mU-PO-mU-PO-mC-PO-mU-PO-1T4-PO-1T4-Hy | 588 | Hy-fA-PS-fG-PS-mA-PO-fA-PO-mU-PO-fA-PO-mU-PO-fC-PO-mC-PO-mU-PO-mC-PO-fC-PO-mU-PO-fC-PO-mC-PO-fA-PO-mU-PO-fC-PO-mU-PS-dT-PS-dT-Hy | 642 |

TABLE 4

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| 042-c-01 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PS-mU-PS-mA-Hy | 643 | Hy-mU-PS-fA-PS-mA-PO-fG-PO-mA-PO-mC-PO-mC-PO-mU-PO-mC-PO-mA-PO-mA-PO-mU-PO-fU-PO-mC-PO-fU-PO-mC-PO-mG-PO-mG-PS-mA-PS-mA-Hy | 697 |
| 042-c-02 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PS-mU-PS-mA-Hy | 644 | Hy-mU-PS-fA-PS-mA-PO-mG-PO-mA-PO-fC-PO-mC-PO-mU-PO-mC-PO-mA-PO-mA-PO-mU-PO-fU-PO-mC-PO-fU-PO-mC-PO-mG-PO-mG-PS-mA-PS-mA-Hy | 698 |
| 042-c-03 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PS-mU-PS-mA-Hy | 645 | Hy-mU-PS-fA-PS-mA-PO-fG-PO-mA-PO-mC-PO-mC-PO-mU-PO-fC-PO-mA-PO-mA-PO-mU-PO-fU-PO-mC-PO-fU-PO-mC-PO-mG-PO-mG-PS-mA-PS-mA-Hy | 699 |
| 042-c-04 | Hy-lgT3-PO-lgT3-PO-lgT3-PO-mC-PO-mC-PO-mG-PO-mA-PO-fG-PO-mA-PO-fA-PO-fU- | 646 | Hy-fU-PS-fA-PS-mA-PO-fG-PO-mA-PO-fC-PO-mC-PO-fU-PO-mC-PO-fA-PO- | 700 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| | PO-fU-PO-mU-PO-mG-PO-mA-<br>PO-mG-PO-mG-PO-mU-PO-mC-<br>PO-mU-PS-mU-PS-mA-Hy | | mA-PO-mA-PO-mU-PO-fU-<br>PO-mC-PO-fU-PO-mC-PO-<br>fG-PO-mG-PS-dT-PS-dT-Hy | |
| 042-c-05 | Hy-lgT3-PO-lgT3-PO-lgT3-<br>PO-1C-PO-1C-PO-mG-PO-mA-<br>PO-fG-PO-mA-PO-fA-PO-fU-<br>PO-fU-PO-mU-PO-mG-PO-mA-<br>PO-mG-PO-mG-PO-mU-PO-mC-<br>PO-mU-PS-mU-PS-mA-Hy | 647 | Hy-mU-PS-fA-PS-mA-PO-<br>fG-PO-mA-PO-mC-PO-mC-<br>PO-mU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 701 |
| 042-c-06 | Hy-lgT3-PO-lgT3-PO-lgT3-<br>PO-1C-PO-1C-PO-mG-PO-mA-<br>PO-fG-PO-mA-PO-fA-PO-fU-<br>PO-fU-PO-mU-PO-mG-PO-mA-<br>PO-mG-PO-mG-PO-mU-PO-mC-<br>PO-mU-PS-mU-PS-mA-Hy | 648 | Hy-mU-PS-fA-PS-mA-PO-<br>mG-PO-mA-PO-fC-PO-mC-<br>PO-mU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 702 |
| 042-c-07 | Hy-lgT3-PO-lgT3-PO-lgT3-<br>PO-1C-PO-1C-PO-mG-PO-mA-<br>PO-fG-PO-mA-PO-fA-PO-fU-<br>PO-fU-PO-mU-PO-mG-PO-mA-<br>PO-mG-PO-mG-PO-mU-PO-mC-<br>PO-mU-PS-mU-PS-mA-Hy | 649 | Hy-mU-PS-fA-PS-mA-PO-<br>fG-PO-mA-PO-mC-PO-mC-<br>PO-mU-PO-fC-PO-mC-PO-<br>mA-PO-mA-PO-mU-PO-fU-<br>PO-mC-PO-fU-PO-mC-PO-<br>mG-PO-mG-PS-mA-PS-mA-Hy | 703 |
| 042-c-08 | Hy-lgT3-PO-lgT3-PO-lgT3-<br>PO-1C-PO-1C-PO-mG-PO-mA-<br>PO-fG-PO-mA-PO-fA-PO-fU-<br>PO-fU-PO-mU-PO-mG-PO-mA-<br>PO-mG-PO-mG-PO-mU-PO-mC-<br>PO-mU-PS-mU-PS-mA-Hy | 650 | Hy-fU-PS-fA-PS-mA-PO-<br>fG-PO-mA-PO-fC-PO-mC-<br>PO-fU-PO-mC-PO-fA-PO-<br>mA-PO-mA-PO-mU-PO-fU-<br>PO-mC-PO-fU-PO-mC-PO-<br>fG-PO-mG-PS-dT-PS-dT-Hy | 704 |
| 042-c-09 | Hy-lgT3-PO-lgT3-PO-lgT3-<br>PO-mC-PO-mC-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 651 | Hy-mU-PS-fA-PS-mA-PO-<br>fG-PO-mA-PO-mC-PO-mC-<br>PO-mU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 705 |
| 042-c-10 | Hy-lgT3-PO-lgT3-PO-lgT3-<br>PO-mC-PO-mC-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 652 | Hy-mU-PS-fA-PS-mA-PO-<br>mG-PO-mA-PO-fC-PO-mC-<br>PO-mU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 706 |
| 042-c-11 | Hy-lgT3-PO-lgT3-PO-lgT3-<br>PO-mC-PO-mC-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 653 | Hy-mU-PS-fA-PS-mA-PO-<br>fG-PO-mA-PO-mC-PO-mC-<br>PO-fU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 707 |
| 042-c-12 | Hy-lgT3-PO-lgT3-PO-lgT3-<br>PO-mC-PO-mC-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 654 | Hy-mU-PS-fA-PS-mA-PO-<br>mG-PO-mA-PO-mC-PO-mC-<br>PO-fU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 708 |
| 042-c-13 | Hy-lgT3-PO-lgT3-PO-lgT3-<br>PO-mC-PO-mC-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 655 | Hy-fU-PS-fA-PS-mA-PO-<br>fG-PO-mA-PO-fC-PO-mC-<br>PO-fU-PO-mC-PO-fA-PO-<br>mA-PO-fA-PO-mU-PO-fU-<br>PO-mC-PO-fU-PO-mC-PO-<br>fG-PO-mG-PS-dT-PS-dT-Hy | 709 |
| 042-c-14 | Hy-lgT3-PO-lgT3-PO-lgT3-<br>PO-1C-PO-1C-PO-mG-PO-mA-<br>PO-fG-PO-mA-PO-fA-PO-mU-<br>PO-fU-PO-fU-PO-fG-PO-mA-<br>PO-mG-PO-mG-PO-mU-PO-mC-<br>PO-mU-PS-mU-PS-mA-Hy | 656 | Hy-mU-PS-fA-PS-mA-PO-<br>fG-PO-mA-PO-mC-PO-mC-<br>PO-mU-PO-mC-PO-mA-PO-<br>mA-PO-mA-PO-mU-PO-fU-<br>PO-mC-PO-fU-PO-mC-PO-<br>mG-PO-mG-PS-mA-PS-mA-Hy | 710 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| 042-c-15 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PS-mU-PS-mA-Hy | 657 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 711 |
| 042-c-16 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PS-mU-PS-mA-Hy | 658 | Hy-mU-PS-fA-PS-mA-PO-fG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 712 |
| 042-c-17 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PS-mU-PS-mA-Hy | 659 | Hy-mU-PS-fA-PS-mA-PO-mG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 713 |
| 042-c-18 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PS-mU-PS-mA-Hy | 660 | Hy-fU-PS-fA-PS-mA-PO-fG-PO-mA-PO-fC-PO-mC-PO-fU-PO-mC-PO-mA-PO-mA-PO-fA-PO-mU-PO-fU-PO-mC-PO-fU-PO-mC-PO-fG-PO-mG-PS-dT-PS-dT-Hy | 714 |
| 042-c-19 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 661 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 715 |
| 042-c-20 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 662 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 716 |
| 042-c-21 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 663 | Hy-mU-PS-fA-PS-mA-PO-fG-PO-mA-PO-mC-PO-mC-PO-mU-PO-fC-PO-mA-PO-mA-PO-mA-PO-mU-PO-fU-PO-mC-PO-fU-PO-mC-PO-mG-PO-mG-PS-mA-PS-mA-Hy | 717 |
| 042-c-22 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 664 | Hy-fU-PS-fA-PS-mA-PO-fG-PO-mA-PO-fC-PO-mC-PO-fU-PO-mC-PO-fA-PO-mA-PO-mA-PO-mU-PO-fU-PO-mC-PO-fU-PO-mC-PO-fG-PO-mG-PS-dT-PS-dT-Hy | 718 |
| 042-c-23 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 665 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 719 |
| 042-c-24 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 666 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 720 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| 042-c-25 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 667 | Hy-mU-PS-fA-PS-mA-PO-fG-PO-mA-PO-mC-PO-mC-PO-mU-PO-fC-PO-mA-PO-mA-PO-mA-PO-mU-PO-fU-PO-mC-PO-fU-PO-mC-PO-mG-PO-mG-PS-mA-PS-mA-Hy | 721 |
| 042-c-26 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-lT4-PO-lT4-Hy | 668 | Hy-fU-PS-fA-PS-mA-PO-fG-PO-mA-PO-fC-PO-mC-PO-fU-PO-mC-PO-fA-PO-mA-PO-mA-PO-mU-PO-fU-PO-mC-PO-fU-PO-mC-PO-fG-PO-mG-PS-dT-PS-dT-Hy | 722 |
| 042-c-27 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 669 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 723 |
| 042-c-28 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 670 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 724 |
| 042-c-29 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 671 | Hy-mU-PS-fA-PS-mA-PO-fG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 725 |
| 042-c-30 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 672 | Hy-mU-PS-fA-PS-mA-PO-mG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 726 |
| 042-c-31 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 673 | Hy-fU-PS-fA-PS-mA-PO-fG-PO-mA-PO-fC-PO-mC-PO-fU-PO-mC-PO-mA-PO-mA-PO-fA-PO-mU-PO-fU-PO-mC-PO-fU-PO-mC-PO-fG-PO-mG-PS-dT-PS-dT-Hy | 727 |
| 042-c-32 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 674 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 728 |
| 042-c-33 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 675 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 729 |
| 042-c-34 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 676 | Hy-mU-PS-fA-PS-mA-PO-fG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 730 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| 042-c-35 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 677 | Hy-mU-PS-fA-PS-mA-PO-mG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 731 |
| 042-c-36 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-lT4-PO-lT4-Hy | 678 | Hy-fU-PS-fA-PS-mA-PO-fG-PO-mA-PO-fC-PO-mC-PO-fU-PO-mC-PO-mA-PO-mA-PO-fA-PO-mU-PO-fU-PO-mC-PO-fU-PO-mC-PO-fG-PO-mG-PS-dT-PS-dT-Hy | 732 |
| 042-c-37 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 679 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 733 |
| 042-c-38 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 680 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 734 |
| 042-c-39 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 681 | Hy-mU-PS-fA-PS-mA-PO-fG-PO-mA-PO-mC-PO-mC-PO-mU-PO-fC-PO-mA-PO-mA-PO-mA-PO-mU-PO-fU-PO-mC-PO-fU-PO-mC-PO-mG-PO-mG-PS-mA-PS-mA-Hy | 735 |
| 042-c-40 | Hy-lgT3-PO-lgT3-PO-lgT3-PO-mC-PO-mC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 682 | Hy-fU-PS-fA-PS-mA-PO-fG-PO-mA-PO-fC-PO-mC-PO-fU-PO-mC-PO-fA-PO-mA-PO-mA-PO-mU-PO-fU-PO-mC-PO-fU-PO-mC-PO-fG-PO-mG-PS-dT-PS-dT-Hy | 736 |
| 042-c-41 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 683 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 737 |
| 042-c-42 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 684 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 738 |
| 042-c-43 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC-PO-mU-PO-mU-PO-mA-PO-lT4-PO-lT4-Hy | 685 | Hy-mU-PS-fA-PS-mA-PO-fG-PO-mA-PO-mC-PO-mC-PO-mU-PO-fC-PO-mA-PO-mA-PO-mA-PO-mU-PO-fU-PO-mC-PO-fU-PO-mC-PO-mG-PO-mG-PS-mA-PS-mA-Hy | 739 |
| 042-c-44 | Hy-lgT3-PO-lgT3-PO-lgT3-PO-lC-PO-lC-PO-mG-PO-mA-PO-fG-PO-mA-PO-fA-PO-fU-PO-fU-PO-mU-PO-mG-PO-mA-PO-mG-PO-mG-PO-mU-PO-mC- | 686 | Hy-fU-PS-fA-PS-mA-PO-fG-PO-mA-PO-fC-PO-mC-PO-fU-PO-mC-PO-fA-PO-mA-PO-mA-PO-mU-PO-fU-PO-mC-PO-fU-PO-mC-PO- | 740 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| | PO-mU-PO-mU-PO-mA-PO-1T4-PO-1T4-Hy | | fG-PO-mG-PS-dT-PS-dT-Hy | |
| 042-c-45 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 687 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 741 |
| 042-c-46 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 688 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 742 |
| 042-c-47 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 689 | Hy-mU-PS-fA-PS-mA-PO-fG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 743 |
| 042-c-48 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 690 | Hy-mU-PS-fA-PS-mA-PO-mG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 744 |
| 042-c-49 | Hy-lgT3-PO-lgT3-PO-lgT3-PO-mC-PO-mC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 691 | Hy-fU-PS-fA-PS-mA-PO-fG-PO-mA-PO-fC-PO-mC-PO-fU-PO-mC-PO-mA-PO-mA-PO-fA-PO-mU-PO-fU-PO-mC-PO-fU-PO-mC-PO-fG-PO-mG-PS-dT-PS-dT-Hy | 745 |
| 042-c-50 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 692 | Hy-mU-PS-fA-PS-mA-PO-fG-PO-mA-PO-mC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 746 |
| 042-c-51 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 693 | Hy-mU-PS-fA-PS-mA-PO-mG-PO-mA-PO-fC-PO-mC-PO-mU-PO-mC-PO-mA-PO-mA-PO-mA-PO-mU-PO-fU-PO-mC-PO-fU-PO-mC-PO-mG-PO-mG-PS-mA-PS-mA-Hy | 747 |
| 042-c-52 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 694 | Hy-mU-PS-fA-PS-mA-PO-fG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 748 |
| 042-c-53 | Hy-lgT3-PO-lgT3-PO-lgT3-PO-lC-PO-lC-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 695 | Hy-mU-PS-fA-PS-mA-PO-mG-PO-mA-PO-mC-PO-mC-PO-fU-PO-mC-PO-mA-PO-mA-PO-mA-PO-mU-PO-fU-PO-mC-PO-fU-PO-mC-PO-mG-PO-mG-PS-mA-PS-mA-Hy | 749 |

TABLE 4-continued

Sequences of Exemplary Modified GalNAc-siRNA Constructs from siRNA#042

| CNST # | Sense strand sequence (5'-3') | SEQ | Antisense strand sequence (5'-3') | SEQ |
|---|---|---|---|---|
| 042-c-54 | Hy-lgT3-PO-lgT3-PO-lgT3-PO-1C-PO-1C-PO-mG-PO-mA-PO-fG-PO-mA-PO-fA-PO-mU-PO-fU-PO-fU-PO-fG-PO-mA-PO-mG-PO-mG-PO-mU-PO-mC-PO-mU-PO-mU-PO-mA-PO-1T4-PO-1T4-Hy | 696 | Hy-fU-PS-fA-PS-mA-PO-fG-PO-mA-PO-fC-PO-mC-PO-fU-PO-mC-PO-mA-PO-mA-PO-fA-PO-mU-PO-fU-PO-mC-PO-fU-PO-mC-PO-fG-PO-mG-PS-dT-PS-dT-Hy | 750 |

While the exemplary siRNAs shown in Tables 2-4 include nucleotide modifications, siRNAs having the same or substantially the same sequences but different numbers, patterns, and/or types of modifications, are also contemplated.

In some embodiments, a dsRNA comprises a sense strand shown in Table 1 with the addition of nucleotides (or modified versions thereof) at either or both of its termini. For example, the dsRNA comprises a sense strand shown in Table 1 with the addition of a 5' CCA and/or a 3' invdT. In some embodiments, a dsRNA comprises an antisense strand shown in Table 1 with the addition of nucleotides (or modified versions thereof) at either or both of its termini. For example, the dsRNA comprises an antisense strand shown in Table 1 with the addition of a 3' dTdT. In certain embodiments, a dsRNA comprises a pair of sense and antisense strands as shown in Table 1, with the addition of a 5' CCA and a 3' invdT to the sense strand and with the addition of a 3' dTdT to the antisense strand. In certain embodiments, a dsRNA comprises a pair of sense and antisense strands as shown in Table 2, with the addition of a 5' lgT3-lgT3-lgT3 and a 3' lT4-lT4 to the sense strand.

In some embodiments, a dsRNA of the present disclosure comprises a sense sequence that is at least 70%, 75%, 80%, 85%, 90%, 95%, 96%, 97%, 98%, or 99% identical in sequence to a sense sequence shown in Table 1. In some embodiments, a dsRNA of the present disclosure comprises an antisense sequence that is at least 70%, 75%, 80%, 85%, 90%, 95%, 96%, 97%, 98%, or 99% identical in sequence to an antisense sequence shown in Table 1. In some embodiments, a dsRNA of the present disclosure comprises sense and antisense sequences that are at least 70%, 75%, 80%, 85%, 90%, 95%, 96%, 97%, 98%, or 99% identical in sequence to sense and antisense sequences, respectively, shown in Table 1. In certain embodiments, the dsRNA comprises sense and antisense strands having the sequences shown in Table 2. In certain embodiments, the dsRNA comprises sense and antisense strands having the sequences shown in Table 3.

The "percentage identity" between two nucleotide sequences is determined by comparing the two optimally-aligned sequences in which the nucleic acid sequence to compare can have additions or deletions compared to the reference sequence for optimal alignment between the two sequences. "Percentage identity" is calculated by determining the number of positions at which the nucleotide residue is identical between the two sequences, preferably between the two complete sequences, dividing the number of identical positions by the total number of positions in the alignment window and multiplying the result by 100 to obtain the percentage identity between the two sequences. For purposes herein, when determining "percentage identity" between two nucleotide sequences, modifications to the nucleotides are not considered. For example, a sequence of 5'-mC-fU-mA-fG-3' is considered having 100% sequence identity as a sequence of 5'-CUAG-3'.

I.5 dsRNA Conjugates

The present dsRNAs may be covalently or noncovalently linked to one or more ligands or moieties. Examples of such ligands and moieties may be found, e.g., in Jeong et al., Bioconjugate Chem. (2009) 20:5-14 and Sebestyén et al., Methods Mol. Biol. (2015) 1218:163-86. In some embodiments, the dsRNA is conjugated/attached to one or more ligands via a linker. Any linker known in the art may be used, including, for example, multivalent (e.g., bivalent, trivalent, or tetravalent) branched linkers. The linker may be cleavable or non-cleavable. Conjugating a ligand to a dsRNA may alter its distribution, enhance its cellular absorption and/or targeting to a particular tissue and/or uptake by one or more specific cell types (e.g., liver cells), and/or enhance the lifetime or half-life of the dsRNA. In some embodiments, a hydrophobic ligand is conjugated to the dsRNA to facilitate direct permeation of the cellular membrane and/or uptake across cells (e.g., liver cells). For ANGPTL8-targeting dsRNAs (e.g., siRNAs), the target tissue may be the liver, including parenchymal cells of the liver (e.g., hepatocytes).

In some embodiments, the dsRNA of the present disclosure is conjugated to a cell-targeting ligand. A cell-targeting ligand refers to a molecular moiety that facilitates delivery of the dsRNA to the target cell, which encompasses (i) increased specificity of the dsRNA to bind to cells expressing the selected target receptors (e.g., target proteins); (ii) increased uptake of the dsRNA by the target cells; and (iii) increased ability of the dsRNA to be appropriately processed once it has entered into a target cell, such as increased intracellular release of an siRNA, e.g., by facilitating the translocation of the siRNA from transport vesicles into the cytoplasm. The ligand may be, for example, a protein (e.g., a glycoprotein), a peptide, a lipid, a carbohydrate, or a molecule having a specific affinity for a co-ligand.

Specific examples of ligands include, without limitation, an antibody or antigen-binding fragment thereof that binds to a specific receptor on a liver cell, thyrotropin, melanotropin, surfactant protein A, mucin carbohydrate, multivalent lactose, multivalent galactose, multivalent mannose, multivalent fucose, N-acetylgalactosamine, N-acetylglucosamine, transferrin, bisphosphonate, a steroid, bile acid, lipopolysaccharide, a recombinant or synthetic molecule such as a synthetic polymer, polyamino acids, an alpha helical peptide, polyglutamate, polyaspartate, lectins, and cofactors. In some embodiments, the ligand is one or more dyes, crosslinkers, polycyclic aromatic hydrocarbons, peptide conjugates (e.g., antennapedia peptide, Tat peptide), polyethylene glycol (PEG), enzymes, haptens, transport/absorption facilitators, synthetic ribonucleases (e.g., imidazole, bisimidazole, histamine, or imidazole clusters), human serum albumin (HSA), or LDL.

In some embodiments, the dsRNA is conjugated to one or more cholesterol derivatives or lipophilic moieties such as cholesterol or a cholesterol derivative; cholic acid; a vitamin (such as folate, vitamin A, vitamin E (tocopherol), biotin, or pyridoxal); bile or fatty acid conjugates, including both saturated and non-saturated (such as lauroyl (C12), myristoyl (C14), palmitoyl (C16), stearoyl (C18) and docosanyl (C22), lithocholic acid and/or lithocholic acid oleylamine conjugate (lithocholic-oleyl, C43)); polymeric backbones or scaffolds (such as PEG, triethylene glycol (TEG), hexaethylene glycol (HEG), poly(lactic-co-glycolic acid) (PLGA), poly(lactide-co-glycolide) (PLG), hydrodynamic polymers); steroids (such as dihydrotestosterone); terpene (such as triterpene); cationic lipids or peptides; and/or a lipid or lipid-based molecule. Such a lipid or lipid-based molecule may bind a serum protein, e.g., human serum albumin (HSA). A lipid-based ligand may be used to modulate (e.g., control) the binding of the conjugate to a target tissue. For example, a lipid or lipid-based ligand that binds to HSA more strongly will be less likely to be targeted to the kidney and therefore less likely to be cleared from the body.

In some embodiments, the cell-targeting moiety or ligand is a N-acetylgalactosamine (GalNAc) derivative. In some embodiments, the dsRNA is attached to one or more (e.g., two, three, four, or more) GalNAc derivatives. The attachment may be via one or more linkers (e.g., two, three, four, or more linkers). In some embodiments, a linker described herein is a multivalent (e.g., bivalent, trivalent, or tetravalent) branched linker. In some embodiments, the dsRNA is attached to two or more GalNAc derivatives via a bivalent branched linker. In some embodiments, the dsRNA is attached to three or more GalNAc derivatives via a trivalent branched linker. In some embodiments, the dsRNA is attached to three or more GalNAc derivatives with or without linkers. In some embodiments, the dsRNA is attached to four or more GalNAc derivatives via four separate linkers. In some embodiments, the dsRNA is attached to four or more GalNAc derivatives via a tetravalent branched linker. In some embodiments, the one or more GalNAc derivatives is attached to the 3'-end of the sense strand, the 3'-end of the antisense strand, the 5'-end of the sense strand, and/or the 5'-end of the antisense strand of the dsRNA. In some embodiments, one or more (e.g., two or three) modified nucleotides of formula (I) are placed in the 5' end and/or 3' end of the sense strand of the dsRNA, where those modified nucleotides each contain a GalNAc derivative moiety (see, e.g., the GalNAc-containing nucleotides shown in Tables A and B). Exemplary and non-limiting conjugates and linkers are described, e.g., in Biessen et al., *Bioconjugate Chem.* (2002) 13(2):295-302; Cedillo et al., *Molecules* (2017) 22(8):E1356; Grijalvo et al., *Genes* (2018) 9(2):E74; Huang et al., *Molecular Therapy: Nucleic Acids* (2017) 6:116-32; Nair et al., *J. Am. Chem. Soc.* (2014) 136:16958-61; Ostergaard et al., *Bioconjugate Chem.* (2015) 26:1451-5; Springer et al., *Nucleic Acid Therapeutics* (2018) 28(3):109-18; and U.S. Pat. Nos. 8,106,022, 9,127,276, and 8,927,705. GalNAc conjugation can be readily performed by methods well known in the art (e.g., as described in the above documents).

II. Methods of Making dsRNAs

A dsRNA of the present disclosure may be synthesized by any method known in the art. For example, a dsRNA may be synthesized by use of an automated synthesizer, by in vitro transcription and purification (e.g., using commercially available in vitro RNA synthesis kits), by transcription and purification from cells (e.g., cells comprising an expression cassette/vector encoding the dsRNA), and the like. In some embodiments, the sense and antisense strands of the dsRNA are synthesized separately and then annealed to form the dsRNA. In some embodiments, the dsRNA comprising modified nucleotides of formula (I) and optionally conjugated to a cell targeting moiety (e.g., GalNAc) may be prepared according to the disclosure of PCT Publication WO 2019/170731.

Ligand-conjugated dsRNAs and ligand molecules bearing sequence-specific linked nucleosides of the present disclosure may be assembled by any method known in the art, including, for example, assembly on a suitable polynucleotide synthesizer utilizing standard nucleotide or nucleoside precursors, or nucleotide or nucleoside conjugate precursors that already bear the linking moiety, ligand-nucleotide, or nucleoside-conjugated precursors that already bear the ligand molecule, or non-nucleoside ligand-bearing building blocks.

Ligand-conjugated dsRNAs of the present disclosure may be synthesized by any method known in the art, including, for example, by the use of a dsRNA bearing a pendant reactive functionality such as that derived from the attachment of a linking molecule onto the dsRNA. In some embodiments, this reactive oligonucleotide may be reacted directly with commercially-available ligands, ligands that are synthesized bearing any of a variety of protecting groups, or ligands that have a linking moiety attached thereto. In some embodiments, the methods facilitate the synthesis of ligand-conjugated dsRNA by the use of nucleoside monomers that have been appropriately conjugated with ligands and that may further be attached to a solid support material. In some embodiments, a dsRNA bearing an aralkyl ligand attached to the 3'-end of the dsRNA is prepared by first covalently attaching a monomer building block to a controlled-pore-glass support via a long-chain aminoalkyl group; then, nucleotides are bonded via standard solid-phase synthesis techniques to the monomer building-block bound to the solid support. The monomer building-block may be a nucleoside or other organic compound that is compatible with solid-phase synthesis.

In some embodiments, functionalized nucleoside sequences of the present disclosure possessing an amino group at the 5'-terminus are prepared using a polynucleotide synthesizer, and then reacted with an active ester derivative of a selected ligand. Active ester derivatives are well known to one of ordinary skill in the art. The reaction of the amino group and the active ester produces an oligonucleotide in which the selected ligand is attached to the 5'-position through a linking group. The amino group at the 5'-terminus can be prepared utilizing a 5'-amino-modifier C6 reagent. In some embodiments, ligand molecules are conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In some embodiments, click chemistry is used to synthesize siRNA conjugates. See, e.g., Astakhova et al., *Mol. Pharm.* (2018) 15(8):2892-9; Mercier et al., *Bioconjugate Chem.* (2011) 22(1):108-14.

III. Compositions and Delivery of dsRNAs

Certain aspects of the present disclosure relate to compositions (e.g., pharmaceutical compositions) comprising a dsRNA as described herein. In some embodiments, the composition further comprises a pharmaceutically acceptable excipient. In some embodiments, the composition is useful for treating a disease or disorder associated with the expression or activity of the ANGPTL8 gene. In some embodiments, the disease or disorder associated with the expression of the ANGPTL8 gene is a lipid metabolism disorder such as hypertriglyceridemia and/or any other condition described herein. Compositions of the present disclosure may be formulated based upon the mode of delivery, including, for example, compositions formulated for delivery to the liver via parenteral administration.

The present dsRNAs can be formulated with a pharmaceutically acceptable excipient. Pharmaceutically acceptable excipients can be liquid or solid, and may be selected with the planned manner of administration in mind so as to provide for the desired bulk, consistency, and other pertinent transport and chemical properties. Any known pharmaceutically acceptable excipient may be used, including, for example, water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), calcium salts (e.g., calcium sulfate, calcium chloride, calcium phosphate, and hydroxyapatite), and wetting agents (e.g., sodium lauryl sulfate).

The present dsRNAs can be formulated into compositions (e.g., pharmaceutical compositions) containing the dsRNA admixed, encapsulated, conjugated, or otherwise associated with other molecules, molecular structures, or mixtures of nucleic acids. For example, a composition comprising one or more dsRNAs as described herein can contain other therapeutic agents such as other lipid lowering agents (e.g., statins). In some embodiments, the composition (e.g., pharmaceutical composition) further comprises a delivery vehicle as described herein.

A dsRNA of the present disclosure may be delivered directly or indirectly. In some embodiments, the dsRNA is delivered directly by administering a pharmaceutical composition comprising the dsRNA to a subject. In some embodiments, the dsRNA is delivered indirectly by administering one or more vectors described below.

A dsRNA of the present disclosure may be delivered by any method known in the art, including, for example, by adapting a method of delivering a nucleic acid molecule for use with a dsRNA (see, e.g., Akhtar et al., *Trends Cell Biol.* (1992) 2(5):139-44; PCT Publication WO 94/02595), or via additional methods known in the art (see, e.g., Kanasty et al., *Nature Materials* (2013) 12:967-77; Wittrup and Lieberman, *Nature Reviews Genetics* (2015) 16:543-52; Whitehead et al., *Nature Reviews Drug Discovery* (2009) 8:129-38; Gary et al., *J Control Release* (2007) 121(1-2):64-73; Wang et al., *AAPS J.* (2010) 12(4):492-503; Draz et al., *Theranostics* (2014) 4(9):872-92; Wan et al., *Drug Deliv Transl Res.* (2013) 4(1):74-83; Erdmann and Barciszewski (eds.) (2010) "RNA Technologies and Their Applications," Springer-Verlag Berlin Heidelberg, DOI 10.1007/978-3-642-12168-5; Xu and Wang, *Asian Journal of Pharmaceutical Sciences* (2015) 10(1):1-12). For in vivo delivery, dsRNA can be injected into a tissue site or administered systemically (e.g., in nanoparticle form via inhalation). In vivo delivery can also be mediated by a beta-glucan delivery system (see, e.g., Tesz et al., *Biochem J.* (2011) 436(2):351-62). In vitro introduction into a cell includes methods known in the art such as electroporation and lipofection.

In some embodiments, a dsRNA of the present disclosure is delivered by a delivery vehicle comprising the dsRNA. In some embodiments, the delivery vehicle is a liposome, lipoplex, complex, or nanoparticle.

III.1 Liposomal Formulations

Liposomes are unilamellar or multilamellar vesicles which have a membrane formed from a lipophilic material and an aqueous interior. In some embodiments, a liposome is a vesicle composed of amphiphilic lipids arranged in a spherical bilayer or bilayers. The aqueous portion contains the composition to be delivered. Cationic liposomes possess the advantage of being able to fuse to the cell wall. Advantages of liposomes include, e.g., that liposomes obtained from natural phospholipids are biocompatible and biodegradable; that liposomes can incorporate a wide range of water and lipid soluble drugs; and that liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes. For example, engineered cationic liposomes and sterically stabilized liposomes can be used to deliver the dsRNA. See, e.g., Podesta et al., *Methods Enzymol.* (2009) 464:343-54; U.S. Pat. No. 5,665,710.

III.2 Nucleic Acid-Lipid Particles

In some embodiments, a dsRNA of the present disclosure is fully encapsulated in a lipid formulation, e.g., to form a nucleic acid-lipid particle such as, without limitation, a SPLP, pSPLP, or SNALP. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. Nucleic acid-lipid particles, e.g., SNALPs, typically contain a cationic lipid, a non-cationic lipid, and a lipid that prevents aggregation of the particle (e.g., a PEG-lipid conjugate). SNALPs and SPLPs are useful for systemic applications, as they exhibit extended circulation lifetimes following intravenous (i.v.) injection and accumulate at distal sites (e.g., sites physically separated from the administration site). SPLPs include "pSPLPs," which include an encapsulated condensing agent-nucleic acid complex as set forth in PCT Publication WO 2000/003683.

In some embodiments, dsRNAs when present in nucleic acid-lipid particles are resistant in aqueous solution to degradation with a nuclease. Nucleic acid-lipid particles and their methods of preparation are disclosed in, e.g., U.S. Pat. Nos. 5,976,567; 5,981,501; 6,534,484; 6,586,410; and 6,815,432; and PCT Publication WO 96/40964.

In some embodiments, the nucleic acid-lipid particles comprise a cationic lipid. Any cationic lipid or mixture thereof known in the art may be used. In some embodiments, the nucleic acid-lipid particles comprise a non-cationic lipid. Any non-cationic lipid or mixture thereof known in the art may be used. In some embodiments, the nucleic acid-lipid particle comprises a conjugated lipid (e.g., to prevent aggregation). Any conjugated lipid known in the art may be used.

III.3 Additional Formulations

Factors that are important to consider in order to successfully deliver a dsRNA molecule in vivo include: (1) biological stability of the delivered molecule, (2) preventing nonspecific effects, and (3) accumulation of the delivered molecule in the target tissue. The nonspecific effects of a dsRNA can be minimized by local administration, for example by direct injection or implantation into a tissue or topically administering the preparation. For administering a dsRNA systemically for the treatment of a disease, the dsRNA may be modified or alternatively delivered using a drug delivery system; both methods act to prevent the rapid degradation of the dsRNA by endo- and exonucleases in vivo. Modification of the RNA or the pharmaceutical excipient may also permit targeting of the dsRNA composition to the target tissue and avoid undesirable off-target effects. As described above, dsRNA molecules may be modified by chemical conjugation to lipophilic groups such as cholesterol to enhance cellular uptake and prevent degradation. In some embodiments, the dsRNA is delivered using drug delivery systems such as a nanoparticle (e.g., a calcium phosphate nanoparticle), a dendrimer, a polymer, liposomes, or a cationic delivery system. Positively charged cationic delivery systems facilitate binding of a dsRNA molecule (negatively charged) and also enhance interactions at the negatively charged cell membrane to permit efficient uptake of a dsRNA by the cell. Cationic lipids, dendrimers, or polymers can either be bound to a dsRNA, or induced to form a vesicle or micelle (See, e.g., Kim et al., *Journal of Controlled Release* (2008) 129(2):107-16) that encases a dsRNA. The formation of vesicles or micelles further prevents degradation of the dsRNA when administered systemically. Methods for making and administering cationic-dsRNA complexes are known in the art. In some embodiments, a dsRNA may form a complex with cyclodextrin for systemic administration.

III.4 Vector-Encoded dsRNAs

A dsRNA of the present disclosure may be delivered to the target cell indirectly by introducing into the target cell a recombinant vector (DNA or RNA vector) encoding the dsRNA. The dsRNA will be expressed from the vector inside the cell, e.g., in the form of shRNA, where the shRNA is subsequently processed into siRNA intracellularly. In some embodiments, the vector is a plasmid, cosmid, or viral vector. In some embodiments, the vector is compatible with expression in prokaryotic cells. In some embodiments, the vector is compatible with expression in *E. coli*. In some embodiments, the vector is compatible with expression in eukaryotic cells. In some embodiments, the vector is compatible with expression in yeast cells. In some embodiments, the vector is compatible with expression in vertebrate cells. Any expression vector capable of encoding dsRNA known in the art may be used, including, for example, vectors derived from adenovirus (AV), adeno-associated virus (AAV), retroviruses (e.g., lentiviruses (LV), Rhabdoviruses, murine leukemia virus, etc.), herpes virus, SV40 virus, polyoma virus, papilloma virus, picornavirus, pox virus (e.g., orthopox or avipox), and the like. The tropism of viral vectors or viral-derived vectors may be modified by pseudotyping the vectors with envelope proteins or other surface antigens from one or more other viruses, or by substituting different viral capsid proteins, as appropriate. For example, lentiviral vectors may be pseudotypes with surface proteins from vesicular stomatitis virus (VSV), rabies, Ebola, Mokola, and the like. AAV vectors may be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes have been described previously (see, e.g., Rabinowitz et al., *J. Virol.* (2002) 76:791-801).

Selection of recombinant vectors, methods for inserting nucleic acid sequences into the vector for expressing a dsRNA, and methods of delivering vectors into one or more cells of interest are known in the art. See, e.g., Domburg, *Gene Therap.* (1995) 2:301-310; Eglitis et al., *Biotechniques* (1998) 6:608-14; Miller, *Hum Gene Therap.* 1:5-14 (1990); Anderson et al., *Nature* (1998) 392:25-30; Xia et al., *Nat. Biotech.* (2002) 20:1006-10; Robinson et al., *Nat Genet.* (2003) 33:401-6; Samulski et al., *J. Virol.* (1987) 61:3096-101; Fisher et al., *J Virol.* (1996) 70:520-32; Samulski et al., *J Virol.* (1989) 63:3822-6; U.S. Pat. Nos. 5,252,479 and 5,139,941; and PCT Publications WO 94/13788 and WO 93/24641.

Vectors useful for the delivery of a dsRNA as described herein may include regulatory elements (e.g., heterologous promoter, enhancer, etc.) sufficient for expression of the dsRNA in the desired target cell or tissue. In some embodiments, the vector comprises one or more sequences encoding the dsRNA linked to one or more heterologous promoters. Any heterologous promoter known in the art capable of expressing a dsRNA may be used, including, for example, the U6 or H1 RNA pol III promoters, the T7 promoter, and the cytomegalovirus promoter. The one or more heterologous promoters may be an inducible promoter, a repressible promoter, a regulatable promoter, and/or a tissue-specific promoter. Selection of additional promoters is within the abilities of one of ordinary skill in the art. In some embodiments, the regulatory elements are selected to provide constitutive expression. In some embodiments, the regulatory elements are selected to provide regulated/inducible/repressible expression. In some embodiments, the regulatory elements are selected to provide tissue-specific expression. In some embodiments, the regulatory elements and sequence encoding the dsRNA form a transcription unit.

A dsRNA of the present disclosure may be expressed from transcription units inserted into DNA or RNA vectors (see, e.g., Couture et al., *TIG* (1996) 12:5-10; PCT Publications WO 00/22113 and WO 00/22114; and U.S. Pat. No. 6,054, 299). Expression may be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann et al., *PNAS* (1995) 92:1292).

In some embodiments, the sense and antisense strands of a dsRNA are encoded on separate expression vectors. In some embodiments, the sense and antisense strands are expressed on two separate expression vectors that are co-introduced (e.g., by transfection or infection) into the same target cell. In some embodiments, the sense and antisense strands are encoded on the same expression vector. In some embodiments, the sense and antisense strands are transcribed from separate promoters which are located on the same expression vector. In some embodiments, the sense and antisense strands are transcribed from the same promoter on the same expression vector. In some embodiments, the sense and antisense strands are transcribed from the same promoter as an inverted repeat joined by a linker polynucleotide sequence such that the dsRNA has a stem and loop structure.

IV. dsRNA Therapy

Certain aspects of the present disclosure relate to methods for inhibiting the expression of the ANGPTL8 gene in a subject (e.g., a primate subject such as a human) comprising administering a therapeutically effective amount of one or more dsRNAs of the present disclosure, one or more vectors of the present disclosure, or one or more pharmaceutical compositions of the present disclosure. Certain aspects of the present disclosure relate to methods of treating and/or preventing one or more conditions described herein (e.g., an ANGPTL8-associated condition such as hypertriglyceridemia) comprising administering one or more dsRNAs of the present disclosure and/or one or more vectors of the present disclosure and/or one or more pharmaceutical compositions comprising one or more dsRNAs as described herein. In some embodiments, downregulating ANGPTL8 expression in a subject alleviates one or more symptoms of a condition described herein (e.g., an ANGPTL8-associated condition such as hypertriglyceridemia) in the subject.

The pharmaceutical composition of the present disclosure may be administered in dosages sufficient to inhibit expression of the ANGPTL8 gene. In some embodiments, a suitable dose of a dsRNA described herein is in the range of 0.001 mg/kg-200 mg/kg body weight of the recipient. In certain embodiments, a suitable dose is in the range of 0.001 mg/kg-50 mg/kg body weight of the recipient, e.g., in the range of 0.001 mg/kg-20 mg/kg body weight of the recipient. Treatment of a subject with a therapeutically effective amount of a pharmaceutical composition can include a single treatment or a series of treatments.

As used herein, the terms "therapeutically effective amount" and "prophylactically effective amount" refer to an amount that provides a therapeutic benefit in the treatment, prevention, or management of pathological processes mediated by ANGPTL8 expression, or an overt symptom of pathological processes mediated by ANGPTL8 expression.

As used herein, the term "ANGPTL8-associated condition" is intended to include any condition in which inhibiting the activity of ANGPTL8 is beneficial. Such a condition may be caused, for example, by excess production of the ANGPTL8 protein, by ANGPTL8 gene mutations that increase ANGPTL8 activity or expression, by abnormal cleavage of the ANGPTL8 protein that increases activity or decreases degradation, and/or by abnormal interactions between ANGPTL8 and other proteins or other endogenous or exogenous substances such that ANGPTL8 activity is increased or degradation is decreased. An ANGPTL8-associated condition may be, e.g., a lipid metabolism disorder.

In some embodiments, a dsRNA described herein is used to treat a subject with a lipid metabolism disorder such as hypertriglyceridemia or any symptoms or conditions associated with hypertriglyceridemia. In certain embodiments, a dsRNA described herein is used to treat a patient with drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, cimetidine-induced hypertriglyceridemia, familial hypertriglyceridemia, acute pancreatitis associated with hypertriglyceridemia, and/or hepatosplenomegaly associated with hypertriglyceridemia.

In some embodiments, a dsRNA described herein is used to treat a subject having one or more conditions selected from: lipidemia (e.g., hyperlipidemia), dyslipidemia (e.g., atherogenic dyslipidemia, diabetic dyslipidemia, or mixed dyslipidemia), hyperlipoproteinemia, hypercholesterolemia, gout associated with hypercholesterolemia, chylomicronemia, lipodystrophy, lipoatrophy, metabolic syndrome, diabetes (Type I or Type II), pre-diabetes, Cushing's syndrome, acromegaly, systemic lupus erythematosus, dysglobulinemia, polycystic ovary syndrome, Addison's disease, glycogen storage disease type 1, hypothyroidism, uremia, adriamycin cardiomyopathy, lipoprotein lipase deficiency, lysosomal acid lipase deficiency, xanthomatosis, eruptive xanthoma, and lipemia retinalis.

Additionally or alternatively, a dsRNA described herein may be used to treat a subject with one or more pathological conditions associated with any of the disorders described herein, such as heart and circulatory conditions (e.g., atherosclerosis, angina, hypertension, congestive heart failure, coronary artery disease, restenosis, myocardial infarction, stroke, aneurysm, cerebrovascular diseases, and peripheral vascular diseases), liver disease, kidney disease, nephrotic syndrome, and chronic renal disease (e.g., uremia, nephrotic syndrome, maintenance dialysis, and renal transplantation).

In some embodiments, a dsRNA described herein may be used to treat a subject with one or more conditions associated with any genetic profile (e.g., familial hypertriglyceridemia, familial combined lipidemia, or familial dysbetalipoproteinemia), treatment (e.g., use of thiazide diuretics, oral contraceptives and other estrogens, certain beta-adrenergic blocking drugs, propofol, HIV medications, isotretinoin, or protease inhibitors), or lifestyle (e.g., cigarette smoking, excessive alcohol consumption, high carbohydrate diet, or high fat diet) that results in or results from elevated blood triglycerides or lipids. Triglyceride levels (e.g., serum triglyceride levels) of over 150 mg/dL are considered elevated for risk of cardiovascular conditions. Triglyceride levels (e.g., serum triglyceride levels) of 500 mg/dL or higher are considered elevated for risk of pancreatitis.

In some embodiments, a dsRNA described herein may be used to manage body weight or reduce fat mass in a subject.

In some embodiments, a dsRNA as described herein inhibits expression of the human ANGPTL8 gene, or both human and cynomolgus ANGPTL8 genes. The expression of the ANGPTL8 gene in a subject may be inhibited, or the ANGPTL8 protein levels in the subject may be reduced, by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% after treatment as compared to pretreatment levels. In some embodiments, expression of the ANGPTL8 gene is inhibited, or the ANGPTL8 protein levels in the subject may be reduced, by at least about 2, at least about 5, at least about 10, at least about 15, at least about 20, at least about 25, at least about 50, at least about 75, or at least about 100 fold after treatment as compared to pretreatment levels. In some embodiments, the ANGPTL8 gene is inhibited or the ANGPTL8 protein levels are reduced in the liver of the subject.

In some embodiments, expression of the ANGPTL8 gene is decreased by the dsRNA for about 12 or more, 24 or more, or 36 or more hours. In some embodiments, expression of the ANGPTL8 gene is decreased for an extended duration, e.g., at least about two, three, four, five, or six days or more, e.g., about one week, two weeks, three weeks, or four weeks or longer.

As used herein, the terms "inhibit the expression of" or "inhibiting expression of," insofar as they refer to the ANGPTL8 gene, refer to the at least partial suppression of the expression of the ANGPTL8 gene, as manifested by a reduction in the amount of mRNA transcribed from the ANGPTL8 gene in a first cell or group of cells treated such that the expression of the ANGPTL8 gene is inhibited, as compared to a second cell or group of cells substantially identical to the first cell or group of cells but which has or have not been so treated (control cells). Such inhibition can be assessed, e.g., by Northern analysis, in situ hybridization, B-DNA analysis, expression profiling, transcription of reporter constructs, and other techniques known in the art. As used herein, the term "inhibiting" is used interchangeably with "reducing," "silencing," "downregulating," "suppressing," and other similar terms, and include any level of inhibition. The degree of inhibition is usually expressed in terms of (((mRNA in control cells)-(mRNA in treated cells))/(mRNA in control cells))×100%.

Alternatively, the degree of inhibition may be given in terms of a reduction of a parameter that is functionally linked to ANGPTL8 gene transcription, e.g., the amount of protein encoded by the ANGPTL8 gene in a cell (as assessed, e.g., by Western analysis, expression of a reporter protein, ELISA, immunoprecipitation, or other techniques known in the art), or the number of cells displaying a certain phenotype, e.g., apoptosis. In principle, ANGPTL8 gene silencing may be determined in any cell expressing the target, either constitutively or by genomic engineering, and by any appropriate assay. However, when a reference is needed in order to determine whether a given dsRNA inhibits the expression of the ANGPTL8 gene by a certain degree and therefore is encompassed by the present disclosure, the assays provided in the Examples below shall serve as such a reference.

In some embodiments, the effect of inhibiting ANGPTL8 gene expression by any of the methods described herein results in a decrease in triglyceride levels in a subject (e.g., in the blood and/or serum of the subject). In some embodiments, triglyceride levels are decreased to below one of the following levels: 500, 450, 400, 350, 300, 250, 200, 190, 180, 170, 160, 150, 140, 130, 120, 110, 100, 90, 80, 70, 60, or 50 mg/dL.

A subject's triglyceride levels may be determined in any of numerous ways known in the art. In some embodiments, a subject's triglyceride levels are determined using a sample from the subject such as blood, serum, or plasma.

A dsRNA or pharmaceutical composition described herein may be administered by any means known in the art, including, without limitation, oral or parenteral routes, including intravenous, intramuscular, subcutaneous, pulmonary, transdermal, and airway (aerosol) administration. Typically, when treating a patient with hypertriglyceridemia, the dsRNA molecules are administered systemically via parenteral means. In some embodiments, the dsRNAs and/or compositions are administered by subcutaneous administration. In some embodiments, the dsRNAs and/or compositions are administered by intravenous administration. In some embodiments, the dsRNAs and/or compositions are administered by pulmonary administration.

As used herein, in the context of ANGPTL8 expression, the terms "treat," "treatment" and the like refer to relief from or alleviation of pathological processes mediated by target gene expression. In the context of the present disclosure, insofar as it relates to any of the conditions recited herein, the terms "treat," "treatment," and the like refer to relieving or alleviating one or more symptoms associated with said condition. For example, in the context of hypertriglyceridemia, treatment may involve a decrease in serum triglyceride levels. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

As used herein, the terms "prevent" or "delay progression of" (and grammatical variants thereof), with respect to a condition relate to prophylactic treatment of a condition, e.g., in an individual suspected to have or be at risk for developing the condition. Prevention may include, but is not limited to, preventing or delaying onset or progression of the condition and/or maintaining one or more symptoms of the disease at a desired or sub-pathological level. For example, in the context of hypertriglyceridemia, prevention may involve maintaining serum triglyceride levels at a desired level in an individual suspected to have or be at risk for developing hypertriglyceridemia.

It is understood that the dsRNAs of the present disclosure may be for use in a treatment as described herein, may be used in a method of treatment as described herein, and/or may be for use in the manufacture of a medicament for a treatment as described herein.

In some embodiments, a dsRNA of the present disclosure is administered in combination with one or more additional therapeutic agents, such as other siRNA therapeutic agents, monoclonal antibodies, and small molecules, to provide a greater improvement to the condition of the patient than administration of the dsRNA alone. In certain embodiments, the additional therapeutic agent provides an anti-inflammatory effect. In certain embodiments, the additional therapeutic agent is an agent that treats hypertriglyceridemia, such as a lipid-lowering agent.

In some embodiments, the additional agent may be one or more of a HMG-CoA reductase inhibitor (e.g., a statin), a fibrate, a bile acid sequestrant, niacin, nicotinic acid, an antiplatelet agent, an angiotensin converting enzyme inhibitor, an angiotensin II receptor antagonist (e.g., losartan potassium), an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, an omega-3 fatty acid (e.g., fish oil or flaxseed oil), and insulin or an insulin analog. Particular examples include, without limitation, atorvastatin, pravastatin, simvastatin, lovastatin, fluvastatin, cerivastatin, rosuvastatin, pitavastatin, ezetimibe, bezafibrate, clofibrate, fenofibrate, gemfibrozil, ciprofibrate, cholestyramine, colestipol, colesevelam, and niacin.

In certain embodiments, a dsRNA as described herein may be administered in combination with another therapeutic intervention such as lipid lowering, weight loss, dietary modification, and/or moderate exercise.

Genetic predisposition plays a role in the development of target gene associated diseases, e.g., hypertriglyceridemia. Therefore, a subject in need of treatment with one or more dsRNAs of the present disclosure may be identified by taking a family history, or, for example, screening for one or more genetic markers or variants. Examples of genes involved in hypertriglyceridemia may include, without limitation, LPL, APOB, APOC2, APOA5, APOE, LMF1, GCKR, GPIHBP1, and GPD1. In certain embodiments, a subject in need of treatment with one or more dsRNAs of the present disclosure may be identified by screening for variants of or loss-of-function mutations in any of these genes or any combination thereof.

A healthcare provider, such as a doctor, nurse, or family member, can take a family history before prescribing or administering a dsRNA of the present disclosure. In addition, a test may be performed to determine a genotype or phenotype. For example, a DNA test may be performed on a sample from the subject, e.g., a blood sample, to identify the ANGPTL8 genotype and/or phenotype before the dsRNA is administered to the subject.

V. Kits and Articles of Manufacture

Certain aspects of the present disclosure relate to an article of manufacture or a kit comprising one or more of the dsRNAs, vectors, or compositions (e.g., pharmaceutical compositions) as described herein useful for the treatment and/or prevention of an ANGPTL8-associated condition (e.g., a lipid metabolism disorder such as hypertriglyceridemia). The article of manufacture or kit may further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating or preventing the disease and may have a sterile access port (for example the container may be an intravenous solution bag or a vial having a stopper pierceable by a hypodermic injection needle). At least one active agent in the composition is a dsRNA as described herein. The label or package insert indicates that the composition is used for treating an ANGPTL8-associated condition. In some embodiments, the condition is a lipid metabolism disorder such as hypertriglyceridemia and/or another condition described herein.

Moreover, the article of manufacture or kit may comprise (a) a first container with a composition contained therein, wherein the composition comprises a dsRNA as described herein; and (b) a second container with a composition contained therein, wherein the composition comprises a second therapeutic agent (e.g., an additional agent as described herein). The article of manufacture or kit in this aspect of the present disclosure may further comprise a package insert indicating that the compositions can be used to treat a particular disease. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and/or user standpoint, including other buffers, diluents, filters, needles, and syringes.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to the manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

EXAMPLES

In order for the present disclosure to be better understood, the following examples are set forth. These examples are for illustration only and are not to be construed as limiting the scope of the present disclosure in any manner.

Example 1: siRNA Synthesis and Purification siRNAs, including non-targeting control siRNAs (NT control), were produced using solid phase oligonucleotide synthesis.
Methods
siRNA Production
RNA oligonucleotides were synthesized at a scale of 1 μmol (in vitro) or 10 μmol (in vivo) on a ABI 394 DNA/RNA or BioAutomation MerMade 12 synthesizer using commercially available 5'-O-DMT-3'-O-(2-cyanoethyl-N,N-diisopropyl) phosphoramidite monomers (SAFC) of uridine, 4-N-acetylcytidine ($C^{Ac}$), 6-N-benzoyladenosine ($A^{Bz}$) and 2-N-isobutyrylguanosine ($G^{iBu}$) with 2'-OMe or 2'-F modification, and the solid supports 5'-O-DMT-thymidine-CPG and 3'-O-DMT-thymidine-CPG (invdT, Link) following standard protocols for solid phase synthesis and deprotection (Beaucage et al., *Curr. Opin. Drug Discov. Devel.* (2008) 11:203-16; Mueller et al., *Curr. Org. Synth.* (2004) 1:293-307).

Phosphoramidite building blocks were used as 0.1 M solutions in acetonitrile and activated with 5-(bis-3,5-trifluoromethylphenyl)-1H-tetrazole (activator 42, 0.25 M in acetonitrile, Sigma Aldrich). Reaction times of 300 s were used for the phosphoramidite couplings. As capping reagents, acetic anhydride in THF (CapA for ABI, Sigma Aldrich) and N-methylimidazole in THF (CapB for ABI, Sigma Aldrich) were used. As oxidizing reagent, iodine in THF/pyridine/water (0.02 M; oxidizer for ABI, Sigma Aldrich) was used. Deprotection of the DMT-protecting group was done using dichloroacetic acid in DCM (DCA deblock, Sigma Aldrich). Final cleavage from solid support and deprotection (acyl- and cyanoethyl-protecting groups) was achieved with $NH_3$ (32% aqueous solution/ethanol, v/v 3:1).

The crude oligonucleotides were analyzed by IEX and LC-MS and purified by anion-exchange high-performance liquid chromatography (IEX-HPLC) using a linear gradient of 10-65% buffer B in 30 min. ÄKTA purifier (Thermo Fisher Scientific DNAPac PA200 semi prep ion exchange column, 8 μm particles, width 22 mm×length 250 mm).
Buffer A: 1.50 L $H_2O$, 2.107 g $NaClO_4$, 438 mg EDTA, 1.818 g TRIS, 540.54 g urea, pH 7.4.
Buffer B: 1.50 L $H_2O$, 105.34 g $NaClO_4$, 438 mg EDTA, 1.818 g TRIS, 540.54 g urea, pH 7.4.
Isolation of the oligonucleotides was achieved by precipitation, induced by the addition of 4 volumes of ethanol and storing at −20° C.

To ensure high fidelity of the data, all single strands were HPLC purified to >85% purity. The purity and identity of the oligonucleotides was confirmed by ion exchange chromatography and LC-MS, respectively.
Duplex Annealing
For the in vitro experiments (100 μM solutions) and in vivo experiments (10 mg/ml), stock solutions of siRNAs in PBS were prepared by mixing equimolar amounts of complementary sense and antisense strands in 1×PBS buffer. The solutions were heated to 90° C. for 10 min and allowed to slowly cool to room temperature to complete the annealing process. siRNAs were further characterized by HPLC and were stored frozen until use.

siRNA Sequences

The sequences of each siRNA, and sequences including nucleotide modifications, are shown in Tables 1 and 2, supra.

siRNA Stability in Mouse Serum

Modified siRNAs were tested for nuclease stability in 50% mouse serum. 160 µL of 2.5 µM siRNA in 1×DPBS (Life Technologies, cat. no. 14190-094) and 160 µL mouse serum (Sigma, cat. no. M5905) were incubated at 37° C. for up to 72 h. At each time-point (0 h, 8 h, 24 h, 32 h, 48 h, 56 h, and 72 h), 20 µL of the reaction was taken out and quenched with a stop solution (Tissue & Cell Lysis Solution (Epicentre, cat. no. MTC096H), Proteinase K (Sigma, cat. no. P2308), water) at 65° C. for 30 min. Prior to HPLC analysis on a Waters 2695 Separation Module and a 2487 Dual Absorbance Detector, RNase-free water was added to each sample. The solution was analyzed by HPLC using a DNAPac PA200 analytical column (Thermo Scientific, cat. no. 063000).

| Time (min) | Flow (mL/min) | % Buffer A* | % Buffer B** |
|---|---|---|---|
| 0 | 1 | 75 | 25 |
| 20 | 1 | 35 | 65 |

Buffer A: 20 mM sodium phosphate (Sigma, Cat. No. 342483), pH 11;
Buffer B: 20 mM sodium phosphate (Sigma, Cat. No. 342483), 1 M sodium bromide (Sigma, Cat. No. 02119), pH 11.

Serum half-lives were estimated for both strands of the siRNA.

Example 2: Identification of siRNAs for Inhibition of Human ANGPTL8 Expression Methods
Cells and Tissue Culture Human Hep3B cells were grown at 37° C., 5% $CO_2$ and 95% relative humidity (RH), and cultivated in EMEM medium (ATCC, cat. no. 30-2003) supplemented with 10% FBS.

siRNA Transfections

For knock-down experiments in Hep3B cells, 20,000 cells/well were used in 96-well plates (Greiner, cat. no. 655180). The cells were transfected with ANGPTL8 siRNAs at 0.1 nM and 1 nM using 0.2 µL/well of Lipofectamine RNAiMAX transfection reagent (Thermo Fisher) according to the manufacturer's protocol in a reverse transfection setup, and incubated for 48 h without medium change. Usually, N=4 technical replicates were carried out per test sample.

mRNA Expression Analysis 48 or 72 hours after siRNA transfection or free siRNA uptake, the cellular RNA was harvested by usage of Promega's SV96 total RNA isolation system (cat. no. Z3500) according to the manufacturer's protocol, including a DNase step during the procedure.

For cDNA synthesis, the Thermo Fisher Reverse Transcriptase kit (cat. no. N8080234) was used. cDNA was synthesized from 30 ng RNA using 1.2 µL 10×RT buffer, 2.64 µL $MgCl_2$ (25 mM), 2.4 µL dNTPs (10 mM), 0.6 µL random hexamers (50 µM), 0.6 µL Oligo(dT)16 (SEQ ID NO: 533) (50 µM), 0.24 µL RNase inhibitor (20 U/µL) and 0.3 µL Multiscribe (50 U/µL) in a total volume of 12 µL. Samples were incubated at 25° C. for 10 minutes and 42° C. for 60 minutes. The reaction was stopped by heating to 95° C. for 5 minutes.

Human and cynomolgus ANGPTL8 mRNA levels were quantified by qPCR using the Thermo Fisher TaqMan Universal PCR Master Mix (cat. no. 4305719) and the following TaqMan Gene Expression assays:

| Human | Hs00218820_m1 |
|---|---|
| Cynomolgus | Hs00218820_m1* *using customized forward primer 5'-GCCCTGCCTACCA AGAATTTG-3' (SEQ ID NO: 534) |

PCR was performed in technical duplicates with an ABI Prism 7900 system under the following PCR conditions: 2 minutes at 50° C., 10 minutes at 95° C., 40 cycles with 95° C. for 15 seconds and 1 minute at 60° C. PCR was set up as a simplex PCR detecting the target gene in one reaction and the housekeeping gene (human/cynomolgus RPL37A) for normalization in a parallel reaction. The final volume for the PCR reaction was 12.5 µL in a 1×PCR master mix; RPL37A primers were used at a final concentration of 50 nM and the probe was used at a final concentration of 200 nM. The ΔΔCt method was applied to calculate relative expression levels of the target transcripts. Percentage of target gene expression was calculated by normalization based on the levels of non-targeting siRNA control treated cells.

$IC_{50}$ Measurements

For $IC_{50}$ measurements, 20,000 human Hep3B cells in 96-well plates were transfected with Lipofectamine RNAiMAX for 48 hours with the indicated ANGPTL8 siRNAs at 7 concentrations starting from 25 nM using 5-8-fold dilution steps. The half maximal inhibitory concentration ($IC_{50}$) for each siRNA was calculated by applying a Biostat-Speed statistical calculation tool. Results were obtained using the 4-parameter logistic model according to Ratkovsky and Reedy (*Biometrics* (1986) 42(3):575-82). The adjustment was obtained by non-linear regression using the Levenberg-Marquardt algorithm in SAS v9.1.3 software.

Cytotoxicity

Cytotoxicity was measured 72 hours after 5 nM and 50 nM siRNA transfections of a culture of 10,000 Hep3B cells per well of a 96-well plate by determining the ratio of cellular viability/toxicity in each sample. Cell viability was measured by determination of the intracellular ATP content using the CellTiter-Glo assay (Promega, cat. no. G7570) according to the manufacturer's protocol. Cell toxicity was measured in the supernatant using the ToxiLight assay (Lonza, cat. no. LT07-217) according to the manufacturer's protocol. 10 nM AllStars Hs Cell Death siRNA (Qiagen, cat. no. SI04381048), 25 µM Ketoconazole (Calbiochem, cat. no. 420600) and 1% Triton X-100 (Sigma, cat. no. T9284) were used as toxic positive controls.

Results

In order to identify siRNAs useful in targeting human ANGPTL8, the following criteria were applied for in silico library generation: First, 19 mers from the human ANGPTL8 mRNA sequence as set forth in NM_018687.6 were identified in silico with an overlap of 18 nucleotides. The resulting pool of 862 19 mers was then aligned to the ANGPTL8 mRNA sequence of *Macaca fascicularis* (cynomolgus monkey), resulting in the exclusion of all sequences having more than 1 mismatch in *M. fascicularis*. This left 401 siRNA sequences with 0 mismatches, and an additional 294 siRNA sequences with 1 mismatch.

For the remaining sequences with a G/C content of 30-55%, an in silico analysis was then carried out to identify any potential off-target transcripts matching either siRNA strand (sense/antisense) in the human transcriptome (RefSeq RNA version 2015-12-22). Human off-target sequences with RNAseq expression (Illumina Body Atlas) FPKM<0.5 in liver tissue were not considered. All siRNA sequences of interest had either greater than three mismatches to any human transcript expressed in liver other than ANGPTL8, or had two mismatches with four or fewer human genes; sequences that did not meet one of these two criteria were filtered out. After this filtration, 132 potential siRNAs were left (see Table 1).

Figure 1A:
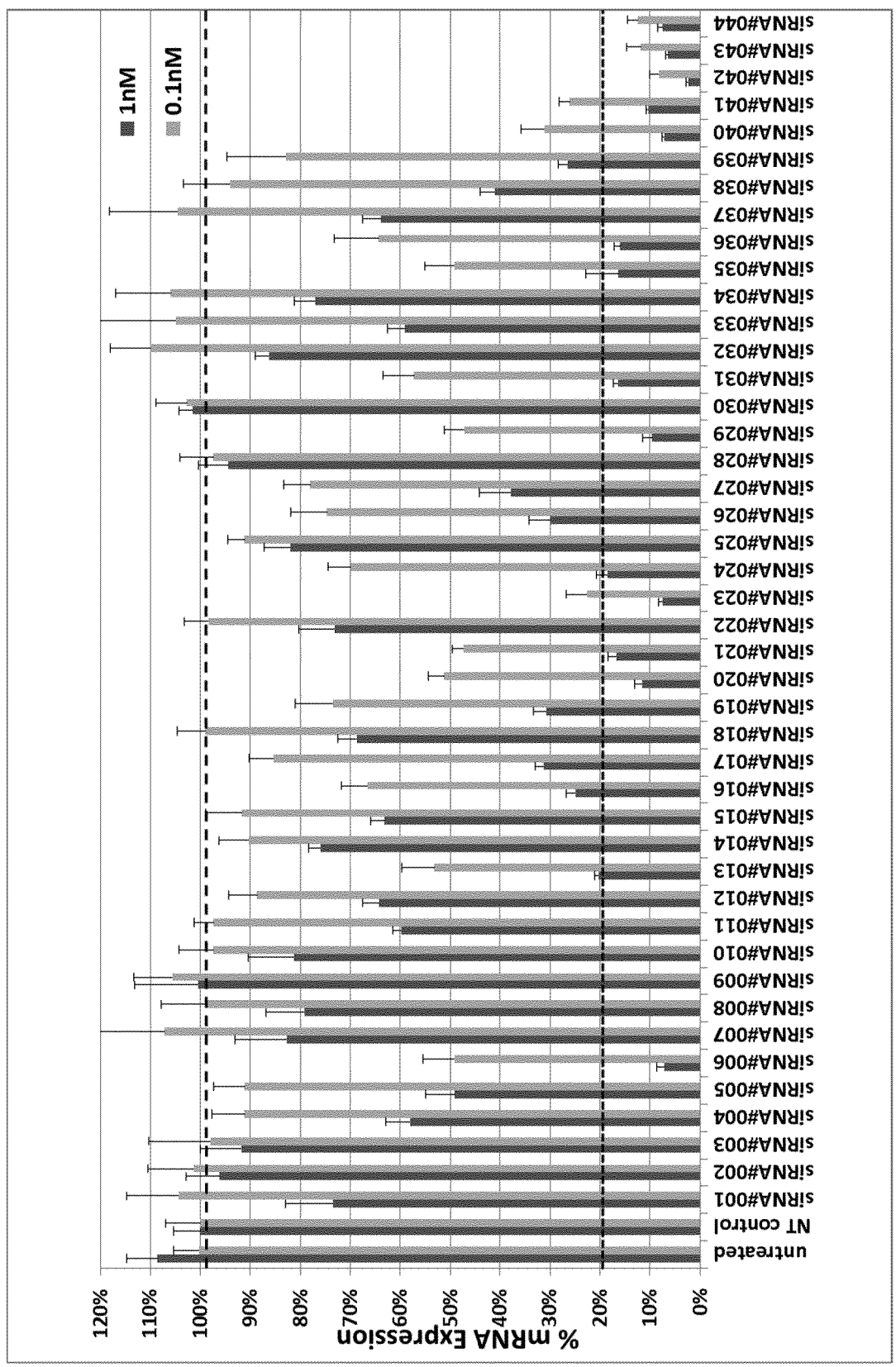
FIGS. 1A, 1B, and 1C are graphs showing RT-qPCR analysis of ANGPTL8 mRNA expression in human Hep3B cell lysates following treatment with 132 test siRNAs as indicated at 0.1 or 1 nM, respectively. Expression of mRNA is represented relative to cells treated with a non-targeting siRNA control. Error bars indicate standard deviation.
Figure 1B:
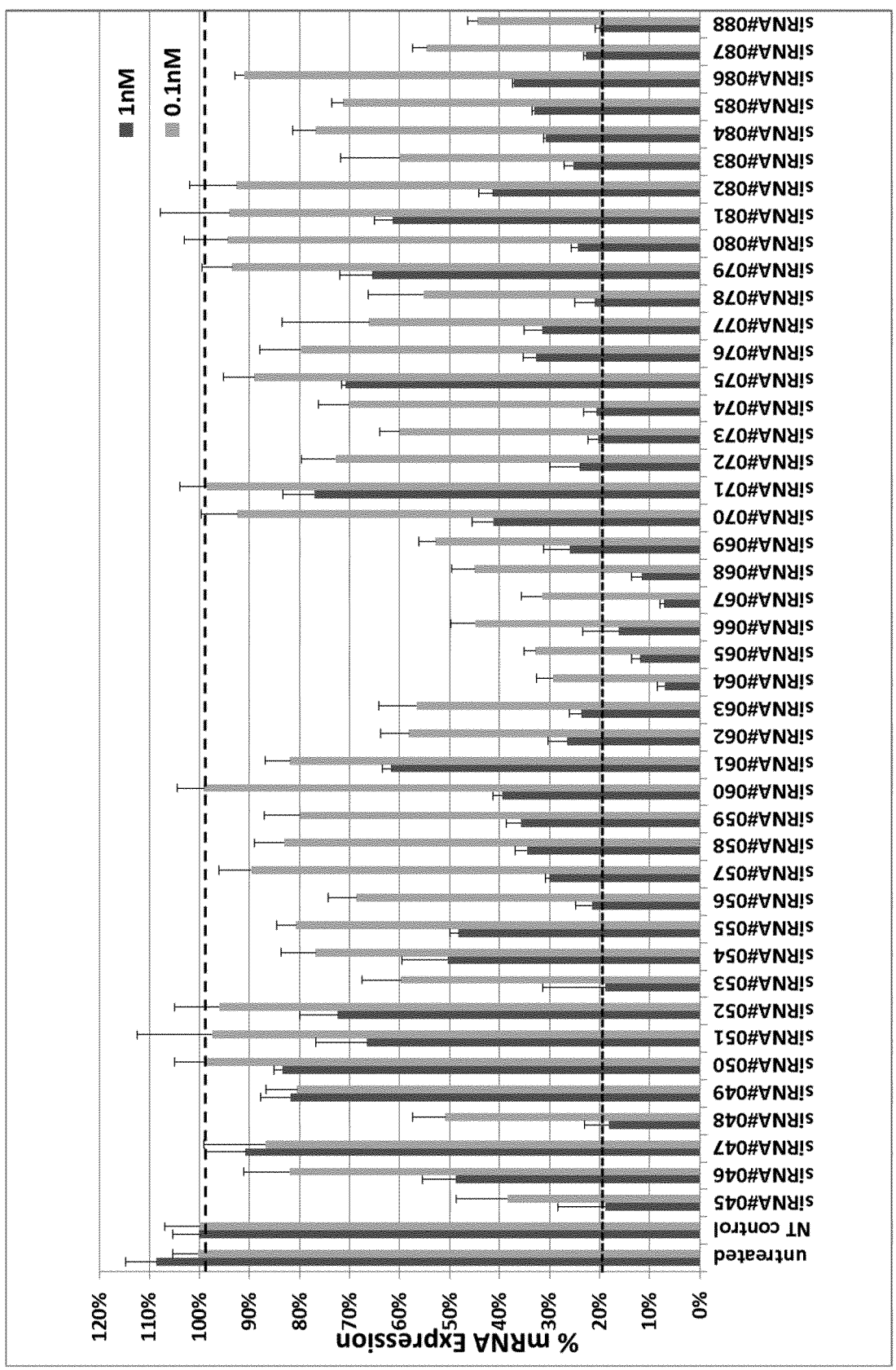
Figure 1C:
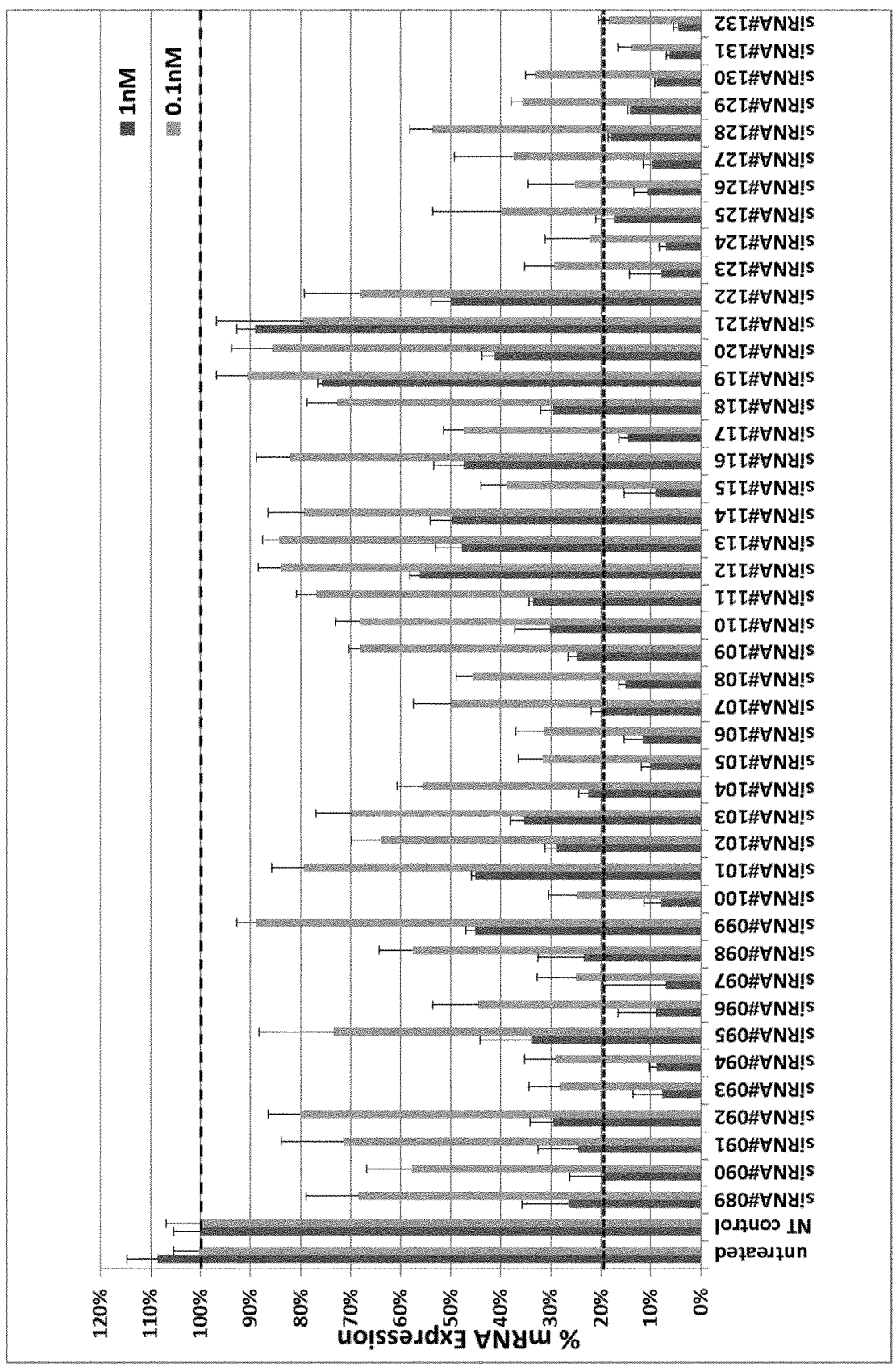

As described above, the 132 siRNAs were produced with nucleotides having a fixed pattern of 2'O-methyl and 2'-fluoro groups (see Table 2). To test the ability of these 132 siRNAs to reduce expression of ANGPTL8, human Hep3B cells were transfected with 0.1 nM or 1.0 nM of each siRNA and incubated for 48 hours. After incubation, mRNA expression of ANGPTL8 was measured in each sample and compared to positive and negative controls (FIGS. 1A-1C). 18 siRNAs that showed reduction of mRNA expression by at least 90% at a concentration of 1.0 nM, or by at least 70% at a concentration of 0.1 nM, were selected for further characterization.

Figure 2:
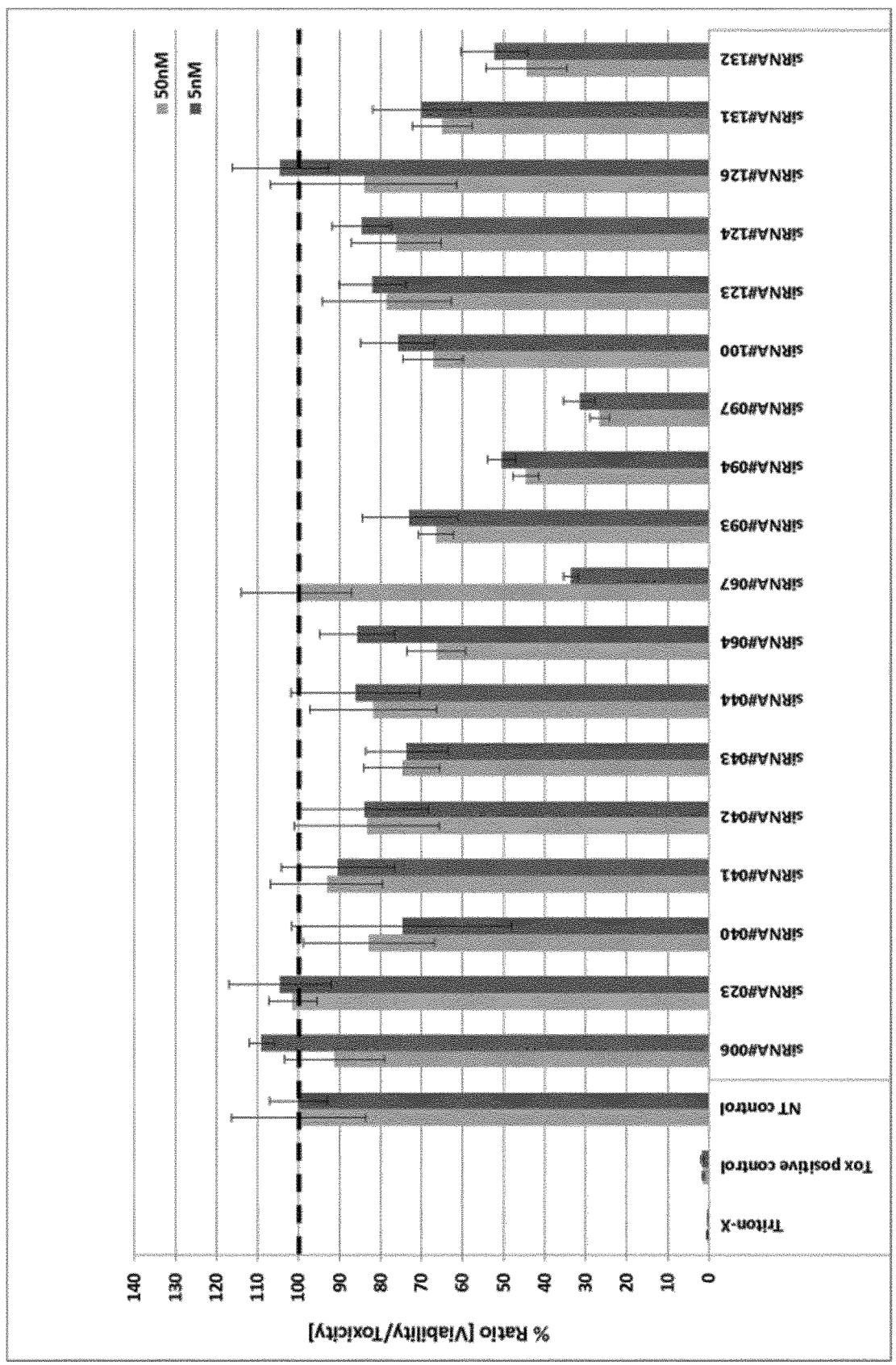
FIG. 2 is a graph showing cytotoxic effects of 18 selected test siRNAs in human Hep3B cells. Cells were treated with siRNAs as indicated at 5 or 50 nM before being analyzed for viability (CellTiter-Glo assay) and toxicity (ToxiLight assay). Ratios of the resulting readings are shown relative to results for a non-targeting siRNA control. Error bars indicate standard deviation.

$IC_{50}$ measurements (Table 5) and a cytotoxicity assay (FIG. 2) were carried out for the selected 18 siRNAs in human Hep3B cells. After removal of 3 siRNAs that showed <50% of NT control Viability/Toxicity ratio (at 50 nM), 12 siRNAs were selected based on their $IC_{50}$ values for conjugation to GalNAc (Table 5):

TABLE 5

Activity and Cytotoxicity of selected siRNAs

| Compound | $I_{max}$ | $IC_{50}$ [nM] | Cytotoxicity detected | Selected for GalNAc conjugation |
|---|---|---|---|---|
| siRNA#006 | 1.004 | 1.37E−01 | | X |
| siRNA#023 | 0.977 | 3.46E−02 | | X |
| siRNA#040 | 0.984 | 2.62E−02 | | X |
| siRNA#041 | 0.956 | 3.33E−02 | | X |
| siRNA#042 | 0.976 | 9.81E−03 | | X |
| siRNA#043 | 0.957 | 1.68E−02 | | X |
| siRNA#044 | 0.956 | 4.15E−02 | | X |
| siRNA#064 | 0.969 | 6.21E−02 | | |
| siRNA#067 | 0.951 | 1.98E−01 | | X |
| siRNA#093 | 0.968 | 5.58E−02 | | |
| siRNA#094 | 0.995 | 5.74E−02 | X | |
| siRNA#097 | 0.992 | 3.70E−02 | X | |
| siRNA#100 | 0.992 | 2.24E−02 | | X |
| siRNA#123 | 0.982 | 4.79E−02 | | X |
| siRNA#124 | 0.976 | 4.79E−02 | | X |
| siRNA#126 | 0.944 | 1.34E−01 | | |
| siRNA#131 | 0.972 | 3.94E−02 | | X |
| siRNA#132 | 0.992 | 1.04E−01 | X | |

Taken together, these results demonstrate the identification of siRNAs capable of potent inhibition of human ANGPTL8 expression without significant cytotoxicity in human cells.

Example 3: Identification of Active GalNAc-Conjugated siRNAs for Inhibition of Human and Cynomolgus ANGPTL8 Expression Methods GalNAc-siRNAs, including non-targeting control siRNAs (NT control), were generated based on the sequences as indicated (see sequence listings above).

Cell Culture and Assays

Human (BioreclamationIVT, cat. no. M00995-P) and cynomolgus (Primacyt, cat. no. CHCP-I-T) primary hepatocytes were cultured as follows: cryopreserved cells were thawed and plated using a plating and thawing kit (Primacyt, cat. no. PTK-1), and were incubated at 37° C., 5% $CO_2$ and 95% RH. 6 hours after plating, the medium was changed to maintenance medium (KaLy-Cell, cat. no. KLC-MM) supplemented with 1% FBS.

mRNA expression analysis was performed as described above in Example 1.

$IC_{50}$ Measurements

For demonstration of dose-activity relationships and $IC_{50}$ measurements in human and cynomolgus primary hepatocytes under free uptake conditions, 50,000-70,000 cells in 96-well plates were incubated for 72 hours without medium change with the siRNAs at concentrations ranging from 10 µM-0.01 nM using 10-fold dilution steps. The half maximal inhibitory concentration ($IC_{50}$) for each siRNA was calculated by applying a Biostat-Speed statistical calculation tool. Results were obtained using the 4-parameter logistic model according to Ratkovsky and Reedy (*Biometrics* (1986) 42(3):575-582). The adjustment was obtained by non-linear regression using the Levenberg-Marquardt algorithm in SAS v9.1.3 software.

Results

Following selection of potent siRNAs, we went on to demonstrate whether the selected molecules retain their activity in the context of a GalNAc-conjugate suitable for liver specific siRNA delivery in vivo. We also assessed whether this activity holds up in cells from *M. fascicularis* (cynomolgus monkey), a pre-clinical species.

The results of the $IC_{50}$ measurements show that all tested siRNA conjugates retain activity when delivered by free uptake to human primary hepatocytes (Table 6), with $IC_{50}$ values ranging from 8.12-475 nM. Surprisingly, however, the performance ranking following free uptake of GalNAc-siRNA differs significantly from that obtained after transfection assisted uptake of unconjugated siRNA (Table 5). This indicates that siRNAs seem to have inherent properties based on their sequence that makes them differentially suited for application in the context of GalNAc conjugates with regard to resulting knock-down potency.

TABLE 6

$I_{max}$ and $IC_{50}$ of selected GalNAc-conjugated siRNAs

| Compound | $I_{max}$ | $IC_{50}$ [nM] |
|---|---|---|
| siRNA#006-c | 0.4301279 | 4.75E+02 |
| siRNA#023-c | 0.8143869 | 3.03E+01 |
| siRNA#040-c | 0.8949594 | 2.70E+01 |
| siRNA#041-c | 0.5851301 | 8.12E+00 |
| siRNA#042-c | 0.946814 | 1.27E+01 |
| siRNA#043-c | 0.9174046 | 1.64E+01 |

TABLE 6-continued $I_{max}$ and $IC_{50}$ of selected GalNAc-conjugated siRNAs

| Compound | $I_{max}$ | $IC_{50}$ [nM] |
|---|---|---|
| siRNA#044-c | 0.958233 | 1.29E+01 |
| siRNA#067-c | 0.3105127 | 3.97E+01 |
| siRNA#100-c | 0.6889424 | 1.28E+01 |
| siRNA#123-c | 0.51566 | 7.04E+01 |
| siRNA#124-c | 0.5422029 | 6.48E+01 |
| siRNA#131-c | 0.7886907 | 1.63E+01 |

Even more surprisingly, the siRNAs show differential dose-activity relationships in cynomolgus hepatocytes that do not correlate with their mismatches to the *M. fascicularis* sequence (FIGS. 5A-D). Contrary to what is expected, the tested siRNAs without mismatch (siRNA#006-c, siRNA#023-c, siRNA#100-c and siRNA#131) overall show an inferior dose-activity relationship compared to the tested siRNAs with one mismatch (particularly siRNA#041-c, siRNA#042-c, siRNA#043-c and siRNA#044-c). This surprising discovery allows the identification of siRNAs that show highest activity in the human target and still allow use in this pre-clinical species.

Example 4: In Vitro and In Vivo Characterization of GalNAc-Conjugated siRNAs for Inhibition of Human ANGPTL8 Expression Methods
Cells and Tissue Culture Human Hep3B cells were grown at 37° C., 5% $CO_2$ and 95% RH, and cultivated in EMEM medium (ATCC, cat. no. 30-2003) supplemented with 10% FBS.

Human (BioreclamationIVT, cat. no. M00995-P) and cynomolgus (Primacyt, cat. no. CHCP-I-T) primary hepatocytes were cultured as follows: cryopreserved cells were thawed and plated using a plating and thawing kit (Primacyt, cat. no. PTK-1), and were incubated at 37° C., 5% $CO_2$ and 95% RH. 6 hours after plating, the medium was changed to maintenance medium (KaLy-Cell, cat. no. KLC-MM) supplemented with 1% FBS.

Human peripheral blood mononuclear cells (PBMCs) were isolated from approximately 16 mL of blood from three healthy donors that were collected in Vacutainer tubes coated with sodium heparin (BD, Heidelberg Germany) according to the manufacturer's instructions.

For transfection of human PBMCs, 100 nM of the siRNAs were reverse transfected into 1×10$^5$ PBMCs with 0.3 µL Lipofectamine 2000 per well of a 96-well plate (N=2) in a total volume of 150 µL serum-free RPMI medium (Thermo Fisher, cat. no. 11875) for 24 hours. Single-stranded RNA ("R-0006") and DNA ("CpG ODN") oligonucleotides, as well as double-stranded unmodified and 2'-O-methyl modified siRNA ("132/161"), were applied as controls.

IFNα Determination

IFNα protein concentration was quantified in the supernatant of human PBMCs as follows: 25 µL of the cell culture supernatant was used for measurement of IFNα concentration applying a self-established electrochemiluminescence assay based on MesoScale Discovery's technology, and using a pan IFNα monoclonal capture antibody (MT1/3/5, Mabtech). Alternatively, a human IFNα2a isoform-specific assay (cat. no. K151VHK) was applied based on MesoScale's U-PLEX platform and according to the supplier's protocol.

Cytotoxicity siRNA cytotoxicity in human primary hepatocytes was measured 72 hours after incubation of 45,000-50,000 cells per well of a 96-well plate with 1 µM, 5 µM and 25 µM siRNA under free uptake conditions by determining the ratio of cellular viability/toxicity in each sample. Cell viability was measured by determination of the intracellular ATP content using the CellTiter-Glo assay (Promega, cat. no. G7570), and cell toxicity was measured in the supernatant using the LDH assay (Sigma, cat. no. 11644793001) according to the manufacturer's protocols. 25 µM Ketoconazole and 1% Triton X-100 were used as positive controls.

Nuclease Stability

The GalNAc-conjugated siRNAs were tested for nuclease stability using the method described in Example 1.

In Vivo Assay

To assess the effect of GalNAc-siRNAs targeting human ANGPTL8 in vivo, a transgene expression system based on adeno-associated viral vectors was applied in mice. To this end, an AAV8 vector with liver specific expression of a bicistronic mRNA, simultaneously encoding human ANGPTL3 and ANGPTL8 from an ApoA2 promoter (Vectalys, Toulouse, France), was administered intravenously to female C57BL/6 mice (Charles River, Germany) before siRNA dosing. GalNAc-conjugated siRNAs (including non-targeting control) were administered subcutaneously at 15 mg/kg (n=8) after serum levels of human ANGPTL3 expressed from the AAV vector reached sufficiently high serum levels. Activity of siRNAs targeting human ANGPTL8 was quantified by measuring human ANGPTL3 as a surrogate.

ANGPTL3 ELISA Assay

Serum ANGPTL3 protein levels in mice treated with siRNAs were quantified by applying R&D Systems' human ANGPTL3 Quantikine ELISA kit (cat. no. DANL30). ANGPTL3 serum levels were calculated relative to the group treated with non-targeting control siRNA.

Results

Figure 3:
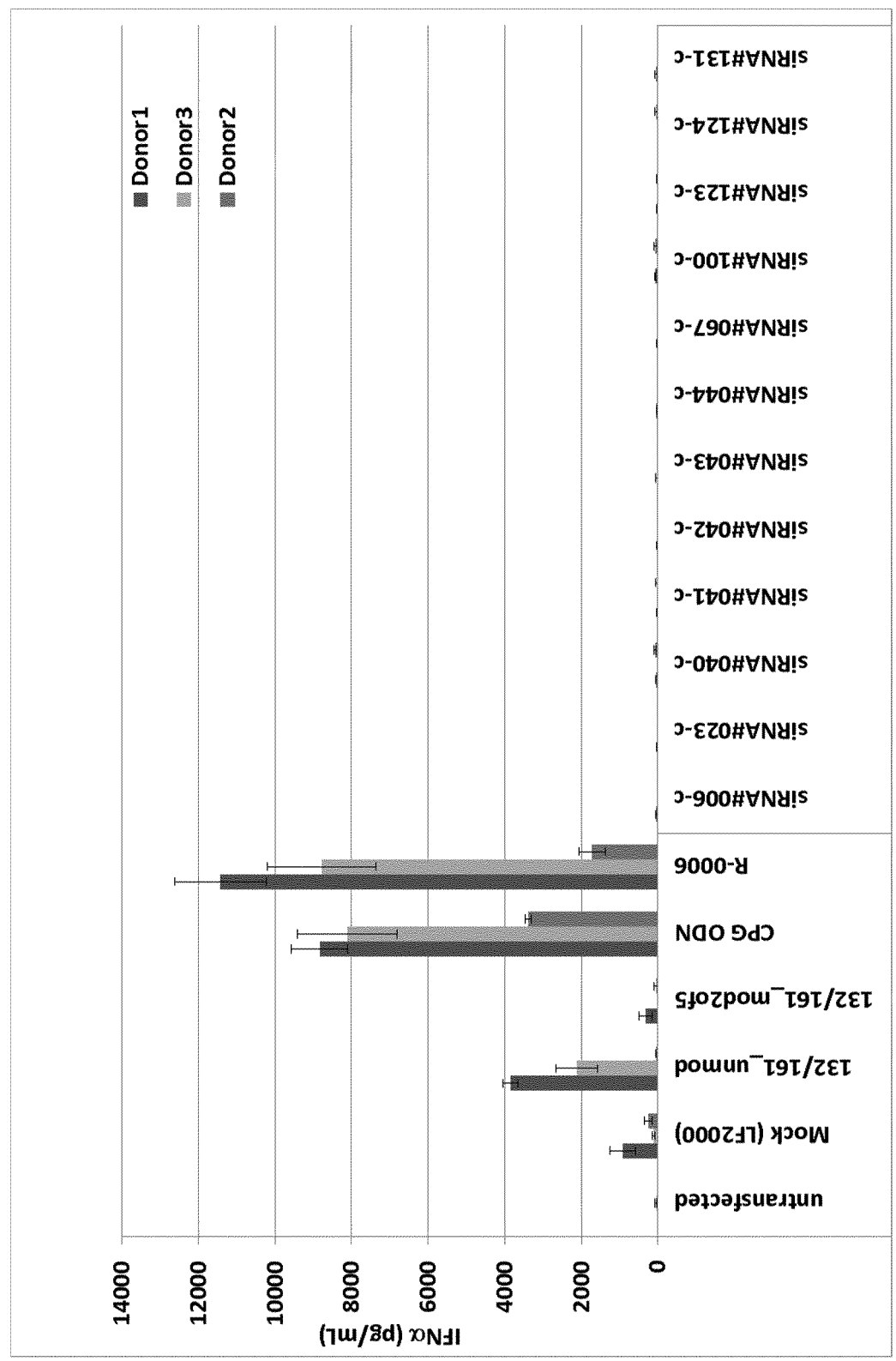
FIG. 3 is a graph of immune stimulation showing the amount of interferon α (IFNα) protein released into the supernatant of human peripheral blood mononuclear cells (PBMCs) isolated from three donors and transfected with selected GalNAc-conjugated siRNAs targeting ANGPTL8 or controls. Protein concentration was determined by ELISA. Error bars indicate standard deviation.

The immune response to 12 GalNAc-siRNAs targeting ANGPTL8 was measured in vitro in human primary cells by examining the production of interferon α secreted from human primary PBMCs isolated from three different healthy donors (FIG. 3) in response to transfection of the siRNAs. No signs of immune stimulation in human PBMCs were observed for any of the tested siRNAs.

The ANGPTL8 GalNAc-siRNAs were also tested for their in vitro nuclease stability in 50% murine serum by determining their relative stability and half-lives (Table 7). Half-lives ranged between 24 h and 72 h.

TABLE 7

In vitro Serum Stability

| Compound | $t_{1/2}$ |
|---|---|
| siRNA#006-c | 72 h |
| siRNA#023-c | 72 h |
| siRNA#040-c | 24 h |
| siRNA#041-c | 32 h |
| siRNA#042-c | 32 h |
| siRNA#043-c | 32 h |
| siRNA#044-c | 56 h |
| siRNA#067-c | 24 h |
| siRNA#100-c | 32 h |
| siRNA#123-c | 32 h |
| siRNA#124-c | 32 h |
| siRNA#131-c | 32 h |

Figure 4:
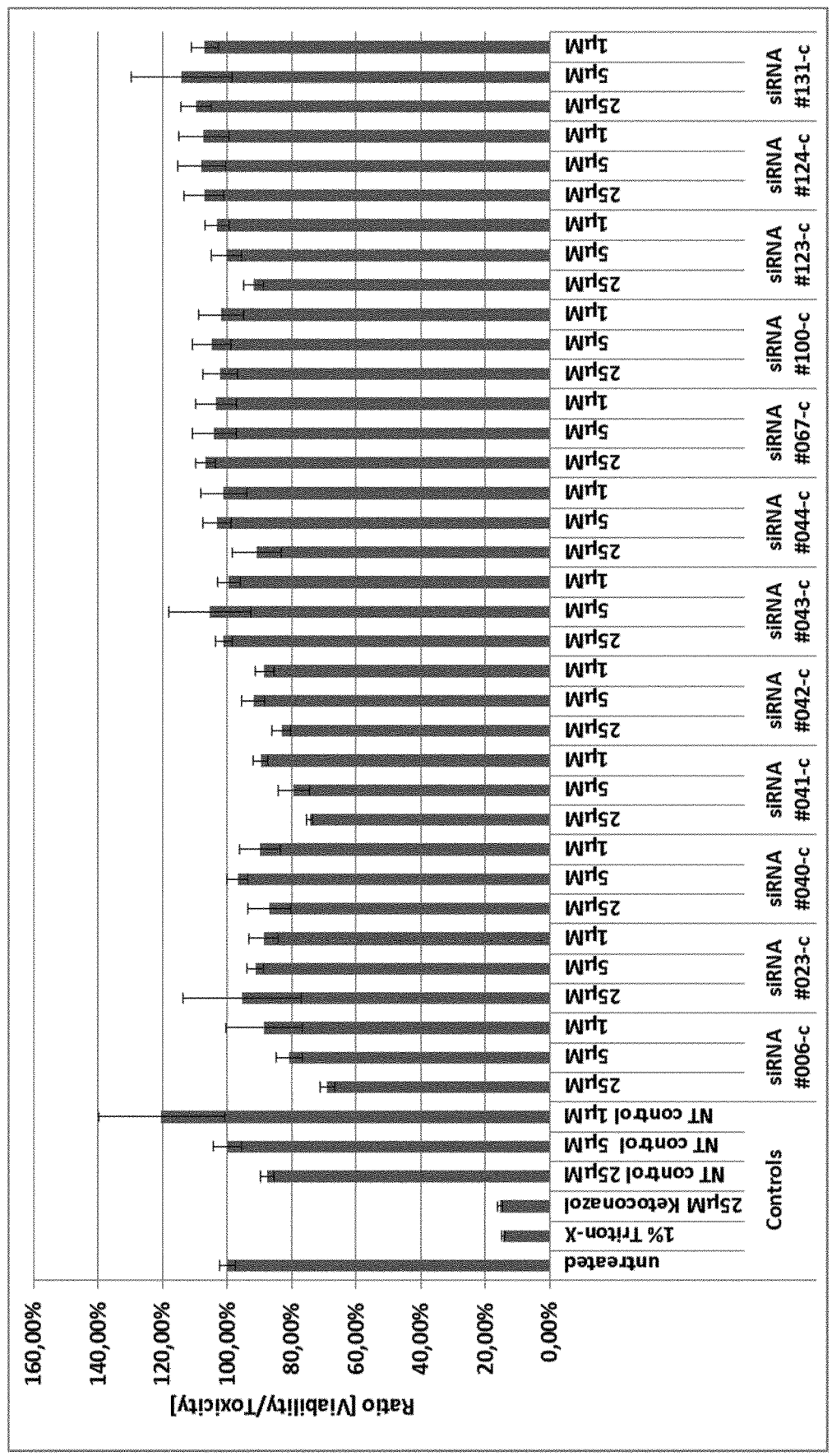
FIG. 4 is a graph showing cytotoxic effects of 12 selected GalNAc-conjugated test siRNAs in human primary hepatocytes following free uptake. Cells were treated with siRNAs as indicated at 1, 5, or 25 μM before being analyzed for viability (CellTiter-Glo assay) and toxicity (ToxiLight assay). Ratios of the resulting readings are shown relative to results for an untreated control and in comparison to toxic positive controls and a non-targeting siRNA control. Error bars indicate standard deviation.
Figure 5A:
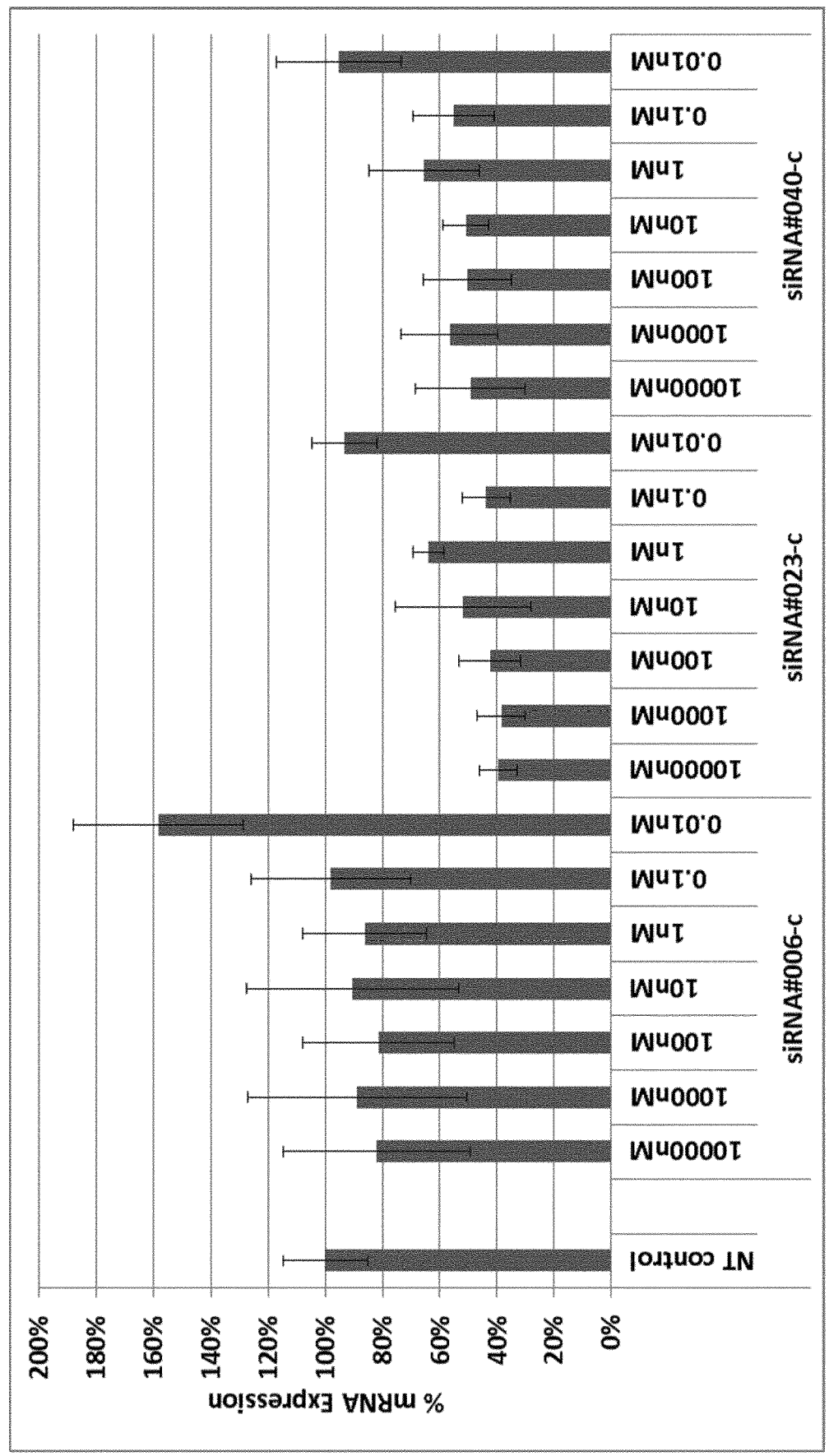
FIGS. 5A-5D are graphs showing RT-qPCR analysis of ANGPTL8 mRNA expression in cynomolgus primary hepatocyte cell lysates following treatment with selected GalNAc-siRNAs at multiple doses as indicated (free uptake). mRNA expression is represented relative to cells treated with a non-targeting siRNA control. Error bars indicate standard deviation.
Figure 5B:
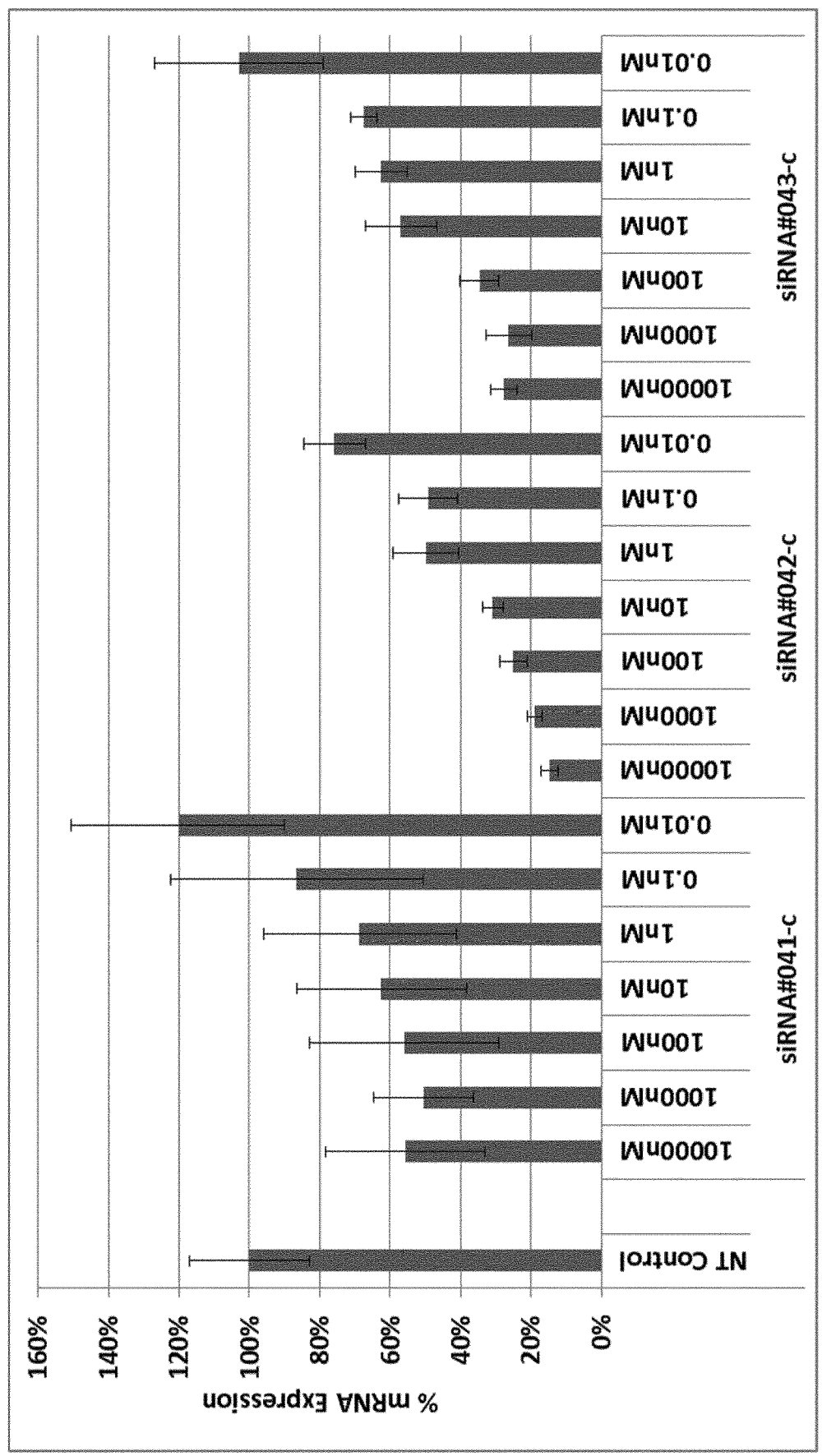
Figure 5C:
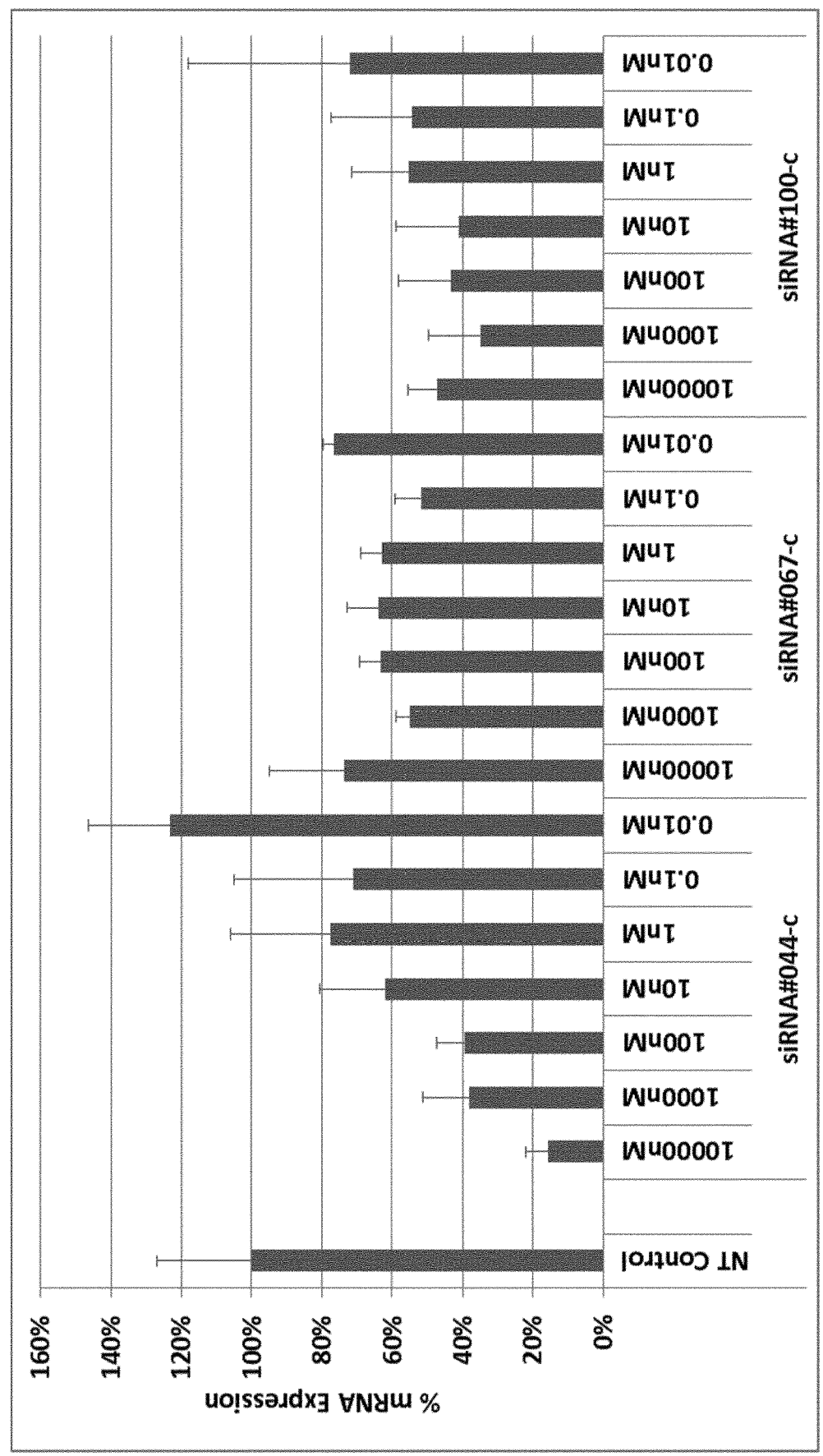
Figure 5D:
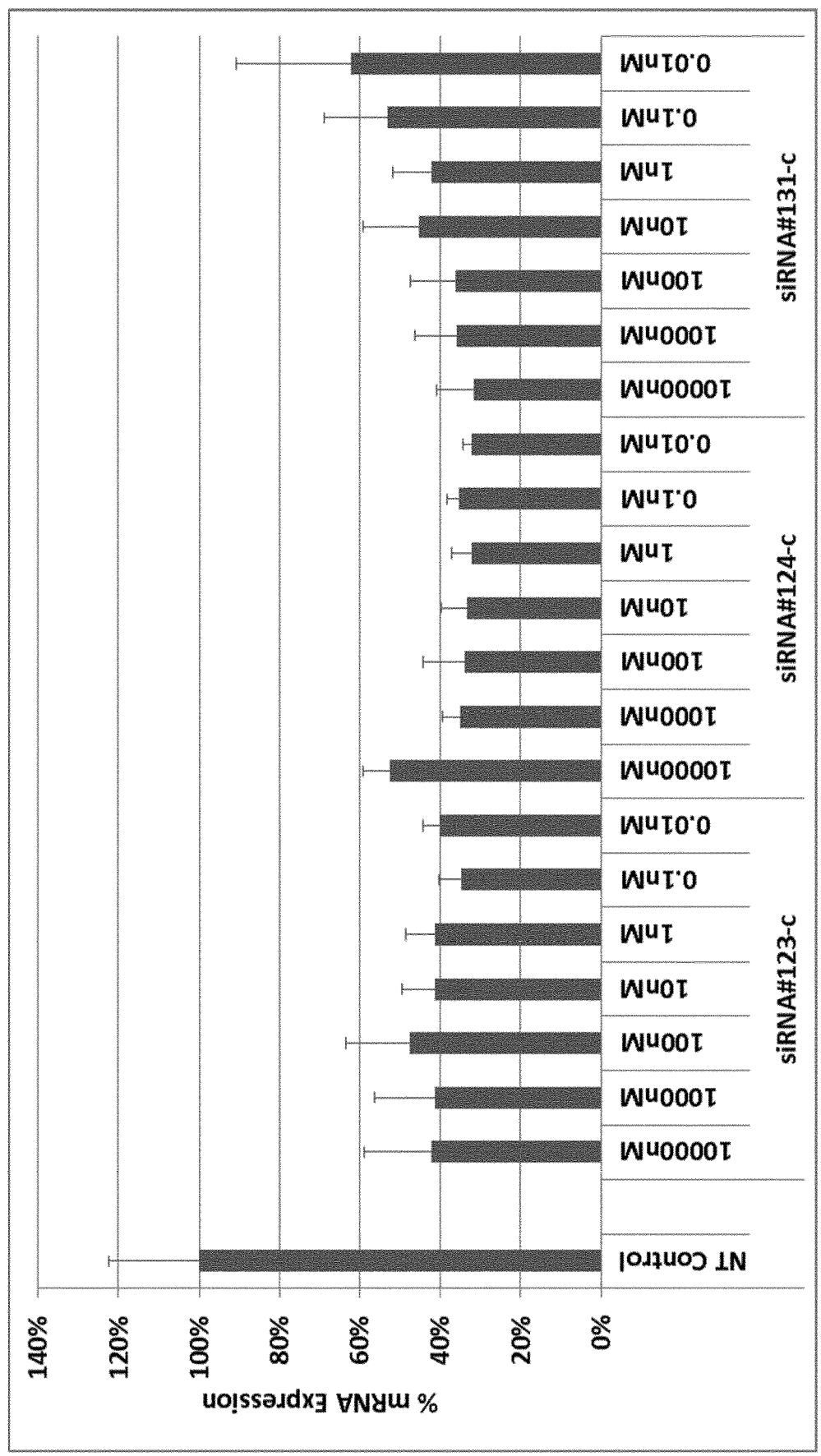

A cytotoxicity assay was carried out in human primary hepatocytes to exclude GalNAc-siRNAs with any toxic potential from further selection (FIG. 4). No obvious toxic effects were observed for most molecules. However, mild, dose-dependent assay effects were observed for siRNA#006-c and siRNA#041-c. These results demonstrate that application of our selected siRNAs in the context of GalNAc-conjugates generally does not confer cytotoxicity.

Figure 6:
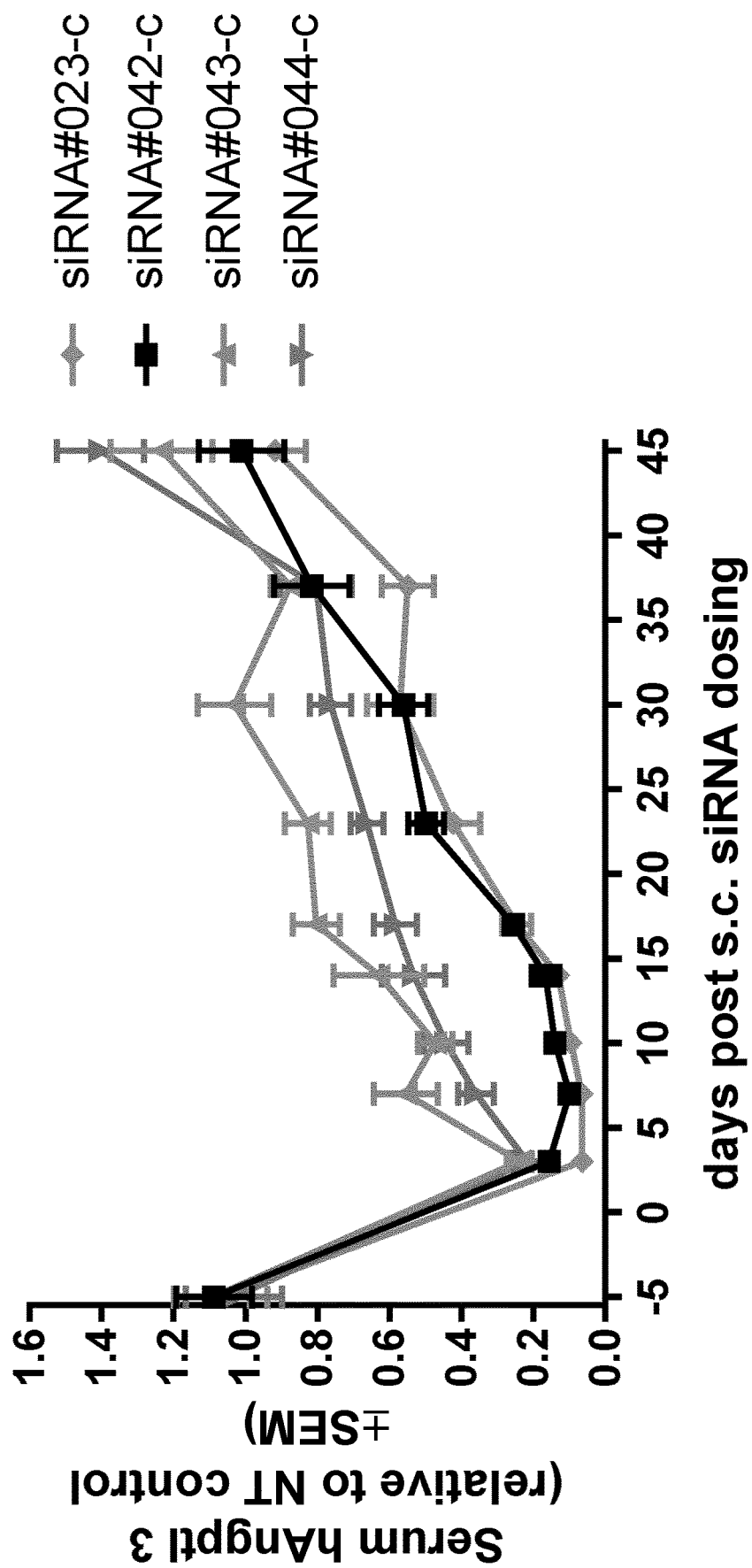
FIG. 6 is a graph showing serum ANGPTL3 protein levels as an indirect monitoring of ANGPTL8 expression from a bicistronic ANGPTL3-ANGPTL8 construct, over time of mice treated subcutaneously with selected GalNAc-siRNAs at 15 mg/kg at day 0. Treated mice express human ANGPTLs 3 and 8 from a liver specific bicistronic adeno-associated viral vector, where knockdown of mRNA leads to reduction of expression of both proteins. Human ANGPTL3 levels were quantified by ELISA. Error bars indicate standard error of the mean. The curve with symbol "♦" corresponds to siRNA#023-c. The curve with symbol "■" corresponds to siRNA#042-c. The curve with symbol "▲" corresponds to siRNA#043-c. The curve with symbol "▼" corresponds to siRNA#044-c.

Finally, four selected GalNAc-siRNAs molecules were tested in vivo using the above-described humanized mouse model expressing human ANGPTL8 mRNA (together with ANGPTL3 from a bicistronic construct) (FIG. 6). After subcutaneous administration of the selected compounds, target protein levels were reduced between 80% and 95% ($KD_{max}$) compared to animals treated with a non-targeting control. Depending on the compound, the levels returned to 50% of the maximum knock-down ($KD_{50}$) between ~d15 and ~d30 post treatment. All groups had returned to baseline by day 45.

In another study, Hep3B cell line overexpressing human ANGPTL8 were transfected with Lipofectamine RNAiMAX with siRNA#042-c for 72 h at 10 concentrations starting from 25 nM, using 2-10-fold dilution steps. Human ANGPTL8 expression was assayed by Western blot in whole cell protein extracts by using a mouse anti-human ANGPTL8 IgG (R&D System, MAB8548) as a primary antibody, a peroxidase-conjugated AffiniPure Goat anti-mouse IgG (JIR Lab. Inc, 11-035-062) as a secondary antibody, and the ECL detection system (GE Healthcare). The data show that siRNA#042-c inhibited human ANGPTL8 expression in Hep3B in a dose-dependent manner, with a half inhibitory concentration ($IC_{50}$) at 0.01 nM and a complete inhibition concentration at 0.1 nM. These results further demonstrate the superior ANGPTL8-inhibitory activity of the tested construct.

Example 5: Optimization of GalNAc-Conjugated ANGPTL8 siRNA Sequences

Methods
Production of Modified GalNAc siRNA Sequences

GalNAc siRNA sequences further optimized with modified nucleotides of formula (I) were synthesized as described in PCT Patent Publication WO 2019/170731. All oligonucleotides were synthesized on an ABI 394 synthesizer. Commercially available (Sigma Aldrich) DNA-, RNA-, 2'-OMe-RNA, and 2'-deoxy-F-RNA-phosphoramidites with standard protecting groups, e.g., 5'-O-dimethoxytrityl-thymidine-3'-O—(N,N-diisopropyl-2-cyanoethyl-phosphoramidite, 5'-O-dimethoxytrityl-2'-O-tert-butyldimethylsilyl-uracile-3'-O—(N,N-diisopropyl-2-cyanoethyl)-phosphoramidite, 5'-O-dimethoxytrityl-2'-O-tert-butyldimethylsilyl-N4-cytidine-3'-O—(N,N-diisopropyl-2-cyanoethyl)-phosphoramidite, 5'-O-dimethoxytrityl-2'-O-tert-butyldimethylsilyl-N6-benzoyl-adenosine-3'-O—(N,N-diisopropyl-2-cyanoethyl)-phosphoramidite, 5'-O-dimethoxytrityl-2'-O-tert-butyldimethylsilyl-N2-isobutyryl-guanosine-3'-O—(N,N-diisopropyl-2-cyanoethyl)-phosphoramidite, 5'-O-dimethoxytrityl-2'-O-methyl-uracile-3'-O—(N,N-diisopropyl-2-cyanoethyl)-phosphoramidite, 5'-O-dimethoxytrityl-2'-O-methyl-N4-cytidine-3'-O—(N,N-diisopropyl-2-cyanoethyl)-phosphoramidite, 5'-O-dimethoxytrityl-2'-O-methyl-N6-benzoyl-adenosine-3'-O—(N,N-diisopropyl-2-cyanoethyl)-phosphoramidite, 5'-O-dimethoxytrityl-2'-O-methyl-N2-isobutyryl-guanosine-3'-O—(N,N-diisopropyl-2-cyanoethyl)-phosphoramidite, 5'-O-dimethoxytrityl-2'-desoxy-fluoro-uracile-3'-O—(N,N-diisopropyl-2-cyanoethyl)-phosphoramidite, 5'-O-dimethoxytrityl-2'-deoxy-fluoro-N4-cytidine-3'-O—(N,N-diiso-propyl-2-cyanoethyl)-phosphoramidite, 5'-O-dimethoxytrityl-2'-deoxy-fluoro-N6-benzoyl-adenosine-3'-O—(N,N-diisopropyl-2-cyanoethyl)-phosphoramidite, and 5'-O-dimethoxytrityl-2'-deoxy-fluoro-N2-isobutyryl-guanosine-3'-O—(N,N-diisopropyl-2-cyanoethyl)-phosphoramidite as well as the corresponding solid support materials (CPG-500 Å, loading 40 mmol/g, ChemGenes) were used for automated oligonucleotide synthesis.

Phosphoramidite building blocks were used as 0.1 M solutions in acetonitrile and activated with 5-(bis-3,5-trifluoromethylphenyl)-1H-tetrazole (activator 42, 0.25 M in acetonitrile, Sigma Aldrich). Reaction times of 200 s were used for standard phosphoramidite couplings. In case of phosphoramidites described herein, coupling times of 300 s were applied. As capping reagents, acetic anhydride in THF (capA for ABI, Sigma Aldrich) and N-methylimidazole in THF (capB for ABI, Sigma Aldrich) were used. As oxidizing reagent, iodine in THF/pyridine/water (0.02 M; oxidizer for ABI, Sigma Aldrich) was used. Alternatively, PS-oxidation was achieved with a 0.05 M solution of 3-((N,N-dimethylaminomethylidene)amino)-3H-1,2,4-dithiazole-5-thione (DDTT) in pyridine/acetonitrile (1:1). Deprotection of the DMT-protecting group was done using dichloroacetic acid in DCM (DCA deblock, Sigma Aldrich). Final cleavage from solid support and deprotection (acyl- and cyanoethyl-protecting groups) was achieved with $NH_3$ (32% aqueous solution/ethanol, v/v 3:1). Treatment with NMP/HF (3:1.5:2) was applied for TBDMS-deprotection.

Oligonucleotides with herein described building blocks at the 3'-end were synthesized on solid support materials shown in Table B or on universal linker-solid support (CPG-500 Å, loading 39 μmol/g, AM Chemicals LLC) and the corresponding phosphoramidites shown in Table A.

Crude products were analyzed by HPLC and single strand purification was performed using ion exchange or preparative HPLC-methods.

Ion exchange: ÄKTA purifier, (Thermo Fisher Scientific DNAPac PA200 semi prep ion exchange column, 8 μm particles, width 22 mm×length 250 mm).

Buffer A: 1.5 L $H_2O$, 2.107 g $NaClO_4$, 438 mg EDTA, 1.818 g TRIS, 540.54 g urea, pH 7.4.

Buffer B: 1.5 L $H_2O$, 105.34 g $NaClO_4$, 438 mg EDTA, 1.818 g TRIS, 40.54 g urea, pH 7.4.

Isolation of the oligonucleotides was achieved by precipitation induced by the addition of 4 volumes of ethanol and storing at −20° C.

Preparative HPLC: Agilent 1100 series prep HPLC (Waters XBridge®BEH C18 OBD™ Prep Column 130 Å, 5 μm, 10 mm×100 mm); Eluent: Triethylammonium acetate (0.1 M in acetonitrile/water). After lyophilization, the products were dissolved in 1.0 mL 2.5 M NaCl solution and 4.0 mL $H_2O$. The corresponding $Na^+$-salts were isolated after precipitation by adding 20 mL ethanol and storing at −20° C. for 18 h.

Final analysis of the single strands was done by LC/MS-TOF methods. For double strand formation, equimolar amounts of sense strands and antisense strands were mixed in 1×PBS buffer and heated to 85° C. for 10 min. Then it was slowly cooled down to room temperature. Final analysis of the siRNA-double strands was done by LC/MS-TOF methods.

Annealing of siRNA duplexes was performed as described in Example 1. The sequences of each siRNA, including nucleotide modifications, are shown in Tables 3 and 4.

siRNA Stability in Mouse Serum

Stability of optimized ANGPTL8 siRNAs was determined as described in Example 1 with the following exceptions: siRNAs were incubated at 37° C. for 0 h, 24 h, 48 h, 72 h, 96 h, and 168 h. Proteinase K was purchased from Qiagen (cat. no. 19133) and HPLC analysis was performed on an Agilent Technologies 1260 Infinity II instrument using a 1260 DAD detector.

Cell Culture and Cell-Based Assays

Human Hep3B cells, primary human hepatocytes, and primary human PBMCs were isolated and cultivated as described in Examples 2-4. Analysis of mRNA was performed as described in Example 2. Cytotoxicity was measured 72 hours after 5 nM and 50 nM siRNA transfections of human Hep3B cells as described in Example 2. IFNα protein concentration was quantified in the supernatant of human PBMCs as described in Example 4.

In Vivo Assay

In vivo activity of modified GalNAc-ANGPTL8 siRNAs was measured in mice transduced with a bicistronic AAV8 vector encoding for human ANGPTL3 and ANGPTL8 mRNA as described in Example 4. In contrast with Example 4, a single siRNA dose of 6 mg/kg was injected subcutaneously into 5 male C57BL/6 mice per treatment group. Serum ANGPTL3 levels were measured by ELISA.

ANGPTL3 ELISA Assay

Serum ANGPTL3 protein levels in mice treated with modified GalNAc-ANGPTL8 siRNAs were used as surrogate for the determination of hepatic in vivo siRNA activities and quantified as described in Example 4.

Results

Fifty-four different siRNA modification patterns were designed and applied to two GalNAc-conjugated siRNA constructs (siRNA#023-c and siRNA#042-c). The library of 2×54 siRNA molecules (siRNA#023-c-01 to siRNA#023-c-54 and siRNA#042-c-01 to siRNA#042-c-54, Tables 3 and 4) was synthesized using three consecutive modified GalNAc-conjugated nucleotides at the 5'-end of the respective siRNA sense strands.

All of the 108 modified ANGPTL8 siRNAs were tested for their nuclease stability in 50% mouse serum (half-life t1l2). As depicted in Table 8, numerous modified constructs displayed significantly improved stability as compared to their parent constructs having a fixed pattern of 2'O-methyl and 2'-fluoro modified nucleotides. For the constructs derived from siRNA#023-c, the serum half-lives improved from approximately 72 h for the parental construct to 168 h or more for the modified constructs. For the constructs derived from siRNA#042-c, serum half-lives improved from approximately 32 h to 96 h or more.

TABLE 8

In vitro Serum Stability

| siRNA Construct | $t_{1/2}$ | siRNA Construct | $t_{1/2}$ |
| --- | --- | --- | --- |
| siRNA#023-c | =72 h | siRNA#042-c | =32 h |
| siRNA#023-c-01 | =72 h | siRNA#042-c-01 | >96 h |
| siRNA#023-c-02 | =72 h | siRNA#042-c-02 | >96 h |
| siRNA#023-c-03 | >48 h | siRNA#042-c-03 | >72 h |
| siRNA#023-c-04 | >48 h | siRNA#042-c-04 | =48 h |
| siRNA#023-c-05 | >48 h | siRNA#042-c-05 | >72 h |
| siRNA#023-c-06 | >48 h | siRNA#042-c-06 | >72 h |
| siRNA#023-c-07 | >96 h | siRNA#042-c-07 | >72 h |
| siRNA#023-c-08 | >48 h | siRNA#042-c-08 | >72 h |
| siRNA#023-c-09 | =96 h | siRNA#042-c-09 | =48 h |
| siRNA#023-c-10 | =96 h | siRNA#042-c-10 | >48 h |
| siRNA#023-c-11 | =96 h | siRNA#042-c-11 | >48 h |
| siRNA#023-c-12 | >96 h | siRNA#042-c-12 | >48 h |
| siRNA#023-c-13 | >72 h | siRNA#042-c-13 | =48 h |
| siRNA#023-c-14 | =168 h | siRNA#042-c-14 | =72 h |
| siRNA#023-c-15 | >72 h | siRNA#042-c-15 | >48 h |
| siRNA#023-c-16 | =168 h | siRNA#042-c-16 | >72 h |
| siRNA#023-c-17 | =96 h | siRNA#042-c-17 | >72 h |
| siRNA#023-c-18 | =72 h | siRNA#042-c-18 | >48 h |
| siRNA#023-c-19 | =72 h | siRNA#042-c-19 | >24 h |
| siRNA#023-c-20 | >48 h | siRNA#042-c-20 | >72 h |
| siRNA#023-c-21 | >48 h | siRNA#042-c-21 | >96 h |
| siRNA#023-c-22 | =72 h | siRNA#042-c-22 | >24 h |
| siRNA#023-c-23 | =72 h | siRNA#042-c-23 | >72 h |
| siRNA#023-c-24 | =96 h | siRNA#042-c-24 | >72 h |
| siRNA#023-c-25 | >24 h | siRNA#042-c-25 | >48 h |
| siRNA#023-c-26 | >48 h | siRNA#042-c-26 | >48 h |
| siRNA#023-c-27 | >72 h | siRNA#042-c-27 | >48 h |
| siRNA#023-c-28 | =72 h | siRNA#042-c-28 | >48 h |
| siRNA#023-c-29 | =72 h | siRNA#042-c-29 | >24 h |
| siRNA#023-c-30 | >48 h | siRNA#042-c-30 | >48 h |
| siRNA#023-c-31 | >72 h | siRNA#042-c-31 | >72 h |
| siRNA#023-c-32 | >72 h | siRNA#042-c-32 | >24 h |
| siRNA#023-c-33 | =72 h | siRNA#042-c-33 | >48 h |
| siRNA#023-c-34 | >72 h | siRNA#042-c-34 | >24 h |
| siRNA#023-c-35 | >48 h | siRNA#042-c-35 | >48 h |
| siRNA#023-c-36 | =72 h | siRNA#042-c-36 | >24 h |
| siRNA#023-c-37 | >72 h | siRNA#042-c-37 | >72 h |
| siRNA#023-c-38 | =72 h | siRNA#042-c-38 | >24 h |
| siRNA#023-c-39 | =72 h | siRNA#042-c-39 | =48 h |
| siRNA#023-c-40 | >48 h | siRNA#042-c-40 | >24 h |
| siRNA#023-c-41 | >96 h | siRNA#042-c-41 | >72 h |
| siRNA#023-c-42 | >96 h | siRNA#042-c-42 | >48 h |
| siRNA#023-c-43 | >48 h | siRNA#042-c-43 | =96 h |
| siRNA#023-c-44 | =72 h | siRNA#042-c-44 | =48 h |
| siRNA#023-c-45 | =96 h | siRNA#042-c-45 | >48 h |
| siRNA#023-c-46 | >96 h | siRNA#042-c-46 | >48 h |
| siRNA#023-c-47 | =72 h | siRNA#042-c-47 | >48 h |
| siRNA#023-c-48 | >72 h | siRNA#042-c-48 | >48 h |
| siRNA#023-c-49 | =72 h | siRNA#042-c-49 | =48 h |
| siRNA#023-c-50 | =96 h | siRNA#042-c-50 | >24 h |
| siRNA#023-c-51 | >168 h | siRNA#042-c-51 | >72 h |
| siRNA#023-c-52 | >72 h | siRNA#042-c-52 | >48 h |
| siRNA#023-c-53 | =72 h | siRNA#042-c-53 | >72 h |
| siRNA#023-c-54 | >72 h | siRNA#042-c-54 | =48 h |

Figure 7A:
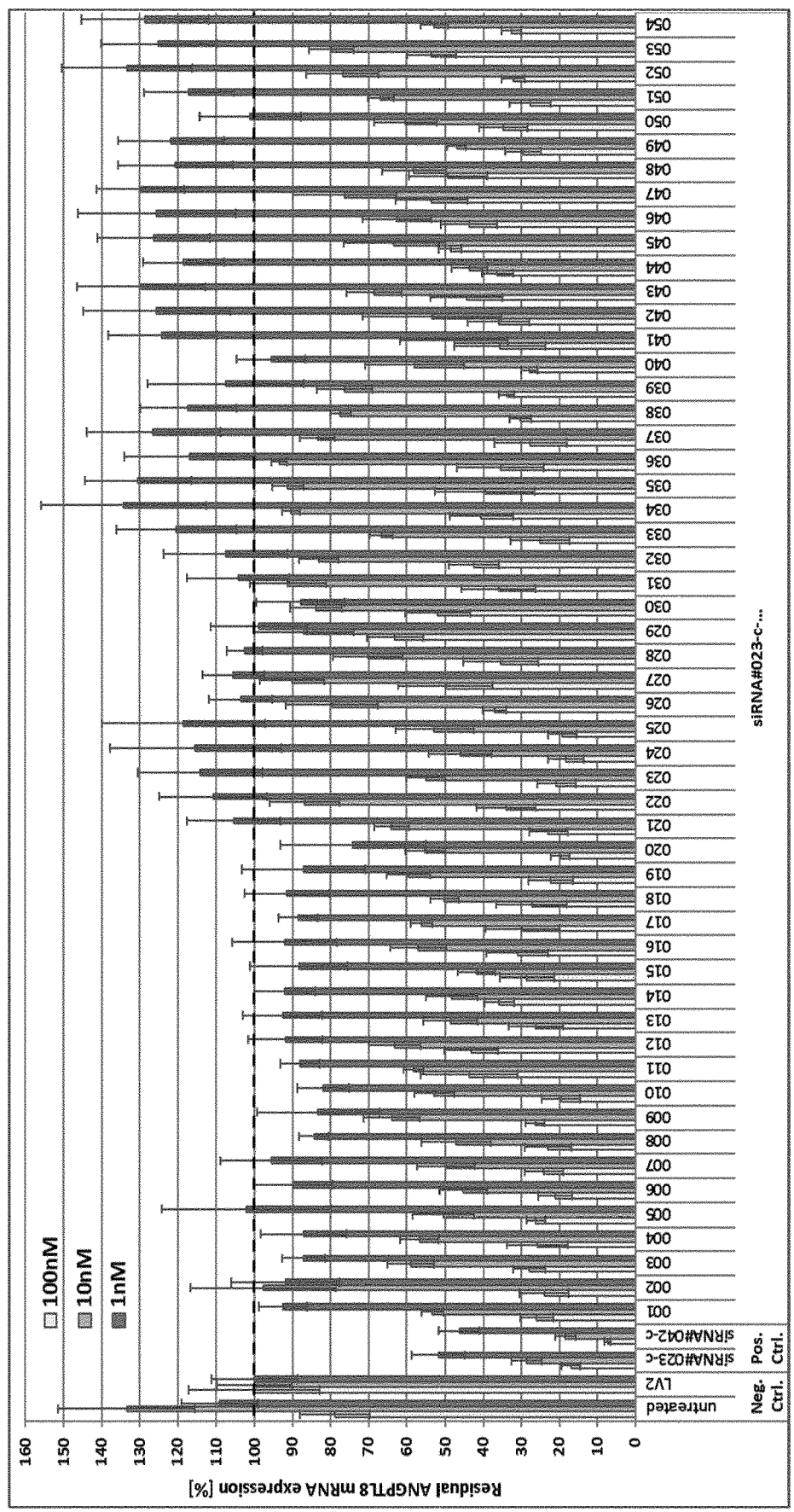
FIGS. 7A and 7B are graphs showing RT-qPCR analysis of ANGPTL8 mRNA expression in primary human hepatocytes following treatment of the cells with 2×54 test siRNAs at 1 nM, 10 nM, or 100 nM, respectively. Neg. Ctrl.: negative control (untreated cells and cells treated with a non-targeting siRNA control LV2). Pos. Ctrl.: cells treated with parent constructs siRNA#023-c and siRNA#042-c.
Figure 7B:
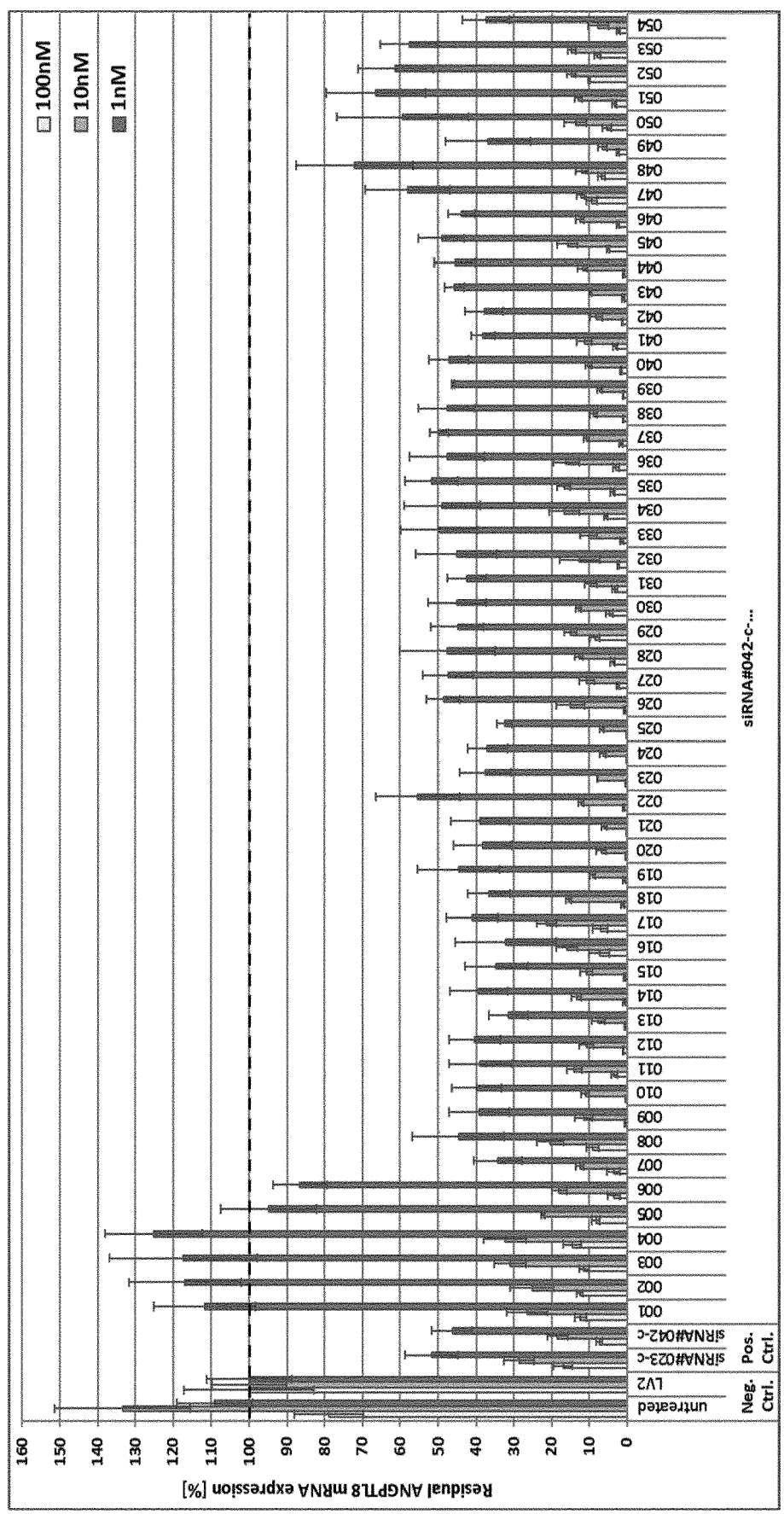

Next, all of the 108 modified GalNAc-siRNAs were evaluated for their knock-down potency in primary human hepatocytes under free uptake conditions using 1 nM, 10 nM, and 100 nM concentrations of the modified siRNAs. The parent constructs siRNA#023-c and siRNA#042-c were used as positive controls. Data are shown in FIGS. 7A and 7B. Surprisingly, most modified variants of siRNA#042-c exhibited strongly improved in vitro knock-down activities as compared to the parent construct (FIG. 7B), while this was not the case for the siRNA#023-c (FIG. 7A).

Based on the in vitro knock-down activity and nuclease stability data, twelve modified variants were selected for each of the two parent constructs. Prior to in vivo activity testing, the 2×12 modified constructs were investigated for their ability to stimulate innate immunity in human PBMCs (FIG. 8) and for their general cytotoxicity in human Hep3B cells (FIG. 9). In both assays, no apparent adverse effects were observed.

Finally, the 2×12 selected modified constructs were tested in vivo as described in Example 4. For this experiment, mice were injected intravenously with a bicistronic AAV8 construct encoding ANGPTL3 and ANGPTL8. Treated mice expressed human ANGPTLs 3 and 8, where knockdown of mRNA led to reduced expression of both proteins. The data show that following the siRNA injection, the protein levels of surrogate biomarker ANGPTL3 were reduced up to 95%

($KD_{max}$) compared to animals treated with PBS (FIGS. 10A and 10B). In fact, the serum level of ANGPTL3 did not return to more than 50% ($KD_{50}$) of the pre-treatment level even on day 70 in animals treated with siRNA#023-c-02, -06, -07, -10, -15, -16, -38, -42, -46, or 51, or with siRNA#042-c-43, or -53. In contrast, the ANGPTL3 levels in animals treated with the parental constructs were indistinguishable from the control animals at that point in time.

In summary, we have demonstrated successful identification of siRNAs that strongly reduce expression of human ANGPTL8 mRNA and protein translated from it in the context of GalNAc-conjugates in vivo and in vitro. Surprisingly, some identified siRNAs further successfully target cynomolgus ANGPTL8 mRNA despite single base sequence mismatch. We have also demonstrated unexpectedly strong improvement of in vivo efficacy of siRNAs by introduction of optimized modification patterns using modified nucleotides.

```
ANGPTL8 Sequences
human ANGPTL8 mRNA sequence
                              (SEQ ID NO: 529)
   1 ataccttaga ccctcagtca tgccagtgcc tgctctgtgc ctgctctggg ccctggcaat 61 ggtgacccgg cctgcctcag cggcccccat gggcggccca gaactggcac agcatgagga 121 gctgaccctg ctcttccatg ggaccctgca gctgggccag gccctcaacg gtgtgtacag 181 gaccacggag ggacggctga caaaggccag gaacagcctg ggtctctatg gccgcacaat 241 agaactcctg gggcaggagg tcagccgggg ccgggatgca gcccaggaac ttcgggcaag 301 cctgttggag actcagatgg aggaggatat tctgcagctg caggcagagg ccacagctga 361 ggtgctgggg gaggtggccc aggcacagaa ggtgctacgg gacagcgtgc agcggctaga 421 agtccagctg aggagcgcct ggctgggccc tgcctaccga gaatttgagg tcttaaaggc 481 tcacgctgac aagcagagcc acatcctatg ggccctcaca ggccacgtgc agcggcagag 541 gcgggagatg gtggcacagc agcatcggct gcgacagatc caggagagac tccacacagc 601 ggcgctccca gcctgaatct gcctggatgg aactgaggac caatcatgct gcaaggaaca 661 cttccacgcc ccgtgaggcc cctgtgcagg gaggagctgc ctgttcactg ggatcagcca 721 gggcgccggg ccccacttct gagcacagag cagagacaga cgcaggcggg gacaaggca
```

```
 781 gaggatgtag ccccattggg gaggggtgga ggaaggacat gtacccttc atgcctacac 841 accctcatt aaagcagagt cgtggcatct caaaaaaaaa aaaaaaaa
human ANGPTL8 polypeptide sequence
                              (SEQ ID NO: 530)
MPVPALCLLW ALAMVTRPAS AAPMGGPELA QHEELTLLFH

GTLQLGQALN GVYRTTEGRL TKARNSLGLY GRTIELLGQE

VSRGRDAAQE LRASLLETQM EEDILQLQAE ATAEVLGEVA

QAQKVLRDSV QRLEVQLRSA WLGPAYREFE VLKAHADKQS

HILWALTGHV QRQRREMVAQ QHRLRQIQER LHTAALPA cynomolgus ANGPTL8 mRNA sequence
                              (SEQ ID NO: 531)
   1 atggggatg ccctccctc cttccctggg gtgcagtcac tgaccggcag ggcctggctg 61 gggtcctcgc ctgtcatgta ctgcactcgc acggcaaggt tgcgcacgga gccctggcgg 121 ctgctgaagt tgaggctgtg cgggtacacg tacagcagac cctcagtcat gctagtgcct 181 gctctgtgcc tgctgtgggc cctggcaatg gtgatccagc ctgcctcagc ggcccccgtg 241 ggcagcccag aactggcaga gcatgaggag ctgaccctgc tcttccatgg gaccctgcag 301 ctgggccagg ccctcaatgg tgtgtacaag accacggagg gacggctgac aaaggccagg 361 aacagcctgg gtctctatgg ccgcacagtg gaactcctgg ggcaggaggt cagccggggc 421 cgggatgcag cccaggaact tcgggcaagc ctgttggaga ctcagatgga ggaggatatt 481 ctgcagctga aggcagaggc catagccgag gtgctggagg aggtggccca ggcacagaag 541 gtgctacagg acagcgtgcg gcggctagaa gtccagctga ggagcgcctg gctgggccct 601 gcctaccaag aatttgaggt cttaaaggct cacgctgaca agcagagcca catcctgtgg 661 gccctcacag gccacgtgca gcggcagagg cgggagatgg tggcacagca gcatcggctg 721 cgacagatcc aggagagaat ccacaaagcg gcgctcccag cctgaatctg cctggatgga 781 actgaggacc aaccatgctg caaggaacac ttccacgccc catgaggccc tgaacaggg 841 aggagctgcc tgttcactgg gatcagccag ggcgcccggc cccacttctg agcacagagc
```

```
901 agagacagac gcaggcaggg acaaaggcag aggacgtagc cccattgggg aggggtggag 961 gaaggatgtg taccctttca tacctacaca ccccccttat taaagcagag tcgtggcatc 1021 tca
``` cynomolgus ANGPTL8 polypeptide sequence
(SEQ ID NO: 532)

```
MLVPALCLLW ALAMVIQPAS AAPVGSPELA EHEELTLLFH
GTLQLGQALN GVYKTTEGRL TKARNSLGLY GRTVELLGQE
VSRGRDAAQE LRASLLETQM EEDILQLKAE AIAEVLEEVA
QAQKVLQDSV RRLEVQLRSA WLGPAYQEFE VLKAHADKQS
HILWALTGHV QRQRREMVAQ QHRLRQIQER IHKAALPA
```

The invention claimed is:

1. A double-stranded ribonucleic acid (dsRNA) that inhibits expression of a human angiopoietin-like protein 8 (ANGPTL8) gene by targeting a target sequence on an RNA transcript of the ANGPTL8 gene, wherein the dsRNA comprises a sense strand comprising a sense sequence, and an antisense strand comprising an antisense sequence, wherein the sense sequence is at least 90% identical to the target sequence, wherein the target sequence is nucleotides 457-475 of SEQ ID NO: 529, and wherein the dsRNA is conjugated to one or more ligands with or without a linker.

2. The dsRNA of claim 1, wherein the sense strand and the antisense strand are complementary to each other over a region of 15-25 contiguous nucleotides, and/or the sense strand and the antisense strand are no more than 30 nucleotides in length.

3. The dsRNA of claim 1, wherein the dsRNA comprises an antisense sequence that is at least 90% identical to the nucleotide sequence of SEQ ID NO: 174.

4. The dsRNA of claim 1, wherein the sense sequence and the antisense sequence are complementary, wherein:
   a) the sense sequence comprises the nucleotide sequence of SEQ ID NO: 42; and/or
   b) the antisense sequence comprises the nucleotide sequence of SEQ ID NO: 174.

5. The dsRNA of claim 1, wherein one or both of the sense strand and the antisense strand further comprise:
   a) a 5' overhang comprising one or more nucleotides; and/or
   b) a 3' overhang comprising one or more nucleotides.

6. The dsRNA of claim 5, wherein an overhang in the dsRNA comprises two or three nucleotides, and/or one or more thymines.

7. The dsRNA of claim 1, wherein the ligand is a cholesterol derivative, a lipophilic moiety, or N-acetylgalactosamine (GalNAc) and the dsRNA is conjugated to one or more GalNAc.

8. The dsRNA of claim 1, wherein the dsRNA is a small interfering RNA (siRNA), or a short hairpin RNA (shRNA).

9. The dsRNA of claim 1, comprising one or more internucleoside linking groups independently selected from the group consisting of phosphodiester, phosphotriester, phosphorothioate, phosphorodithioate, alkyl-phosphonate and phosphoramidate backbone linking groups, or a pharmaceutically acceptable salt thereof.

10. A pharmaceutical composition comprising the dsRNA of claim 1 and a pharmaceutically acceptable excipient.

11. The dsRNA of claim 1, wherein the dsRNA comprises one or more modified nucleotides,
 wherein at least one of the one or more modified nucleotides is 2'-deoxy-2'-fluoro-ribonucleotide, 2'-deoxyribonucleotide, or 2'-O-methyl-ribonucleotide, and/or
 wherein the dsRNA comprises an inverted 2'-deoxyribonucleotide at the 3'-end of its sense or antisense strand, and/or
 wherein the sense sequence and the antisense sequence comprise alternating 2'-O-methyl ribonucleotides and 2'-deoxy-2'-fluoro ribonucleotides.

12. The dsRNA of claim 1, wherein:
 a) the sense sequence comprises a nucleotide sequence selected from the group consisting of SEQ ID NOs: 643-696; and/or
 b) the antisense sequence comprises a nucleotide sequence selected from the group consisting of SEQ ID NOs: 697-750.

13. A double-stranded ribonucleic acid (dsRNA) that inhibits expression of a human angiopoietin-like protein 8 (ANGPTL8) gene by targeting a target sequence on an RNA transcript of the ANGPTL8 gene, wherein the dsRNA comprises a sense strand comprising a sense sequence, and an antisense strand comprising an antisense sequence, wherein the sense sequence is at least 90% identical to the target sequence, wherein the target sequence is nucleotides 457-475 of SEQ ID NO: 529, and wherein the dsRNA comprises one or more modified nucleotides,
 wherein at least one of the one or more modified nucleotides is 2'-deoxy-2'-fluoro-ribonucleotide, 2'-deoxyribonucleotide, or 2'-O-methyl-ribonucleotide, and/or
 wherein the dsRNA comprises an inverted 2'-deoxyribonucleotide at the 3'-end of its sense or antisense strand, and/or
 wherein the sense sequence and the antisense sequence comprise alternating 2'-O-methyl ribonucleotides and 2'-deoxy-2'-fluoro ribonucleotides.

14. A pharmaceutical composition comprising the dsRNA of claim 13 and a pharmaceutically acceptable excipient.

15. A double-stranded ribonucleic acid (dsRNA) that inhibits expression of a human angiopoietin-like protein 8 (ANGPTL8) gene by targeting a target sequence on an RNA transcript of the ANGPTL8 gene, wherein the dsRNA comprises a sense strand comprising a sense sequence, and an antisense strand comprising an antisense sequence, wherein the sense sequence is at least 90% identical to the target sequence, wherein the target sequence is nucleotides 457-475 of SEQ ID NO: 529, and wherein:
 a) the sense sequence comprises a nucleotide sequence selected from the group consisting of SEQ ID NOs: 643-696; and/or
 b) the antisense sequence comprises a nucleotide sequence selected from the group consisting of SEQ ID NOs: 697-750.

16. A pharmaceutical composition comprising the dsRNA of claim 15 and a pharmaceutically acceptable excipient.

* * * * *